US007101977B2

(12) United States Patent
Rosenblum et al.

(10) Patent No.: US 7,101,977 B2
(45) Date of Patent: Sep. 5, 2006

(54) THERAPEUTIC AGENTS COMPRISING PRO-APOPTOTIC PROTEINS

(75) Inventors: Michael G. Rosenblum, Houston, TX (US); Yuying Liu, Houston, TX (US)

(73) Assignee: Research Development Foundation, Carson City, NV (US)

( * ) Notice: Subject to any disclaimer, the term of this patent is extended or adjusted under 35 U.S.C. 154(b) by 446 days.

(21) Appl. No.: 10/196,793

(22) Filed: Jul. 17, 2002

(65) Prior Publication Data

US 2003/0086919 A1 May 8, 2003

Related U.S. Application Data

(60) Provisional application No. 60/360,361, filed on Feb. 28, 2002, provisional application No. 60/332,886, filed on Nov. 6, 2001, provisional application No. 60/306,091, filed on Jul. 17, 2001.

(51) Int. Cl.
*C07K 16/00* (2006.01)
*C12N 9/00* (2006.01)

(52) U.S. Cl. .................................... 530/387.1; 435/183

(58) Field of Classification Search ............ 530/387.1; 435/183
See application file for complete search history.

(56) References Cited

U.S. PATENT DOCUMENTS 4,263,279 A 4/1981 Sela et al. .................... 424/85
4,414,148 A 11/1983 Jansen et al. ............ 530/391.9
4,522,918 A 6/1985 Schlom et al. ................ 435/68
4,590,071 A 5/1986 Scannon et al. .............. 424/85
4,650,674 A 3/1987 Aggarwal et al. ............ 424/85
4,671,958 A 6/1987 Rodwell et al. .............. 424/85
4,677,064 A 6/1987 Mark et al. .................... 435/68
4,753,894 A 6/1988 Frankel et al. .............. 436/548
4,771,128 A 9/1988 Ferris et al. ............. 530/391.7
4,801,578 A 1/1989 Monsigny et al. ............. 514/8
4,831,122 A 5/1989 Buchsbaum et al. ..... 530/391.3
4,863,726 A 9/1989 Stevens et al. ............ 424/85.2
4,870,163 A 9/1989 Rubin et al. ................ 530/413
4,888,415 A 12/1989 Lambert et al. ............ 530/390
4,894,225 A 1/1990 Zimmerman ............... 424/85.1
4,894,227 A 1/1990 Stevens et al. ............ 424/85.2
4,894,443 A 1/1990 Greenfield et al. ......... 530/388
4,935,233 A 6/1990 Bell et al. .................. 424/85.5
4,946,778 A 8/1990 Landner et al. ............ 435/69.6
4,962,188 A 10/1990 Frankel ...................... 530/389
4,963,354 A 10/1990 Shepard et al. ............ 424/85.1
4,980,457 A 12/1990 Jansen et al. ............... 530/391
5,017,371 A 5/1991 Cummins .................. 424/85.6
5,019,368 A 5/1991 Epstein et al. ............... 424/1.1
5,032,521 A 7/1991 White et al. ........... 435/240.27
5,134,075 A 7/1992 Hellstrom et al. ....... 530/387.3
5,359,046 A 10/1994 Capon et al. .............. 536/23.4
5,624,827 A 4/1997 Rosenblum et al. ....... 435/91.5
5,631,348 A 5/1997 Rosenblum et al. ........ 530/370
5,720,954 A 2/1998 Hudziak et al. ......... 424/130.1
5,744,580 A 4/1998 Better et al. ................ 530/377
5,770,195 A 6/1998 Hudziak et al. ......... 424/130.1
5,837,491 A 11/1998 Better et al. ............... 435/69.1
5,851,829 A * 12/1998 Marasco et al. ............ 435/328
6,084,073 A 7/2000 Piatak, Jr. ................... 530/370
6,099,842 A 8/2000 Pastan et al. ............ 424/183.1
6,140,066 A * 10/2000 Lorberboum-Galski et al. ......................... 435/7.23
6,214,974 B1 4/2001 Rosenblum et al. ..... 530/391.9
6,306,626 B1 10/2001 Rosenblum et al. ..... 435/70.21
RE37,462 E 12/2001 Rosenblum et al. ........ 530/370
6,531,133 B1 * 3/2003 Lorberboum-Galski et al. ..................... 424/197.11
6,599,505 B1 7/2003 Rosenblum .............. 424/134.1
6,669,938 B1 12/2003 Rosenblum et al. ..... 424/183.1
6,750,329 B1 6/2004 Rosenblum et al. ..... 530/391.7
2002/0090374 A1 * 7/2002 Yarkoni et al. .......... 424/178.1
2003/0073163 A1 4/2003 Fernandez et al. ......... 435/69.1
2003/0134302 A1 7/2003 Fernandez et al. ............. 435/6
2003/0176331 A1 * 9/2003 Rosenblum et al. .......... 514/12
2003/0186384 A1 10/2003 Barth et al. ................ 435/69.5
2004/0009477 A1 1/2004 Fernandez et al. ............. 435/6
2004/0013691 A1 1/2004 Rosenblum .............. 424/234.1

FOREIGN PATENT DOCUMENTS

AU B79527/87 4/1988
AU B82047/87 6/1988
AU A13017/88 9/1988
AU A21725/88 3/1989
AU A30753/89 8/1989
EP 0118365 3/1984
EP 0160446 4/1985
EP 0150126 7/1985
EP 0184369 11/1985
EP 0226418 12/1986
EP 0222360 5/1987
EP 0256714 2/1988
EP 0281070 9/1988
EP 0305967 3/1989

(Continued)

OTHER PUBLICATIONS

U.S. Appl. No. 10/676,725, filed Oct. 1, 2003, Rosenblum.

(Continued)

*Primary Examiner*—Karen Cochrane Carlson
(74) *Attorney, Agent, or Firm*—Fulbright & Jaworski, L.L.P.

(57) ABSTRACT

The present invention relates to targeted killing of a cell utilizing a chimeric polypeptide comprising a cell-specific targeting moiety and a signal transduction pathway factor. In a preferred embodiment, the signal transduction pathway factor is an apoptosis-inducing factor, such as granzyme B, granzyme A, or Bax.

23 Claims, 34 Drawing Sheets

FOREIGN PATENT DOCUMENTS

| | | |
|---|---|---|
| EP | 0336631 | 10/1989 |
| EP | 0350230 | 1/1990 |
| EP | 0396387 | 11/1990 |
| GB | 1564666 | 1/1978 |
| GB | 2148299 | 5/1985 |
| JP | 86121 | 7/1981 |
| JP | 62209098 | 12/1986 |
| JP | 190200 | 8/1987 |
| WO | WO 85/00974 | 8/1984 |
| WO | WO 86/05098 | 7/1985 |
| WO | WO 86/02945 | 5/1986 |
| WO | WO 87/00056 | 6/1986 |
| WO | WO 88/09343 | 12/1988 |
| WO | WO 88/09344 | 12/1988 |
| WO | WO 89/00999 | 2/1989 |
| WO | WO 89/06692 | 7/1989 |
| WO | WO 90/00405 | 1/1990 |
| WO | WO 91/16071 | 10/1991 |
| WO | WO 94/26910 | 11/1994 |
| WO | IB-97/22364 A1 | 6/1997 |
| WO | IB-97/46259 A2 | 12/1997 |
| WO | IB-98/37901 A1 | 9/1998 |
| WO | WO 99/40198 | 8/1999 |
| WO | IB-99/45128 A2 | 9/1999 |
| WO | IB-99-49059 A2 | 9/1999 |
| WO | WO 99/43840 | 9/1999 |
| WO | WO 99/51620 | 10/1999 |
| WO | WO 99/51766 | 10/1999 |
| WO | WO 00/34317 | 6/2000 |
| WO | WO 03/002598 | 1/2003 |

OTHER PUBLICATIONS

U.S. Appl. No. 10/926,731, filed Aug. 26, 2004, Rosenblum.

Bendig, "Humanization of rodent monoclonal antibodies by CDR grafting," *METHODS: A Companion to Methods in Enzymology*, 8:83-93, 1995.

Berkower, "The promise and pitfalls of monoclonal antibody therapeutics," *Current Opinion in Biotechnology*, 7:622-628, 1996.

Bird et al., "Single-chain antigen-binding proteins," *Science*, 242:423-426, 1988.

Bjorn et al., "Evaluation of monoclonal antibodies for the development of breast cancer immunotoxins," *Cancer Res.*, 45:1214-1221, 1985.

Blair et al., "Linkage of cytotoxic agents to immunoglobulins," *J. Immunol. Methods*, 59:129-143, 1983.

Blakely et al., "Antibody toxin conjugates: a perspective," *Monoclonal Antibody Therapy*. Waldmann (ed). 45:50-90, 1988.

Bolognesi et al., "In vitro anti-tumour activity of anti-CD80 and anti-CD86 immunotoxins containing type 1 ribosome-inactivating proteins," *Br. J. Haematol.*, 110(2):351-361, 2000.

Bradford et al., "A rapid and sensitive method for the quantitation of microgram quantities of protein utilizing the principle of protein-dye binding," Analy. Biochem., 72:248-252, 1976.

Bumol et al., "Biosynthetic studies of proteoglycans in human melanoma cells with a monoclonal antibody to a core glycoprotein of chondroitin sulfate proteoglycans," J. Biol. Chem., 259:12733-12741, 1984.

Chan et al., "Comparison of gallium-67 versus indium-111 monoclonal antibody (96.5, ZME-018) in detection of human melanoma in athymic mice," *J. Nucl. Med.*, 28:1441-1446, 1987.

Chaudhary et al., "A recombinant immunotoxin consisting of two antibody variable domains fused to Pseudomonas exotoxin," *Nature*, 339:394-397, 1989.

Collen et al., "Recombinant staphylokinase variants with altered immunoreactivity," *Circulation*, 94:197-206, 1996.

Cotton et al., "Somatic mutation and the origin of the antibody diversity. Clonal variability of the immunoglobulin produced by MOPC 21 cells in culture," *Eur. J. Immunol.*, 3:135-140, 1973.

DeLand et al, "A perspective of monoclonal antibodies: past, present, and future," *Seminars in Nuc. Med.*, 19(3):158-165.

Dermer, "Another anniversary for the war on cancer," *Bio/technology*, 12:320, 1994.

Dillman, "Monoclonal antibodies for treating cancer," *Ann. Intern. Med.*, 111:592-603. 1989.

Dumontet, "[Immunotherapy and cancer: the role of monoclonal antibodies]," *J. Chir.* (Paris), 126:682-686, 1989.

Engert et al., "Resistance of myeloid leukaemia cell lines to ricin A-chain immunotoxins," *Leuk. Res.*, 15:1079-1086, 1991.

Falasca et al., "Properties of the ribosome-inactivating proteins gelonin, Momordica charantia inhibitor, and dianthins," *Biochem. J.*, 207:505-509, 1982.

Fiers et al. "Tumor necrosis factor: a potential anti tumor agent," *J. Interferon Res.*, 7:627-634, 1987.

Flannery et al., "Immunomodulation: NK cells activated by interferon-conjugated monoclonal antibody against human osteosarcoma" *Eur. J. Cancer Clin. Oncol.*, 20:791-798, 1984.

Frankel et al., "Prospects for immunotoxin therapy in cancer," *Ann. Rev. Med.*, 37:125-142, 1986.

Freshney, "Culture of animal cells, a manual of basic technique," Alan R. Liss, Inc, 1983.

Friedman et al., "BR96 sFv-PE40, a potent single-chain immunotoxin that selectively kills carcinoma cells," *Cancer Res.*, 53:334-339, 1993.

Frontiera et al., "Sequential use of indium-111 labeled monoclonal antibodies 96.5 and ZME-018 does not increase detection sensitivity for metastatic melanoma," *Clin. Nucl, Med.*, 14:357-366, 1989.

Gallego et al., "Preparation of four daunomycin-monoclonal antibody 791T/36 conjugates with anti-tumour activity," *Int. J. Cancer*, 33:737-744, 1984.

Gase et al., "Functional significance of NH2- and COOH- terminal regions of staphylokinase in plasminogen activation," *Thrombosis and Haemostasis*, 76(5):755-760, 1996.

GenBank Accession No. L12243.

Giacomini et al., "Modulation by recombinant DNA leukocyte (alpha) and fibroblast (beta) interferons of the expression and shedding of HLA- and tumor-associated antigens by human melanoma cells," *J. Immunol.*, 133(3):1649-1655, 1984.

Gillies et al., "Antigen binding and biological activities of engineered mutant chimeric antibodies with human tumor specificities," *Hum. Antibodies Hybridomas.*, 1:47-54, 1990.

Gould et al., "Phase I study of an anti-breast cancer immunotoxin by continuous infusion: report of a targeted toxic effect not predicted by animal studies," *J. Natl. Cancer Inst.*, 81:775-781, 1989.

Green et al., "Monoclonal antibody therapy for solid tumors," *Cancer Treat Rev.*, 26:269-286, 2000.

Greiner et al., "Differential effects of recombinant human leukocyte interferons on cell surface antigen expression," *Cancer Res.*, 46:4984-4990, 1986.

Greiner et al., "Enhanced expression of surface tumor-associated antigens on human breast and colon tumor cells after recombinant human leukocyte alpha-interferon treatment," *Cancer Res.*, 44:3208-3214, 1984.

Hamburger and Salmon, "Primary bioassay of human tumor stem cells," *Science*, 197:461-463, 1977.

Hann et al., "Building 'validated' mouse models of human cancer," *Curr. Opin. Cell Biol.*, 13:778-784, 2001.

Harlow et al., *Antibodies: A laboratory Manuel*, Cold Spring Harbor Press, pp. 72-77, 92-97, 128-135, and 141-157, 1988.

Hertler et al., "A phase I study of T101-ricin A chain immunotoxin in refractory chronic lymphocytic leukemia," *J. Biol. Response Mod.*, 7:97-113, 1987.

Hoogenboom et al., "Targeting of tumor necrosis factor to tumor cells: secretion by myeloma cells of a genetically engineered antibody-tumor necrosis factor hybrid molecule," *Biochim Biophys Acta.*, 1096:345-354, 1991.

Huston et al., "Single-chain immunotechnology of Fv analogues and fusion proteins," in *Immunotechnology*, Gosling and Reen (eds), p. 47-60, 1993.

Imai et al, "[Current status of monoclonal antibodies to human melanoma and its application]," *Gan To Kagaku Ryoho.*, 10:852-860, 1983 (abstract in English).

Imai et al., "Differential effect of interferon on the expression of tumor-associated antigens and histocompatibility antigens on human melanoma cells: relationship to susceptibility to immune lysis mediated by monoclonal antibodies," *J. Immunol.*, 127(2):505-509, 1981.
Juhl et al., "New approaches in gastric cancer research: I. Monoclonal antibodies in diagnosis and therapy," *Hepatogastroenterol*, 36:27-32, 1989.
Julius et al., "Induction of resting B cells to DNA synthesis by soluble monoclonal anti-immunoglobulin," *Eur. J. Immunol.*, 14:753-757, 1984.
Kaneta et al., "Effect of gelonin immunoconjugate with monoclonal antibody MSN-1 to endometrial adenocarcinoma on antigen-producing tumor cells in vivo," *Jpn J. Cancer Res.*, 89(5):583-588, 1998.
Kim and Weaver, "Construction of a recombinant expression plasmid encoding a staphylococcal protein A-ricin A fusion protein," *Gene*; 68:315-321, 1988.
Kimmel et al., "In vitro drug sensitivity testing in human gliomas," *J. Neurosurg.* 66:161-171, 1987.
Kipriyanov et al., "Recombinant single-chain Fv fragments carrying c-terminal cysteine residues: production of bivalent and biotinylated miniantibodies," *Molecular Immunology*, 31:1047-1058, 1994.
Kirkwood et al., "Scintigraphic detection of metastatic melanoma using indium 111/DTPA conjugated anti-gp240 antibody (ZME-018)," *J. Clin. Oncol.*, 5:1247-1255, 1987.
Koizumi et al., "Immunoscintigraphy and pharmacokinetics of indium-111-labeled ZME-018 monoclonal antibody in patients with malignant melanoma," *Japanese J of Cancer Res*, 79:973-981, 1988.
Kovarik et al., "Biochemical and histochemical characteristic of target antigen detected by monoclonal antibody HBCa-12 against a membrane component of human mammary carcinoma cell line," *Neoplasma*, 31(6):625-630, 1984.
Kudlicki et al., "Elongation and folding of nascent ricin chains as peptidyl-rRNA on ribosomes: the effect of amino acid deletions on these processes," *J. Mol. Biol.*, 252:203-212, 1995.
Kufe et al., "Differential reactivity of a novel monoclonal anitbody (DF3) with human malignant vs. benign breast tumors," *Hybridoma*, 3(3):223-232, 1984.
Kung et al., "A mouse IgM allotypic determinant (Igh-6.5) recognized by a monoclonal rat antibody," *J. Immunol.* 127:873-876, 1981.
Kurucz et al., "A bacterial expressed single-chain Fv construct from the 2B4 T-cell receptor," *Proc Natl Acad Sci USA*; 90: 3830-3834, 1993.
Lambert et al., "Immunotoxins containing single chain ribosome-inactivating proteins," in *Immunotoxins*, Frankel ed., p. 175-209, 1988.
Lambert et al., "Purified immunotoxins that are reactive with human lymphoid cells. Monoclonal antibodies conjugated to the ribosome-inactivating proteins gelonin and the pokeweed antiviral proteins," *J. Biol. Chem.*, 260(22):12035-12041, 1985.
Lazar et al., "Tranforming growth factor alpha: mutation of aspartic acid 47 and leucine 48 results in different biological activities," *Mol. Cell. Biol.*, 8:1247-1252, 1988.
Leibovitz et al., "A hypo-osmotic medium to disaggregate tumor cell clumps into viable and clonogenic single cells for the human stem cell clonogenic assay," *Int. J. Cell Cloning*, 1:478-485, 1983.
Levy et al., "Retroviral transfer and expression of a humanized, red-shifted green fluorescent protein gene into human tumor cells," *Nat. Biotechnol.*, 14:610-614, 1996.
Lewis and Crowe, "Generation of humanized monoclonal antibodies by 'best' fit framework selection and recombinant polymerase chain reaction," *Year Immunol.*, 7:110-118, 1993.
Lubin et al., "Analysis of the human factor VIII A2 inhibitor epitope by alanine scanning mutagenesis," *J. Biol. Chem.*, 272(48)30191-30195, 1997.
Macey et al., "Uptake of Indium-111-labeled monoclonal antibody ZME-018 as a function of tumor size in a patient with melanoma," *Am J of Physiologic Imaging*; 3:1-6, 1988.
Mazurier et al., "Rapid analysis and efficient selection of human transduced primitive hematopoetic cells using the humanized S65T green fluorescent protein," *Gene Ther.*, 5:556-562, 1998.
McCartney et al., "Engineering disulfide-linked singl-chain Fv dimers [(sFv')2] with improved solution and targeting properties: anti-digoxin 26-10 (sFv')2 and anti-c-erbB-2 741F8 (sFv')2 made by protein folding and bonded through C-terminal cysteinyl peptides," *Protein Engineering*; 8:301-314, 1994.
Miescher-Granger et al., "Biological activities of human recombinant interferon alpha/beta targeted by anti-Epstein-Barr virus monoclonal antibodies," *FEBS Lett.*, 179:29-33, 1985.
Mihich, "Future perspectives for biological response modifiers: a viewpoint," *Sem Oncol.*, 13:234-254, 1986.
Montanaro et al., "A metalloproteinase associated with gelonin, a ribosome inactivating protein," *Ital. J. Biochem.*, p. 1-10, 1984.
Moola et al., "Erwinia chrysanthemi L-asparaginase: epitope mapping and production of antigenically modified enzymes," *Biochem J.*, 302( Pt 3):921-7, 1994.
Morris and Wool, "Determination by systematic deletion of the amino acids essential for catlysis by ricin A chain," *Proc. Natl. Acad. Sci. USA*, 89:4869-4873, 1992.
Mujoo et al., "Pharmacokinetics, tissue distribution, and in vivo antitumor effects of the antimelanoma immunotoxin ZME-gelonin," *Cancer Immunology, Immunotherapy*; 40:339-345, 1995.
Mujoo et al., "Pharmacology and therapeutic studies with ZME-gelonin immunotoxin," *Proc. Am Assoc. Cancer Res*, 32:266, #1580, 1991.
Muldoon et al., "Tracking and quantitation of retroviral-mediated transfer using a completely humanized, red-shifted green fluorescent protein gene," *Biotechniques*, 22:162-167, 1997.
Munishkin and Wool, "Systematic deletion analysis of ricin A-chain function," *J Biol. Chem.*, 270:30581-30587, 1995.
Murray et al., "Clinical parameters related to optimal tumor localization of indium-111-labeled mouse antimelanoma monoclonal antibody ZME-018" *J. Nuclear Med.*, 28:25-33,1987.
Murray et al., "Differential in vitro effects of alpha recombinant interferon and gamma recombinant on the expression of melanoma-associated antigens and 240 Kd on melanoma cell line Ts294," *AACR*, 27:313, 1986.
Murray et al., "Differential in vitro effects of recombinant alpha-interferon and recombinant gamma-interferon alone or in combination on the expression of melanoma-associated surface antigens," *J. Biol. Response Modifiers*, 7:152-161, 1988.
Nechushtan et al., "Conformation of the Bax C-termimus regulates subcellular location and cell death," *EMBO Journal*, 18:2330-2341, 1999.
Neville et al., "Monoclonal antibody-ricin or ricin A chain hybrids: kinetic analysis of cell killing for tumor therapy," *Immunol. Rev.*, 62:75-91, 1982.
Nolan et al., "Cloning and expression of a gene encoding gelonin, a ribosome-inactivating protein from Gelonium multiflorum," *Gene*, 134:223-227, 1993.
Nuti et al., "A monoclonal antibody (B72.3) defines patterns of distribution of a novel tumor-associated antigen in human mammary carcinoma cell populations," *Int. J. Cancer*, 29(5):539-546, 1982.
O'Boyle et al., "Potentiation of anitproliferative effects of monoclonal antibody IYm-1 and immunoconjugate Lym-1-gelonin on human Burkitt's lymphoma cells with μ-interferon and tumor necrosis factor," *Journal of Immunotherapy*; 18:221-230, 1995.
O'Hare et al., "Cytotoxicity of a recombinant ricin-A-chain fusion protein containing a proteolytically-cleavable spacer sequence," *FEBS Lett.*, 273:200-204, 1990.
Owens and Young, "The genetic engineering of monclonal antibodies," *Journal of Immunological Methods*; 168:149-165, 1994.
Ozawa et al., "Selective killing of squamous carcinoma cells by an immunotoxin that recognizes the EGF receptor," *Int. J. Cancer*, 43:152-157, 1989.
Pagliaro et al., "Humanized M195 monoclonal antibody conjugated to recombinant gelonin: an anti-CD33 immunotoxin with antileukemic activity," *Clin. Cancer Res.*, 4(8):1971-1976, 1998.
Pai and Pastan "Immunotoxin therapy for cancer," *JAMA*, 269:78-81, 1993.
Panchagnula et al., "Monoclonal antibodies in drug targeting," *Journal of Clinical Pharmacy & Therapeutics*, 22:7-19, 1997.

Pastan et al., "Recombinant toxins for cancer treatment," *Science*, 254:1173-1177, 1991.
Pearson et al., "Enhanced therapeutic efficacy against an ovarian tumor xenograft of immunotoxins used in conjunction with recombinant alpha-interferon," *Cancer Res.* 50:6379-6388, 1990.
Pelham et al., "Interferon-alpha conjugation to human osteogenic sarcoma monoclonal antibody 791T/36," *Cancer Immunol. Immunother.*, 15:210-216, 1983.
Peterson and Krohn, "Mapping of B cell epitopes on steroid 17 α-hydroxylase, and autoantigen in autoimmune polyglandular syndrome type I," *Clin. Exp. Immunol.*, 98:104-109, 1994.
Porter, "Human immune response to recombinant human proteins," *J. Pharmaceutical Sciences*, 90:1-11, 2001.
Pullyblank and Monson, "Monoclonal antibody treatment of colorectal cancer," *British Journal of Surgery*; 84:1511-1517, 1997.
Ramakrishnan and Houston, "Prevention of growth of leukemia cells in mice by monoclonal antibodies directed against Thy 1.1 antigen disulfide linked to two ribosomal inhibitors: pokeweed antiviral protein or ricin A chain," *Cancer Res.*, 44(4):1398-404, 1984.
Raso et al., "Monoclonal antibody-ricin A chain conjugate selectively cytotoxic for cells bearing the common acute lymphoblastic leukemia antigen." *Cancer Res.*, 42:457-464, 1982.
Reimann et al., "In vivo administration of lymphocyte-specific monoclonal antibodies in nonhuman primates. IV. Cytotoxic effect of an anti-T11-gelonin immunotoxin," *J. Clin. Invest.*, 82:129-138, 1988.
Roselli et al., "Clinical value of radiolabeled monoclonal antibodies in the management of carcinoma patients," *In Vivo*, 7:615-622, 1993.
Rosenblum et al., "Comparative cytotoxicity and pharmacokinetics of antimelanoma immunotoxins containing either natural or recombinant gelonin," *Cancer Chemotherapy and Pharmacology*; 44:343-348, 1999.
Rosenblum et al, "A specific and potent immunotoxin composed of antibody ZME-018 and the plant toxin gelonin," , *Mol. Biother.* 3:6-13, 1991.
Rosenblum et al., "A gelonin-containing immunotoxin directed against human breast carcinoma," *Mol. Biother.* 4:122-129, 1992.
Rosenblum et al., "Amino acid sequence analysis, gene construction, cloning, and expression of gelonin, a toxin derived from Gelonium multiflorum," *J Interferon Cytokine Res.*, 15(6):547-555, 1995.
Rosenblum et al., "Antibody-mediated delivery of tumor necrosis factor (TNF-α)," *Proc. Am Cancer Res.*, 30:410, #1522, 1987.
Rosenblum et al., "Antibody-mediated delivery of tumor necrosis factor (TNF-alpha): improvement of cytotoxicity and reduction of cellular resistance," *Cancer Commun.* 3:21-27, 1991.
Rosenblum et al., "Growth inhibitory effects of interferon-beta but not interferon-alpha on human glioma cells: correlation of receptor binding, 2'5'-oligoadenylate synthetase and protein kinase activity," *Interferon Res.*, 10:141-151, 1990.
Rosenblum et al., "Monoclonal Antibodies for delivery of cytokines," *Cancer Bull*, 46(1):34-39, 1994.
Rosenblum et al., "An antimelanoma immunotoxin composed of antibody AMI-018 and the plant toxin gelonin," , *Proc. Am. Assoc. Cancer Res. Annu. Meet.*, 29:427, #1700, 1988 (Abstract).
Rosenblum et al., "Recombinant immunotoxins directed against the c-erb-2/HER2/neu oncogene product: in vitro cytotoxicity, pharmacokinetics, and in vivo efficacy studies in Xenograft models," *Clin Cancer Res*; 5:865-874, 1999.
Rosenblum et al., "Tumor necrosis factor a: multifaceted peptide hormone," *Critical Reviews in Immunology*, pp. 21-44, 1989.
Ross et al., "Increased toxicity of diphtheria toxin for human lymphoblastoid cells following covalent linkage to anti-(human lymphocyte) globulin or its F(ab')2 fragment," *Eur. J. Biochem.* 104:381-390, 1980.
Rowlinson-Busza et al., "Target delivery of biologic and other antineoplastic agents," *Current Opinion in Oncology*, 4:1142-1148, 1992.
Roy et al., "Anti-MY9-blocked-ricin: an immunotoxin for selective targeting of acute myeloid leukemia cells," *Blood*, 77:2404-2412, 1991.
Salmon and Liu "Effects of granulocyte-macrophage colony-stimulating factor on in vitro growth of human solid tumors," J. Clin. Oncol., 7:1346-1350, 1989.
Salmon et al., "Evaluation of an automated image analysis system for counting human tumor colonies," *Internat. J. Cell Cloning*, 2:142-160, 1984.
Salmon et al., "Quantitation of differential sensativity of human-tumor stem cells to anticancer drugs," *New Eng. J. Med.*, 298:1321-1327, 1978.
Schienberg et al., "Monoclonal Antibody M195:A diagnostic marker for acute myelogenous leukemia," *Leukemia*, 3(6):440-445, 1989.
Scholz et al., "Correlation of drug response in patients and in the clonogenic assay with solid human tumour xenografts," *Eur. J. Cancer*, 26(8):901-905, 1990.
Schulz et al., "Monoclonal antibody-directed effector cells selectively lyse human melanoma cells in vitro and in vivo," Proc. Natl. Acad. Sci. USA, 80:5407-5411, 1983.
Scott et al., "An immunotoxin composed of a monoclonal antitransferrin receptor antibody linked by a disulfide bond to the ribosome-inactivating protein gelonin: potent in vitro and in vivo effects against human tumors," *J. Natl. Cancer Inst.*, 79:1163-1172, 1987.
Shoemaker et al, "Application of a human tumor colony-forming assay to new drug screening," *Cancer Res.*, 45:2145-2153, 1985.
Singh et al., "Hormonotoxins. Preparation and characterization of ovine luteinizing hormone-gelonin conjugate," *J. Biol. Chem.*, 264(6):3089-3095, 1989.
Sivam et al., "Immunotoxins to a human melanoma-associated antigen: comparison of gelonin with ricin and other A chain conjugates," *Cancer Res.*, 47:3169-3173, 1987.
Soule et al., "Membrane 126-kilodalton phosphoglycoprotein associated with human carcinomas identified by a hybridoma antibody to mammary carcinoma cells," *Proc. Natl. Acad. Sci. USA*, 80:1332-1336, 1983.
Spitler et al., "Immunotoxin therapy of malignant melanoma," *Med Oncol Tumor Pharmacother.*, 3:147-152, 1986.
Spitler et al., "Therapy of patients with malignant melanoma using a monoclonal antimelanoma antibody-ricin A chain immunotoxin," *Cancer Res.*, 47:1717-1723, 1987.
Spitler et al., "Therapy of metastatic malignant melanoma using XomaZyme Mel, a murine monoclonal anti-melanoma ricin A chain immunotoxin," *Nuc. Med. And Biol.s.*, 16:625-627, 1989.
Stirpe et al., "Gelonin, a new inhibitor of protein synthesis, nontoxic to intact cells. Isolation, characterization, and preparation of cytotoxic complexes with concanavalin A," *J. Biol. Chem.*, 255:6947-6953, 1980.
Tao et al., "Studies of aglycosylated chimeric mouse-human IgG. Role of carbohydrate in the structure and effector functions mediated by the human IgG constant region," *J. Immunol.*, 143:2595-2601, 1989.
Tedder et al., "Epstein Barr virus binding induces internalization of the C3d receptor: a novel immunotoxin delivery system," *J. Immunol.* 137(4):1387-1391, 1986.
Thorpe et al., "An immunotoxin composed of monoclonal anti-thy 1.1 antibody and a ribosome-inactivating protein from saponaria oddicinalis: potent antitumor effects in vitro and in vivo," *J. Natl. Cancer Inst*, 75(1):151-159, 1985.
Thorpe et al., "Cytotoxicity acquired by conjugation of an anti-Thy 1.1 monoclonal antibody and the ribosome-inactivating protein, gelonin," *Eur. J. Biochem.*, 116:447-454, 1981.
Thorpe et al., "Monoclonal antibodies: clinical and regulatory issues," *Trends Biotechnol.* 11:40-42, 1993.
Till et al., "An assay that predicts the ability of monoclonal antibodies to form potent ricin A chain-containing immunotoxins," *Cancer Res.* 48:1119-1123, 1988.
Trowbridge et al., "Anti-transferrin receptor monoclonal antibody and toxin-antibody conjugates affect growth of human tumour cells," *Nature*, 294:171-173, 1981.
Vitetta et al., "neoplastic B cells as targets for antibody-ricin A chain immunotoxins," ., 62:15-183, 1982.
Vitetta et al., "Redesigning nature's poisons to create anti-tumor reagents," *Science*, 238:1098-1104, 1987.

Vogel et al., "In vivo studies with covalent conjugates of cobra venom factor and monoclonal antibodies to human tumors," *Hematology and Blood Transfusion*, 29:514-517, 1989.

Von Hoff, "Human tumor cloning assays: applications in clinical oncology and new antineoplastic agent development," Cancer and Metastasis Reviews, 7:357-371, 1988.

Wahl et al., "Experimental radioimmunotherapy," *Cancer*, 73:989-992, 1994.

Waldenamn, "Multichain interleukin-2 receptor: a target for immunotherapy in lymphoma," *J. Natl. Cancer Inst.* 81:914-923, 1989.

Waldmann et al., "Monoclonal antibodies in diagnosis and therapy," *Science*, 252:1657-1662, 1991.

Wels et al., "Diminution of antibodies directed against tumor cell surface epitopes: a single chain Fv fusion molecule specifically recognizes the extracellular of the c-erbB-2 receptor," *Journal of Steroid Biochemistry & Molecular Biology*, 43:1-7, 1992.

White et al., "Two monoclonal antibodies selective for human mammary carcinoma" *Cancer Res.*, 45:1337-1343, 1985.

Williams et al., "Targeting and therapy of human glioma xenografts in vivo utilizing radiolabeled antibodies," *Cancer Res*, 50:974s-979s, 1990.

Wilson et al, "Distribution and molecular characterization of a cell-surface and a cytoplasmic antigen detectable in human melanoma cells with monoclonal antibodies," *Int. J. Cancer*, 28:293-300, 1981.

Wool et al., "Structure and evolution of mammalian ribosomal proteins," *Biochem Cell Biol.*, 73:933-947, 1995.

Worn and Pluckthun, "Mutual stabilization of $V_L$ and $V_H$ in single-chain antibody fragments, investigated with mutants engineered for stability," *Biochemistry*; 37:13120-13127, 1998.

Xu et al., "Antileukemic activity of recombinant humanized M195-gelonin immunotoxin in nude mice," *Leukemia*, 10:321-326, 1996.

Yeung et al., "Trichosanthin, α-momorcharin and β-momorcharin: identity of aborifacient and ribosome-inactivating proteins," *Int. J. Pept. Protein Res.*, 31(3):265-8, 1988.

Yokota et al., "Synergistic potentiation of in vivo antitumor activity of anti-human T-leukemia immunotoxins by recombinant alpha-interferon and daunorubicin," *Cancer Res.*, 50:32-37, 1990.

Yung et al., "In vitro chemosensitivity testing and its clinical application in human gliomas," *Neurosurg. Rev.*, 12:197-203, 1989.

Zuckerman et al., "Preparation and biological activity of recombinant leukocyte interferon A [rIFN alpha A] conjugated to an antimelanoma murine monoclonal antibody [ZME-018]," *Proc. Amer. Assoc. Cancer Res.*, 28:384, 1987.

Aboud-Pirak et al., "Cytotoxic activity of daunorubicin or vindesine conjugated to a monoclonal antibody on cultured MCF-7 breast carcinoma cells," *Biochem. Pharmacol.*, 38:641-648, 1989.

Aggarwal and Kohr, "Human tumor necrosis factor," *Methods and Enzymology*, 116:448-456, 1986.

Alfthan et al., "Properties of single-chain antibody containing different linker peptides," *Protein Engineering*; 8:725-731, 1995.

Alkan et al., "Antiviral and antiproliferative effects of interferons delivered via monoclonal antibodies," *J. Interferon Res.*, 4(3):355-363, 1984.

Alley et al., "Feasibility of drug screening with panels of human tumor cell lines using a microculture tetrazolium assay," *Cancer Res.*, 48:589-601, 1988.

Arnon et al., "Monoclonal antibodies for immunotargeting of drugs in cancer therapy," Monoclonal Antibodies and Cancer Therapy, Alan R. Liss, Inc. pp. 243-256, 1985.

Atkinson et al., "Conjugation of folate via gelonin carbohydrate residues retains ribosomal-activating properties of the toxin and permits targeting to folate receptor positive cells," *Biochem Molec. Biol.*, 276(30):29730-29735, 2001.

Barbieri and Stirpe, "Ribosome-inactivating proteins from plants: Properties and possible uses," *Cancer Surveys*, 1(3):489-520.

Batra et al., "Antitumor activity in mice of an immunotoxin made with anti-transferrin receptor and a recombinant form of Pseudomonas exotoxin," *Proc. Natl. Acad. Sci.*, 86:8545-8549, 1989.

Batra et al., "Single-chain immunotoxins directed at the human transferrin receptor containing Pseudomonas exotoxin A or diphtheria toxin: anti-TFR(Fv)-PE40 and DT388-anti-TFR(Fv)," *Mol. Cell. Biol.* 11:2200-2205, 1991.

Brunet et al., "The inducible cytotoxic T-lymphocyte-associated gene transcript CTLA-1 sequence and gene localization to mouse chromosome 14," *Nature*, 322 (6076):268-271, 1986.

Crosby et al., "A complex of serine protease gene expressed preferentially in cytotoxic T-lymphoyocytes is closely linked to the T-cell receptor alpha- and delta-chain genes on mouse chromosome 14," *Genomics*, 6(2):252-259, 1990.

Dahl et al., "Isolation of a cDNA clone encoding a novel form of granzyme B from human NK cells and mapping to chromosome 14," *Hum. Genet.*, 84(5):465-470, 1990.

Haddad et al., "Structural organization of the hCTLA-1 gene encoding human granzyme B," *Gene*, 87(2):265-271, 1990.

Hanson et al., "A cluster of hematopoietic serine protease genes is found on the same chromosomal band as the human α/δ T-cell receptor locus," *Proc. Natl. Acad. Sci., USA*, 87:960-963, 1990.

Harper et al., "Proximity of the CTLA-1 serine esterase and Tcr alpha loci in mouse and man," *Immunogenetics*, 28(6):439-444, 1988.

Klein et al., "Genomic organization and chromosomal assignment for a serine protease gene (CSPB) expressed by human cytotoxic lymphocytes," *Genomics*, 5(1):110-117, 1989.

Lin et al., "Chromosomal localization of two human serine protease genes to region 14q11.2—q12 by in situ hybridization," *Cytogenet Cell Genet.*, 53(2-3):169-171, 1990.

Motyka et al., "Mannose 6-phosphate/insulin-like growth factor II receptor is a death receptor for granzyme B during cytotoxic T cell-induced apoptosis," *Cell*, 103(3):491-500, 2000.

Rissoan et al., "Subtractive hybridization reveals the expression of immunoglobulinlike transcript 7, Eph-B1, granzyme B and 3 novel transcripts in human plasmacytoid dendiritic cells," *Blood*, 100(9):3295-3303, 2002.

Henkart, Pierre A.; Mechanism of Lymphocyte-mediated Cytotoxicity; Ann. Rev. Immunol., vol. 3, pp. 31-58, 1985.

Young, John Ding-E, et al.; Cell-Mediated Killing: A common Mechanism??; Cell, vol. 46, pp. 641-642, Aug. 29, 1986.

Smyth, Mark J., et al.; Granzymes: exogenous proteinases that induce target cell apoptosis; Immunology Today, vol. 16 (4), pp. 202-206, 1995.

Adams, Jerry M., et al.; The Bcl-2 Protein Family: Arbiters of Cell Survival; Science, vol. 281, pp. 1322-1326, Aug. 28, 1998.

Tai, Yu-Tzu, et al.; In Vivo Cytotoxicity of Ovarian Cancer Cells through Tumor-selective Expression of the BAX Gene; Cancer Research, vol. 59, pp. 2121-2126, May 1, 1999.

Kagawa, Shunsuke, et al.; Antitumor Effect of Adenovirus-mediated Bax Gene Transfer on p53-sensitive and p53-resistant Cancer Lines; Cancer Research, vol. 60, pp. 1157-1161, Mar. 1, 2000.

Kagawa, S., et al.; A binary adenoviral vector system for expressing high levels of the proapoptotic gene bax; Gene Therapy, vol. 7, pp. 75-79, 2000.

Blink, Elizabeth J., et al.; Curtin Conference: Perforin-dependent nuclear targeting of granzymes: A central role in the nuclear events of granule-exocytosis-mediated apoptosis? Immunology and Cell Biology, vol. 77, pp. 206-215, 1999.

Aqeilan, Rami, et al.; Interleukin 2-Bax: a novel prototype of human chimeric proteins for targeted therapy; FEBS Letters, vol. 457, pp. 271-276, 1999.

Panchal, Rekha G.; Novel Therapeutic Strategies to Selectively Kill Cancer Cells; Biochemical Pharmacology, vol. 55, pp. 247-252, 1998.

Johnson, D.E.; Review: Noncaspase proteases in apoptosis; Leukemia, vol. 14, pp. 1695-1703, 2000.

Kam, Chih-Min, et al.; Review; Granzymes (lymphocyte serine proteases): characterization with natural and synthetic substrates and inhibitors; Biochimica et Biophysica Acta, vol. 1477, pp. 307-323, 2000.

Arora, "Vascular endothelial growth facto chimeric toxin is highly active against endothelial cells," *Cancer Research*, 59:183-188, 1999.

Liu, "Mechanistic studies of a novel, human fusion toxin composed of vascular endothelial growth factor $(VEGF)_{121}$ and the serine protease granzyme B: Directed apoptotic events in vascular endothelial cells," *Molecular Cancer Therapeutics*, 949-959, 2003.

* cited by examiner

```
1/1                                                                    54/18
ATG CAA CCA ATC CTG CTT CTG CTG GCC TTC CTC CTG CTG CCC AGG GCA GAT GCA
 M   Q   P   I   L   L   L   L   A   F   L   L   L   P   R   A   G   A
55/19                                                                 108/36
GGG GAG ATC ATC GGG GGA CAT GAG GCC AAG CCC CAC TCC CGC CCC TAC ATG GCT
 G   E   I   I   G   G   H   E   A   K   P   H   S   R   P   Y   M   A
109/37                                                                162/54
TAT CTT ATG ATC TGG GAT CAG AAG TCT CTG AAG AGG TGC GGT GGC TTC CTG ATA
 Y   L   M   I   W   D   Q   K   S   L   K   R   C   G   G   F   L   I
163/55                                                                216/72
CAA GAC GAC TTC GTG CTG ACA GCT GCT CAC TGT TGG GGA AGC TCC ATA AAT GTC
 Q   D   D   F   V   L   T   A   A   H   C   W   G   S   S   I   N   V
217/73                                                                270/90
ACC TTG GGG GCC CAC AAT ATC AAA GAA CAG GAG CCG ACC CAG CAG TTT ATC CCT
 T   L   G   A   H   N   I   K   E   Q   E   P   T   Q   Q   F   I   P
271/91                                                               324/108
GTG AAA AGA CCC ATC CCC CAT CCA GCC TAT AAT CCT AAG AAC TTC TCC AAC GAC
 V   K   R   P   I   P   H   P   A   Y   N   P   K   N   F   S   N   D
325/109                                                              381/127
ATC ATG CTA CTG CAG CTG GAG AGA AAG GCC AAG CGG ACC AGA GCT GTG CAG CCC
 I   M   L   L   Q   L   E   R   K   A   K   R   T   R   A   V   Q   P
382/128                                                              438/146
CTC AGG CTA CCT AGC AAC AAG GCC CAG GTG AAG CCA GGG CAG ACA TGC AGT GTG
 L   R   L   P   S   N   K   A   Q   V   K   P   G   Q   T   C   S   V
439/147                                                              492/164
GCC GGC TGG GGG CAG ACG GCC CCC CTG GGA AAA CAC TCA CAC ACA CTA CAA GAG
 A   G   W   G   Q   T   A   P   L   G   K   H   S   H   T   L   Q   E
493/165                                                              546/182
GTG AAG ATG ACA GTG CAG GAA GAT CGA AAG TGC GAA TCT GAC TTA CGC CAT TAT
 V   K   M   T   V   Q   E   D   R   K   C   E   S   D   L   R   H   Y
547/183                                                              600/200
TAC GAC AGT ACC ATT GAG TTG TGC GTG GGG GAC CCA GAG ATT AAA AAG ACT TCC
 Y   D   S   T   I   E   L   C   V   G   D   P   E   I   K   K   T   S
601/201                                                              654/218
TTT AAG GGG GAC TCT GGA GGC CCT CTT GTG TGT AAC AAG GTG GCC CAG GGC ATT
 F   K   G   D   S   G   G   P   L   V   C   N   K   V   A   Q   G   I
655/219                                                             705/235
GTC TCC TAT GGA CGA AAC AAT GGC ATG CCT CCA CGA GCC TGC ACC AAA  GTC
 V   S   Y   G   R   N   N   G   M   P   P   R   A   C   T   K   V
706/236                                        747/249
TCA AGC TTT GTA CAC TGG ATA AAG AAA ACC ATG AAA CGC TAC TAA
 S   S   F   V   H   W   I   K   K   T   M   K   R   Y   -
```

FIG. 2

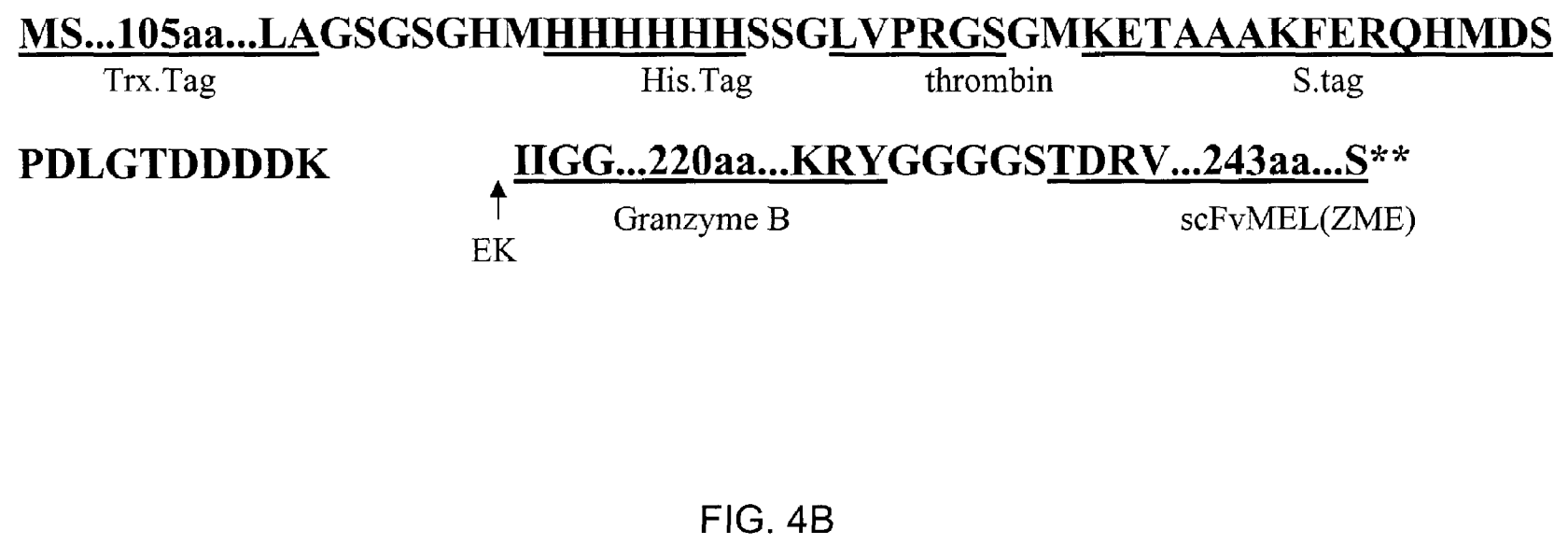

MS...105aa...LAGSGSGHMHHHHHHSSGLVPRGSGMKETAAAKFERQHMDS

Trx.Tag His.Tag thrombin S.tag

PDLGTDDDDK IIGG...220aa...KRYGGGGSTDRV...243aa...S**

EK Granzyme B scFvMEL(ZME)

FIG. 4B

```
1/1                                                        54/18
ATC ATC GGG GGA CAT GAG GCC AAG CCC CAC TCC CGC CCC TAC ATG GCT TAT CTT
 I   I   G   G   H   E   A   K   P   H   S   R   P   Y   M   A   Y   L

55/19                                                      108/36
ATG ATC TGG GAT CAG AAG TCT CTG AAG AGG TGC GGT GGC TTC CTG ATA CAA GAC
 M   I   W   D   Q   K   S   L   K   R   C   G   G   F   L   I   Q   D

109/37                                                     162/54
GAC TTC GTG CTG ACA GCT GCT CAC TGT TGG GGA AGC TCC ATA AAT GTC ACC TTG
 D   F   V   L   T   A   A   H   C   W   G   S   S   I   N   V   T   L

163/55                                                     216/72
GGG GCC CAC AAT ATC AAA GAA CAG GAG CCG ACC CAG CAG TTT ATC CCT GTG AAA
 G   A   H   N   I   K   E   Q   E   P   T   Q   Q   F   I   P   V   K

217/73                                                     270/90
AGA CCC ATC CCC CAT CCA GCC TAT AAT CCT AAG AAC TTC TCC AAC GAC ATC ATG
 R   P   I   P   H   P   A   Y   N   P   K   N   F   S   N   D   I   M

271/91                                                     324/108
CTA CTG CAG CTG GAG AGA AAG GCC AAG CGG ACC AGA GCT GTG CAG CCC CTC AGG
 L   L   Q   L   E   R   K   A   K   R   T   R   A   V   Q   P   L   R

325/109                                                    378/126
CTA CCT AGC AAC AAG GCC CAG GTG AAG CCA GGG CAG ACA TGC AGT GTG GCC GGC
 L   P   S   N   K   A   Q   V   K   P   G   Q   T   C   S   V   A   G

379/127                                                    432/144
TGG GGG CAG ACG GCC CCC CTG GGA AAA CAC TCA CAC ACA CTA CAA GAG GTG AAG
 W   G   Q   T   A   P   L   G   K   H   S   H   T   L   Q   E   V   K

433/145                                                    486/162
ATG ACA GTG CAG GAA GAT CGA AAG TGC GAA TCT GAC TTA CGC CAT TAT TAC GAC
 M   T   V   Q   E   D   R   K   C   E   S   D   L   R   H   Y   Y   D

487/163                                                    540/180
AGT ACC ATT GAG TTG TGC GTG GGG GAC CCA GAG ATT AAA AAG ACT TCC TTT AAG
 S   T   I   E   L   C   V   G   D   P   E   I   K   K   T   S   F   K
```

FIG. 4C

```
541/181                                                          594/198
GGG GAC TCT GGA GGC CCT CTT GTG TGT AAC AAG GTG GCC CAG GGC ATT GTC TCC
 G   D   S   G   G   P   L   V   C   N   K   V   A   Q   G   I   V   S

595/199                                                          648/216
TAT GGA CGA AAC AAT GGC ATG CCT CCA CGA GCC TGC ACC AAA GTC TCA AGC TTT
 Y   G   R   N   N   G   M   P   P   R   A   C   T   K   V   S   S   F

649/217                                                          702/234
GTA CAC TGG ATA AAG AAA ACC ATG AAA CGC TAC GGT GGC GCT GGC TCC GCA CCC
 V   H   W   I   K   K   T   M   K   R   Y   G   G   G   G   S   A   P

703/235                                                          756/252
ATG GCA GAA GGA GGA GGG CAG AAT CAT CAC GAA GTG GTG AAG TTC ATG GAT GTC
 M   A   E   G   G   G   Q   N   H   H   E   V   V   K   F   M   D   V

757/253                                                          810/270
TAT CAG CGC AGC TAC TGC CAT CCA ATC GAG ACC CTG GTG GAC ATC TTC CAG GAG
 Y   Q   R   S   Y   C   H   P   I   E   T   L   V   D   I   F   Q   E

811/271                                                          864/288
TAC CCT GAT GAG ATC GAG TAC ATC TTC AAG CCA TCC TGT GTG CCC CTG ATG CGA
 Y   P   D   E   I   E   Y   I   F   K   P   S   C   V   P   L   M   R

865/289                                                          918/306
TGC GGG GGC TGC TGC AAT GAC GAG GGC CTG GAG TGT GTG CCC ACT GAG GAG TCC
 C   G   G   C   C   N   D   E   G   L   E   C   V   P   T   E   E   S

919/307                                                          972/324
AAC ATC ACC ATG CAG ATT ATG CGG ATC AAA CCT CAC CAA GGC CAG CAC ATA GGA
 N   I   T   M   Q   I   M   R   I   K   P   H   Q   G   Q   H   I   G

973/325                                                         1026/342
GAG ATG AGC TTC CTA CAG CAC AAC AAA TGT GAA TGC AGA CCA AAG AAA GAT AGA
 E   M   S   F   L   Q   H   N   K   C   E   C   R   P   K   K   D   R

1027/343                              1059/353
GCA AGA CAA GAA AAT TGT GAC AAG CCG AGG CGG
 A   R   Q   E   N   C   D   K   P   R   R
```

FIG. 4D

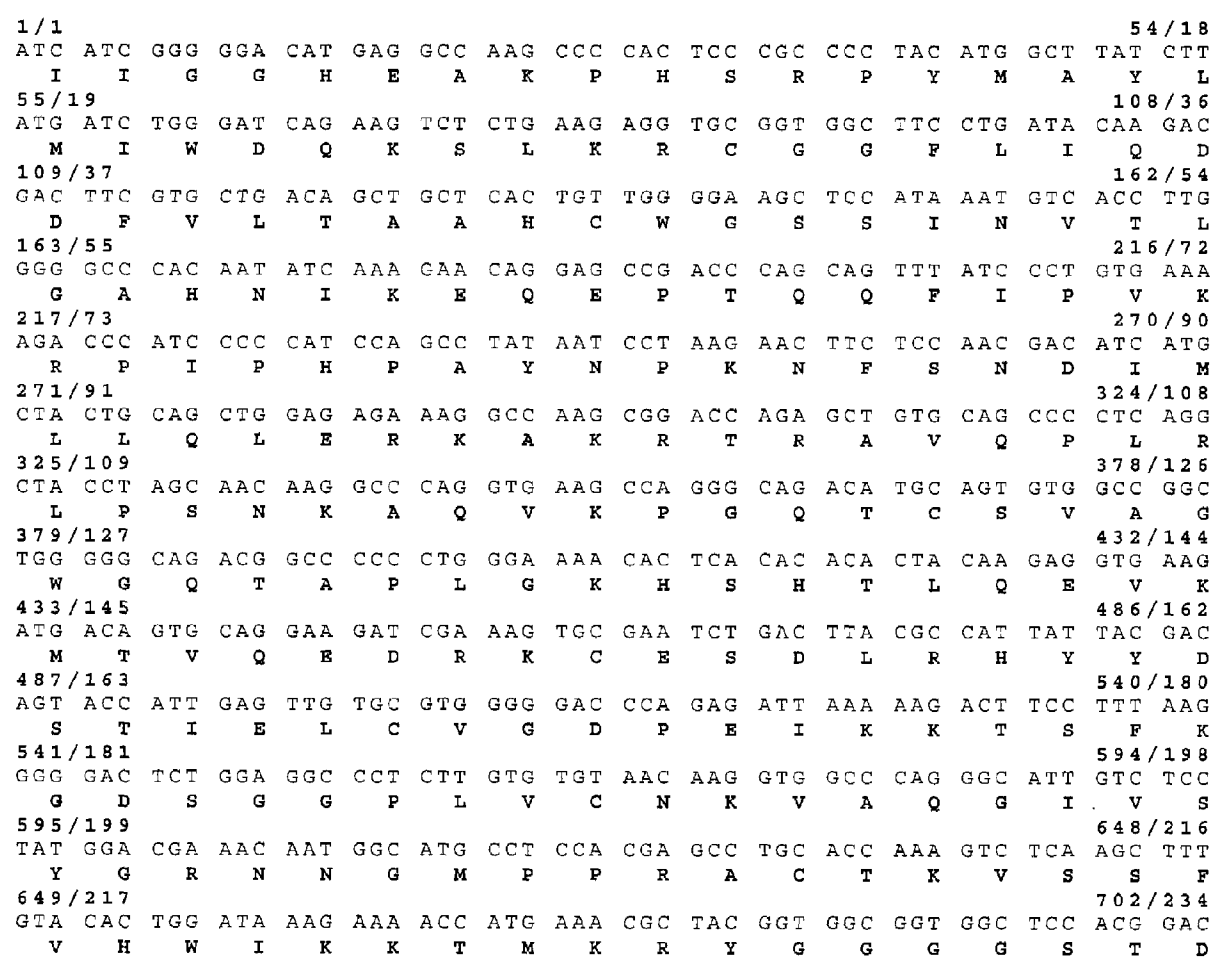

```
1/1                                                                  54/18
ATC ATC GGG GGA CAT GAG GCC AAG CCC CAC TCC CGC CCC TAC ATG GCT TAT CTT
 I   I   G   G   H   E   A   K   P   H   S   R   P   Y   M   A   Y   L
55/19                                                               108/36
ATG ATC TGG GAT CAG AAG TCT CTG AAG AGG TGC GGT GGC TTC CTG ATA CAA GAC
 M   I   W   D   Q   K   S   L   K   R   C   G   G   F   L   I   Q   D
109/37                                                              162/54
GAC TTC GTG CTG ACA GCT GCT CAC TGT TGG GGA AGC TCC ATA AAT GTC ACC TTG
 D   F   V   L   T   A   A   H   C   W   G   S   S   I   N   V   T   L
163/55                                                              216/72
GGG GCC CAC AAT ATC AAA GAA CAG GAG CCG ACC CAG CAG TTT ATC CCT GTG AAA
 G   A   H   N   I   K   E   Q   E   P   T   Q   Q   F   I   P   V   K
217/73                                                              270/90
AGA CCC ATC CCC CAT CCA GCC TAT AAT CCT AAG AAC TTC TCC AAC GAC ATC ATG
 R   P   I   P   H   P   A   Y   N   P   K   N   F   S   N   D   I   M
271/91                                                             324/108
CTA CTG CAG CTG GAG AGA AAG GCC AAG CGG ACC AGA GCT GTG CAG CCC CTC AGG
 L   L   Q   L   E   R   K   A   K   R   T   R   A   V   Q   P   L   R
325/109                                                            378/126
CTA CCT AGC AAC AAG GCC CAG GTG AAG CCA GGG CAG ACA TGC AGT GTG GCC GGC
 L   P   S   N   K   A   Q   V   K   P   G   Q   T   C   S   V   A   G
379/127                                                            432/144
TGG GGG CAG ACG GCC CCC CTG GGA AAA CAC TCA CAC ACA CTA CAA GAG GTG AAG
 W   G   Q   T   A   P   L   G   K   H   S   H   T   L   Q   E   V   K
433/145                                                            486/162
ATG ACA GTG CAG GAA GAT CGA AAG TGC GAA TCT GAC TTA CGC CAT TAT TAC GAC
 M   T   V   Q   E   D   R   K   C   E   S   D   L   R   H   Y   Y   D
487/163                                                            540/180
AGT ACC ATT GAG TTG TGC GTG GGG GAC CCA GAG ATT AAA AAG ACT TCC TTT AAG
 S   T   I   E   L   C   V   G   D   P   E   I   K   K   T   S   F   K
541/181                                                            594/198
GGG GAC TCT GGA GGC CCT CTT GTG TGT AAC AAG GTG GCC CAG GGC ATT GTC TCC
 G   D   S   G   G   P   L   V   C   N   K   V   A   Q   G   I   V   S
595/199                                                            648/216
TAT GGA CGA AAC AAT GGC ATG CCT CCA CGA GCC TGC ACC AAA GTC TCA AGC TTT
 Y   G   R   N   N   G   M   P   P   R   A   C   T   K   V   S   S   F
649/217                                                            702/234
GTA CAC TGG ATA AAG AAA ACC ATG AAA CGC TAC GGT GGC GGT GGC TCC ACG GAC
 V   H   W   I   K   K   T   M   K   R   Y   G   G   G   G   S   T   D
```

FIG. 4E

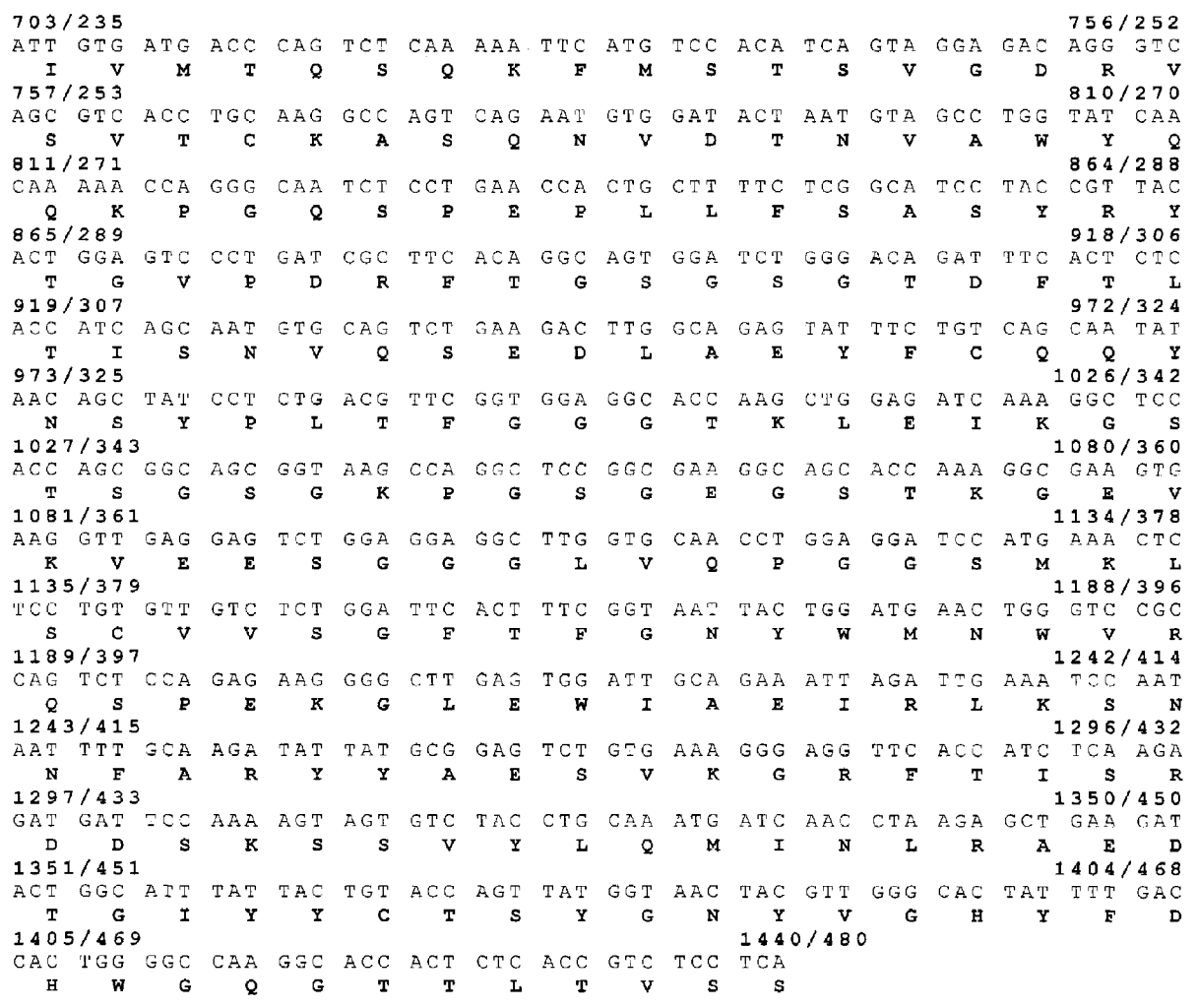

```
703/235                                                     756/252
ATT GTG ATG ACC CAG TCT CAA AAA TTC ATG TCC ACA TCA GTA GGA GAC AGG GTC
 I   V   M   T   Q   S   Q   K   F   M   S   T   S   V   G   D   R   V
757/253                                                     810/270
AGC GTC ACC TGC AAG GCC AGT CAG AAT GTG GAT ACT AAT GTA GCC TGG TAT CAA
 S   V   T   C   K   A   S   Q   N   V   D   T   N   V   A   W   Y   Q
811/271                                                     864/288
CAA AAA CCA GGG CAA TCT CCT GAA CCA CTG CTT TTC TCG GCA TCC TAC CGT TAC
 Q   K   P   G   Q   S   P   E   P   L   L   F   S   A   S   Y   R   Y
865/289                                                     918/306
ACT GGA GTC CCT GAT CGC TTC ACA GGC AGT GGA TCT GGG ACA GAT TTC ACT CTC
 T   G   V   P   D   R   F   T   G   S   G   S   G   T   D   F   T   L
919/307                                                     972/324
ACC ATC AGC AAT GTG CAG TCT GAA GAC TTG GCA GAG TAT TTC TGT CAG CAA TAT
 T   I   S   N   V   Q   S   E   D   L   A   E   Y   F   C   Q   Q   Y
973/325                                                    1026/342
AAC AGC TAT CCT CTG ACG TTC GGT GGA GGC ACC AAG CTG GAG ATC AAA GGC TCC
 N   S   Y   P   L   T   F   G   G   G   T   K   L   E   I   K   G   S
1027/343                                                   1080/360
ACC AGC GGC AGC GGT AAG CCA GGC TCC GGC GAA GGC AGC ACC AAA GGC GAA GTG
 T   S   G   S   G   K   P   G   S   G   E   G   S   T   K   G   E   V
1081/361                                                   1134/378
AAG GTT GAG GAG TCT GGA GGA GGC TTG GTG CAA CCT GGA GGA TCC ATG AAA CTC
 K   V   E   E   S   G   G   G   L   V   Q   P   G   G   S   M   K   L
1135/379                                                   1188/396
TCC TGT GTT GTC TCT GGA TTC ACT TTC GGT AAT TAC TGG ATG AAC TGG GTC CGC
 S   C   V   V   S   G   F   T   F   G   N   Y   W   M   N   W   V   R
1189/397                                                   1242/414
CAG TCT CCA GAG AAG GGG CTT GAG TGG ATT GCA GAA ATT AGA TTG AAA TCC AAT
 Q   S   P   E   K   G   L   E   W   I   A   E   I   R   L   K   S   N
1243/415                                                   1296/432
AAT TTT GCA AGA TAT TAT GCG GAG TCT GTG AAA GGG AGG TTC ACC ATC TCA AGA
 N   F   A   R   Y   Y   A   E   S   V   K   G   R   F   T   I   S   R
1297/433                                                   1350/450
GAT GAT TCC AAA AGT AGT GTC TAC CTG CAA ATG ATC AAC CTA AGA GCT GAA GAT
 D   D   S   K   S   S   V   Y   L   Q   M   I   N   L   R   A   E   D
1351/451                                                   1404/468
ACT GGC ATT TAT TAC TGT ACC AGT TAT GGT AAC TAC GTT GGG CAC TAT TTT GAC
 T   G   I   Y   Y   C   T   S   Y   G   N   Y   V   G   H   Y   F   D
1405/469                                1440/480
CAC TGG GGC CAA GGC ACC ACT CTC ACC GTC TCC TCA
 H   W   G   Q   G   T   T   L   T   V   S   S
```

FIG. 4F

Human Bax gene, 573 bps DNA

```
Exon 1 (31 bp)                            Exon 2 (53 bp)
GAC GGG TCC GGG GAG CAG CCC AGA GGC GGG GGG CCC ACC AGC TCT GAG CAG ATC
D   G   S   G   E   Q   P   R   G   G   G   P   T   S   S   E   Q   I
                                         Exon 3 (147 bp)
ATG AAG ACA GGG GCC CTT TTG CTT CAG GGT TTC ATC CAG GAT CGA GCA GGG CGA
M   K   T   G   A   L   L   L   Q   G   F   I   Q   D   R   A   G   R

ATG GGG GGG GAG GCA CCC GAG CTG GCC CTG GAC CCG GTG CCT CAG GAT GCG TCC
M   G   G   E   A   P   E   L   A   L   D   P   V   P   Q   D   A   S

ACC AAG AAG CTG AGC GAG TGT CTC AAG CGC ATC GGG GAC GAA CTG GAC AGT AAC
T   K   K   L   S   E   C   L   K   R   I   G   D   E   L   D   S   N
                            BH3 (7aa)

                     Exon 4 (135 bp)
ATG GAG CTG CAG AGG ATG ATT GCC GCC GTG GAC ACA GAC TCC CCC CGA GAG GTC
M   E   L   Q   R   M   I   A   A   V   D   T   D   S   P   R   E   V

TTT TTC CGA GTG GCA GCT GAC ATG TTT TCT GAC GGC AAC TTC AAC TGG GGC CGG
F   F   R   V   A   A   D   M   F   S   D   G   N   F   N   W   G   R
                                        BH1 (11aa)
                                                         Exon 5 (105 bp)
GTT GTC GCC CTT TTC TAC TTT GCC AGC AAA CTG GTG CTC AAG GCC CTG TGC ACC
V   V   A   L   F   Y   F   A   S   K   L   V   L   K   A   L   V   T

AAG GTG CCG GAA CTG ATC AGA ACC ATC ATG GGC TGG ACA TTG GAC TTC CTC CGG
K   V   P   E   L   I   R   T   I   M   G   W   T   L   D   F   L   R
                                                     Exon 6 (102 bp)
GAG CGG CTG TTG GGC TGG ATC CAA GAC CAG GGT GGT TGG GAC GGC CTC CTC TCC
E   R   L   L   G   W   I   Q   D   Q   G   G   W   D   G   L   L   S
                    BH2 (9aa)

TAC TTT GGG ACG CCC ACG TGG CAG ACC GTG ACC ATC TTT GTG GCG GGA GTG CTC
Y   F   G   T   P   T   W   Q   T   V   T   I   F   V   A   G   V   L

ACC GCC TCG CTC ACC ATC TGG AAG AAG ATG GGC
T   A   S   L   T   I   W   K   K   M   G
```

PAE cells flk-1 flt-1

Treatment a 0 24 h 0 24 h b a: λDNAHindIII
b: 1kb DNA ladder

THERAPEUTIC AGENTS COMPRISING PRO-APOPTOTIC PROTEINS

The present invention claims priority to U.S. Provisional Patent Application Ser. No. 60/306,091, filed Jul. 17, 2001; to U.S. Provisional Patent Application Ser. No. 60/332,886, filed Nov. 6, 2001; and to U.S. Provisional Patent Application Ser. No. 60/360,361, filed Feb. 28, 2002, all of which are incorporated by reference herein in their entirety.

FIELD OF THE INVENTION

The present invention is directed to the fields of cellular and molecular biology and cancer biology. More particularly, the present invention provides methods and compositions concerning therapeutic agents comprising a pro-apoptosis moiety and a cell-specific targeting moiety.

BACKGROUND OF THE INVENTION

The selective destruction of an individual cell is often desirable in a variety of clinical settings. A multitude of signal transduction pathways in the cell are linked to its death and survival, and delivery of a limiting and/or crucial component of the pathway can be productive in terms of its destruction. A classic example of such a signal transduction pathway is apoptosis, and a variety of elements of apoptotic pathways would be useful to target a cell for death. Apoptosis, or programmed cell death, is a fundamental process controlling normal tissue homeostasis by regulating a balance between cell proliferation and death (Vaux et al., 1994; Jacobson et al., 1997).

The serine protease granzyme B (GrB) (Lobe et al., 1986; Schmid and Weissman, 1987; Trapani et al., 1988) is integrally involved in apoptotic cell death induced in target cells upon their exposure to the contents of lysosome-like cytoplasmic granules (or cytolytic granules) found in cytotoxic T-lymphocytes (CTL) and natural killer (NK) cells (Henkart, 1985; Young and Cohn, 1986; Smyth and Trapani, 1995). Cytotoxic lymphocyte granules contain perforin, a pore-forming protein, and a family of serine proteases, termed granzymes (Table 1). Perforin has some structural and functional resemblance to the complement proteins C6, C7, C8 and C9, members of complement membrane attack complex (Shinkai et al., 1988). In lymphocyte-mediated cytolysis, perforin is inserted into the target cell membranes and appears to polymerize to form pores (Podack, 1992; Yagita et al., 1992), which mediates access of granzyme B to the target cell cytoplasm. Once inside, granzyme B induces apoptosis by directly activating caspases and inducing rapid DNA fragmentation (Shi et al., 1992).

TABLE 1

GRANZYMES (LYMPHOCYTE SERINE PROTEASES)

| Names | Species | Other Names | Enzyme Activity |
|---|---|---|---|
| A | Mouse | Hanukah factor, MTSP, SE-1, CTLA-3 | Tryptase |
| | Rat | RNKP-2, fragmentin 1 | |
| | Human | Hanukah factor, HTSP-1, granzyme 1 | |
| B | Mouse | CCP-1, CTLA-1 | Asp-ase |
| | Rat | Fragmentin 2, RNKP-1 | |
| | Human | HLP, granzyme 2, HSE26.1, CSPB | |
| C | Mouse | CCP-2 | Unknown |
| | Rat | RNKP-4 | |
| D | Mouse | CCP-5 | Unknown |
| E | Mouse | CCP-3, MCSP2 | Unknown |
| F | Mouse | CCP-4, MCSP3 | Unknown |
| G | Mouse | MCSP1 | Unknown |
| H | Human | CCP-X, CSP-C | Chymase |
| I | Rat | GLP I and II | Unknown |
| J | Rat | RNKP-5 | Unknown |
| K | Rat | Tryptase 2, fragmentin 3 | Tryptase |
| | Human | Granzyme 3 | Tryptase |
| M | Rat | RNK-Met-1 | Met-ase |
| | Human | Met-ase | |

The granzymes are structurally related, but have diverse substrate preference. Through its unique ability to cleave after aspartate residues, granzyme B can cleave many procaspases in vitro, and it has been an important tool in analyzing the maturation of caspase-3 (Darmon et al., 1995; Quan et al., 1996; Martin et al., 1996), caspase-7 (Chinnaiyan et al., 1996; Gu et al., 1996; Femandes-Alnemri et al., 1995), caspase-6 (Orth et al., 1996; Ferrandes-Alnemri et al., 1995), caspase-8 (Muzio et al., 1996), caspase-9 (Duan et al., 1996), and caspase-10a/b (Fernandes-Alnemri et al., 1996; Vincenz and Dixit, 1997). Furthermore, it is highly toxic to target cells (Shi et al., 1992). It has been assumed until now that granzyme B kills cells by direct caspase activated, supplemented under certain circumstances by direct damage to downstream caspase substrates (Andrade et al., 1998). Having gained access to the cytosol, granzyme B is rapidly translocated to the nucleus (Jans et al., 1996; Trapani et al., 1996) and can cleave poly (ADP-ribose) polymerase and nuclear matrix antigen, sometimes using different cleavage sites than those preferred by caspases (Andrade et al., 1998). Although many procaspases are efficiently cleaved in vitro, granzyme B-induced caspase activation occurs in a hierarchical manner in intact cells, commencing at the level of executioner caspases such as caspase-3, followed by caspase-7 (Yang et al., 1998). This is in contrast to FasL-mediated killing, which relies on a membrane signal generated through apical caspases such as caspase-8 (Muzio et al., 1996; Sarin et al., 1997). In addition, some studies showed that granzyme B can also induce death through a caspase-independent mechanism that involves direct damage to nonnuclear structures, although the key substrates in this pathway have yet to be elucidated (Sarin et al., 1997; Trapani et al., 1998; Heibein et al., 1999; Beresford et al., 1999).

Studies by Froelich and co-workers suggest that GrB is internalized by receptor-mediated endocytosis, and that the role of perforin is to mediate release of granzyme B from endocytic vesicles. In fact, perforin can be replaced by other vesicle-disrupting factors such as those produced by adenovirus (Froelich et al., 1996; Pinkoski et al., 1998; Browne et al., 1999).

Granzymes in general are highly homologous, with 38–67% homology to GrB (Haddad et al., 1991), and they contain the catalytic triad (His-57, Asp-102, and Ser-195) of trypsin family serine proteases. Other features include the mature, N-terminal Ile-Ile-Gly-Gly sequence, three or four disulfide bridges, and a conserved motif (PHSRPYMA), which also appears in neutrophil cathepsin G and mast cell chymases. The carbohydrate moieties of granzymes are Asn-linked (Griffiths and Isaaz, 1993). The granzyme mRNA transcripts are translated as pre-pro-proteases. The pre- or leader sequence is cleaved by signal peptidase at the endoplasmic reticulum. When the propeptides are removed, the inactive progranzymes (zymogens) become active proteases. The granzyme propeptides sequences start after the leader peptide and end before the N-terminal Ile needed for the protease to fold into a catalytic conformation (Kam et al., 2000).

Among the various apoptotic factors identified so far, members of the Bcl-2 family represent some of the most well-defined regulators of this death pathway. Some members of the Bcl-2 family, including Bcl-2, Bcl-XL, Ced-9, Bcl-w and so forth, promote cell survival, while other members including Bax, Bcl-Xs, Bad, Bak, Bid, Bik and Bim have been shown to potentiate apoptosis (Adams and Cory, 1998). A number of diverse hypotheses have been proposed so far regarding the possible biological functions of the Bcl-2 family members. These include dimer formation (Oltvai et al., 1993), protease activation (Chinnaiyan et al., 1996), mitochondrial membrane depolarization (6), generation of reactive oxygen intermediates (Hockenbery et al., 1993), regulation of calcium flux (Lam et al., 1994; Huiling et al., 1997), and pore formation (Antonsson et al., 1997; Marzo et al., 1998).

Bax, a 21 kDa death-promoting member of the Bcl-2 family, was first identified as a protein that co-immunoprecipated with Bcl-2 from different cell lines (Oltvai et al., 1993). Overexpression of Bax accelerates cell death in response to a wide range of cytotoxic results. Determination of the amino acid sequence of the Bax protein showed it to be highly homologous to Bcl-2. The Bax gene consists of six exons and produces alternative transcripts, the predominant form of which encodes a 1.0 kb mRNA and is designated Baxα. Like Bcl-2 and several other members of the Bcl-2 family, the Bax protein has highly conserved regions, BH1, BH2 and BH3 domains, and hydropathy analysis of the sequences of these proteins indicates the presence of a hydrophobic transmembrane segment at their C-terminal ends (Oltvai et al., 1993).

Bax is widely expressed without any apparent tissue specificity. However, on the induction of apoptosis, Bax translocates into mitochondria, resulting in mitochondria dysfinction and release of cytochrome c, which subsequently activates caspase pathways (Hsu and Youle, 1997; Wolter et al., 1997; Gross et al., 1998). This translocation process is rapid and occurs at an early stage of apoptosis (Wolter et al., 1997). Selective overexpression of Bax in human ovarian cancer through adenoviral gene transfer resulted in significant tumor cell kill in vivo (Tai et al., 1999). Overexpression of the Bax gene by a binary adenovirus system in cultured cell lines from human lung carcinoma results in caspase activation, apoptosis induction, and cell growth suppression. Moreover, intratumoral injection of adenovirus vector expressing the Bax gene suppressed growth of human lung cancer xenografts established in nude mice (Kagawa et al., 2000; Kagawa et al., 2000).

WO 99/45128 and Aqeilan et al. (1999) are directed to chimeric proteins having cell-targeting specificity and apoptosis-inducing activities, particularly the recombinant chimeric protein IL-2-Bax, which specifically targets IL2 receptor-expressing cells and induces cell-specific apoptosis.

WO 99/49059 relates to a chimeric toxin comprised of gonadotropin releasing hormone (GnRH) and Pseudomonas exotoxin A (PE) to detect a tumor-associated epitope expressed by human adenocarcinoma.

WO 97/46259 concerns targeted chimeric toxins comprising cell targeting moieties and cell killing moieties directed to neoplastic cells. In a specific example, the chimeric toxin comprises gonadotropin releasing hormone homologs and *Pseudomonas* Exotoxin A.

WO 97/22364 addresses targeted treatment of allergy responses, whereby a chimeric cytotoxin $Fc_{2'-3}$-$PE_{40}$ is directed to targeted elimination of cells expressing the FcεRI receptor.

While some chimeric protein compositions have been described, other methods and compositions are needed for improved therapies involving the killing of cells.

SUMMARY OF THE INVENTION

The present invention is directed to methods and compositions involving the delivery of chimeric polypeptides comprising signal transduction pathway factors that induce death of a targeted cell. In a preferred embodiment, this factor is a pro-apoptotic factor.

Almost all cells contain mechanisms responsible for mediating cell-death (apoptosis). Thus, in some embodiments, the present invention addresses delivery of certain pro-apoptotic proteins that are central mediators of this effect to the interior of target cells, which will result in cell death through apoptotic mechanisms. The apoptosis-inducing moiety induces programmed cell death upon entry into the target cell of the chimeric polypeptide, which is delivered for binding to the target cell by the cell-specific targeting moiety. In some embodiments of the present invention and as an advantage over known methods in the art, pro-apoptotic polypeptides are delivered as proteins and not as nucleic acid molecules to be translated to produce the desired polypeptides. As an additional advantage, human sequences are utilized in the chimeric polypeptides of the present invention to circumvent any undesirable immune responses from a foreign polypeptide.

In further embodiments, granzyme A or granzyme B is a mediator for inducing apoptosis. In specific embodiments, recombinant ligand (VEGF) and/or recombinant antibody (scFvMEL) moieties are fused as nucleic acid sequences to those sequences that encode a granzyme or a Bcl-2 family member. The inventors present data herein demonstrating that chimeric polypeptides, such as granzymeB-vegf121 and granzymeB-scFvMEL, are cytotoxic to target cells. Given that a skilled artisan recognizes that there are multiple similar cell-targeting and pro-apoptotic examples that may be used interchangeably with the specific examples herein, this indicates that constructs containing pro-apoptotic proteins have significant therapeutic potential for the treatment of disease states and represent a new class of therapeutic agents with a novel mechanism of action.

In an embodiment in which pro-apoptotic proteins are utilized as the killing moiety in chimeric proteins, recombinant antibody (scFvMEL) that binds to the cell-surface antigen gp240 of melanoma cells and is internalized efficiently is utilized. The inventors fused the genes encoding scFvMEL to genes encoding Bax, truncated Bax1-5, and Bax 345, respectively (designated as scFvMEL-bax, scFvMEL-Bax1-5 and scFvMEL-Bax 345, respectively). These genes were inserted into protein-expression vectors and transformed into bacteria. The fusion proteins were purified, tested against target cells in culture, and shown to be cytotoxic to target cells. This suggests that constructs containing the pro-apoptotic protein Bax have significant therapeutic potential for the treatment of diseases and present a new class of therapeutic agents with a novel mechanism of action.

In an object of the present invention, there is a chimeric polypeptide comprising a cell-specific targeting moiety and a signal transduction pathway factor.

In another object of the present invention, there is a chimeric polypeptide comprising a cell-specific targeting moiety and an apoptosis-inducing factor, wherein said apoptosis-inducing factor is a granzyme. In a specific embodiment, the granzyme is granzyme B. In another specific embodiment, the amino acid sequence of said granzyme B is selected from the group consisting of SEQ ID NO:11, SEQ ID NO:12, SEQ ID NO:13, SEQ ID NO:14, SEQ ID NO:15, and SEQ ID NO:16. In another specific embodiment, the amino acid sequence of said granzyme B is SEQ ID NO:60, SEQ ID NO:60 further comprising an N-terminal extension of SEQ ID NO:61, or SEQ ID NO:60 wherein the first twenty amino acids are absent. In a further specific embodiment, the amino acid sequence of said granzyme B is at least 100 contiguous amino acids from SEQ ID NO:11, SEQ ID NO:12, SEQ ID NO:13, SEQ ID NO:14, SEQ ID NO:15, SEQ ID NO:16, or SEQ ID NO:60. In a further specific embodiment, the amino acid sequence of said granzyme B is at least 75 contiguous amino acids from SEQ ID NO:11, SEQ ID NO:12, SEQ ID NO:13, SEQ ID NO:14, SEQ ID NO:15, SEQ ID NO:16, or SEQ ID NO:60. In a further specific embodiment, the amino acid sequence of said granzyme B is at least 40 contiguous amino acids from SEQ ID NO:11, SEQ ID NO:12, SEQ ID NO:13, SEQ ID NO:14, SEQ ID NO:15, SEQ ID NO:16, or SEQ ID NO:60. In an additional specific embodiment, the granzyme is granzyme A. In a further specific embodiment, the amino acid sequence of said granzyme A is selected from the group consisting of SEQ ID NO:23, SEQ ID NO:24 and SEQ ID NO:25. In a further specific embodiment, the amino acid sequence of said granzyme A is at least 100 contiguous amino acids from SEQ ID NO:23, SEQ ID NO:24 or SEQ ID NO:25. In a further specific embodiment, the amino acid sequence of said granzyme A is at least 75 contiguous amino acids from SEQ ID NO:23, SEQ ID NO:24 or SEQ ID NO:25. In a further specific embodiment, the amino acid sequence of said granzyme A is at least 40 contiguous amino acids from SEQ ID NO:23, SEQ ID NO:24 or SEQ ID NO:25. In an additional specific embodiment, the cell-specific targeting moiety is a cytokine, an antibody, a ligand, or a hormone. In a further specific embodiment, the ligand is VEGF. In a further specific embodiment, the VEGF is vegf121. In a further specific embodiment, the antibody is a single chain antibody. In a further specific embodiment, the single chain antibody is scFvMEL. In an additional specific embodiment, the granzyme is granzyme B and said cell-specific targeting moiety is vegf121. In another specific embodiment, the granzyme is granzyme B and said cell-specific targeting moiety is scFvMEL. In a further specific embodiment, the polypeptide further comprises a linker, such as SEQ ID NO:50, SEQ ID NO:51, or SEQ ID NO:52. In a specific embodiment, the polypeptide is encoded by a recombinant polynucleotide.

In an additional object of the present invention, there is an expression cassette comprising a polynucleotide encoding a chimeric polypeptide comprising a cell-specific targeting moiety and an apoptosis-inducing factor, wherein said apoptosis-inducing factor is a granzyme, and wherein said polynucleotide is under control of a regulatory sequence operable in a host cell. In specific embodiments, the granzyme is granzyme A or granzyme B. In a specific embodiment, the granzyme A is encoded by a polynucleotide of SEQ ID NO:26, SEQ ID NO:27, or SEQ ID NO:28. In another specific embodiment, the granzyme B is encoded by a polynucleotide of SEQ ID NO:17, SEQ ID NO:18, SEQ ID NO:19, SEQ ID NO:20, SEQ ID NO:21, or SEQ ID NO:22. In an additional specific embodiment, the cassette is comprised in a recombinant viral vector, such as an adenoviral vector, an adeno-associated viral vector, or a retroviral vector.

In an additional object of the present invention, there is a host cell comprising an expression cassette comprising a polynucleotide encoding a chimeric polypeptide comprising a cell-specific targeting moiety and an apoptosis-inducing factor, wherein said apoptosis-inducing factor is a granzyme. In specific embodiments, the cell is further defined as a prokaryotic host cell or an eukaryotic host cell.

In another object of the present invention, there is a method of using a host cell comprising an expression cassette comprising a polynucleotide encoding a chimeric polypeptide comprising a cell-specific targeting moiety and an apoptosis-inducing factor, wherein said apoptosis-inducing factor is a granzyme, comprising culturing the host cell under conditions suitable for the expression of the chimeric polypeptide.

In an additional object of the present invention, there is a method of inducing apoptosis in a cell, comprising administering to said cell an effective amount of a chimeric polypeptide comprising a cell-specific targeting moiety and a granzyme. In specific embodiments, the granzyme is granzyme A or granzyme B. In specific embodiments, the cell is in vivo and/or in a human.

In another object of the present invention, there is a method of inducing apoptosis in a cell, comprising administering to said cell an effective amount of a chimeric polypeptide comprising a cell-specific targeting moiety and a granzyme, wherein said cell-specific targeting moiety is scFvMEL and said granzyme is granzyme B. It is contemplated that the cell-specific targeting moiety acts by targeting specific cells, for example, cells that express on their surface a peptide or polypeptide that is capable of specifically binding the targeting moiety. The compound that allows the cell to be specifically targeted may be referred herein as the target. Thus, in some embodiments of the invention, cells may have a target to which the cell-specific targeting moiety recognizes.

In another object of the present invention, there is a method of inducing apoptosis in a cell, comprising administering to said cell an effective amount of a chimeric polypeptide comprising a cell-specific targeting moiety and a granzyme, wherein said cell-specific targeting moiety is vegf121 and said granzyme is granzyme B.

In an additional object of the present invention, there is a method of inducing apoptosis in a cell, comprising administering to said cell an effective amount of a chimeric polypeptide comprising a cell-specific targeting moiety and a pro-apoptotic member of the Bcl-2 family. In a specific embodiment, the pro-apoptotic member of the Bcl-2 family is Bax or a fragment thereof. In specific embodiments, the cell is in vivo and/or in a human. In a specific embodiment, the fragment of Bax lacks at least part of a polypeptide encoded by exon 6 in a Bax polynucleotide sequence.

In another object of the present invention, there is a method of inducing apoptosis in a cell, comprising administering to said cell an effective amount of a chimeric polypeptide comprising a cell-specific targeting moiety and a pro-apoptotic member of the Bcl-2 family, wherein said cell-specific targeting moiety is scFvMEL and said pro-apoptotic member of the Bcl-2 family is Bax or a fragment of Bax. In a specific embodiment, the fragment of Bax lacks at least part of exon 6 in a Bax polynucleotide sequence.

In an additional object of the present invention, there is a method of treating a disease in an individual, comprising the steps of administering to said individual a therapeutically effective amount of a composition comprising a chimeric polypeptide comprising an apoptosis-inducing moiety and a cell-specific targeting moiety; and a pharmaceutical carrier. In a specific embodiment, the pharmaceutical carrier comprises a lipid. In another specific embodiment, the disease is cancer, diabetes, arthritis, or inflammatory bowel disease, atherosclerosis, or diabetic retinopathy. In an additional specific embodiment, the disease is cancer. In a further specific embodiment, the apoptosis-inducing moiety is a granzyme. In a further specific embodiment, the granzyme is granzyme B or a fragment thereof. In an additional specific embodiment, the apoptosis-inducing moiety is a pro-apoptotic member of the Bcl-2 family. In another specific embodiment, the pro-apoptotic member of the Bcl-2 family is Bax or a fragment thereof. In an additional specific embodiment, the fragment of Bax lacks at least part of a polypeptide encoded by exon 6 in a Bax polynucleotide sequence. In another specific embodiment, the fragment of Bax lacks at least part of a polypeptide encoded by exons selected from the group consisting of 4, 5, and 6. In an additional specific embodiment, the administration is by intravenous injection. In another specific embodiment, the administration is by inhalation. In a further specific embodiment, the administration is intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, by inhalation (e.g. aerosol inhalation), by injection, by infusion, by continuous infusion, by localized perfusion bathing target cells directly, via a catheter, via a lavage, in a creme, or in a lipid composition. In a specific embodiment, the method further comprises administering to said individual an anti-inflammatory composition, chemotherapy, surgery, radiation, hormone therapy, or gene therapy.

It is contemplated that aspects of the invention discussed in the context of one embodiment of the invention may be employed with respect to any other embodiments of the invention.

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein.

FIG. 2 shows the nucleotide sequence encoding human pre-mature granzyme B (SEQ ID NO:54) and amino acid sequence (SEQ ID NO:55).

FIG. 3A shows the construction of pET32GrB-vegf121. FIG. 3B shows the construction of pET32GrB-scFvMEL. The full length genes were ligated into the Xba I/Xho I site of the expression vector pET-32a(+).

FIGS. 4A, 4B, 4C, 4D, 4E and 4F demonstrate the predicted structure of recombinant granzyme B-vegf121 (FIG. 4A), granzyme B-scFvMEL (FIG. 4B) in pET32a vector expressed in *E. coli* and the sequences of granzyme B-vegf121 (FIGS. 4C and 4D) (SEQ ID NO:56 for nucleic acid sequence and SEQ ID NO:57 for amino acid sequence), granzyme B-scFvMEL (FIGS. 4E and 4F) (SEQ ID NO:58 for nucleic acid sequence and SEQ ID NO:59 for amino acid sequence). The pET32a(+) vector contains a T7 promoter for high-level expression. Expression of the nucleic acid includes sequence containing the Trx.tag, followed by a His.tag, a thrombin cleavage site, and an enterokinase cleavage site for final removal of the protein purification tag.

In FIG. 5B, there is shown SDS-PAGE Coomassie blue staining of granzyme B-scFvMEL. In Panel C, lane 1 shows protein molecular marker; lane 2 shows non-induced total cell lysates; lane 3 shows induced total cell lysates; lane 4 shows non-induced soluble; lane 5 shows induced soluble; lane 6 shows non-induced insoluble; lane 7 shows induced insoluble. In Panel D, lane 1 shows protein molecular marker; lane 2 shows pro-granzyme B-scFvMEL (IMAC-eluate from Nickel NTA); lane 3 shows granzyme B-scFvMEL (after rEK cut).

FIG. 10 illustrates the human Bax gene, its exons, and domains BH1, BH2, and BH3.

DETAILED DESCRIPTION OF THE INVENTION

Figure 1:
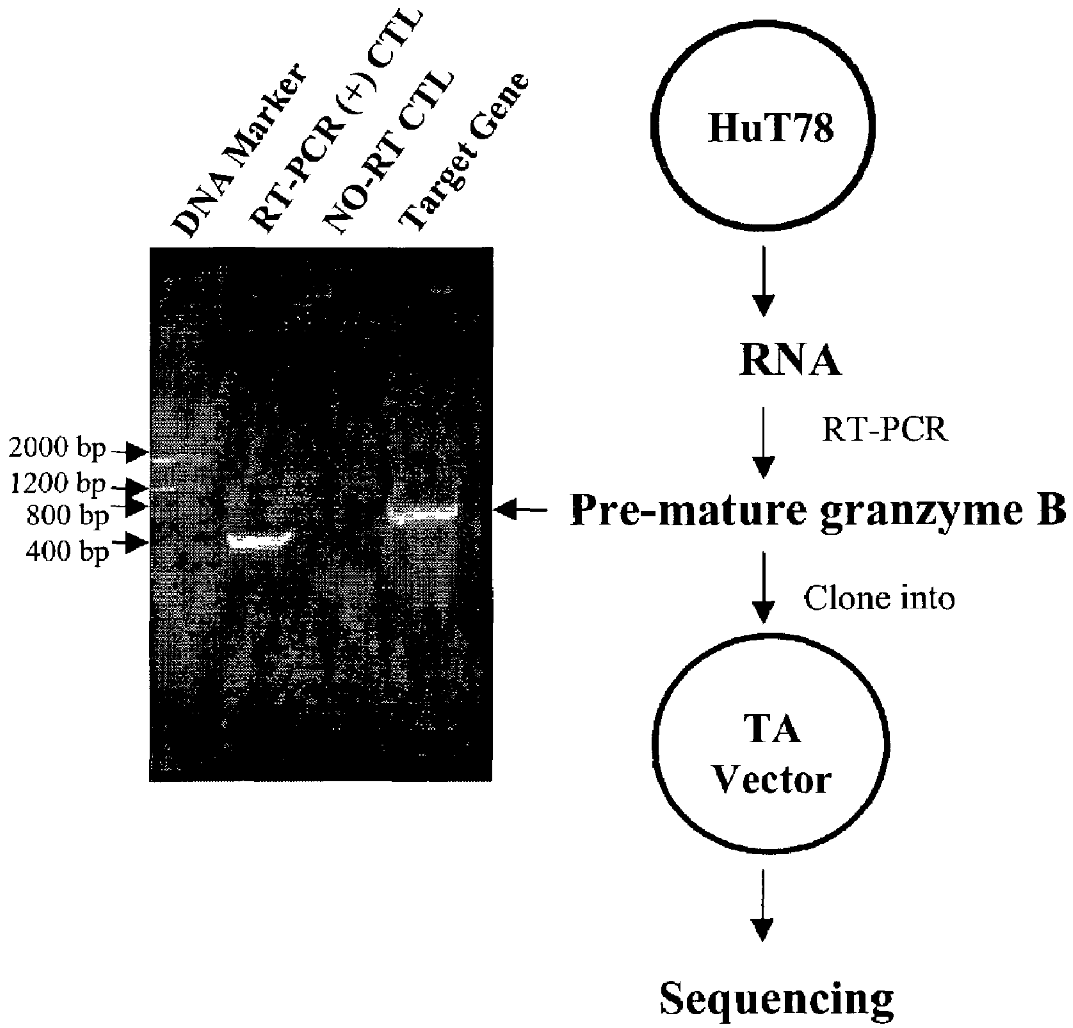
FIG. 1 illustrates human pre-mature granzyme B cDNA from Hut78 cells. A 1% agarose gel electrophoresis demonstrates human pre-mature granzyme B cDNA synthesized from Hut78 cells by RT-PCR. Lane 1 represents a low mass DNA molecular marker; lane 2 represents control synthesized cDNA (~500 bp); lane 3 represents no RT control; and lane 4 represents human pre-mature granzyme B cDNA (~800 bp).

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

As used herein the specification, “a” or “an” may mean one or more. As used herein in the claim(s), when used in conjunction with the word “comprising”, the words “a” or “an” may mean one or more than one. As used herein “another” may mean at least a second or more.

The term “apoptosis” as used herein is defined as programmed cell death; an endogenous cell death program results in the death of the cell.

The term “cytokine” as used herein is defined as an agent made by a cell that affects the behavior of another cell. In a specific embodiment, the agent is a polypeptide. For example, cytokines made by lymphocytes are often called lymphokines or interleukins (IL). Furthermore, cytokines act on specific cytokine receptors on the cells that they affect. In a specific embodiment, the term “cytokine” includes growth factors.

The term “granzyme” as used herein is defined as an enzyme from the granules of cytotoxic lymphocytes that, upon entry into the cytosol of a cell, induce apoptosis and/or nuclear DNA fragmentation. In a specific embodiment, the granzyme is a lymphocyte serine protease. In some embodiments, the granzyme is full-length, whereas in other embodiments the granzyme is partial.

The term “signal transduction pathway factor” as used herein is defined as an enzyme, substrate, cofactor or other protein which influences biological activity of another enzyme, cofactor or protein. In a specific embodiment, the factor is associated with receptor-mediated signaling that transmits a signal from outside the cell membrane to modulate a growth response within the cell. In one embodiment, the growth response that is modulated is a pro-growth response. In an alternative embodiment, the growth response that is modulated is an anti-growth response, such as induction of apoptosis.

The present invention relates to chimeric proteins with cell-targeting specificity and cell-destruction moieties, such as from signal transduction pathways linked, either directly or indirectly, to cell death. In some embodiments, the cell-destruction moieties are apoptosis-inducing activities. The chimeric proteins of the invention are composed of a cell-specific targeting moiety and an apoptosis-inducing moiety. The cell-specific targeting moiety provides cell-specific binding properties to the chimeric protein, while the apoptosis-inducing moiety induces programmed cell death upon entry into a target cell. In some embodiments, the chimeric proteins of the invention are delivered as polypeptides and are produced by recombinant expression of a fusion polynucleotide between a coding sequence of a cell-targeting moiety and a coding sequence of an apoptosis-inducing protein. Such chimeric proteins are likely to be superior to the immunotoxins currently used in the art because they are of human origin and thus are expected to have reduced immunogenicity in a human recipient. In addition, chimeric proteins kill target cells by inducing apoptosis which does not cause a release of cellular organelles into the extracellular environment to result in an inflammatory response. When cells die by the apoptotic pathway, they shrink and condense, but the organelles and plasma membranes retain their integrity, and the dead cells are rapidly phagocytosed by neighboring cells or macrophages before there is leakage of the cells’ contents, thereby eliciting minimal tissue or systemic response.

The invention also relates to pharmaceutical compositions of the chimeric proteins, methods of producing such proteins and methods of using the same in vitro and in vivo, especially for eliminating specific undesirable target cells, and for the treatment of a variety of disease conditions as well as the use of the proteins for disease diagnosis.

In the present invention, methods and compositions regarding targeted destruction of a cell utilizing a chimeric polypeptide are disclosed. The chimeric polypeptide is comprised of at least two moieties: one moiety is the effectual component for killing of the cell; the second moiety is the delivery component of the chimeric polypeptide to target the killing component to the cell of interest. In some embodiments of the present invention, at least one of the moieties, and preferably both, are of human origin, which eliminates an immune response from the individual to whom the chimeric polypeptide is administered. In one embodiment, the moiety for killing the cell is a component of a signal transduction pathway, such as one which is a limiting factor or restriction point in the pathway. Delivery of the signal transduction pathway bypasses the requirement to elicit upstream steps of the pathway, and the resultant administration of this restriction point ends in the same effect, which is destruction of the cell. A skilled artisan recognizes that types of agents which could be delivered intracellularly to mediate signal transduction include enzymes, such as kinases (for example, protein kinase B (PKB,AKT), which mediates insulin signaling; protein kinase C, which is involved in numerous signaling events; and phosphatidylinositol 3-kinase, which is involved in numerous signaling events); phosphatases; proteases (such as caspase 3); nucleases (such as caspase-activated deoxyribonuclease (CAD), which is a mediator of apoptosis); phospholipases; NCKAP1 (which is an apoptosis-related protein downregulated in the brain tissues of Alzheimer's patients; Suzuki et al., 2000) or co-factors, such as cytochrome c (which is involved in apoptosis signaling) and cyclic AMP (which is involved in numerous pathways).

In a specific embodiment, the signal transduction pathway factor is an enzyme. The enzyme may be a hydrolase (e.g., deaminase, esterase, glycosidase, lipase, nuclease, peptidase, phosphatase, phosphodiesterase, and proteinase); isomerase (e.g., epimerase, mutase, and racemase); ligase or synthetase (e.g., acyl-CoA synthetase, amino-acyl-tRNA synthetase, and carboxylase); lyase (e.g., aldolase, decarboxylase, dehydratase, and nucleotide cyclase); oxidoreductase (e.g., dehydrogenase, dioxygenase, hydrogenase, monooxygenase, nitrogenase, oxidase, and reductase); and/or transferase (e.g., acyltransferase, aminotransferase, glycosyltransferase, kinase, methyltransferase, nucleotidyltransferase, phosphorylase, and sulphotransferase). In specific embodiments, the enzyme is classified as a toxin, which means it is toxic to a cell, tissue, or organism.

In some embodiments, the signal transduction pathway factor is an apoptosis-inducing factor. Almost all cells contain mechanisms responsible for mediating cell death (apoptosis). In a specific embodiment, and as demonstrated in the Examples herein, delivery of granzyme B protein into the interior of target cells results in cell death through apoptotic mechanisms. Using recombinant ligand (VEGF) and recombinant antibody (scFvMEL), which bind to the cell-surface of tumor cells and internalize efficiently, the inventors designed two novel granzyme B-related fusion proteins: GrB-vegf121 to specifically target the endothelial cells; and GrB-scFvMEL to specifically target the melanoma cells.

A skilled artisan recognizes particular cell-specific targeting moieties which would be useful in the chimeric polypeptide to target a cell of interest. For example, the cell-specific targeting moieties may be antibodies to a particular cell marker(s), growth factor(s), hormone(s), or cytokine(s).

A skilled artisan is aware that nucleic acid sequences and amino acid sequences useful for generating the chimeric polypeptide of the present invention are readily obtainable, particularly through public databases, such as the National Center for Biotechnology Information's (NCBI) GenBank database, or commercially available databases such as from Celera Genomics, Inc. (Rockville, Md.). For example, granzyme B amino acid sequences useful in the present invention may include, followed by their GenBank Accession number, at least: P10144 (SEQ ID NO:11); XP_012328 (SEQ ID NO:12); A61021 (SEQ ID NO:13); NP_004122 (SEQ ID NO:14); CAA01810 (SEQ ID NO:15); and/or AAA75490 (SEQ ID NO:16). SEQ ID NO:60 is human granzyme B sequence reflecting variances seen in SEQ ID NO:11 through SEQ ID NO:16, such as at residue 55 (a Gln or an Arg), at residue 94 (a Pro or an Ala), as an N-terminal extension comprising SEQ ID NO:61 (MKSLSLLHLFPLPRAKREQGGNNSSSNQGSLPEK), and/or as a deletion of residues 1 through 20.

Granzyme B nucleic acid sequences useful in the present invention may include at least: XM_012328 (SEQ ID NO:17); BF589964 (SEQ ID NO:18); BF221604 (SEQ ID NO:19); NM_004131 (SEQ ID NO:20); A26437 (SEQ ID NO:21); and/or M28879 (SEQ ID NO:22). Granzyme A amino acid sequences useful in the present invention may include, followed by their GenBank Accession number, at least: P12544 or NP_006135 (SEQ ID NO:23) or XP_003652 (SEQ ID NO:24). SEQ ID NO:25 comprises a human granzyme A amino acid sequence and reflects variance in SEQ ID NO:23 and SEQ ID NO:24 at residue 121 (Thr or Met, respectively). Granzyme A nucleic acid sequences useful in the present invention may include at least: XM_003652 (SEQ ID NO:26); NM_006144 (SEQ ID NO:27); and/or U40006 (SEQ ID NO:28). A skilled artisan recognizes how to retrieve these and related sequences from the NCBI GenBank database.

I. Apoptosis-Inducing Proteins

Strictly regulated cell death is required for the development of multilineage organisms and the maintenance of homeostasis within tissues. Differentiation status of an individual cell directly affects whether it can execute a suicidal response following a death stimulus varies. Both positive and negative regulators of programmed cell death (apoptosis) have been identified. Bcl-2 is a repressor of programmed cell death (Vaux et al., 1988), and recently, other Bcl-2 homologues were shown to inhibit apoptosis. However, one homolog of Bcl-2, Bax, mediates an opposite effect through acceleration of apoptosis. In the Bcl-2 family there is notable homology clustered within two conserved regions: Bcl-2 homology domains 1 and 2 (BH1 and BH2) (Oltvai et al., 1993; Boise et al., 1993; Kozopas et al., 1993; Lin et al., 1993). Members of the Bcl family include Bax, Bcl-$X_L$, Mc1-1, A1 and several open reading frames in DNA viruses. Another conserved domain in Bax, distinct from BH1 and BH2, is termed BH3 and mediates cell death and protein binding functions (Chittenden et al., 1995). A subset of the pro-apoptotic proteins contains only the BH3 domain, implying that this particular domain may be uniquely important in the promotion of apoptosis (Diaz et al., 1997).

In vivo Bax homodimerizes and also forms heterodimers with BCL-2, and overexpressed Bax overrides the death repressor activity of BCL-2 (Oltvai et al., 1993). Bax expression levels higher than Bcl-2 expression levels in bladder tumors correlates to an improved patient prognosis. In patients whose tumors expressed more Bcl-2 than Bax mRNA, early relapses were much more frequently observed (Gazzaniga et al., 1996).

Recently it was reported that a splice variant of Bax, Bax-alpha, was expressed in high amount in normal breast epithelium, whereas only weak or no expression was detected in 39 out of 40 cancer tissue samples examined (Bargou et al., 1996), and downregulation of Bax-alpha was detected in different histological subtypes. Furthermore, when Bax-alpha was transfected into breast cancer cell lines under the control of a tetracycline-dependent expression system, Bax restored sensitivity of the cancer cells toward both serum starvation and APO-I/Fas-triggered apoptosis, significantly reducing tumor growth in SCID mice. Therefore, it was proposed that disruption of apoptosis pathway may contribute to the pathogenesis of breast cancer at least in part due to an imbalance between members of the Bcl-2 gene family (Bargou et al., 1996).

Additional members of the Bcl-2 family of apoptosis-inducing proteins have been identified. Bak, a new member of the Bcl-2 family, is expressed in a wide variety of cell types and binds to the Bcl-2 homologue Bcl-x2 in yeast (Farrow et al., 1995; Chittenden et al., 1995). A domain in Bak was identified as both necessary and sufficient for cytotoxicity activity and binding to Bcl-x1. Furthermore, sequences similar to this domain that are distinct from BH1 and BH2 have been identified in Bax and Bipl. This domain is critical for mediating the function of multiple cell death-regulatory proteins that interact with Bcl-2 family members (Chittenden et al., 1995).

Overexpression of Bak in sympathetic neurons deprived of nerve growth factor accelerated apoptosis and blocked the protective effect of co-injected E1B 19K. The adenovirus E1B 19K protein is known to inhibit apoptosis induced by E1A, tumor-necrosis factor-alpha, FAS antigen and nerve growth factor deprivation (Farrow et al., 1995). Expression of Bak induced rapid and extensive apoptosis of serum-deprived fibroblasts, which suggests that Bak is directly involved in activating the cell death machinery (Chittenden et al., 1995). In the normal and neoplastic colon, mucosal expression of immunoreactive Bak co-localized with sites of epithelial cell apoptosis. Induction of apoptosis in the human colon cancer cell line HT29 and the rat normal small intestinal cell line 1EC 18 in culture was accompanied by increased Bak expression without consistent changes in expression of other Bcl-2 homologous proteins (Moss et al., 1996). Therefore, Bak was also suggested to be the endogenous Bcl-2 family member best correlated with intestinal cell apoptosis (Moss et al., 1996).

Unlike Bax, however, Bak can inhibit cell death in an Epstein-Barr-virus-transformed cell line. Tissues with unique distribution of Bak messenger RNA include those containing long-lived, terminally differentiated cell types (Krajewski, et al., 1996), suggesting that cell-death-inducing activity is broadly distributed, and that tissue-specific modulation of apoptosis is controlled primarily by regulation of molecules that inhibit apoptosis (Kiefer et al., 1995).

Another member of the Bcl2 family, Bad, possesses the key amino acid motifs of BH1 and BH2 domains. Bad lacks the classical C-terminal signal-anchor sequence responsible for the integral membrane positions of other family members. Bad selectively dimerizes with Bcl-$x_L$ as well as Bcl-2, but not with Bax, Bcl-Xs-Mcl1, A1 or itself. Bad reverses the death repressor activity of Bcl-$X_L$, but not that of Bcl-2 (Yang et al., 1995; Ottilie et al., 1997; Zha et al., 1997).

Bik, another member of the Bcl-2 family, interacts with the cellular survival-promoting proteins, Bcl-2 and Bcl-$X_L$ as well as the viral survival-promoting proteins, Epstein Barr virus-BHRF1 and adenovirus E1B-19 kDa. In transient transfection assays, Bik promotes cell death in a manner similar to Bax and Bak, other pro-apoptotic members of the Bcl-2 family. This pro-apoptosis activity of Bik can be suppressed by coexpression of Bcl-2, Bcl-$X_L$, EBV-BHRF1 and E1B-19 kDa proteins, which suggests that Bik may be a common target for both cellular and viral anti-apoptotic proteins. While Bik does not contain overt homology to the BH1 and BH2 conserved domains characteristic of the Bcl-2 family, it shares a 9 amino acid domain (BH3) with Bax and Bak, which may be a critical determinant for the death-promoting activity of these proteins (Boyd et al., 1995; Han et al., 1996).

The Bcl-2 family is composed of various pairs of antagonist and agonist proteins that regulate apoptosis, although whether their function is interdependent remains unclear. Utilizing gain-and loss of function models of Bcl-2 and Bax, Knudson et al. (1997), demonstrated that apoptosis and thymic hypoplasia, characteristic of Bcl-2-deficient mice, are largely absent in mice also deficient in Bax. A single copy of Bax promoted apoptosis in the absence of Bcl-2. However, overexpression of Bcl-2 still repressed apoptosis in the absence of Bax. While an in vivo competition exists between Bax and Bcl-2, each is able to regulate apoptosis independently. Bax has been shown to form channels in lipid membranes and trigger the release of liposome-encapsulated carboxyluorescein at both neutral and acidic pH. At physiological pH, release could be blocked by Bcl-2. In planer lipid bilayers, Bax formed pH- and voltage-dependent ion-conduction channels. Thus, the pro-apoptotic effects of Bax may be elicited through an intrinsic pore-forming activity that can be antagonized by Bcl-2 (Antonsson et al., 1997). Two other members of this family, Bcl-2 and Bcl-1, were also shown to form pores in lipid membranes (Schendel et al., 1997).

II. Granzyme B and Apoptosis

Host defenses against viruses, parasitic agents, and transformed cells require cytotoxic T lymphocytes (CTLs) and natural killer (NK) cells (Berke, 1995; Kagi et al., 1996), which induce apoptosis in target cells using at least two separate mechanisms. In the first mechanism, there is stimulation of cell surface death receptors (such as Fas) on the target cells by death ligands expressed on the surface of the effector cell (Nagata and Golstein, 1995; Ashkenazi and Dixit, 1998), which then leads to activation of caspase cascades in the target cell. In the second mechanism, denoted “granule exocytosis,” there is vectoral transfer of the contents of effector cell cytoplasmic granules into the target cell (Doherty, 1993; Shresta et al., 1995a; Shresta et al., 1995b). Perforin and the granzyme family of serine proteases are important components of these granules.

Perforin is a 70 kDa protein that binds in a calcium-dependent manner to membrane phosphorylcholine groups (Masson and Tshopp, 1985; Young et al., 1986; Tschopp et al., 1989). Subsequent to binding, perforin inserts into the membrane and oligomerizes, resulting in the formation of pores. This permeabilization of the membrane likely makes possible the entry of other molecules, such as granzymes, into the target cell.

Granzymes A and B are particularly abundant (Smyth et al., 1996) within the granules of CTLs and NK cells. Granzyme B, which is also called fragmentin or cytotoxic T cell protease (CCP), is similar to caspases having the characteristic of cleaving substrate proteins after aspartate residues (Zunino et al., 1990; Lobe et al., 1986; Odake et al., 1991; Poe et al., 1991; Shi et al., 1992). Mice that are granzyme B knockouts demonstrate an important role for granzyme B in the induction of target cell apoptosis. CTLs and NK cells derived from granzyme $B^{-/-}$ mice have a severely reduced capacity to induce apoptotic DNA fragmentation in target cells (Shresta et al., 1995a; Heusel et al., 1994). Although earlier complementary studies showed that purified granzyme B alone did not promote apoptosis when added to target cells, cotreatment with purified granzyme B and perforin proteins induced marked DNA fragmentation and apoptotic features in four lymphoma target cell lines (Shi et al., 1992). Therefore, it is possible that granzyme B gains entry into target cells through perforin-generated pores, although this is controversial. Several studies have shown that granzyme B is internalized by target cells in the absence of added perforin (Froelich et al., 1996; Jans et al., 1996; Shi et al., 1997; Pinkoski et al., 1998; Pinkoski et al., 2000). The internalized granzyme B has been reported to reside in the cytoplasm, (Jans et al., 1996; Shi et al., 1997) or in a novel vesicular compartment. (Pinkoski et al., 1998), although the triggering of apoptosis in cells that have internalized granzyme B requires further addition of perforin to the cells (Froelich et al., 1996; Jans et al., 1996; Shi et al., 1997; Pinkoski et al., 1998; Pinkoski et al., 2000). It is possible that perforin is required for the release of granzyme B to the target cell from internal vesicles. Other studies have indicated that perforin facilitates translocation of granzyme B to the nucleus, and that nuclear localization is critical to the ability of granzyme B to cause apoptosis (Jans et al., 1996; Shi et al., 1997; Pinkoski et al., 1998; Pinkoski et al., 2000; Pinkoski et al., 1996; Trapani et al., 1996).

Although the importance of granzyme B subcellular localization remains controversial, it is certain that granzyme B has the ability to affect the caspase pathway of apoptosis. In vitro studies have shown that granzyme B is capable of cleaving procaspase3, -6, -7, -8m -9 and -10, (Darmon et al., 1996; Darmon et al., 1996; Martin et al., 1996; Quan et al., 1996; Fernandes-Alnemri et al., 1995; Orth et al., 1996; Fernandes-Alnemri et al., 1995; Chinnaiyan et al., 1996; Gu et al., 1996; Boldin et al., 1996; Muzio et al., 1996; Duan et al., 1996; Fernandes-Alnemri et al., 1996; Medema et al., 1997; Van de Craen et al., 1997; Talanian et al., 1997). In the case of procaspases-3, -7 and -9, granzyme B-mediated processing has been shown to generate active caspase enzymes (Darmon et al., 1995; Quan et al., 1996; Gu et al., 1996; Duan et al., 1996). More importantly, studies with whole cells have shown that caspases are activated in target cells following coincubation with granzyme B and perforin (Darmon et al., 1996; Talanian et al., 1997; Shi et al., 1996). It remains to be determined, however, which caspases are the preferred in vivo substrates for granzyme B. In any event, it is reasonable to propose that granzyme B may promote apoptosis simply by cleaving and activating endogenous caspases in the target cell.

Cleavage of the caspase substrate proteins PARP, lamin B, and U1–70 kDa is also observed in cells undergoing granzyme B/perforin-mediated apoptosis (Medema et al., 1997; Talanian et al., 1997; Shi et al., 1996; Andrade et al., 1998). These cleavage events are likely due to caspases activated by cleavage by granzyme B, since cleavage of all three proteins is inhibited by 100 μM DEVD- or VAD-containing peptides, which inhibit caspases, but not granzyme B (Darmon et al., 1996; Medema et al., 1997; Talanian et al., 1997; Shi et al., 1996; Andrade et al., 1998). Two additional caspase substrate proteins, DNA-$PK_{cs}$ and NuMA, are also cleaved in granzyme B/perforin-treated cells, but cleavage of these proteins is insensitive to DEVD or VAD peptide inhibitors (Andrade et al., 1998) Moreover, the sizes of the DNA-$PK_{cs}$ and NuMA proteolytic fragments generated by granzyme B differ from those resulting from caspase cleavage, which suggests that during granzyme B-mediated apoptosis, important cellular substrates are cleaved in a caspase-independent manner. The significance of these caspase-independent cleavage events is unknown. However, given that granzyme B/perforin-mediated DNA fragmentation and apoptotic death is significantly delayed by 100 μM DEVD/VAD, (Darmon et al., 1996; Talanian et al., 1997; Shi et al., 1996) this emphasizes the necessity for caspase activation during this form of apoptosis.

III. Granzyme A and Apoptosis

The mature granzyme A enzyme is a disulphide cross-linked homodimer of 50 kDa that cleaves substrate proteins following lysine or arginine residues (Odake et al., 1991; Gershenfeld et al., 1986; Masson et al., 1986), and granzyme A is the most abundant protease found in the granules of CTL cells. The mechanism of action of this protease differs significantly from that of granzyme B, although granzyme A is capable of inducing apoptosis after loading into target cells. Furthermore, it is thought that the role of granzyme A in CTL-induced apoptosis is significantly more subtle than that of granzyme B. For example, mice which are deficient in granzyme A expression (granzyme $A^{-/-}$ mice) exhibit relatively normal CTL-mediated cytotoxicity (Andrade et al., 1998), although they are unable to clear the mouse pox virus Ectromelia (Mulbacher et al., 1996). In contrast, CTLs from granzyme $B^{-/-}$ mice are capable of inducing target cell death only after prolonged coincubation (Heusel et al., 1994), and, therefore, granzyme B is critically important for rapid CTL killing. Recent experiments using mice deficient in both granzyme A and granzyme B suggest that granzyme A does have some role in CTL-mediated killing. CTLs from granzyme $A^{-/-}$/granzyme $B^{-/-}$ mice are unable to induce target cell DNA fragmentation, even after prolonged coincubation (Shresta et al., 1999), which indicates that granzyme A activity accounts for the ability of granzyme $B^{-/-}$ CTLs to induce target cell apoptosis following prolonged exposure. Therefore, granzyme A may allow CTLs to kill target cells under conditions where granzyme B activity is inhibited (e.g. target cells that express granzyme B inhibitors).

In studies with recombinant proteins, coincubation of granzyme A and perforin with target cells leads to rapid (within 2 hours) accumulation of DNA single-strand breaks (Hayes et al., 1980; Beresford et al., 1999), which contrasts with the rapid degradation of DNA to oligonucleosomal-length fragments seen in cells treated with granzyme B and perforin. Granzyme A/perforin treatment also leads to nuclear condensation (Beresford et al., 1999). These effects which occur in response to granzyme A are insensitive to caspase inhibitors, indicating that these actions of granzyme A are caspase-independent (Beresford et al., 1999). In a consistent manner, granzyme A/perforin treatment does not result in processing/activation of procaspase-3 or cleavage of the caspase substrate proteins PARP, lamin B, or rho-GTPase (Beresford et al., 1999) However, granzymeB-induced DNA fragmentation is strictly dependent on the activation of caspases. Both granzyme A and granzyme B (in conjunction with perforin) also induce target cell cytolysis, both cases of which are caspase-independent events. Thus, current evidence indicates that granzyme B is the primary CTL mediator of target cell DNA fragmentation and apoptotic death, and that the apoptotic effects of this protease are mediated primarily through the activation of caspase. Alternatively, granzyme A may be more of a default or specialized mediator of target cell apoptosis, with the pathways initiated by granzyme A being distinctly different from those initiated by granzyme B.

IV. Generation of Chimeric Molecules

While the chimeric proteins of the present invention may be produced by chemical synthetic methods or by chemical linkage between the two moieties, it is preferred that they are produced by fusion of a coding sequence of a cell-specific targeting moiety and a coding sequence of an apoptosis-inducing protein under the control of a regulatory sequence which directs the expression of the fusion polynucleotide in an appropriate host cell. In preferred embodiments, each of the components of the chimeric protein comprise functional activity for their respective parts being a cell-specific targeting moiety and a signal transduction pathway factor (such as an apoptosis-inducing protein).

The fusion of two full-length coding sequences can be achieved by methods well known in the art of molecular biology. It is preferred that a fusion polynucleotide contain only the AUG translation initiation codon at the 5' end of the first coding sequence without the initiation codon of the second coding sequence to avoid the production of two separate encoded products. In addition, a leader sequence may be placed at the 5' end of the polynucleotide in order to target the expressed product to a specific site or compartment within a host cell to facilitate secretion or subsequent purification after gene expression. The two coding sequences can be fused directly without any linker or by using a flexible polylinker, such as one composed of the pentamer Gly-Gly-Gly-Gly-Ser (SEQ ID NO:50) repeated 1 to 3 times. Such linker has been used in constructing single chain antibodies (scfv) by being inserted between $V_H$ and $V_L$ (Bird et al., 1988; Huston et al., 1988). The linker is designed to enable the correct interaction between two beta-sheets forming the variable region of the single chain antibody. Other linkers which may be used include Glu-Gly-Lys-Ser-Ser-Gly-Ser-Gly-Ser-Glu-Ser-Lys-Val-Asp (SEQ ID NO:51) (Chaudhary et al., 1990) and Lys-Glu-Ser-Gly-Ser-Val-Ser-Ser-Glu-Gln-Leu-Ala-Gln-Phe-Arg-Ser-Leu-Asp (SEQ ID NO:52)(Bird et al., 1988).

A. Cell-Specific Targeting Moieties

The chimeric proteins of the invention are composed of a cell-specific targeting moiety and an apoptosis-inducing moiety. The cell-specific targeting moiety confers cell-type specific binding to the molecule, and it is chosen on the basis of the particular cell population to be targeted. A wide variety of proteins are suitable for use as cell-specific targeting moieties, including but not limited to, ligands for receptors such as growth factors, hormones and cytokines, and antibodies or antigen-binding fragments thereof.

Since a large number of cell surface receptors have been identified in hematopoietic cells of various lineages, ligands or antibodies specific for these receptors may be used as cell-specific targeting moieties. IL2 may be used as a cell-specific targeting moiety in a chimeric protein to target $IL2R^+$ cells. Alternatively, other molecules such as B7-1, B7-2 and CD40 may be used to specifically target activated T cells (The Leucocyte Antigen Facts Book, 1993, Barclay et al. (eds.), Academic Press). Furthermore, B cells express CD19, CD40 and IL4 receptor and may be targeted by moieties that bind these receptors, such as CD40 ligand, IL4, IL5, IL6 and CD28. The elimination of immune cells such as T cells and B cells is particularly useful in the treatment of autoimmunity, hypersensitivity, transplantation rejection responses and in the treatment of lymphoid tumors. Examples of autoimmune diseases are multiple sclerosis, rheumatoid arthritis, insulin-dependent diabetes mellitus, systemic lupus crythemotisis, scleroderma, and uviatis. More specifically, since myelin basic protein is known to be the major target of immune cell attack in multiple sclerosis, this protein may be used as a cell-specific targeting moiety for the treatment of multiple sclerosis (WO 97/19179; Becker et al., 1997).

Other cytokines that may be used to target specific cell subsets include the interleukins (IL1 through IL15), granulocyte-colony stimulating factor, macrophage-colony stimulating factor, granulocyte-macrophage colony stimulating factor, leukemia inhibitory factor, tumor necrosis factor, transforming growth factor, epidermal growth factor, insulin-like growth factors, and/or fibroblast growth factor (Thompson (ed.), 1994, The Cytokine Handbook, Academic Press, San Diego).

A skilled artisan recognizes that there are a variety of known cytokines, including hematopoietins (four-helix bundles) (such as Epo (erythropoietin), IL-2 (T-cell growth factor), IL-3 (multicolony CSF), IL-4 (BCGF-1, BSF-1), IL-5 (BCGF-2), IL-6 IL-4 (IFN-$\beta_2$, BSF-2, BCDF), IL-7, IL-8, IL-9, IL-11, IL-13 (P600), G-CSF, IL-15 (T-cell growth factor), GM-CSF (granulocyte macrophage colony stimulating factor), OSM (OM, oncostatin M), and LIF (leukemia inhibitory factor)); interferons (such as IFN-γ, IFN-α, and IFN-β); immunoglobin superfamily (such as B7.1 (CD80), and B7.2 (B70, CD86)); TNF family (such as TNF-α (cachectin), TNF-β (lymphotoxin, LT, LT-α), LT-β, CD40 ligand (CD40L), Fas ligand (FasL), CD27 ligand (CD27L), CD30 ligand (CD30L), and 4-1BBL)); and those unassigned to a particular family (such as TGF-β, IL-1α, IL-1β, IL-1 RA, IL-10 (cytokine synthesis inhibitor F), IL-12 (NK cell stimulatory factor), MIF, IL-16, IL-17 (mCTLA-8), and/or IL-18 (IGIF, interferon-γ inducing factor)).

Additionally, certain cell surface molecules are highly expressed in tumor cells, including hormone receptors such as human chorionic gonadotropin receptor and gonadotropin releasing hormone receptor (Nechushtan et al., 1997). Therefore, the corresponding hormones may be used as the cell-specific targeting moieties in cancer therapy.

Thus, in some embodiments of the invention, no antibodies are utilized in the chimeric polypeptides. However, antibodies are extremely versatile and useful cell-specific targeting moieties because they can be generated against any cell surface antigen of interest. Monoclonal antibodies have been generated against cell surface receptors, tumor-associated antigens, and leukocyte lineage-specific markers such as CD antigens. Antibody variable region genes can be readily isolated from hybridoma cells by methods well known in the art.

Over the past few years, several monoclonal antibodies have been approved for therapeutic use and have achieved significant clinical and commercial success. Much of the clinical utility of monoclonal antibodies results from the affinity and specificity with which they bind to their targets, as well as long circulating life due to their relatively large size. Monoclonal antibodies, however, are not well suited for use in indications where a short half-life is advantageous or where their large size inhibits them physically from reaching the area of potential therapeutic activity.

Moreover, antibodies in their native form, consisting of two different polypeptide chains that need to be generated in approximately equal amounts and assembled correctly, are poor candidates for therapeutic purposes. However, it is possible to create a single polypeptide which can retain the antigen binding properties of a monoclonal antibody.

Single chain antibodies (SCAs) are genetically engineered proteins designed to expand on the therapeutic and diagnostic applications possible with monoclonal antibodies. SCAs have the binding specificity and affinity of monoclonal antibodies and, in their native form, are about one-fifth to one-sixth of the size of a monoclonal antibody, typically giving them very short half-lives. Human SCAs offer many benefits compared to most monoclonal antibodies, including more specific localization to target sites in the body, faster clearance from the body, and a better opportunity to be used orally, intranasally, transdermally or by inhalation. In addition to these benefits, fully-human SCAs can be isolated directly from human SCA libraries without the need for costly and time consuming "humanization" procedures. SCAs are also readily produced through intracellular expression (inside cells) allowing for their use in gene therapy applications where SCA molecules act as specific inhibitors of cell function.

The variable regions from the heavy and light chains (VH and VL) are both approximately 110 amino acids long. They can be linked by a 15 amino acid linker with the sequence $(SEQ\ ID\ NO{:}50)_3$, which has sufficient flexibility to allow the two domains to assemble a functional antigen binding pocket. In specific embodiments, addition of various signal sequences allows the scFv to be targeted to different organelles within the cell, or to be secreted. Addition of the light chain constant region (Ck) allows dimerization via disulfide bonds, giving increased stability and avidity. Thus, for a single chain Fv (scFv) SCA, although the two domains of the Fv fragment are coded for by separate genes, it has been proven possible to make a synthetic linker that enables them to be made as a single protein chain scFv (Bird et al., 1988; Huston et al., 1988) by recombinant methods. Furthermore, they are frequently used due to their ease of isolation from phage display libraries and their ability to recognize conserved antigens (for review, see Adams and Schier, 1999). For example, scFv is utilized to target suicide genes to carcinoembryonic antigen (CEA)-expressing tumor cells by a retrovector displaying anti-CEA scFv (Kuroki et al., 2000).

Finally, the Fc portion of the heavy chain of an antibody may be used to target Fc receptor-expressing cells such as the use of the Fc portion of an IgE antibody to target mast cells and basophils. The use of antibodies to target a polypeptide or peptide of interest by antibody-directed therapy or immunological-directed therapy is currently approved and in use in the present therapeutic market.

Thus, it is preferred that a scFv be used as a cell-specific targeting moiety in the present invention.

B. Apoptosis-Inducing Moieties

The pro-apoptotic proteins in the BCL2 family are particularly suitable for use as the apoptosis-inducing moieties in the present invention. Such human proteins are expected to have reduced immunogenicity over many immunotoxins composed of bacterial toxins. Although Bax is a useful apoptosis-inducing moiety in one embodiment of the present invention, other members in this family are suitable for use in the present invention and include Bak (Farrow et al., 1995; Chittenden et al., 1995; Kiefer et al., 1995), Bcl-$X_S$, (Boise et al., 1993; Fang et al., 1994), Bad (Yang et al., 1995), Bid (Wang et al., 1996), Bik (Boyd et al., 1995), Hrk (Inohara et al., 1997) and/or Bok (Hsu et al., 1997). The nucleotide sequences encoding these proteins are known in the art and are readily obtainable from databases such as GenBank, and thus cDNA clones can be readily obtained for fusion with a coding sequence for a cell-specific targeting moiety in an expression vector.

Specific domains of particular members of the Bcl-2 family have been studied regarding their apoptosis-inducing activities. For example, the GD domain of Bak is involved in the apoptosis function (U.S. Pat. No. 5,656,725). In addition, Bax and Bipla share a homologous domain. Therefore, any biologically active domains of the Bcl-2 family may be used as an apoptosis-inducing moiety for the practice of the present invention.

Caspases also play a central role in apoptosis and may well constitute part of the consensus core mechanism of apoptosis. Caspases are implicated as mediators of apoptosis. Since the recognition that CED-3, a protein required for developmental cell death, has sequence identity with the mammalian cysteine protease interleukin-1 beta-converting enzyme (ICE), a family of at least 10 related cysteine proteases has been identified. These proteins are characterized by almost absolute specificity for aspartic acid in the P1 position. All the caspases (ICE-like proteases) contain a conserved QACKG (where X is R, Z or G) pentapeptide active-site motif. Caspases are synthesized as inactive proenzymes comprising an N-terminal peptide (Prodomain) together with one large and one small subunit. The crystal structures of both caspase-1 and caspase-3 show that the active enzyme is a heterotetramer, containing two small and two large subunits. Activation of caspases during apoptosis results in the cleavage of critical cellular substrates, including poly (ADP-riose) polymerase and lamins, so precipitating the dramatic morphological changes of apoptosis (Cohen, 1997, Biochem. J. 326:1–16). Therefore, it is also within the scope of the present invention to use a caspase as an apoptosis-inducing moiety.

Recently a few new proteins were cloned and identified as factors required for mediating activity of proteins, mainly caspases, involved in the apoptosis pathway. One factor was identified as the previously known electron transfer protein, cytochrome c (Lin et al., 1996, Cell 86:147–157), designed as Apaf-2. In addition to cytochrome c the activation of caspase-3 requires two other cytosolic factors-Apaf-1 and Apaf-3. Apaf-1 is a protein homologous to *C. elegans* CED-4, and Apaf-3 was identified as a member of the caspase family, caspase-9. Both factors bind to each other via their respective NH2-terminal CED-3 homologous domains, in the presence of cytochrome c, an event that leads to caspase-9 activation. Activated caspase-9 in turn cleaves and activates caspase-3 (Liu et al., 1996; Zou et al., 1997; Li et al., 1997). Another protein involved in the apoptotic pathway is DNA fragmentation factor (DFF), a heterodimer of 45 and 40 kd subunits that functions downstream of caspase-3 to trigger fragmentation of genomic DNA into nucleosomal segments (Liu et al., 1997).

C. Chimeric Polypeptide Production

In accordance with the objects of the present invention, a polynucleotide that encodes a chimeric protein, mutant polypeptide, biologically active fragment of chimeric protein, or functional equivalent thereof, may be used to generate recombinant DNA molecules that direct the expression of the chimeric protein, chimeric peptide fragments, or a functional equivalent thereof, in appropriate host cells.

Due to the inherent degeneracy of the genetic code, other DNA sequences that encode substantially the same or a functionally equivalent amino acid sequence, may be used in the practice of the invention of the cloning and expression of the chimeric protein. Such DNA sequences include those capable of hybridizing to the chimeric sequences or their complementary sequences under stringent conditions. In one embodiment, the phrase "stringent conditions" as used herein refers to those hybridizing conditions that (1) employ low ionic strength and high temperature for washing, for example, 0.015 M NaCl/0.0015 M sodium citrate/0.1% SDS at 50° C.; (2) employ during hybridization a denaturing agent such as formamide, for example, 50% (vol/vol) formamide with a 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.; or (3) employ 50% formamide, 5×SSC (0.75 M NaCl, 0.075 M Sodium pyrophosphate, 5× Denhardt's solution, sonicated salmon sperm DNA (50 μg/ml), 0.1% SDS, and 10% dextran sulfate at 42° C., with washes at 42° C. in 0.2×SSC and 0.1% SDS.

Altered DNA sequences that may be used in accordance with the invention include deletions, additions or substitutions of different nucleotide residues resulting in a sequence that encodes the same or a functionally equivalent fusion gene product. The gene product itself may contain deletions, additions or substitutions of amino acid residues within a chimeric sequence, which result in a silent change thus producing a functionally equivalent chimeric protein. Such amino acid substitutions may be made on the basis of similarity in polarity, charge, solubility, hydrophobicity, hydrophilicity, and/or the amphipathic nature of the residues involved. For example, negatively charged amino acids include aspartic acid and glutamic acid; positively charged amino acids include lysine, histidine and arginine; amino acids with uncharged polar head groups having similar hydrophilicity values include the following: glycine, asparagine, glutamine, serine, threonine, tyrosine; and amino acids with nonpolar head groups include alanine, valine, isoleucine, leucine, phenylalanine, proline, methionine, tryptophan.

The DNA sequences of the invention may be engineered in order to alter a chimeric coding sequence for a variety of ends, including but not limited to, alterations which modify processing and expression of the gene product. For example, mutations may be introduced using techniques which are well known in the art, e.g., site-directed mutagenesis, to insert new restriction sites, to alter glycosylation patterns, phosphorylation, etc.

In an alternate embodiment of the invention, the coding sequence of the chimeric protein could be synthesized in whole or in part, using chemical methods well known in the art. (See, for example, Caruthers et al., 1980; Crea and Horn, 1980; and Chow and Kempe, 1981). For example, active domains of the moieties can be synthesized by solid phase techniques, cleaved from the resin, and purified by preparative high performance liquid chromatography followed by chemical linkage to form a chimeric protein. (e.g., see Creighton, 1983, *Proteins Structures And Molecular Principles*, W.H. Freeman and Co., N.Y. pp. 50–60). The composition of the synthetic peptides may be confirmed by amino acid analysis or sequencing (e.g., the Edman degradation procedure; see Creighton, 1983, *Proteins, Structures and Molecular Principles*, W.H. Freeman and Co., N.Y. pp. 34–49). Alternatively, the two moieties of the chimeric protein produced by synthetic or recombinant methods may be conjugated by chemical linkers according to methods well known in the art (Brinkmann and Pastan, 1994).

In order to express a biologically active chimeric protein, the nucleotide sequence coding for a chimeric protein, or a functional equivalent, is inserted into an appropriate expression vector, i.e., a vector which contains the necessary elements for the transcription and translation of the inserted coding sequence. The chimeric gene products as well as host cells or cell lines transfected or transformed with recombinant chimeric expression vectors can be used for a variety of purposes. These include but are not limited to generating antibodies (i.e., monoclonal or polyclonal) that bind to epitopes of the proteins to facilitate their purification.

Methods that are well known to those skilled in the art can be used to construct expression vectors containing the chimeric protein coding sequence and appropriate transcriptional/translational control signals. These methods include in vitro recombinant DNA techniques, synthetic techniques and in vivo recombination/genetic recombination. See, for example, the techniques described in Sambrook et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y.

A variety of host-expression vector systems may be utilized to express the chimeric protein coding sequence. These include but are not limited to microorganisms such as bacteria transformed with recombinant bacteriophage DNA, plasmid DNA or cosmid DNA expression vectors containing the chimeric protein coding sequence; yeast transformed with recombinant yeast expression vectors containing the chimeric protein coding sequence; insect cell systems infected with recombinant virus expression vectors (e.g., baculovirus) containing the chimeric protein coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the chimeric protein coding sequence; or animal cell systems. It should be noted that since most apoptosis-inducing proteins cause programmed cell death in mammalian cells, it is preferred that the chimeric protein of the invention be expressed in prokaryotic or lower eukaryotic cells. Section 6 illustrates that IL2-Bax may be efficiently expressed in *E. coli.*

The expression elements of each system vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter; cytomegalovirus promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll α/β binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the chimeric DNA, SV40-, BPV- and EBV-based vectors may be used with an appropriate selectable marker.

In bacterial systems a number of expression vectors may be advantageously selected depending upon the use intended for the chimeric protein expressed. For example, when large quantities of chimeric protein are to be produced, vectors which direct the expression of high levels of protein products that are readily purified may be desirable. Such vectors include but are not limited to the pHL906 vector (Fishman et al., 1994), the *E. coli* expression vector pUR278 (Ruther et al., 1983), in which the chimeric protein coding sequence may be ligated into the vector in frame with the lacZ coding region so that a hybrid AS-lacZ protein is produced; pIN vectors (Inouye and Inouye, 1989; Van Heeke and Schuster, 1989); and the like.

An alternative expression system which could be used to express chimeric protein is an insect system. In one such system, *Autographa californica* nuclear polyhidrosis virus (AcNPV) is used as a vector to express foreign genes. The virus grows in *Spodoptera frugiperda* cells. The chimeric protein coding sequence may be cloned into non-essential regions (for example the polyhedrin gene) of the virus and placed under control of an AcNPV promoter (for example the polyhedrin promoter). Successful insertion of the chimeric protein coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (e.g., see Smith et al., 1983; U.S. Pat. No. 4,215,051).

Specific initiation signals may also be required for efficient translation of the inserted chimeric protein coding sequence. These signals include the ATG initiation codon and adjacent sequences. In cases where the entire chimeric gene, including its own initiation codon and adjacent sequences, is inserted into the appropriate expression vector, no additional translational control signals may be needed. However, in cases where the chimeric protein coding sequence does not include its own initiation codon, exogenous translational control signals, including the ATG initiation codon, must be provided. Furthermore, the initiation codon must be in phase with the reading frame of the chimeric protein coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. The presence of consensus N-glycosylation sites in a chimeric protein may require proper modification for optimal chimeric protein function. Different host cells have characteristic and specific mechanisms for the post-translational processing and modification of proteins. Appropriate cell lines or host systems can be chosen to ensure the correct modification and processing of the chimeric protein. To this end, eukaryotic host cells which possess the cellular machinery for proper processing of the primary transcript, glycosylation, and phosphorylation of the chimeric protein may be used. Such mammalian host cells include but are not limited to CHO, VERO, BHK, HeLa, COS, MDCK, 293, W138, and the like.

For long-term, high-yield production of recombinant chimeric proteins, stable expression is preferred. For example, cell lines which stably express the chimeric protein may be engineered. Rather than using expression vectors which contain viral originals of replication, host cells can be transformed with a chimeric coding sequence controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including but not limited to the herpes simplex virus thymidine kinase (Wigler et al., 1977), hypoxanthine-guanine phosphoribosyltransferase (Szybalski and Szybalski, 1962), and adenine phosphoribosyltransferase (Lowy et al., 1980) genes can be employed in tk-, hgprt- or aprt-cells, respectively. Also, antimetabolite resistance can be used as the basis of selection for dhfr, which confers resistance to methotrexate (Wigler et al., 1980; O'Hare et al., 1981); gpt, which confers resistance to mycophenolic acid (Mulligan and Berg, 1981); neo, which confers resistance to the aminoglycoside G-418 (Colbere-Garapin et al., 1981); and hygro, which confers resistance to hygromycin (Santerre et al., 1984) genes. Additional selectable genes have been described, namely trpB, which allows cells to utilize indole in place of tryptophan; hisD, which allows cells to utilize histinol in place of histidine (Hartman and Mulligan, 1988); and ODC (ornithine decarboxylase) which confers resistance to the ornithine decarboxylase inhibitor, 2-(difluoromethyl)-DL-ornithine, DFMO (McConlogue L, 1987, In: Current Communications in Molecular Biology, Cold Spring Harbor Laboratory ed.).

D. Protein Purification

The chimeric proteins of the invention can be purified by art-known techniques such as high performance liquid chromatography, ion exchange chromatography, gel electrophoresis, affinity chromatography and the like. The actual conditions used to purify a particular protein will depend, in part, on factors such as net charge, hydrophobicity, hydrophilicity, etc., and will be apparent to those having skill in the art.

For affinity chromatography purification, any antibody which specifically binds the protein may be used. For the production of antibodies, various host animals, including but not limited to rabbits, mice, rats, etc., may be immunized by injection with a chimeric protein or a fragment thereof. The protein may be attached to a suitable carrier, such as bovine serum albumin (BSA), by means of a side chain functional group or linkers attached to a side chain functional group. Various adjuvants may be used to increase the immunological response, depending on the host species, including but not limited to, Freund's (complete and incomplete), mineral gels such as aluminum hydroxide, surface active substances such as lysolecithin, pluronic polyols, polyanions, peptides, oil emulsions, keyhold limpet hemocyanin, dinitrophenol, and potentially useful human adjuvants such as BCG (bacilli Calmetter-Guerin) and *Corynebacterium parvum.*

Monoclonal antibodies to a chimeric protein may be prepared using any technique which provides for the production of antibody molecules by continuous cell lines in culture. These include but are not limited to the hybridoma technique originally described by Koehler and Milstein (1975), the human B-cell hybridoma technique, (Kosbor et al., 1983; Cote et al., 1983) and the EBV-hybridoma technique (Cole et al., 1985). In addition, techniques developed for the production of "chimeric antibodies" (Morrison et al., 1984; Neuberger et al., 1984; Takeda et al., 1985) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce chimeric protein-specific single chain antibodies for chimeric protein purification and detection.

V. Uses of Chimeric Polypeptide

Once a chimeric protein is expressed and purified, its identity and functional activities can be readily determined by methods well known in the art. For example, antibodies to the two moieties of the protein may be used to identify the protein in Western blot analysis. In addition, the chimeric protein can be tested for specific binding to target cells in binding assays using a fluorescent-labeled or radiolabelled secondary antibody.

A. In Vitro and Ex Vivo Uses

The chimeric polypeptides of the invention are useful for targeting specific cell types in a cell mixture, and eliminating the target cells by inducing apoptosis. The chimeric polypeptides of the invention are also useful as a diagnostic reagent. The binding of a chimeric protein to a target cell can be readily detected by using a secondary antibody specific for the apoptosis-inducing moiety. In that connection, the secondary antibody or the chimeric protein enzyme or a radioisotope to facilitate the detection of binding of the chimeric protein to a cell.

B. In Vivo Uses

In some embodiments, an effective amount of the chimeric polypeptides of the present invention are administered to a cell. In other embodiments, a therapeutically effective amount of the chimeric polypeptides of the present invention are administered to an individual for the treatment of disease. The term "effective amount" as used herein is defined as the amount of the chimeric polypeptides of the present invention which are necessary to result in a physiological change in the cell or tissue to which it is administered. The term "therapeutically effective amount" as used herein is defined as the amount of the chimeric polypeptides of the present invention that eliminate, decrease, delay, or minimize adverse effects of a disease, such as cancer. A skilled artisan readily recognizes that in many cases the chimeric polypeptide may not provide a cure but may only provide partial benefit. In some embodiments, a physiological change having some benefit is also considered therapeutically beneficial. Thus, in some embodiments, an amount of chimeric polypeptide that provides a physiological change is considered an "effective amount" or a "therapeutically effective amount."

The chimeric proteins of the invention may be administered to a subject per se or in the form of a pharmaceutical composition for the treatment of cancer, autoimmunity, transplantation rejection, post-traumatic immune responses and infectious diseases by targeting viral antigens, such as gp120 of HIV. More specifically, the chimeric polypeptides may be useful in eliminating cells involved in immune cell-mediated disorder, including lymphoma; autoimmunity, transplantation rejection, graft-versus-host disease, ischemia and stroke. Pharmaceutical compositions comprising the proteins of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations which can be used pharmaceutically. Proper formulation is dependent upon the route of administration chosen.

For topical administration the proteins of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, inhalation, oral or pulmonary administration.

For injection, the proteins of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents.

Alternatively, the proteins may be in powder form for constitution with a suitable vehicle, e.g., sterile pyrogen-free water, before use.

For transmucosal administration, penetrants appropriate to the barrier to be permeated are used in the formulation. Such penetrants are generally known in the art.

For oral administration, the proteins can be readily formulated by combining the proteins with pharmaceutically acceptable carriers well known in the art. Such carriers enable the proteins of the invention to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, e.g. lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate.

If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like may be added.

For buccal administration, the proteins may take the form of tablets, lozenges, etc. formulated in conventional manner.

For administration by inhalation, the proteins for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator may be formulated containing a powder mix of the protein and a suitable powder base such as lactose or starch.

The proteins may also be formulated in rectal or vaginal compositions such as suppositories or retention enemas, e.g., containing conventional suppository bases such as cocoa butter or other glycerides.

In addition to the formulations described previously, the proteins may also be formulated as a depot preparation. Such long acting formulations may be administered by implantation (for example subcutaneously or intramuscularly) or by intramuscular injection. Thus, for example, the proteins may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well known examples of delivery vehicles that may be used to deliver proteins of the invention. Certain organic solvents such as dimethylsulfoxide also may be employed, although usually at the cost of greater toxicity. Additionally, the proteins may be delivered using a sustained-release system, such as semipermeable matrices of solid polymers containing the therapeutic agent. Various of sustained-release materials have been established and are well known by those skilled in the art. Sustained-release capsules may, depending on their chemical nature, release the proteins for a few weeks up to over 100 days. Depending on the chemical nature and the biological stability of the chimeric protein, additional strategies for protein stabilization may be employed.

As the proteins of the invention may contain charged side chains or termini, they may be included in any of the above-described formulations as the free acids or bases or as pharmaceutically acceptable salts. Pharmaceutically acceptable salts are those salts which substantially retain the biologic activity of the free bases and which are prepared by reaction with inorganic acids. Pharmaceutical salts tend to be more soluble in aqueous and other protic solvents than are the corresponding free base forms.

1. Effective Dosages

The proteins of the invention will generally be used in an amount effective to achieve the intended purpose. For use to treat or prevent a disease condition, the proteins of the invention, or pharmaceutical compositions thereof, are administered or applied in a therapeutically effective amount. A therapeutically effective amount is an amount effective to ameliorate or prevent the symptoms, or prolong the survival of, the patient being treated. Determination of a therapeutically effective amount is well within the capabilities of those skilled in the art, especially in light of the detailed disclosure provided herein.

For systemic administration, a therapeutically effective dose can be estimated initially from in vitro assays. For example, a dose can be formulated in animal models to achieve a circulating concentration range that includes the $IC_5$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the proteins which are sufficient to maintain therapeutic effect. Usual patient dosages for administration by injection range from about 0.1 to 5 mg/kg/day, preferably from about 0.5 to 1 mg/kg/day. Therapeutically effective serum levels may be achieved by administering multiple doses each day.

In cases of local administration or selective uptake, the effective local concentration of the proteins may not be related to plasma concentration. One having skill in the art will be able to optimize therapeutically effective local dosages without undue experimentation.

The amount of protein administered will, of course, be dependent on the subject being treated, on the subject's weight, the severity of the affliction, the manner of administration and the judgment of the prescribing physician.

The therapy may be repeated intermittently while symptoms detectable or even when they are not detectable. The therapy may be provided alone or in combination with other drugs. In the case of autoimmune disorders, the drugs that may be used in combination with IL2-Bax of the invention include, but are not limited to, steroid and non-steroid anti-inflammatory agents.

2. Toxicity

Preferably, a therapeutically effective dose of the chimeric proteins described herein will provide therapeutic benefit without causing substantial toxicity.

Toxicity of the proteins described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Proteins which exhibit high therapeutic indices are preferred. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, In: *The Pharmacological Basis of Therapeutics*, Ch. 1, p. 1).

VI. Biological Functional Equivalents

As modifications and/or changes may be made in the structure of the polynucleotides encoding the chimeric polypeptides of the present invention and/or the chimeric polypeptides themselves according to the present invention, while obtaining molecules having similar or improved characteristics, such biologically functional equivalents are also encompassed within the present invention.

A. Modified Polynucleotides and Polypeptides

The biological functional equivalent may comprise a polynucleotide that has been engineered to contain distinct sequences while at the same time retaining the capacity to encode the "wild-type" or standard protein. This can be accomplished to the degeneracy of the genetic code, i.e., the presence of multiple codons, which encode for the same amino acids. In one example, one of skill in the art may wish to introduce a restriction enzyme recognition sequence into a polynucleotide while not disturbing the ability of that polynucleotide to encode a protein.

In another example, a polynucleotide encoding the chimeric polypeptide may be (and may encode) a biological functional equivalent with more significant changes. Certain amino acids may be substituted for other amino acids in a protein structure without appreciable loss of interactive binding capacity with structures such as, for example, antigen-binding regions of antibodies, binding sites on substrate molecules, receptors, and the like. So-called "conservative" changes do not disrupt the biological activity of the polypeptide, as the structural change is not one that impinges of the polypeptide's ability to carry out its designed function. It is thus contemplated by the inventors that various changes may be made in the sequence of genes and proteins disclosed herein, while still fulfilling the goals of the present invention.

In terms of functional equivalents, it is well understood by the skilled artisan that, inherent in the definition of a "biologically functional equivalent" protein and/or polynucleotide, is the concept that there is a limit to the number of changes that may be made within a defined portion of the molecule while retaining a molecule with an acceptable level of equivalent biological activity. Biologically functional equivalents are thus defined herein as those polypeptides (and polynucleotides) in selected amino acids (or codons) may be substituted. Functional activity comprises the ability to kill a target cell for the signal transduction pathway factor moiety or the ability to target a cell specifically for the cell-specific targeting moiety.

In general, the shorter the length of the molecule, the fewer changes that can be made within the molecule while retaining function. Longer domains may have an intermediate number of changes. The full-length protein will have the most tolerance for a larger number of changes. However, it must be appreciated that certain molecules or domains that are highly dependent upon their structure may tolerate little or no modification.

Amino acid substitutions are generally based on the relative similarity of the amino acid side-chain substituents, for example, their hydrophobicity, hydrophilicity, charge, size, and/or the like. An analysis of the size, shape and/or type of the amino acid side-chain substituents reveals that arginine, lysine and/or histidine are all positively charged residues; that alanine, glycine and/or serine are all a similar size; and/or that phenylalanine, tryptophan and/or tyrosine all have a generally similar shape. Therefore, based upon these considerations, arginine, lysine and/or histidine; alanine, glycine and/or serine; and/or phenylalanine, tryptophan and/or tyrosine; are defined herein as biologically functional equivalents.

To effect more quantitative changes, the hydropathic index of amino acids may be considered. Each amino acid has been assigned a hydropathic index on the basis of their hydrophobicity and/or charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and/or arginine (−4.5).

The importance of the hydropathic amino acid index in conferring interactive biological function on a protein is generally understood in the art (Kyte & Doolittle, 1982, incorporated herein by reference). It is known that certain amino acids may be substituted for other amino acids having a similar hydropathic index and/or score and/or still retain a similar biological activity. In making changes based upon the hydropathic index, the substitution of amino acids whose hydropathic indices are within ±2 is preferred, those which are within ±1 are particularly preferred, and/or those within ±0.5 are even more particularly preferred.

It also is understood in the art that the substitution of like amino acids can be made effectively on the basis of hydrophilicity, particularly where the biological functional equivalent protein and/or peptide thereby created is intended for use in immunological embodiments, as in certain embodiments of the present invention. U.S. Pat. No. 4,554,101, incorporated herein by reference, states that the greatest local average hydrophilicity of a protein, as governed by the hydrophilicity of its adjacent amino acids, correlates with its immunogenicity and/or antigenicity, i.e., with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0): threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids whose hydrophilicity values are within ±2 is preferred, those which are within ±1 are particularly preferred, and/or those within ±0.5 are even more particularly preferred.

B. Altered Amino Acids

The present invention, in many aspects, relies on the synthesis of peptides and polypeptides in cyto, via transcription and translation of appropriate polynucleotides. These peptides and polypeptides will include the twenty "natural" amino acids, and post-translational modifications thereof. However, in vitro peptide synthesis permits the use of modified and/or unusual amino acids. A table of exemplary, but not limiting, modified and/or unusual amino acids is provided herein below.

TABLE 2

Modified and/or Unusual Amino Acids

| Abbr. | Amino Acid | Abbr. | Amino Acid |
|---|---|---|---|
| Aad | 2-Aminoadipic acid | EtAsn | N-Ethylasparagine |
| BAad | 3-Aminoadipic acid | Hyl | Hydroxylysine |
| BAla | beta-alanine, beta-Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | Aile | allo-Isoleucine |
| Aib | 2-Aminoisobutyric acid | MeGly | N-Methylglycine, sarcosine |
| BAib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

C. Mimetics

In addition to the biological functional equivalents discussed above, the present inventors also contemplate that structurally similar compounds may be formulated to mimic the key portions of peptide or polypeptides of the present invention. Such compounds, which may be termed peptidomimetics, may be used in the same manner as the peptides of the invention and, hence, also are functional equivalents.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Some successful applications of the peptide mimetic concept have focused on mimetics of β-turns within proteins, which are known to be highly antigenic. Likely β-turn structure within a polypeptide can be predicted by computer-based algorithms, as discussed herein. Once the component amino acids of the turn are determined, mimetics can be constructed to achieve a similar spatial orientation of the essential elements of the amino acid side chains.

Other approaches have focused on the use of small, multidisulfide-containing proteins as attractive structural templates for producing biologically active conformations that mimic the binding sites of large proteins. Vita et al. (1998). A structural motif that appears to be evolutionarily conserved in certain toxins is small (30–40 amino acids), stable, and high permissive for mutation. This motif is composed of a beta sheet and an alpha helix bridged in the interior core by three disulfides.

Beta II turns have been mimicked successfully using cyclic L-pentapeptides and those with D-amino acids. Weisshoff et al. (1999). Also, Johannesson et al. (1999) report on bicyclic tripeptides with reverse turn inducing properties.

Methods for generating specific structures have been disclosed in the art. For example, alpha-helix mimetics are disclosed in U.S. Pat. Nos. 5,446,128; 5,710,245; 5,840,833; and 5,859,184. Theses structures render the peptide or protein more thermally stable, also increase resistance to proteolytic degradation. Six, seven, eleven, twelve, thirteen and fourteen membered ring structures are disclosed.

Methods for generating conformationally restricted beta turns and beta bulges are described, for example, in U.S. Pat. Nos. 5,440,013; 5,618,914; and 5,670,155. Beta-turns permit changed side substituents without having changes in corresponding backbone conformation, and have appropriate termini for incorporation into peptides by standard synthesis procedures. Other types of mimetic turns include reverse and gamma turns. Reverse turn mimetics are disclosed in U.S. Pat. Nos. 5,475,085 and 5,929,237, and gamma turn mimetics are described in U.S. Pat. Nos. 5,672,681 and 5,674,976.

D. Liposome Targeting

Association of the chimeric polypeptide with a liposome may improve biodistribution and other properties of the chimeric polypeptide. For example, liposome-mediated nucleic acid delivery and expression of foreign DNA in vitro has been very successful (Nicolau and Sene, 1982; Fraleyet al., 1979; Nicolauet al., 1987). The feasibility of liposome-mediated delivery and expression of foreign DNA in cultured chick embryo, HeLa and hepatoma cells has also been demonstrated (Wong et al., 1980). Successful liposome-mediated gene transfer in rats after intravenous injection has also been accomplished (Nicolau et al., 1987).

It is contemplated that a liposome/chimeric polypeptide composition may comprise additional materials for delivery to a tissue. For example, in certain embodiments of the invention, the lipid or liposome may be associated with a hemagglutinating virus (HVJ). This has been shown to facilitate fusion with the cell membrane and promote cell entry of liposome-encapsulated DNA (Kaneda et al., 1989). In another example, the lipid or liposome may be complexed or employed in conjunction with nuclear non-histone chromosomal proteins (HMG-1) (Kato et al., 1991). In yet further embodiments, the lipid may be complexed or employed in conjunction with both HVJ and HMG-1.

Targeted delivery is achieved by the addition of ligands without compromising the ability of these liposomes deliver large amounts of chimeric polypeptide. It is contemplated that this will enable delivery to specific cells, tissues and organs. The targeting specificity of the ligand-based delivery systems are based on the distribution of the ligand receptors on different cell types. The targeting ligand may either be non-covalently or covalently associated with the lipid complex, and can be conjugated to the liposomes by a variety of methods.

E. Cross-Linkers

Bifunctional cross-linking reagents have been extensively used for a variety of purposes including preparation of affinity matrices, modification and stabilization of diverse structures, identification of ligand and receptor binding sites, and structural studies. Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino, sulfhydryl, guanidino, indole, carboxyl specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

Exemplary methods for cross-linking ligands to liposomes are described in U.S. Pat. No. 5,603,872 and U.S. Pat. No. 5,401,511, each specifically incorporated herein by reference in its entirety). Various ligands can be covalently bound to liposomal surfaces through the cross-linking of amine residues. Liposomes, in particular, multilamellar vesicles (MLV) or unilamellar vesicles such as microemulsified liposomes (MEL) and large unilamellar liposomes (LUVET), each containing phosphatidylethanolamine (PE), have been prepared by established procedures. The inclusion of PE in the liposome provides an active functional residue, a primary amine, on the liposomal surface for cross-linking purposes. Ligands such as epidermal growth factor (EGF) have been successfully linked with PE-liposomes. Ligands are bound covalently to discrete sites on the liposome surfaces. The number and surface density of these sites will be dictated by the liposome formulation and the liposome type. The liposomal surfaces may also have sites for non-covalent association. To form covalent conjugates of ligands and liposomes, cross-linking reagents have been studied for effectiveness and biocompatibility. Cross-linking reagents include glutaraldehyde (GAD), bifunctional oxirane (OXR), ethylene glycol diglycidyl ether (EGDE), and a water soluble carbodiimide, preferably 1-ethyl-3-(3-dimethylaminopropyl) carboddiimide (EDC). Through the complex chemistry of cross-linking, linkage of the amine residues of the recognizing substance and liposomes is established.

In another example, heterobifunctional cross-linking reagents and methods of using the cross-linking reagents are described (U.S. Pat. No. 5,889,155, specifically incorporated herein by reference in its entirety). The cross-linking reagents combine a nucleophilic hydrazide residue with an electrophilic maleimide residue, allowing coupling in one example, of aldehydes to free thiols. The cross-linking reagent can be modified to cross-link various functional groups and is thus useful for cross-linking polypeptides and sugars. Table 3 details certain hetero-bifunctional cross-linkers considered useful in the present invention.

TABLE 3

HETERO-BIFUNCTIONAL CROSS-LINKERS

| Linker | Reactive Toward | Advantages and Applications | Spacer Arm Length\after cross-linking |
|---|---|---|---|
| SMPT | Primary amines<br>Sulfhydryls | Greater stability | 11.2 A |
| SPDP | Primary amines<br>Sulfhydryls | Thiolation<br>Cleavable cross-linking | 6.8 A |
| LC-SPDP | Primary ammes<br>Sulfhydryls | Extended spacer arm | 15.6 A |
| Sulfo-LC-SPDP | Primary amines<br>Sulfhydryls | Extended spacer arm<br>Water-soluble | 15.6 A |
| SMCC | Primary amines<br>Sulfhydryls | Stable maleimide reactive group<br>Enzyme-antibody conjugation<br>Hapten-carrier protein conjugation | 11.6 A |
| Sulfo-SMCC | Primary amines<br>Sulfhydryls | Stable maleimide reactive group<br>Water-soluble<br>Enzyme-antibody conjugation | 11.6 A |
| MBS | Primary amines<br>Sulfhydryls | Enzyme-antibody conjugation<br>Hapten-carrier protein conjugation | 9.9 A |

TABLE 3-continued

HETERO-BIFUNCTIONAL CROSS-LINKERS

| Linker | Reactive Toward | Advantages and Applications | Spacer Arm Length\after cross-linking |
|---|---|---|---|
| Sulfo-MBS | Primary amines Sulfhydryls | Water-soluble | 9.9 A |
| SIAB | Primary amines Sulfhydryls | Enzyme-antibody conjugation | 10.6 A |
| Sulfo-SIAB | Primary amines Sulfhydryls | Water-soluble | 10.6 A |
| SMPB | Primary amines Sulfhydryls | Extended spacer arm Enzyme-antibody conjugation | 14.5 A |
| Sulfo-SMPB | Primary amines Sulfhydryls | Extended spacer arm Water-soluble | 14.5 A |
| EDC/Sulfo-NHS | Primary amines Carboxyl groups | Hapten-Carrier conjugation | 0 |
| ABH | Carbohydrates Nonselective | Reacts with sugar groups | 11.9 A |

In instances where a particular polypeptide does not contain a residue amenable for a given cross-linking reagent in its native sequence, conservative genetic or synthetic amino acid changes in the primary sequence can be utilized.

VII. Combination Treatments/Cancer Therapies

In order to increase the effectiveness of a chimeric polypeptide of the present invention, or expression construct coding therefor, it may be desirable to combine these compositions with other agents effective in the treatment of hyperproliferative disease, such as anti-cancer agents. A hyperproliferative disease includes diseases and conditions that are associated with any sort of abnormal cell growth or abnormal growth regulation. In methods of the present invention, preferably the patient is a human. A variety of hyperproliferative diseases can be treated according to the methods of the present invention. Some of the hyperproliferative diseases contemplated for treatment in the present invention are psoriasis, rheumatoid arthritis (RA), inflammatory bowel disease (IBD), osteoarthritis (OA) and pre-neoplastic lesions in the mouth, prostate, breast, lung etc. The present invention has important ramifications particularly with respect to one hyperproliferative disease: cancer.

Thus, in certain embodiments, the hyperproliferative disease is further defined as cancer. In still further embodiments, the cancer is melanoma, non-small cell lung, small-cell lung, lung, hepatocarcinoma, retinoblastoma, astrocytoma, glioblastoma, gum, tongue, leukemia, neuroblastoma, head, neck, breast, pancreatic, prostate, renal, bone, testicular, ovarian, mesothelioma, cervical, gastrointestinal, lymphoma, brain, colon, sarcoma or bladder. The cancer may include a tumor comprised of tumor cells. In other embodiments, the hyperproliferative disease is rheumatoid arthritis, inflammatory bowel disease, osteoarthritis, leiomyomas, adenomas, lipomas, hemangiomas, fibromas, vascular occlusion, restenosis, atherosclerosis, pre-neoplastic lesions (such as adenomatous hyperplasia and prostatic intraepithelial neoplasia), carcinoma in situ, oral hairy leukoplakia, or psoriasis.

An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cells with the expression construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s).

Tumor cell resistance to chemotherapy and radiotherapy agents represents a major problem in clinical oncology. One goal of current cancer research is to find ways to improve the efficacy of chemo- and radiotherapy by combining it with gene therapy. For example, the herpes simplex-thymidine kinase (HS-tK) gene, when delivered to brain tumors by a retroviral vector system, successfully induced susceptibility to the antiviral agent ganciclovir (Culver, et al., 1992). In the context of the present invention, it is contemplated that chimeric polypepides could be used similarly in conjunction with chemotherapeutic, radiotherapeutic, gene therapy, or immunotherapeutic intervention, in addition to other pro-apoptotic or cell cycle regulating agents.

Alternatively, the therapy may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one may contact the cell with both modalities within about 12–24 h of each other and, more preferably, within about 6–12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed, gene therapy is "A" and the secondary agent, such as radio- or chemotherapy, is "B":

A/B/A B/A/B B/B/A A/A/B A/B/B B/A/A A/B/B/B B/A/B/B B/B/B/A B/B/A/B A/A/B/B A/B/A/B A/B/B/A B/B/A/A B/A/B/A B/A/A/B A/A/A/B B/A/A/A A/B/A/A A/A/B/A

Administration of the therapeutic expression constructs of the present invention to a patient will follow general protocols for the administration of chemotherapeutics, taking into account the toxicity, if any, of the vector. It is expected that the treatment cycles would be repeated as necessary. It also is contemplated that various standard therapies, as well as surgical intervention, may be applied in combination with the described hyperproliferative cell therapy.

A. Chemotherapy

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing.

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

C. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with gene therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

D. Genes

In yet another embodiment, the secondary treatment is a gene therapy in which a therapeutic polynucleotide is administered before, after, or at the same time as a chimeric polypeptide of the present invention. Delivery of a chimeric polypeptide in conjuction with a second vector encoding one of the following gene products will have a combined anti-hyperproliferative effect on target tissues. Alternatively, a single vector encoding both genes may be used. A variety of proteins are encompassed within the invention, some of which are described below.

1. Inducers of Cellular Proliferation

The proteins that induce cellular proliferation further fall into various categories dependent on function. The commonality of all of these proteins is their ability to regulate cellular proliferation. For example, a form of PDGF, the sis oncogene, is a secreted growth factor. Oncogenes rarely arise from genes encoding growth factors, and at the present, sis is the only known naturally-occurring oncogenic growth factor. In one embodiment of the present invention, it is contemplated that anti-sense mRNA directed to a particular inducer of cellular proliferation is used to prevent expression of the inducer of cellular proliferation.

The proteins FMS, ErbA, ErbB and neu are growth factor receptors. Mutations to these receptors result in loss of regulatable function. For example, a point mutation affecting the transmembrane domain of the Neu receptor protein results in the neu oncogene. The erbA oncogene is derived from the intracellular receptor for thyroid hormone. The modified oncogenic ErbA receptor is believed to compete with the endogenous thyroid hormone receptor, causing uncontrolled growth.

The largest class of oncogenes includes the signal transducing proteins (e.g., Src, Abl and Ras). The protein Src is a cytoplasmic protein-tyrosine kinase, and its transformation from proto-oncogene to oncogene in some cases, results via mutations at tyrosine residue 527. In contrast, transformation of GTPase protein ras from proto-oncogene to oncogene, in one example, results from a valine to glycine mutation at amino acid 12 in the sequence, reducing ras GTPase activity.

The proteins Jun, Fos and Myc are proteins that directly exert their effects on nuclear functions as transcription factors.

2. Inhibitors of Cellular Proliferation

The tumor suppressor oncogenes function to inhibit excessive cellular proliferation. The inactivation of these genes destroys their inhibitory activity, resulting in unregulated proliferation. The tumor suppressors p53, p16 and C-CAM are described below.

High levels of mutant p53 have been found in many cells transformed by chemical carcinogenesis, ultraviolet radiation, and several viruses. The p53 gene is a frequent target of mutational inactivation in a wide variety of human tumors and is already documented to be the most frequently mutated gene in common human cancers. It is mutated in over 50% of human NSCLC (Hollstein et al., 1991) and in a wide spectrum of other tumors.

The p53 gene encodes a 393-amino acid phosphoprotein that can form complexes with host proteins such as large-T antigen and E1B. The protein is found in normal tissues and cells, but at concentrations which are minute by comparison with transformed cells or tumor tissue Wild-type p53 is recognized as an important growth regulator in many cell types. Missense mutations are common for the p53 gene and are essential for the transforming ability of the oncogene. A single genetic change prompted by point mutations can create carcinogenic p53. Unlike other oncogenes, however, p53 point mutations are known to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg, 1991).

Another inhibitor of cellular proliferation is p16. The major transitions of the eukaryotic cell cycle are triggered by cyclin-dependent kinases, or CDK's. One CDK, cyclin-dependent kinase 4 (CDK4), regulates progression through the $G_1$. The activity of this enzyme may be to phosphorylate Rb at late $G_1$. The activity of CDK4 is controlled by an activating subunit, D-type cyclin, and by an inhibitory subunit, the p16$^{INK4}$ has been biochemically characterized as a protein that specifically binds to and inhibits CDK4, and thus may regulate Rb phosphorylation (Serrano et al., 1993; Serrano et al., 1995). Since the p16$^{INK4}$ protein is a CDK4 inhibitor (Serrano, 1993), deletion of this gene may increase the activity of CDK4, resulting in hyperphosphorylation of the Rb protein. p16 also is known to regulate the function of CDK6.

p16$^{INK4}$ belongs to a newly described class of CDK-inhibitory proteins that also includes p16$^B$, p19, p21$^{WAF1}$, and p27$^{KIP1}$. The p16$^{INK4}$ gene maps to 9p21, a chromosome region frequently deleted in many tumor types. Homozygous deletions and mutations of the p16$^{INK4}$ gene are frequent in human tumor cell lines. This evidence suggests that the p16$^{INK4}$ gene is a tumor suppressor gene. This interpretation has been challenged, however, by the observation that the frequency of the p16$^{INK4}$ gene alterations is much lower in primary uncultured tumors than in cultured cell lines (Caldas et al., 1994; Cheng et al., 1994; Hussussian et al., 1994; Kamb et al., 1994; Kamb et al., 1994; Mori et al., 1994; Okamoto et al., 1994; Nobori et al., 1995; Orlow et al., 1994; Arap et al., 1995). Restoration of wild-type p16$^{INK4}$ function by transfection with a plasmid expression vector reduced colony formation by some human cancer cell lines (Okamoto, 1994; Arap, 1995).

Other genes that may be employed according to the present invention include Rb, APC, DCC, NF-1, NF-2, WT-1, MEN-I, MEN-II, zac1, p73, VHL, MMAC1/PTEN, DBCCR-1, FCC, rsk-3, p27, p27/p16 fusions, p21/p27 fusions, anti-thrombotic genes (e.g., COX-1, TFPI), PGS, Dp, E2F, ras, myc, neu, raf, erb, fms, trk, ret, gsp, hst, abl, E1A, p300, genes involved in angiogenesis (e.g., VEGF, FGF, thrombospondin, BAI-1, GDAIF, or their receptors) and MCC.

3. Regulators of Programmed Cell Death

Apoptosis, or programmed cell death, is an essential process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al, 1985; Tsujimoto and Croce, 1986). The evolutionarily conserved Bcl-2 protein now is recognized to be a member of a family of related proteins, which can be categorized as death agonists or death antagonists.

Subsequent to its discovery, it was shown that Bcl-2 acts to suppress cell death triggered by a variety of stimuli. Also, it now is apparent that there is a family of Bcl-2 cell death regulatory proteins which share in common structural and sequence homologies. These different family members have been shown to either possess similar functions to Bcl-2 (e.g., Bcl$_{XL}$, Bcl$_W$, Bcl$_S$, Mcl-1, A1, Bfl-1) or counteract Bcl-2 function and promote cell death (e.g., Bax, Bak, Bik, Bim, Bid, Bad, Harakiri).

E. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

F. Other agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adehesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abililties of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyerproliferative efficacy of the treatments. Inhibitors of cell adehesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

VIII. Pharmaceutical Preparations

Pharmaceutical compositions of the present invention comprise an effective amount of one or more chimeric polypeptides or chimeric polypeptides and at least one additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one chimeric polypeptide or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289–1329, incorporated herein by reference). Except insofar as any conventional carrier is incompatible with the active ingredient, its use in the therapeutic or pharmaceutical compositions is contemplated.

The chimeric polypeptide may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g. aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The chimeric polypeptide may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments, the chimeric polypeptide is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

IX. Lipid Compositions

In certain embodiments, the present invention employs a novel composition comprising one or more lipids associated with at least one chimeric polypeptide. A lipid is a substance that is characteristically insoluble in water and extractable with an organic solvent. Lipids include, for example, the substances comprising the fatty droplets that naturally occur in the cytoplasm as well as the class of compounds which are well known to those of skill in the art which contain long-chain aliphatic hydrocarbons and their derivatives, such as fatty acids, alcohols, amines, amino alcohols, and aldehydes. Of course, compounds other than those specifically described herein that are understood by one of skill in the art as lipids are also encompassed by the compositions and methods of the present invention.

A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof.

A. Lipid Types

A neutral fat may comprise a glycerol and a fatty acid. A typical glycerol is a three carbon alcohol. A fatty acid generally is a molecule comprising a carbon chain with an acidic moeity (e.g., carboxylic acid) at an end of the chain. The carbon chain may of a fatty acid may be of any length, however, it is preferred that the length of the carbon chain be of from about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, to about 30 or more carbon atoms, and any range derivable therein. However, a preferred range is from about 14 to about 24 carbon atoms in the chain portion of the fatty acid, with about 16 to about 18 carbon atoms being particularly preferred in certain embodiments. In certain embodiments the fatty acid carbon chain may comprise an odd number of carbon atoms, however, an even number of carbon atoms in the chain may be preferred in certain embodiments. A fatty acid comprising only single bonds in its carbon chain is called saturated, while a fatty acid comprising at least one double bond in its chain is called unsaturated.

Specific fatty acids include, but are not limited to, linoleic acid, oleic acid, palmitic acid, linolenic acid, stearic acid, lauric acid, myristic acid, arachidic acid, palmitoleic acid, arachidonic acid ricinoleic acid, tuberculosteric acid, lactobacillic acid. An acidic group of one or more fatty acids is covalently bonded to one or more hydroxyl groups of a glycerol. Thus, a monoglyceride comprises a glycerol and one fatty acid, a diglyceride comprises a glycerol and two fatty acids, and a triglyceride comprises a glycerol and three fatty acids.

A phospholipid generally comprises either glycerol or an sphingosine moiety, an ionic phosphate group to produce an amphipathic compound, and one or more fatty acids. Types of phospholipids include, for example, phophoglycerides, wherein a phosphate group is linked to the first carbon of glycerol of a diglyceride, and sphingophospholipids (e.g., sphingomyelin), wherein a phosphate group is esterified to a sphingosine amino alcohol. Another example of a sphingophospholipid is a sulfatide, which comprises an ionic sulfate group that makes the molecule amphipathic. A phopholipid may, of course, comprise further chemical groups, such as for example, an alcohol attached to the phosphate group. Examples of such alcohol groups include serine, ethanolamine, choline, glycerol and inositol. Thus, specific phosphoglycerides include a phosphatidyl serine, a phosphatidyl ethanolamine, a phosphatidyl choline, a phosphatidyl glycerol or a phosphatidyl inositol. Other phospholipids include a phosphatidic acid or a diacetyl phosphate. In one aspect, a phosphatidylcholine comprises a dioleoylphosphatidylcholine (a.k.a. cardiolipin), an egg phosphatidylcholine, a dipalmitoyl phosphalidycholine, a monomyristoyl phosphatidylcholine, a monopalmitoyl phosphatidylcholine, a monostearoyl phosphatidylcholine, a monooleoyl phosphatidylcholine, a dibutroyl phosphatidylcholine, a divaleroyl phosphatidylcholine, a dicaproyl phosphatidylcholine, a diheptanoyl phosphatidylcholine, a dicapryloyl phosphatidylcholine or a distearoyl phosphatidylcholine.

A glycolipid is related to a sphinogophospholipid, but comprises a carbohydrate group rather than a phosphate group attached to a primary hydroxyl group of the sphingosine. A type of glycolipid called a cerebroside comprises one sugar group (e.g., a glucose or galactose) attached to the primary hydroxyl group. Another example of a glycolipid is a ganglioside (e.g., a monosialoganglioside, a GM1), which comprises about 2, about 3, about 4, about 5, about 6, to about 7 or so sugar groups, that may be in a branched chain, attached to the primary hydroxyl group. In other embodiments, the glycolipid is a ceramide (e.g., lactosylceramide).

A steroid is a four-membered ring system derivative of a phenanthrene. Steroids often possess regulatory functions in cells, tissues and organisms, and include, for example, hormones and related compounds in the progestagen (e.g., progesterone), glucocoricoid (e.g., cortisol), mineralocorticoid (e.g., aldosterone), androgen (e.g., testosterone) and estrogen (e.g., estrone) families. Cholesterol is another example of a steroid, and generally serves structural rather than regulatory functions. Vitamin D is another example of a sterol, and is involved in calcium absorption from the intestine.

A terpene is a lipid comprising one or more five carbon isoprene groups. Terpenes have various biological functions, and include, for example, vitamin A, coenyzme Q and carotenoids (e.g., lycopene and β-carotene).

B. Charged and Neutral Lipid Compositions

In certain embodiments, a lipid component of a composition is uncharged or primarily uncharged. In one embodiment, a lipid component of a composition comprises one or more neutral lipids. In another aspect, a lipid component of a composition may be substantially free of anionic and cationic lipids, such as certain phospholipids (e.g., phosphatidyl choline) and cholesterol. In certain aspects, a lipid component of an uncharged or primarily uncharged lipid composition comprises about 95%, about 96%, about 97%, about 98%, about 99% or 100% lipids without a charge, substantially uncharged lipid(s), and/or a lipid mixture with equal numbers of positive and negative charges.

In other aspects, a lipid composition may be charged. For example, charged phospholipids may be used for preparing a lipid composition according to the present invention and can carry a net positive charge or a net negative charge. In a non-limiting example, diacetyl phosphate can be employed to confer a negative charge on the lipid composition, and stearylamine can be used to confer a positive charge on the lipid composition.

C. Making Lipids

Lipids can be obtained from natural sources, commercial sources or chemically synthesized, as would be known to one of ordinary skill in the art. For example, phospholipids can be from natural sources, such as egg or soybean phosphatidylcholine, brain phosphatidic acid, brain or plant phosphatidylinositol, heart cardiolipin and plant or bacterial phosphatidylethanolamine. In another example, lipids suitable for use according to the present invention can be obtained from commercial sources. For example, dimyristyl phosphatidylcholine ("DMPC") can be obtained from Sigma Chemical Co., dicetyl phosphate ("DCP") is obtained from K & K Laboratories (Plainview, N.Y.); cholesterol ("Chol") is obtained from Calbiochem-Behring; dimyristyl phosphatidylglycerol ("DMPG") and other lipids may be obtained from Avanti Polar Lipids, Inc. (Birmingham, Ala.). In certain embodiments, stock solutions of lipids in chloroform or chloroform/methanol can be stored at about −20° C. Preferably, chloroform is used as the only solvent since it is more readily evaporated than methanol.

D. Lipid Composition Structures

In a preferred embodiment of the invention, the chimeric polypeptide may be associated with a lipid. A chimeric polypeptide associated with a lipid may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure. A lipid or lipid/chimeric polypeptide associated composition of the present invention is not limited to any particular structure. For example, they may also simply be interspersed in a solution, possibly forming aggregates which are not uniform in either size or shape. In another example, they may be present in a bilayer structure, as micelles, or with a "collapsed" structure. In another non-limiting example, a lipofectamine (Gibco BRL)-chimeric polypeptide or Superfect (Qiagen)-chimeric polypeptide complex is also contemplated.

In certain embodiments, a lipid composition may comprise about 1%, about 2%, about 3%, about 4% about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about about 85%, about 86%, about 87%, about 88%, about 90%, about 91%, about 92%, about 93%, about 94%, about 95%, about 96%, about 97%, about 98%, about 99%, about 100%, or any range derivable therein, of a particular lipid, lipid type or non-lipid component such as a drug, protein, sugar, nucleic acids or other material disclosed herein or as would be known to one of skill in the art. In a non-limiting example, a lipid composition may comprise about 10% to about 20% neutral lipids, and about 33% to about 34% of a cerebroside, and about 1% cholesterol. In another non-limiting example, a liposome may comprise about 4% to about 12% terpenes, wherein about 1% of the micelle is specifically lycopene, leaving about 3% to about 11% of the liposome as comprising other terpenes; and about 10% to about 35% phosphatidyl choline, and about 1% of a drug. Thus, it is contemplated that lipid compositions of the present invention may comprise any of the lipids, lipid types or other components in any combination or percentage range.

1. Emulsions

A lipid may be comprised in an emulsion. A lipid emulsion is a substantially permanent heterogenous liquid mixture of two or more liquids that do not normally dissolve in each other, by mechanical agitation or by small amounts of additional substances known as emulsifiers. Methods for preparing lipid emulsions and adding additional components are well known in the art (e.g., Modem Pharmaceutics, 1990, incorporated herein by reference).

For example, one or more lipids are added to ethanol or chloroform or any other suitable organic solvent and agitated by hand or mechanical techniques. The solvent is then evaporated from the mixture leaving a dried glaze of lipid. The lipids are resuspended in aqueous media, such as phosphate buffered saline, resulting in an emulsion. To achieve a more homogeneous size distribution of the emulsified lipids, the mixture may be sonicated using conventional sonication techniques, further emulsified using microfluidization (using, for example, a Microfluidizer, Newton, Mass.), and/or extruded under high pressure (such as, for example, 600 psi) using an Extruder Device (Lipex Biomembranes, Vancouver, Canada).

2. Micelles

A lipid may be comprised in a micelle. A micelle is a cluster or aggregate of lipid compounds, generally in the form of a lipid monolayer, and may be prepared using any micelle producing protocol known to those of skill in the art (e.g., Canfield et al., 1990; El-Gorab et al, 1973; Colloidal Surfactant, 1963; and Catalysis in Micellar and Macromolecular Systems, 1975, each incorporated herein by reference). For example, one or more lipids are typically made into a suspension in an organic solvent, the solvent is evaporated, the lipid is resuspended in an aqueous medium, sonicated and then centrifuged.

3. Liposomes

In particular embodiments, a lipid comprises a liposome. A "liposome" is a generic term encompassing a variety of single and multilamellar lipid vehicles formed by the generation of enclosed lipid bilayers or aggregates. Liposomes may be characterized as having vesicular structures with a bilayer membrane, generally comprising a phospholipid, and an inner medium that generally comprises an aqueous composition.

A multilamellar liposome has multiple lipid layers separated by aqueous medium. They form spontaneously when lipids comprising phospholipids are suspended in an excess of aqueous solution. The lipid components undergo self-rearrangement before the formation of closed structures and entrap water and dissolved solutes between the lipid bilayers (Ghosh and Bachhawat, 1991). Lipophilic molecules or molecules with lipophilic regions may also dissolve in or associate with the lipid bilayer.

In certain less preferred embodiments, phospholipids from natural sources, such as egg or soybean phosphatidylcholine, brain phosphatidic acid, brain or plant phosphatidylinositol, heart cardiolipin and plant or bacterial phosphatidylethanolamine are preferably not used as the primary phosphatide, i.e., constituting 50% or more of the total phosphatide composition or a liposome, because of the instability and leakiness of the resulting liposomes.

In particular embodiments, a lipid and/or chimeric polypeptide may be, for example, encapsulated in the aqueous interior of a liposome, interspersed within the lipid bilayer of a liposome, attached to a liposome via a linking molecule that is associated with both the liposome and the chimeric polypeptide, entrapped in a liposome, complexed with a liposome, etc.

a. Making Liposomes

A liposome used according to the present invention can be made by different methods, as would be known to one of ordinary skill in the art. Phospholipids can form a variety of structures other than liposomes when dispersed in water, depending on the molar ratio of lipid to water. At low ratios the liposome is the preferred structure.

For example, a phospholipid (Avanti Polar Lipids, Alabaster, Ala.), such as for example the neutral phospholipid dioleoylphosphatidylcholine (DOPC), is dissolved in tert-butanol. The lipid(s) is then mixed with the chimeric polypeptide, and/or other component(s). Tween 20 is added to the lipid mixture such that Tween 20 is about 5% of the composition's weight. Excess tert-butanol is added to this mixture such that the volume of tert-butanol is at least 95%. The mixture is vortexed, frozen in a dry ice/acetone bath and lyophilized overnight. The lyophilized preparation is stored at −20° C. and can be used up to three months. When required the lyophilized liposomes are reconstituted in 0.9% saline. The average diameter of the particles obtained using Tween 20 for encapsulating the chimeric polypeptide is about 0.7 to about 1.0 μm in diameter.

Alternatively, a liposome can be prepared by mixing lipids in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 min. to 2 hours, depending on the desired volume of the liposomes. The composition can be dried further in a desiccator under vacuum. The dried lipids generally are discarded after about 1 week because of a tendency to deteriorate with time.

Dried lipids can be hydrated at approximately 25–50 mM phospholipid in sterile, pyrogen-free water by shaking until all the lipid film is resuspended. The aqueous liposomes can be then separated into aliquots, each placed in a vial, lyophilized and sealed under vacuum.

In other alternative methods, liposomes can be prepared in accordance with other known laboratory procedures (e.g., see Bangham et al., 1965; Gregoriadis, 1979; Deamer and Uster 1983, Szoka and Papahadjopoulos, 1978, each incorporated herein by reference in relevant part). These methods differ in their respective abilities to entrap aqueous material and their respective aqueous space-to-lipid ratios.

The dried lipids or lyophilized liposomes prepared as described above may be dehydrated and reconstituted in a solution of inhibitory peptide and diluted to an appropriate concentration with an suitable solvent, e.g., DPBS. The mixture is then vigorously shaken in a vortex mixer. Unencapsulated additional materials, such as agents including but not limited to hormones, drugs, nucleic acid constructs and the like, are removed by centrifugation at 29,000×g and the liposomal pellets washed. The washed liposomes are resuspended at an appropriate total phospholipid concentration, e.g., about 50–200 mM. The amount of additional material or active agent encapsulated can be determined in accordance with standard methods. After determination of the amount of additional material or active agent encapsulated in the liposome preparation, the liposomes may be diluted to appropriate concentrations and stored at 4° C. until use. A pharmaceutical composition comprising the liposomes will usually include a sterile, pharmaceutically acceptable carrier or diluent, such as water or saline solution.

The size of a liposome varies depending on the method of synthesis. Liposomes in the present invention can be a variety of sizes. In certain embodiments, the liposomes are small, e.g., less than about 100 nm, about 90 nm, about 80 nm, about 70 nm, about 60 nm, or less than about 50 nm in external diameter. In preparing such liposomes, any protocol described herein, or as would be known to one of ordinary skill in the art may be used. Additional non-limiting examples of preparing liposomes are described in U.S. Pat. Nos. 4,728,578, 4,728,575 4,737,323, 4,533,254, 4,162,282, 4,310,505, and 4,921,706; International Applications PCT/US85/01161 and PCT/US89/05040; U.K. Patent Application GB 2193095 A; Mayer et al., 1986; Hope et al., 1985; Mayhew et al. 1987; Mayhew et al., 1984; Cheng et al., 1987; and Liposome Technology, 1984, each incorporated herein by reference).

A liposome suspended in an aqueous solution is generally in the shape of a spherical vesicle, having one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules may form a bilayer, known as a lamella, of the arrangement XY-YX. Aggregates of lipids may form when the hydrophilic and hydrophobic parts of more than one lipid molecule become associated with each other. The size and shape of these aggregates will depend upon many different variables, such as the nature of the solvent and the presence of other compounds in the solution.

The production of lipid formulations often is accomplished by sonication or serial extrusion of liposomal mixtures after (I) reverse phase evaporation (II) dehydration-rehydration (III) detergent dialysis and (IV) thin film hydration. In one aspect, a contemplated method for preparing liposomes in certain embodiments is heating sonicating, and sequential extrusion of the lipids through filters or membranes of decreasing pore size, thereby resulting in the formation of small, stable liposome structures. This preparation produces liposomal/chimeric polypeptide or liposomes only of appropriate and uniform size, which are structurally stable and produce maximal activity. Such techniques are well-known to those of skill in the art (see, for example Lang et al., 1990).

Once manufactured, lipid structures can be used to encapsulate compounds that are toxic (e.g., chemotherapeutics) or labile (e.g., nucleic acids) when in circulation. The physical characteristics of liposomes depend on pH, ionic strength and/or the presence of divalent cations. Liposomes can show low permeability to ionic and/or polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and/or results in an increase in permeability to ions, sugars and/or drugs. Liposomal encapsulation has resulted in a lower toxicity and a longer serum half-life for such compounds (Gabizon et al., 1990).

Liposomes interact with cells to deliver agents via four different mechanisms: Endocytosis by phagocytic cells of the reticuloendothelial system such as macrophages and/or neutrophils; adsorption to the cell surface, either by nonspecific weak hydrophobic and/or electrostatic forces, and/or by specific interactions with cell-surface components; fusion with the plasma cell membrane by insertion of the lipid bilayer of the liposome into the plasma membrane, with simultaneous release of liposomal contents into the cytoplasm; and/or by transfer of liposomal lipids to cellular and/or subcellular membranes, and/or vice versa, without any association of the liposome contents. Varying the liposome formulation can alter which mechanism is operative, although more than one may operate at the same time.

Numerous disease treatments are using lipid based gene transfer strategies to enhance conventional or establish novel therapies, in particular therapies for treating hyperproliferative diseases. Advances in liposome formulations have improved the efficiency of gene transfer in vivo (Templeton et al., 1997) and it is contemplated that liposomes are prepared by these methods. Alternate methods of preparing lipid-based formulations for nucleic acid delivery are described (WO 99/18933).

In another liposome formulation, an amphipathic vehicle called a solvent dilution microcarrier (SDMC) enables integration of particular molecules into the bi-layer of the lipid vehicle (U.S. Pat. No. 5,879,703). The SDMCs can be used to deliver lipopolysaccharides, polypeptides, nucleic acids and the like. Of course, any other methods of liposome preparation can be used by the skilled artisan to obtain a desired liposome formulation in the present invention.

b. Targeting Ligands

The targeting ligand can be either anchored in the hydrophobic portion of the complex or attached to reactive terminal groups of the hydrophilic portion of the complex. The targeting ligand can be attached to the liposome via a linkage to a reactive group, e.g., on the distal end of the hydrophilic polymer. Preferred reactive groups include amino groups, carboxylic groups, hydrazide groups, and thiol groups. The coupling of the targeting ligand to the hydrophilic polymer can be performed by standard methods of organic chemistry that are known to those skilled in the art. In certain embodiments, the total concentration of the targeting ligand can be from about 0.01 to about 10% mol.

Targeting ligands are any ligand specific for a characteristic component of the targeted region. Preferred targeting ligands include proteins such as polyclonal or monoclonal antibodies, antibody fragments, or chimeric antibodies, enzymes, or hormones, or sugars such as mono-, oligo- and poly-saccharides (see, Heath et al., Chem. Phys. Lipids 40:347 (1986)) For example, disialoganglioside GD2 is a tumor antigen that has been identified neuroectodermal origin tumors, such as neuroblastoma, melanoma, small-cell lung carcinoma, glioma and certain sarcomas (Mujoo et al., 1986, Schulz et al., 1984). Liposomes containing anti-disialoganglioside GD2 monoclonal antibodies have been used to aid the targeting of the liposomes to cells expressing the tumor antigen (Montaldo et al., 1999; Pagan et al., 1999). In another non-limiting example, breast and gynecological cancer antigen specific antibodies are described in U.S. Pat. No. 5,939,277, incorporated herein by reference. In a further non-limiting example, prostate cancer specific antibodies are disclosed in U.S. Pat. No. 6,107,090, incorporated herein by reference. Thus, it is contemplated that the antibodies described herein or as would be known to one of ordinary skill in the art may be used to target specific tissues and cell types in combination with the compositions and methods of the present invention. In certain embodiments of the invention, contemplated targeting ligands interact with integrins, proteoglycans, glycoproteins, receptors or transporters. Suitable ligands include any that are specific for cells of the target organ, or for structures of the target organ exposed to the circulation as a result of local pathology, such as tumors.

In certain embodiments of the present invention, in order to enhance the transduction of cells, to increase transduction of target cells, or to limit transduction of undesired cells, antibody or cyclic peptide targeting moieties (ligands) are associated with the lipid complex. Such methods are known in the art. For example, liposomes have been described further that specifically target cells of the mammalian central nervous system (U.S. Pat. No. 5,786,214, incorporated herein by reference). The liposomes are composed essentially of N-glutarylphosphatidylethanolamine, cholesterol and oleic acid, wherein a monoclonal antibody specific for neuroglia is conjugated to the liposomes. It is contemplated that a monoclonal antibody or antibody fragment may be used to target delivery to specific cells, tissues, or organs in the animal, such as for example, brain, heart, lung, liver, etc.

Still further, a chimeric polypeptide may be delivered to a target cell via receptor-mediated delivery and/or targeting vehicles comprising a lipid or liposome. These take advantage of the selective uptake of macromolecules by receptor-mediated endocytosis that will be occurring in a target cell. In view of the cell type-specific distribution of various receptors, this delivery method adds another degree of specificity to the present invention.

Thus, in certain aspects of the present invention, a ligand will be chosen to correspond to a receptor specifically expressed on the target cell population. A cell-specific chimeric polypeptide delivery and/or targeting vehicle may comprise a specific binding ligand in combination with a liposome. The chimeric polypeptide to be delivered are housed within a liposome and the specific binding ligand is functionally incorporated into a liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In certain embodiments, a receptor-mediated delivery and/or targeting vehicles comprise a cell receptor-specific ligand and a chimeric polypeptide-binding agent. Others comprise a cell receptor-specific ligand to which chimeric polypeptide to be delivered has been operatively attached. For example, several ligands have been used for receptor-mediated gene transfer (Wu and Wu, 1987; Wagner et al., 1990 Perales et al., 1994; Myers, EPO 0273085), which establishes the operability of the technique. In another example, specific delivery in the context of another mammalian cell type has been described (Wu and Wu, 1993; incorporated herein by reference).

In still further embodiments, the specific binding ligand may comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al., 1987). The asialoglycoprotein, asialofetuin, which contains terminal galactosyl residues, also has been demonstrated to target liposomes to the liver (Spanjer and Scherphof, 1983; Hara et al., 1996). The sugars mannosyl, fucosyl or N-acetyl glucosamine, when coupled to the backbone of a polypeptide, bind the high affinity manose receptor (U.S. Pat. No. 5,432,260, specifically incorporated herein by reference in its entirety). It is contemplated that the cell or tissue-specific transforming constructs of the present invention can be specifically delivered into a target cell or tissue in a similar manner.

In another example, lactosyl ceramide, and peptides that target the LDL receptor related proteins, such as apolipoprotein E3 ("Apo E") have been useful in targeting liposomes to the liver (Spanjer and Scherphof, 1983; WO 98/0748).

Folate and the folate receptor have also been described as useful for cellular targeting (U.S. Pat. No. 5,871,727). In this example, the vitamin folate is coupled to the complex. The folate receptor has high affinity for its ligand and is overexpressed on the surface of several malignant cell lines, including lung, breast and brain tumors. Anti-folate such as methotrexate may also be used as targeting ligands. Transferrin mediated delivery systems target a wide range of replicating cells that express the transferrin receptor (Gilliland et al., 1980).

c. Liposome/Nucleic Acid Combinations

In certain embodiments, a liposome/chimeric polypeptide may comprise a nucleic acid, such as, for example, an oligonucleotide, a polynucleotide or a nucleic acid construct (e.g., an expression vector). Where a bacterial promoter is employed in the DNA construct that is to be transfected into eukaryotic cells, it also will be desirable to include within the liposome an appropriate bacterial polymerase.

It is contemplated that when the liposome/chimeric polypeptide composition comprises a cell or tissue specific nucleic acid, this technique may have applicability in the present invention. In certain embodiments, lipid-based non-viral formulations provide an alternative to viral gene therapies. Although many cell culture studies have documented lipid-based non-viral gene transfer, systemic gene delivery via lipid-based formulations has been limited. A major limitation of non-viral lipid-based gene delivery is the toxicity of the cationic lipids that comprise the non-viral delivery vehicle. The in vivo toxicity of liposomes partially explains the discrepancy between in vitro and in vivo gene transfer results. Another factor contributing to this contradictory data is the difference in liposome stability in the presence and absence of serum proteins. The interaction between liposomes and serum proteins has a dramatic impact on the stability characteristics of liposomes (Yang and Huang, 1997). Cationic liposomes attract and bind negatively charged serum proteins. Liposomes coated by serum proteins are either dissolved or taken up by macrophages leading to their removal from circulation. Current in vivo liposomal delivery methods use aerosolization, subcutaneous, intradermal, intratumoral, or intracranial injection to avoid the toxicity and stability problems associated with cationic lipids in the circulation. The interaction of liposomes and plasma proteins is largely responsible for the disparity between the efficiency of in vitro (Felgner et al., 1987) and in vivo gene transfer (Zhu et al., 1993; Philip et al., 1993; Solodin et al., 1995; Liu et al., 1995; Thierry et al., 1995; Tsukamoto et al., 1995; Aksentijevich et al., 1996).

An exemplary method for targeting viral particles to cells that lack a single cell-specific marker has been described (U.S. Pat. No. 5,849,718). In this method, for example, antibody A may have specificity for tumor, but also for normal heart and lung tissue, while antibody B has specificity for tumor but also normal liver cells. The use of antibody A or antibody B alone to deliver an anti-proliferative nucleic acid to the tumor would possibly result in unwanted damage to heart and lung or liver cells. However, antibody A and antibody B can be used together for improved cell targeting. Thus, antibody A is coupled to a gene encoding an anti-proliferative nucleic acid and is delivered, via a receptor mediated uptake system, to tumor as well as heart and lung tissue. However, the gene is not transcribed in these cells as they lack a necessary transcription factor. Antibody B is coupled to a universally active gene encoding the transcription factor necessary for the transcription of the anti-proliferative nucleic acid and is delivered to tumor and liver cells. Therefore, in heart and lung cells only the inactive anti-proliferative nucleic acid is delivered, where it is not transcribed, leading to no adverse effects. In liver cells, the gene encoding the transcription factor is delivered and transcribed, but has no effect because no an anti-proliferative nucleic acid gene is present. In tumor cells, however, both genes are delivered and the transcription factor can activate transcription of the anti-proliferative nucleic acid, leading to tumor-specific toxic effects.

The addition of targeting ligands for gene delivery for the treatment of hyperproliferative diseases permits the delivery of genes whose gene products are more toxic than do non-targeted systems. Examples of the more toxic genes that can be delivered includes pro-apoptotic genes such as Bax and Bak plus genes derived from viruses and other pathogens such as the adenoviral E4orf4 and the *E.coli* purine nucleoside phosphorylase, a so-called "suicide gene" which converts the prodrug 6-methylpurine deoxyriboside to toxic purine 6-methylpurine. Other examples of suicide genes used with prodrug therapy are the *E. coli* cytosine deaminase gene and the HSV thymidine kinase gene.

It is also possible to utilize untargeted or targeted lipid complexes to generate recombinant or modified viruses in vivo. For example, two or more plasmids could be used to introduce retroviral sequences plus a therapeutic gene into a hyperproliferative cell. Retroviral proteins provided in trans from one of the plasmids would permit packaging of the second, therapeutic gene-carrying plasmid. Transduced cells, therefore, would become a site for production of non-replicative retroviruses carrying the therapeutic gene. These retroviruses would then be capable of infecting nearby cells. The promoter for the therapeutic gene may or may not be inducible or tissue specific.

Similarly, the transferred nucleic acid may represent the DNA for a replication competent or conditionally replicating viral genome, such as an adenoviral genome that lacks all or part of the adenoviral E1a or E2b region or that has one or more tissue-specific or inducible promoters driving transcription from the E1a and/or E1b regions. This replicating or conditional replicating nucleic acid may or may not contain an additional therapeutic gene such as a tumor suppressor gene or anti-oncogene.

d. Lipid Administration

The actual dosage amount of a lipid composition (e.g., a liposome-chimeric polypeptide) administered to a patient can be determined by physical and physiological factors such as body weight, severity of condition, idiopathy of the patient and on the route of administration. With these considerations in mind, the dosage of a lipid composition for a particular subject and/or course of treatment can readily be determined.

The present invention can be administered intravenously, intradermally, intraarterially, intraperitoneally, intralesionally, intracranially, intraarticularly, intraprostaticaly, intrapleurally, intratracheally, intranasally, intravitreally, intravaginally, rectally,topically, intratumorally, intramuscularly, intraperitoneally, subcutaneously, intravesicularlly, mucosally, intrapericardially, orally, topically, locally and/or using aerosol, injection, infusion, continuous infusion, localized perfusion bathing target cells directly or via a catheter and/or lavage.

X. Antibody Preparation

A. Polyclonal Antibodies

Polyclonal antibodies are useful in the present invention regarding multiple embodiments for the chimeric polypeptides. Polyclonal antibodies to the chimeric polypeptides generally are raised in animals by multiple subcutaneous (sc) or intraperitoneal (ip) injections of the chimeric polypeptide and an adjuvant. It may be useful to conjugate the chimeric polypeptides or a fragment containing the target amino acid sequence to a protein that is immunogenic in the species to be immunized, e.g. keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glytaraldehyde, succinic anhydride, $SOCl_2$, or $R^1N{=}C{=}NR$, where R and $R^1$ are different alkyl groups.

Animals are immunized against the immunogenic conjugates or derivatives by combining 1 mg of 1 μg of conjugate (for rabbits or mice, respectively) with 3 volumes of Freud's complete adjuvant and injecting the solution intradermally at multiple sites. One month later the animals are boosted with 1/5 to 1/10 the original amount of conjugate in Freud's complete adjuvant by subcutaneous injection at multiple sites. 7 to 14 days later the animals are bled and the serum is assayed for anti-chimeric polypeptides antibody titer. Animals are boosted until the titer plateaus. Preferably, the animal boosted with the conjugate of the same chimeric polypeptides, but conjugated to a different protein and/or through a different cross-linking reagent. Conjugates also can be made in recombinant cell culture as protein fusions. Also, aggregating agents such as alum are used to enhance the immune response.

B. Monoclonal Antibodies

Monoclonal antibodies are obtained from a population of substantially homogeneous antibodies, i.e., the individual antibodies comprising the population are identical except for possible naturally-occurring mutations that may be present in minor amounts. Thus, the modifier "monoclonal" indicates the character of the antibody as not being a mixture of discrete antibodies.

For example, the anti-chimeric polypeptide monoclonal antibodies of the invention may be made using the hybridoma method first described by Kohler and Milstein (1975), or may be made by recombinant DNA methods [Cabilly et al., U.S. Pat. No. 4,816,567].

In the hybridoma method, a mouse or other appropriate host animal, such as hamster is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell [Goding, Monoclonal Antibodies: Principles and Practice, pp. 59–103 (Academic Press, 1986)].

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high level expression of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA.

Culture medium in which hybridoma cells are growing is assayed for production of monoclonal antibodies directed against chimeric polypeptides. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson and Pollard (1980).

After hybridoma cells are identified that produce antibodies of the desired specificity, affinity, and/or activity, the clones may be subcloned by limiting dilution procedures and grown by standard methods. Goding, Monoclonal Antibodies: Principles and Practice, pp. 59–104 (Academic Press, 1986). Suitable culture media for this purpose include, for example, Dulbecco's Modified Eagle's Medium or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (Morrison et al., 1984), or by covalently joining to the immunoglobulin coding sequence all or part of the coding sequence for a non-immunoglobulin polypeptide. In that manner, "chimeric" or "hybrid" antibodies are prepared that have the binding specificity of an anti-chimeric polypeptide monoclonal antibody herein.

Typically such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for a chimeric polypeptide and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

For diagnostic applications, the antibodies of the invention typically will be labeled with a detectable moiety. The detectable moiety can be any one which is capable of producing, either directly or indirectly, a detectable signal. For example, the detectable moiety may be a radioisotope, such as $^{3}H$, $^{14}C$, $^{32}P$, $^{35}S$, or $^{125}I$, a fluorescent or chemiluminescent compound, such as fluorescein isothiocyanate, rhodamine, or luciferin; biotin; radioactive isotopic labels, such as, e.g., $^{125}I$, $^{32}P$, $^{14}C$, or $^{3}H$, or an enzyme, such as alkaline phosphatase, beta-galactosidase or horseradish peroxidase.

Any method known in the art for separately conjugating the antibody to the detectable moiety may be employed, including those methods described by Hunter et al., (1962); David et al. (1974); Pain et al. (1981); and Nygren (1982).

The antibodies of the present invention may be employed in any known assay method, such as competitive binding assays, direct and indirect sandwich assays, and immunoprecipitation assays. Zola, Monoclonal Antibodies: A Manual of Techniques, pp. 147–158 (CRC Press, Inc., 1987).

Competitive binding assays rely on the ability of a labeled standard (which may be a chimeric polypeptide or an immunologically reactive portion thereof) to compete with the test sample analyte (chimeric polypeptides) for binding with a limited amount of antibody. The amount of chimeric polypeptides in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three part complex (U.S. Pat. No. 4,376,110). The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

C. Humanized Antibodies

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986); Riechmann et al. (1988); Verhoeyen et al. (1988)), by substituting rodent CDRs or CDR sequences for the corresponding sequences of a human antibody. Accordingly, such "humanized" antibodies are chimeric antibodies (Cabilly, supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

It is important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding. For further details see U.S. application Ser. No. 07/934,373 filed Aug. 21, 1992, which is a continuation-in-part of application Ser. No. 07/715,272 filed Jun. 14, 1991.

D. Human Antibodies

Human monoclonal antibodies can be made by the hybridoma method. Human myeloma and mouse-human heteromyeloma cell lines for the production of human monoclonal antibodies have been described, for example, by Kozbor (1984), and Brodeur et al., Monoclonal Antibody Production Techniques and Applications, pp. 51–63 (Marcel Dekker, Inc., New York, 1987).

It is now possible to produce transgenic animals (e.g. mice) that are capable, upon immunization, of producing a repertoire of human antibodies in the absence of endogenous immunoglobulin production. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g. Jakobovits et al. (1993).

Alternatively, the phage display technology (McCafferty et al. (1990) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle.

Because the filamentous particle contains a single-stranded DNA copy of the phage genome, selections based on the functional properties of the antibody also result in selection of the gene encoding the antibody exhibiting those properties. Thus, the phage mimicks some of the properties of the B-cell. Phage display can be performed in a variety of formats; for their review see, e.g. Johnson and Chiswell (1993). Several sources of V-gene segments can be used for phage display. Clackson et al. (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al. (1991), or Griffith et al. (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling" (Marks et al., 1992). In this method, the affinity of "primary" human antibodies obtained by phage display can be improved by sequentially replacing the heavy and light chain V region genes with repertoires of naturally occurring variants (repertoires) of V domain genes obtained from unimmunized donors. This techniques allows the production of antibodies and antibody fragments with affinities in the nM range. A strategy for making very large phage antibody repertoires (also known as "the mother-of-all libraries") has been described by Waterhouse et al. (1993), and the isolation of a high affinity human antibody directly from such large phage library is reported by Griffith et al. (1994). Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable capable of restoring a functional antigen-binding site, i.e. the epitope governs (imprints) the choice of partner. When the process is repeated in order to replace the remaining rodent V domain, a human antibody is obtained (see PCT patent application WO 93/06213, published Apr. 1, 1993). Unlike traditional humanization of rodent antibodies by CDR grafting, this technique provides completely human antibodies, which have no framework or CDR residues of rodent origin.

E. Bispecific Antibodies

Bispecific antibodies are monoclonal, preferably human or humanized, antibodies that have binding specificities for at least two different antigens. In the present case, one of the binding specificities is for a chimeric polypeptide, the other one is for any other antigen, and preferably for another receptor or receptor subunit. For example, bispecific antibodies specifically binding a chimeric polypeptide and neurotrophic factor, or two different chimeric polypeptides are within the scope of the present invention.

F. Methods for Making Bispecific Antibodies are Known in the Art

Traditionally, the recombinant production of bispecific antibodies is based on the coexpression of two immunoglobulin heavy chain-light chain pairs, where the two heavy chains have different specificities (Milstein and Cuello (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in PCT application publication No. WO 93/08829 (published May 13, 1993), and in Traunecker et al. (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, $CH_2$ and $CH_3$ regions. It is preferred to have the first heavy chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in copending application Ser. No. 07/931,811 filed Aug. 17, 1992.

For further details of generating bispecific antibodies see, for example, Suresh et al. (1986).

G. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (PCT application publication Nos. WO 91/00360 and WO 92/200373; EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

EXAMPLES

The following is an illustration of preferred embodiments for practicing the present invention. However, they are not limiting examples. Other examples and methods are possible in practicing the present invention.

Example 1

Materials

The following materials were utilized for multiple Examples described herein. The PCR reagents were obtained from Fisher Scientific (Pittsburgh, Pa.), and the molecular biology enzymes were purchased from Boehringer Mannheim (Indianapolis, Ind.) or New England Biolabs (Beverly, Mass.). Bacterial strains, pET bacterial expression plasmids and recombinant enterokinase were obtained from Novagen (Madison, Wis.). All other chemicals were from Sigma Chemical Company (St. Louis, Mo.) or Fisher Scientific (Pittsburg, Pa.). Metal affinity resin (Talon or Nichel agrose) was obtained from Clontech Laboratories (Palo Alto, Calif.). Tissue culture reagents were from Gibco BRL (Gaithersburg, Md.).

Human cutaneous T cell lymphoma (Hut78) from American Type Culture Collection (ATCC, Manassas, Va.) cultured in RPMI 1640 medium containing 10% fetal bovine serum (FBS). Porcine aortic endothelial cells transfected with either flt-1 receptor (PAE-Flt-1) or the flk-1/KDR receptor (PAE-Flk-1) were a gift from Dr. J. Waltenberger and cultured in F12 Nutrient Mixture (HAM) with 10% FBS. The human melanoma A375M cell-line was obtained from Dr. I. J. Fidler of the University of Texas MD Anderson Cancer Center (Houston, Tex.) and were cultured in MEM supplemented with 10% FBS.

Example 2

Methods—Cloning Human Granzyme B Gene

The following methods were utilized at least for Example 13. Hut78 RNA was isolated using GlassMAX RNA Microisolation Spin Cartridge System (Gibco BRL), and the quanitity of total RNA was then determined. Genomic DNA was then removed by incubating the sample with DNase I for 15 min at room temperature. The DNase I was inactivated by adding EDTA solution heating for 15 min at 65° C. The SUPERSCRIPT First-Strand Synthesis System for RT-PCR (Gibco BRL) was used to synthesize the first-strand with oligo (dT). The target cDNA (pre-mature human Granzyme B cDNA) was amplified using the primers: NcoIgb (5' to 3'): GGTGGCGGTGGCTCCATGGAACCAATCCTGCTTCTG (SEQ ID NO:1) and CxhoIgb (5' to 3'): GCCACCGCCTCCCTCGAGCTATTAGTAGCGTTTCATGGT (SEQ ID NO:2) by PCR. PCR conditions included denaturation at 95° C. for 5 min, PCR cycle of 94° C. for 1 min, 50° C. for 1 min, 72° C. for 1 min, for a total of 30 cycles; extension step was 72° C. for 5 min. A 1% agarose gel was run to confirm the PCR product. The PCR product was then cloned into PCR 2.1 TA vector (Invitrogen; Carlsbad, Calif.) and designated gbTA. The gbTA was transformed into INVαF' competent cells, and the positive clones were screened by blue/white colony screening or by PCR methods. The DNAs for positive clones were isolated by using QIAprep Spin prep kit (Qiagen; Valencia, Calif.) and sequenced to confirm human granzyme B gene; the correct clone was identified as gbTA-2 (clone #2).

Example 3

Methods—Construction of Granzyme B-VEGF121 or Granzyme B-SCFVMEL Fusion Genes

The following fusion constructs were utilized in multiple Examples described herein. The fusion construct Granzyme B-vegf121 was an Ek-Granzyme B-G4S linker-Vegf121 format. The construction was based on over-lap PCR method. Briefly, granzyme B coding sequence was amplified from gbTA-2 by PCR using the primers: NgbEK (5' to 3'): GGTACCGACGACGACGACAAGAT-CATCGGGGGACATGAG, Cgb (5' to 3') (SEQ ID NO:3) and GGAGCCACCGCCACCGTAGCGTTTCATGGT (SEQ ID NO:4). These were designed to delete the signal sequence of pre-mature granzyme B and insert an enterokinase cleavage site at the N-terminus, in addition to adding a G4S linker sequence to the C-terminus in order to link to vegf121 gene. Vegf121 sequence was amplified from a plasmid pET22-vegf121 (a gift from Dr. Phil Thorpe's group, the University of Texas Southwest Medical School, Dallas, Tex.) by PCR using primers: Nvegf (5' to 3') GGTG-GCGGTGGCTCCGCACCCATGGCAGAA (SEQ ID NO:5) and Cxhol veg (5' to 3') AAGGCTCGTGTCGAC-CTCGAGTCATTACCGCCTCGGCTTGTC (SEQ ID NO:6). ScFvMEL sequence was amplified from a plasmid pET32-scFvMEL/TNF by PCR using primers: Nzme2 (5' to 3') GGTGGCGGTGGCTCCACGGACATTGT-GATGACCCAGTCTCAAAAATTC (SEQ ID NO:7) and Czme2 (5' to 3') GGAGCCACCGCCACCCTCGAGCTAT-CATGAGGAGACGGTGAGAGTGGT (SEQ ID NO:8). These primers added G4S linker sequence to the N-terminus to overlap PCR link to the C-terminus of granzyme B, and a Xho I site was incorporated at the C-terminus to facilitate subsequent cloning steps. Two stop codons were added at the C-terminus just before the Xho I site. The fused genes were linked together by the second PCR using primers NgbEK and Cxholveg (for granzyme B-vegf121) or NgbEK and Czme2 (for granzyme B-scFvMEL). In order to clone the fused genes into pET32a (+) vector with an enterokinase site at the N-terminus of granzyme B, the fragment from pET32a (+) was amplified by PCR using primers T7 promoter (5' to 3') TAATACGACTCACTATAG (SEQ ID NO:9) and CpET32EK (5' to 3') CTTGTCGTCGTCGTCG-GTACCCAGATCTGG (SEQ ID NO:10). The primer has an enterokinase site at the C-terminus overlapping with the N-terminus of fused gene. By overlap PCR, the fusion genes EK-Granzyme B-vegf121 were constructed using primers T7 promoter and CxhoIveg, and the fusion genes EK-Granzyme B-scFvMEL were constructed using primers T7 promoter and Czme2. The PCR reactions were performed by thirty cycles of 94° C. for 1 min, 50° C. for 1 min and 72° C. for 1 min, with an extension reaction at 72° C. for 5 min. Amplified fragments were separated by 1% agarose gel electrophoresis and purified by PCR purification kit (Qiagen). The purified PCR products were digested with Xba I and Xho I at 37° C. for 3 hrs and then separated by 1% agarose gel electrophoresis, purified from the gels and cloned into pET32a (+) vector, designated pET32GrB-vegf121 or pET32GrB-scFvMEL. The ligation mixture was transformed into DH5α competent cells, the positive clones were screened by PCR, and then sequenced. A clone having the T7 promoter, lac operator, rbs, Trx.tag, His.tag, S-tag, and enterokinase sites to granzyme B-G4S-vegf121 or granzyme B-G4S-scFvMEL, with no second site mutations, was chosen for transformation into AD494 (DE3)pLysS competent cells for further induction and expression.

Example 4

Method—Induction and Expression of Granzyme B-VEGF121 or Granzyme B-SCFVMEL Fusion Proteins in *E. coli*

The fusion constructs of Example 3 were induced and expressed as described herein for utilization in multiple Examples elsewhere herein, including at least Examples 17 and 18. Bacterial colonies transformed with the constructed plasmid were grown in Luria Broth (LB) growth media containing 200 μg/ml ampicillin, 70 μg/ml chloramphenicol, and 15 μg/ml kanamycin, at 37° C. overnight at 240 rpm shaking. The cultures were then diluted 1:100 in fresh LB media plus antibiotics and grown to $A_{600}$ of 0.5 at 37° C. Thereafter, the cultures were induced by addition of IPTG to a final concentration of 0.25 mM at 37° C. for 1.5 hrs. The cells were harvested and resuspended in 10 mM Tris (pH 8.0) and stored frozen at −80° C. for later purification.

Example 5

Methods—Purification of Granzyme B-VEGF121 or Granzyme B-SCFVMEL Fusion Protein

The fusion constructs induced and expressed in Example 4 were purified as described herein for utilization in multiple Examples elsewhere herein, including at least Examples 17 and 18. The resuspension culture was lysed by addition of lysozyme to a final concentration of 100 μg/ml with agitation for 30 min at 4° C., which was followed by sonication. Extracts were centrifuged at 10,800 g for 30 min, and the supernatant was further centrifuged at 40,000 rpm for 1 hr. The supernatant containing only soluble protein was adjusted to 40 mM Tris, pH 8.0, 10 mM imidazole and applied to a nickel-NTA agarose equilibrated with the same buffer. After washing the nickel-NTA agarose with 500 mM NaCl and 20 mM imidazole, the bound proteins were eluted with 500 mM NaCl, and 500 mM imidazole. Absorbance (280 nM) and SDS-PAGE analyses were performed to identify the polyhistidine-tagged protein, designated Pro-granzyme B-vegf121 or Pro-granzyme B-scFvMEL, respectively. The eluted pro-granzymeB-vegf121 or pro-granzymeB-scFvMEL protein was dialyzed against 20 mM Tris-HCl (pH 8.0) and 50 mM NaCl. Progranzyme B moiety of granzyme B-vegf121 or granzyme B-scFvMEL was activated by the addition of recombinant bovine enterokinase (rEK) to remove the polyhistidine-tag according to the manufacturer's instruction (1 unit of rEK cleavage 50 μg protein, incubated at room temperature for 16 hrs). The rEK was removed by EK capture agarose. The final protein was analyzed by SDS-PAGE and stored at 4° C.

Example 6

Methods—SDS-Page and Western Blot Analysis

The following methods were performed for experiments as described in, for example, Example 15. Protein samples were analyzed by electrophoresis on an 8.5% SDS-PAGE under reducing conditions. The gels were stained with coomassie blue. For western blotting analysis, proteins were transferred from gels into nitrocellulose membranes. The membranes were blocked with 5% non-fat milk and incubated for 1 hr at room temperature with mouse anti-granzyme B monoclonal antibody (1.0 μg/ml) or mouse anti-vegf121 polyclonal antibody (1:2000 dilution) or rabbit anti-scFvzme polyclonal antibody (1:2000 dilution). After washing, the membranes were incubated with goat anti-mouse/horseradish peroxidase conjugate (HRP-GAM, 1:5000 dilution) or goat anti-rabbit/horseradish peroxidase conjugate (HRP-GAR, 1:5000 dilution). After further washing, the membrane was developed using the Amersham (Piscataway, N.J.) ECL detection system and exposed to X-ray film.

Example 7

Methods—Enzyme Assays

The enzymatic activity of granzyme B was determined in a continuous calorimetric assay, with BAADT (N-α-t-butoxycarbonyl-L-alanyl-L-alanyl-L-aspartyl-thiobenzyl ester) as substrate. Assays were performed in 200 μl and consisted of enzyme in 100 mM HEPES, pH7.5, 10 mM $CaCl_2$, 1 mM 5,5'-dithiobis-2-nitrobenzoic acid, 0.2 mM substrate at 25° C. The change in absorbance at $OD_{405}$ was measured on a Thermomax plate reader. Absorbance increases were converted to enzymatic rates by using an extinction coefficient of 13, 100 cm-1M-1 that differed from the usual extinction coefficient of 13, 600 cm-1M-1 at 412 nm reported by Ellman.

Example 8

Methods—Detection of SCFVMEL Moiety of Granzyme B-SCFVMEL

Reacti-Bind™ Protein L Coated Plates from PIERCE (Rockford, Ill.) were used for detection of scFvMEL moiety of GranzymeB-scFvMEL, based on ELISA method. Briefly, pre-coated Protein L was blocked by 5% BSA, and the reaction was purified with Granzyme B-scFvMEL or other scFvMEL fusion proteins at various concentrations, respectively. After washing, the proteins were incubated with rabbit ant-scFvZME antibody, followed by HRP-GAR, then substrate 2,2'-azino-bis-3-ethylbenzthiazoline-6-sulfonic acid (ABTS) solution with 1 μg/ml 30% $H_2O_2$ was added. Absorbance at 405 nm was measured after 30 min.

Example 9

Methods—Cytotoxicity Assays in Vitro against PAE-FLT-1 and PAE-FLK-1 for Granzyme B-VEGF121 and Against A375-M for Granzyme B-SCFVMEL PAE cells in Ham's F-12 medium with 10% FBS or A375-M cells in MEM medium with 10% FBS were plated into 96-well plates at a density of $2.5\times10^3$ cells per well and allowed to adhere for 24 hr at 37° C. in 5% $CO_2$. After 24 hr, the medium was replaced with medium containing different concentrations of granzymeB-vegf121 or granzyme B-scFvMEL. After 72 hr, the effect of granzymeB-vegf121 or granzymeB-scFvMEL on the growth of cells in culture was determined using crystal violet staining. Surviving adherent cells were stained by adding 100 μl of crystal violet (0.5% (w:v) in ethanol). The stain was incubated on the plates for 0.5 hr, excess stain was removed, and the plates were washed with water and allowed to air-dry. The remaining dye was solubilized by addition of 150 μl of Sornson's buffer (0.1 M sodium citrate, pH4.2). Plates were read on a microplate ELISA reader at 630 nM.

Example 10

In Vitro Transcription and Translation and in Vitro Cleavage of Procaspase 3 or DFF45 by Granzyme B or Bax Fusion Protein An expression plasmid containing cDNA encoding procaspase-3 or DFF45 will be linearized with a restriction endonuclease digested and $^{35}$S-labeled procaspase-3 or DFF45 protein will be generated using an in vitro rabbit reticulocyte TNT kit (Promega) according to the manufacturer's instructions. In brief, the linear plasmid containing cDNA encoding procaspase-3 or DFF45 (1 μg) will be incubated with the TNT reaction mixture containing 25 μl of rabbit reticulocyte lysate, 2 μl of TNT reaction buffer, 1 μl of T7 RNA polymerase, 1 mM amino acid mixture minus cysteine, 2 μl of [$^{35}$S] cysteine or 2 μl of [$^{35}$S] methionine (10 mCi/ml) and 40 U of RNase inhibitor (Amersham Pharmacia Biotech, Inc.) in a total volume of 50 μl for 90 min at 30° C. For in vitro cleavage, the translation products will be incubated in the presence of granzyme B fusion or Bax fusion proteins in 150 mM NaCl. The reactions will be performed at 30° C. in a final volume of 10 μl for various time intervals. The reactions will be then stopped by the addition of an equal volume of 2× Laemmli buffer. Cleavage products will be then separated by 15% SDS-PAGE and detected either by immunoblotting or phosphorimaging of the dried gels.

Example 11

Apoptosis Assays

Cell Morphology:

A375-M or AAB527 cells (for Granzyme B-scFvMEL) and PAE-Flk1 or PAE-Flt1 cells (for Granzyme B-vegf121) will be grown in appropriate cell culture media. Cell death will be monitored by XTT assay. To visually monitor granzyme B-mediated or Bax-mediated apoptosis of these cells, $1\times10^4$ cells will be plated in each well of a 12-well microscope slide. Forty-eight hours later, cells will be washed once in PBS, then treated with 25 μl of serum-free medium supplemented with 1 μg/ml DTT and granzyme B fusion proteins or Bax fusion proteins. Following incubation at 37° C. for 1 hr, supernatants will be removed and replaced with 50 μl of complete medium. After a further 2 h at 37° C., cells will be gently washed with PBS and fixed with acetone: methanol (1:1) for 2 min at room temperature. Apoptosis of adherent cells will be visualized by phase-contrast microscopy.

Assay of DNA Fragmentation:

To monitor DNA fragmentation, $5\times10^5$ cells in 50 μl of serum-free medium will be supplemented with 1 μg/ml DTT and granzyme B fusion proteins or Bax fusion proteins. Following incubation at 37° C. for 1 hr, they will be washed once in PBS. Fragmented DNA will be extracted using a phenol/chloroform extraction assay. Briefly, the cell pellet will be re-suspended in 25 μl of PBS, and an equal volume of pheno/chloroform/isoamylalcohol (1:1:0.1) added. Following gentle agitation and centrifugation (10,000 g for 2 min), fragmented DNA will be recovered, treated with RNase A for 1 hr at 37° C. and analyzed on 2% agarose gels containing ethidium bromide.

Facs Analysis:

Cells ($5\times10^5$/10 ml) will be centrifuged at 450×g for 6 min, washed with cold PBS and resuspended in 300 μl of PBS. The cells will be fixed with 5 ml methanol and left at −20° C. for at least 1 hr. The cells will be then centrifuged at 800×g for 5 min., resuspended in 100 μl PBS and diluted to a final volume of 1 ml with PBS. Cells will be incubated on ice for an additional 30 min, centrifuged at 800×g for 5 min and resuspended in 0.5 ml PBS. 10 μl RNase (50 μg/ml) and propidium iodide (PI, 5 μg/ml) will be added to the cell samples which will be then FACS analyzed for DNA content as a function of cell number.

Cleavage of Caspase-3, PARP and DFF Detected in Cell Samples Treated with Fusion Proteins vs. Non-Treated with Fusion Proteins within Different Time Course or Dose by Using Western Blot Analysis:

For western blotting, samples will be separated by electrophoresis using 14% SDS-PAGE. The proteins will be transferred from gels into nitrocellulose membranes. The membranes will be blocked with 5% non-fat milk, and incubated for 1 hr at room temperature with anti-caspase-3 or cleaved caspase-3, or anti-PARP or anti-cleaved DFF antibody (obtained from Cell Signaling Technology). After washing, the membranes will be incubated with goat anti-rabbit or goat anti-mouse/horseradish peroxidase conjugate. After further washing, the membranes will be developed using the Amersham ECL detection system and exposed to X-ray film.

Example 12

Signal Transduction Pathway-Non-Apoptosis Assays

In the following example, experiments are described which are performed to analyze insulin signal transduction pathways, which are non-apoptotic pathways, in cells treated with a delivery vehicle containing protein kinase B, which is a critical point in the insulin signal transduction cascade leading to modulation of the enzyme glycogen synthetase kinase-3 (GSK-3). In the present invention, a fusion construct of the cytokine human hepatocyte growth factor(HCF) and the signal transduction regulator protein kinase B(PKB) will be generated. The HCF component serves to bind to hepatocytes and to deliver active PKB to the cellular cytoplasm. From there, activation of the downstream modulators of insulin signaling (GSK-3) will be assessed as described below.

Anti-GSK3 antibodies are obtained from Transduction Laboratory. Phosphotyrosine antibody 4G10 and anti-PKB antibody will be obtained from Upstate Biotechnology. Phosphospecific antibody against Ser-9 of GSK3 will be obtained from Quality Controlled Biochemicals.

Cultures of hepatocytes in media will be treated with various doses of HCF or the HCF/PKB fusion construct. At various times after drug addition, cells will be harvested. To prepare cytosolic fractions, cells will be washed and collected in ice-cold phosphate-buffered saline. Cell pellets will be resuspended in ice-cold hypotonic buffer (25 mM Tris, pH 7.5, 1 mM EDTA, 25 mM NaF, 1 mM dithiothreitol) with Complete protease inhibitor mixture (Roche Molecular Biochemicals; Indianapolis, Ind.). Cells will be lysed after incubating on ice for 10 min (verified by microscope analysis). The lysates will be subjected to ultracentrifugation at 100,000×g for 30 minutes at 4° C., and the supernatant will be collected. For immunoprecipitation, cells will be washed twice in ice-cold phosphate-buffered saline, and then lysed in IP buffer (125 mM NaCl, 25 mM NaF, 25 mM Tris, pH 7.5, 1 mM EDTA, 1 mM EGTA, 1% Triton X-100, 10 mM -glycerol phosphate, 5 mM sodium pyrophosphate, 1 mM NaVO3, 200 nM okadaic acid, 1 mM dithiothreitol) with Complete protease inhibitor mixture. Anti-GSK3 antibody will be added to clarified lysates for 1 h at 4° C., and then Protein G beads (Sigma) will be added for another 1 h. Immunoprecipitates will be washed three times with IP buffer.

For GSK3 kinase assays, cells treated with the delivery vehicle containing active protein kinase B fusion construct GSK3 immunoprecipitates will be washed once with kinase buffer (25 mM Tris, pH 7.5, 10 mM MgC12) first. Kinase reactions will be performed in kinase buffer with 100 μM [γ-$^{32}$ P]ATP and 100 μM 2BSP peptide as the substrate (synthesized by the Biomedical Resource Center, University of California, San Francisco, Calif.). 2BSP is based on the GSK3 target site in eIF2B. After 20 min at 30° C., the reactions will be spotted on phosphocellulose P81 paper (Whatman), washed four times with 100 mM phosphoric acid, and counted in scintillation counter.

Example 13

Human Granzyme B Gene Cloning from Hut78

Native human granzyme B is a cytotoxic lymphocyte granule serine proteinase produced by cytotoxic T cells and natural killer cells. Initial attempts to clone human granzyme B gene from HL-60 cells, which are promyelocytic leukemia cells from human peripheral blood, were unsuccessful. However, the targeted cDNA, as a pre-mature granzyme B gene, was obtained from human cutaneous T cell lymphoma Hut78 cells, by isolating RNA and using RT-PCR. A 1% agarose gel electrophoresis showed that human pre-mature granzyme B cDNA was ~800 bp (FIG. 1). The gene sequence and amino acid sequence (FIG. 2) showed that the first 20 amino acids are signal sequence. The human granzyme B sequence with signal sequence is designated pre-mature granzyme B. In cytotoxic cells, active granzyme B is generated from a zymogen by dipeptidyl peptidase I (DPPI)-mediated proteolysis (Smyth et al., 1995). This removes the two-residue ($Gly^{19}Glu^{20}$) propeptide and exposes $Ile^{21}$ to become the mature, N-terminal Ile-Ile-Gly-Gly sequence granzyme B.

Example 14

Construction of Granzyme B-VEGF121 or Granzyme B-SCFVMEL

Figure 3A:
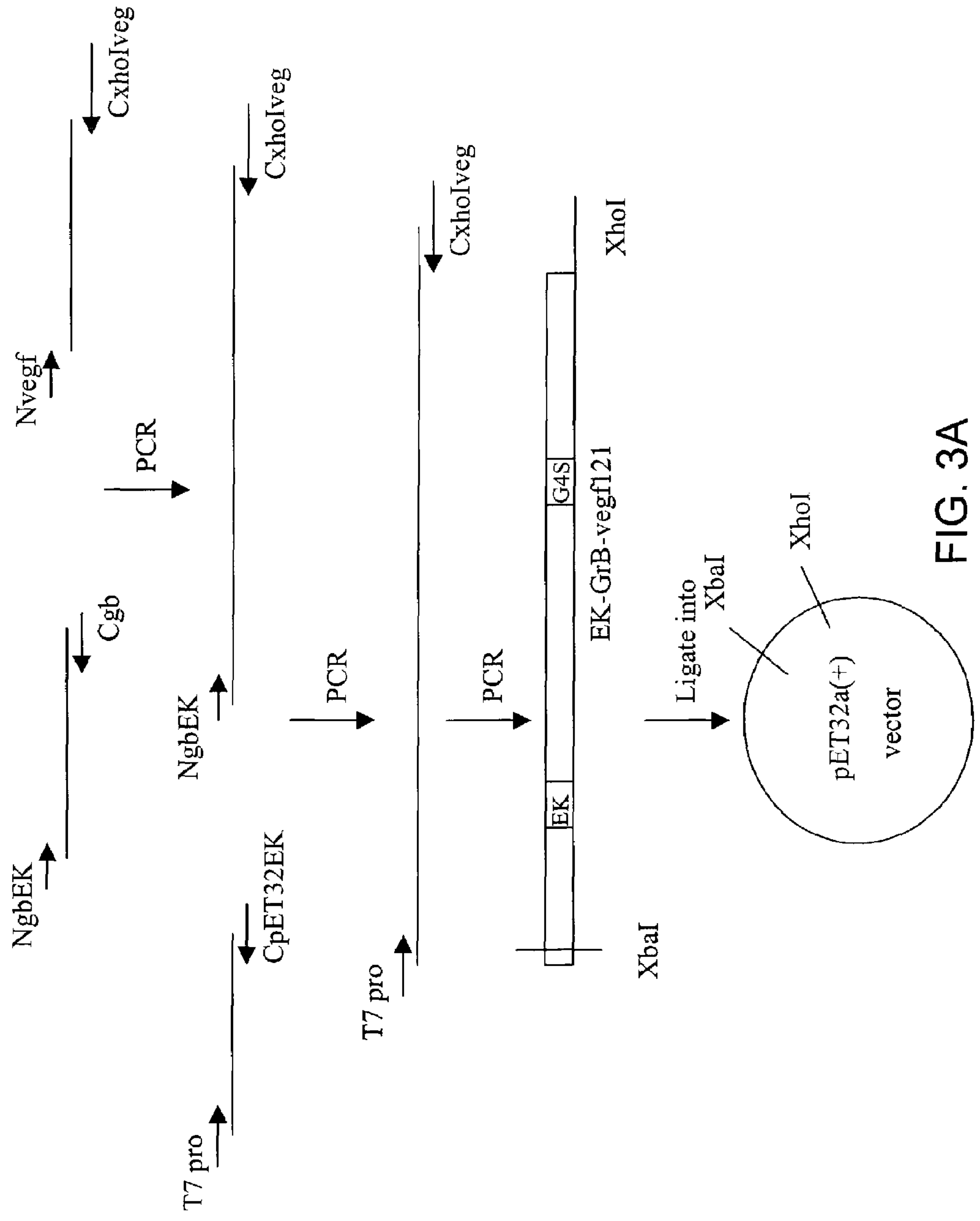
FIGS. 3A and 3B illustrate construction of pET32GrB-vegf121 and pET32GrB-scFvMEL fusion constructs. Construction of these fusion constructs was based on a PCR method.
Figure 3B:
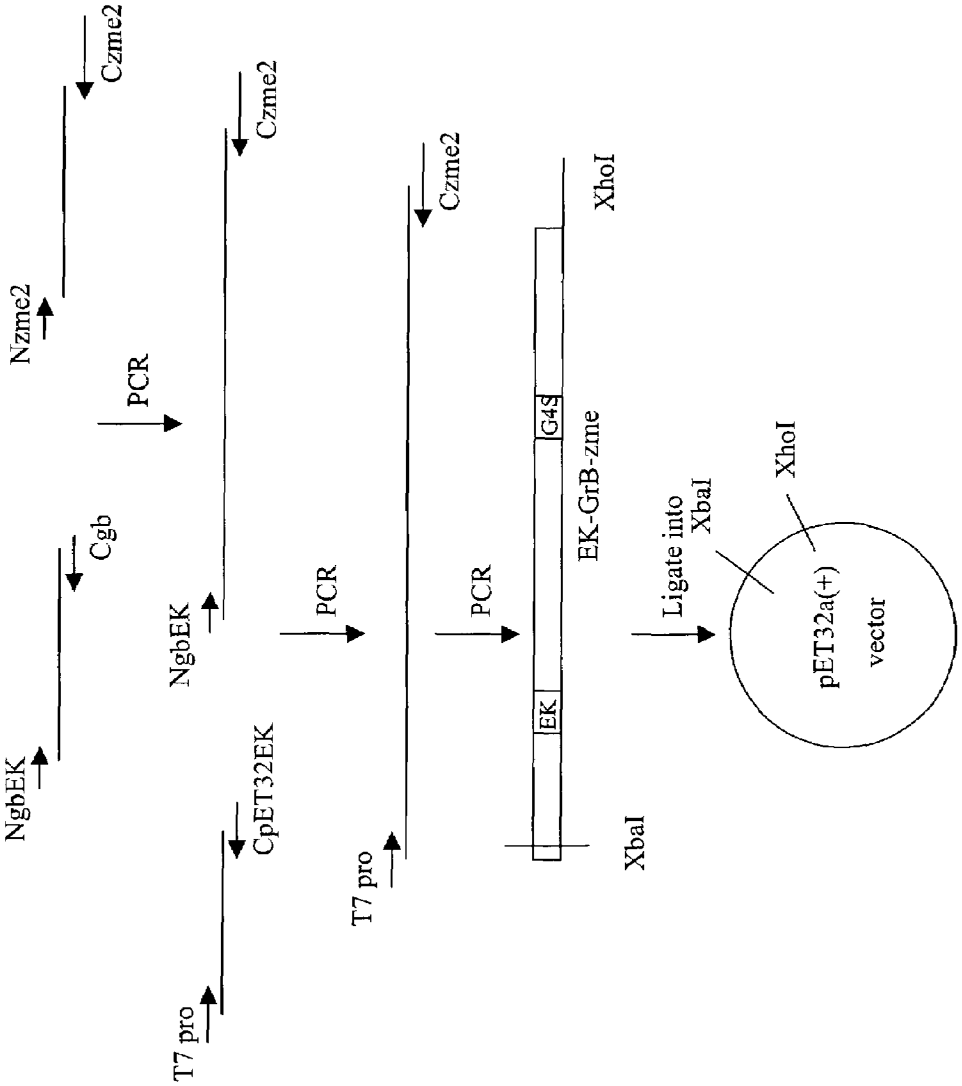
Figure 4A:
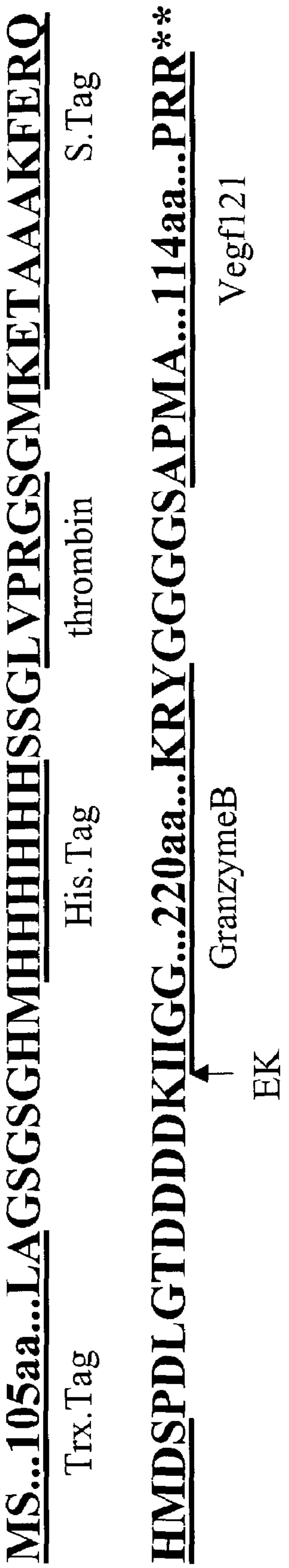

PCR was used to amplify the coding sequence of granzyme B from $Ile^{21}$, which is the first residue of the mature enzyme, effectively deleting the signal sequence and GlyGlu domain. Concomitantly, a cleavage site was inserted for enterokinase (AspAspAspLys; SEQ ID NO:53) upstream and adjacent to $Ile^{21}$. Granzymne B was attached to the recombinant Vegf121 or scFvMEL via flexible tether (G4S). The fused gene fragment was then introduced into the Xba I and Xho I sites of the pET32a (+) to form the expression vector pET32GrB-vegf121 (FIG. 3A) and pET32GrB-scFvMEL (FIG. 3B). This vector contains a T7 promoter for high-level expression followed by a Trx.tag, a His.tag, a thrombin cleavage site, and an enterokinase cleavage site for final removal of the protein purification tag (FIG. 4A and 4B). Once the protein tag is removed by recombinant enterokinase, the first residue Ile of mature granzyme was exposed, and the granzyme B moiety of granzyme B-vegf121 or granzyme B-scFvMEL was activated. The nucleotide sequences and amino acid sequences of granzyme B-vegf121(1059 base pairs, 353 aa) (FIGS. 4C and 4D) and granzyme B-scFvMEL (1440 base pairs, 480 aa) (FIGS. 4E and 4F) were confirmed.

Example 15

Expression and Purification of Granzyme B-VEGF121 or Granzyme B-SCFVMEL Fusion Protein The recombinant protein granzyme B-vegf121or granzyme B-scFvMEL was expressed as polyhistidine-tagged protein designed pro-granzymeB-vegf121 or pro-granzyme B-scFvMEL and then purified by Nickel-NTA metal affinity chromatography. The his-tag was cleaved by addition of rEK to form granzymeB-vegf121 or granzyme B-scFvMEL. One liter of the culture typically yielded approximately 100 μg of the final purified granzymeB-vegf121 product and 150 μg of the final purified granzyme B-scFvMEL product.

Figure 5A:
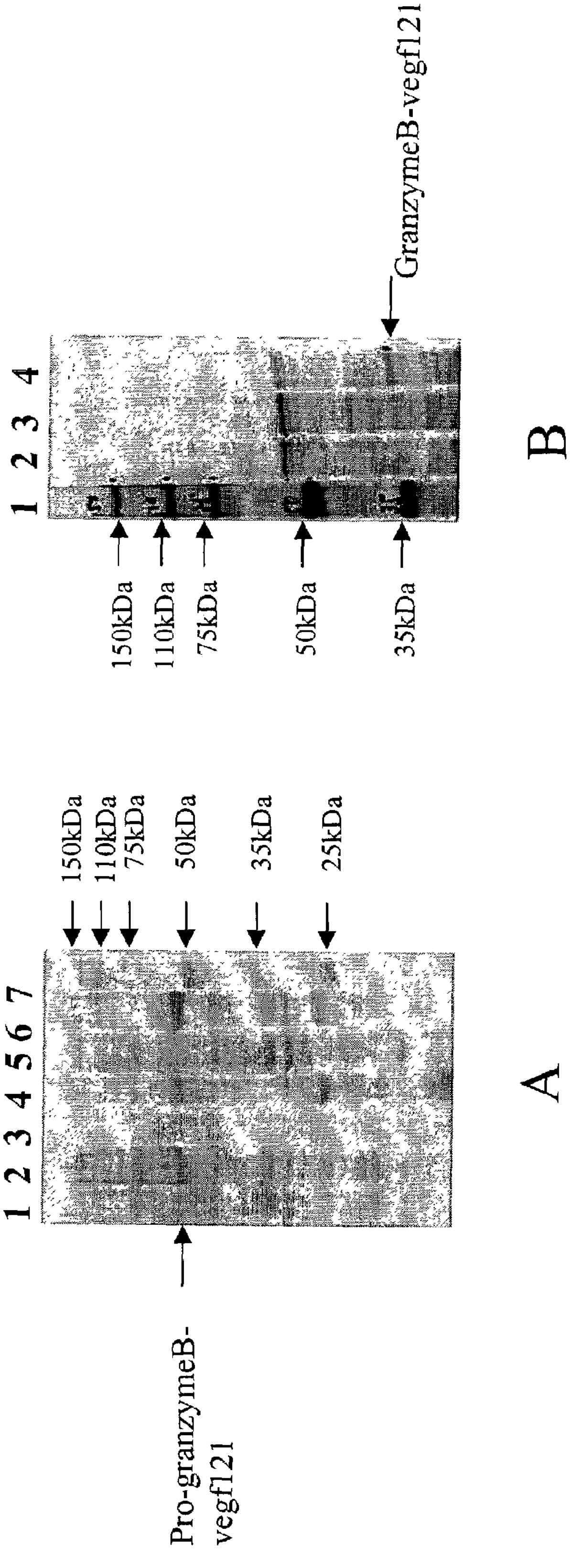
FIGS. 5A and 5B show SDS-PAGE analyses of the expression of the fusion proteins SDS-PAGE Coomassie Blue staining of granzyme B-vegf121 (FIG. 5A) and granzyme B-scFvMEL (FIG. 5B) under reducing conditions. Panel A of FIG. 5A shows SDS-PAGE Coomassie Blue staining of Granzyme B-vegf121. Lane 1 shows non-induced total cell lysates; lane 2 shows induced total cell lysates; lane 3 shows non-induced soluble; lane 4 shows induced soluble; lane 5 shows non-induced insoluble; lane 6 shows induced insoluble; lane 7 shows protein molecular marker. In Panel B, lane 1 shows protein molecular marker; lane 2 shows pro-granzyme B-vegf121 (IMAC-eluate from Talon Resin); lane 3 shows pro-granzyme B-vegf121 (IMAC-Elute from Nickel NTA), Lane 4: Granzyme B-vegf121 (after rEK cut).
Figure 5B:
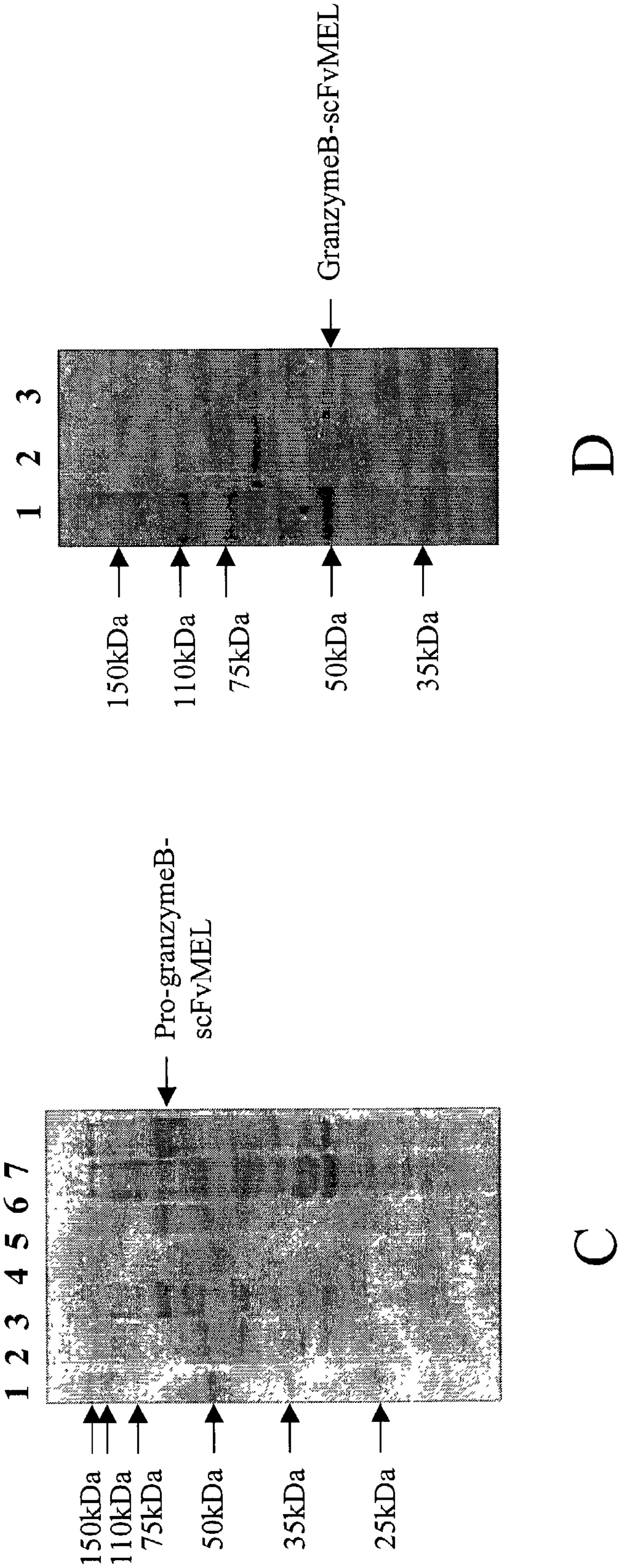

The results showed induced expression of granzyme B-related fusion constructs. The induced band at ~55 kDa for granzyme B-vegf121 and at ~72 kDa for Granzyme B-scFvMEL represent, respectively, the granzyme B-vegf121 or granzyme B-scFvMEL construct containing a ~18 kDa purification tag. Enzymatic digestion of the tag using recombinant enterokinase (rEK) resulted in appearance of a band migrating at ~38 kDa for granzyme B-vegf121 and at ~53 kDa for granzyme B-scFvMEL representing native proteins. Thus, SDS-PAGE showed that the final purified granzymeB-vegf121 fusion construct migrated under reducing conditions as a band at the expected molecular weight of 38 kDa (FIG. 5A) and granzyme B-scFvMEL fusion construct showed the band at the expected molecular weight of 53 kDa (FIG. 5B).

Figure 6:
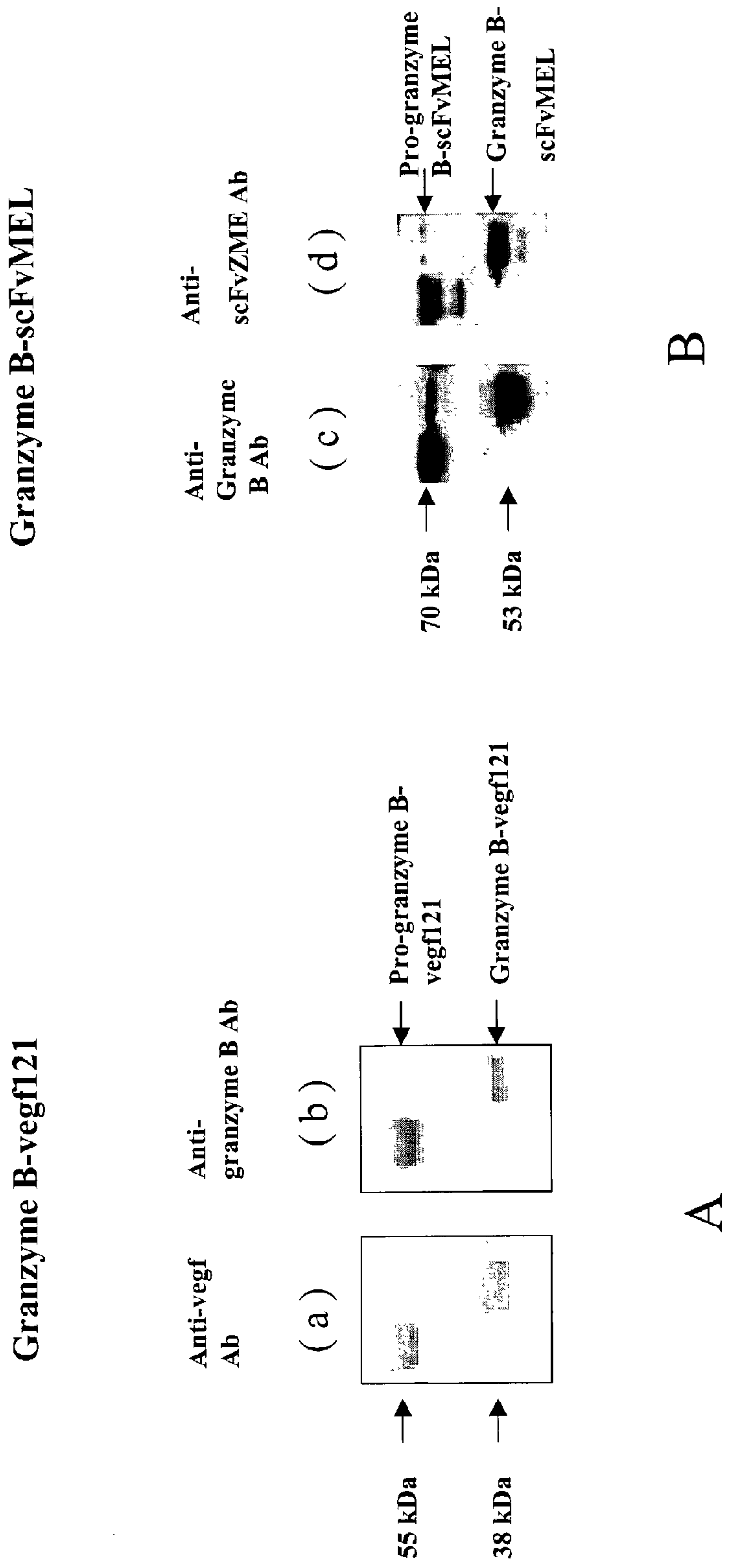
FIG. 6 demonstrates a Western blot analysis of granzyme B-vegf121 and granzyme B-scFvMEL.

Specificity of the cleaved fusion protein was confirmed by Western blot using either mouse anti-granzyme B monoclonal antibody, mouse anti-vegf121 polyclonal antibody, or rabbit anti-scFvZME polyclonal antibody (FIG. 6). The results showed that granzyme B-vegf121 fusion construct (FIG. 6A) could specifically bind to either mouse anti-vegf121 antibody (FIG. 6A (a)) or mouse anti-granzyme B monoclonal antibody (FIG. 6A (b)). The molecular weights of pro-granzyme B-vegf121 and Granzyme B-vegf121 are approximately 55 kDa and 38 kDa, respectively. Granzyme B-scFvMEL fusion construct (FIG. 6B) could specifically bind to either mouse anti-granzyme B monoclonal antibody (FIG. 6B (c)) or rabbit anti-scFvMEL polyclonal antibody (FIG. 6B (d)). The molecular weights of Pro-granzyme B-scFvMEL and Granzyme B-scFvMEL are approximately 70 kDa and 53 kDa, respectively.

Example 16

Bindging Activity of SCFVMEL Moiety of Granzyme B-SCFVMEL Fusion Protein

Figure 7:
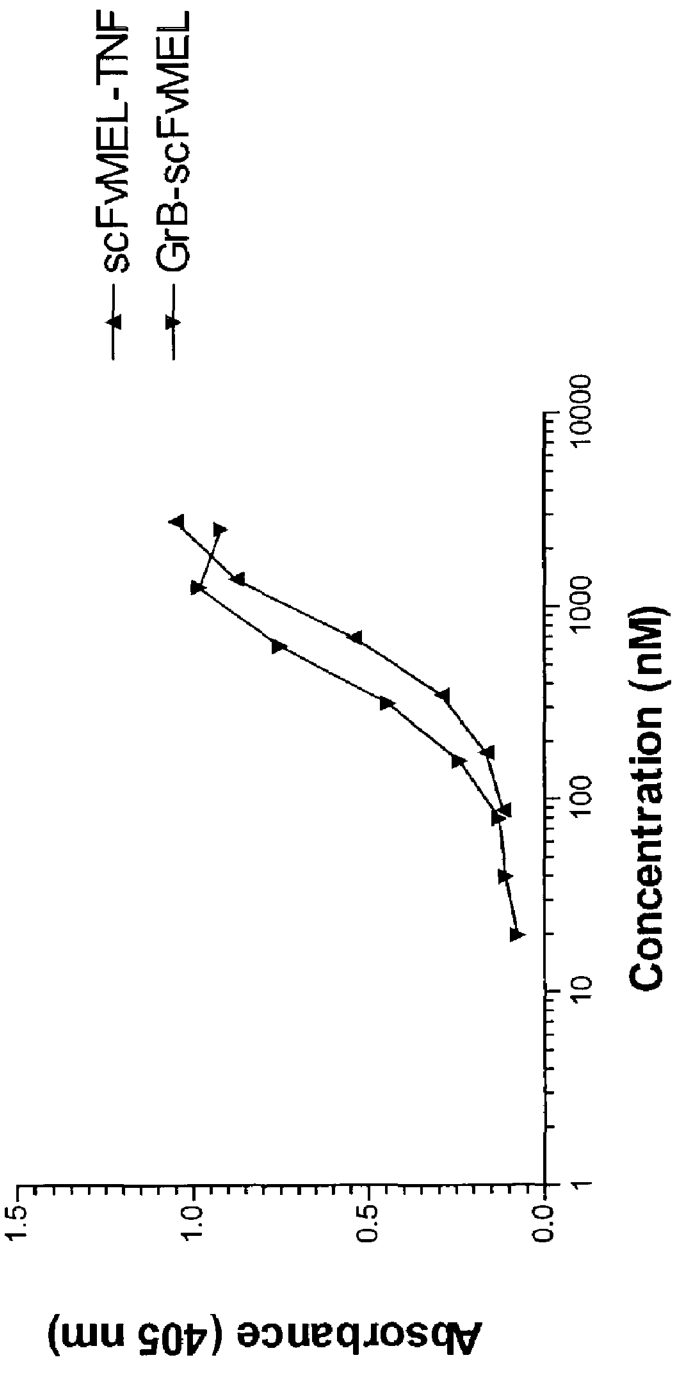
FIG. 7 shows binding activity of scFvMEL moiety of granzyme B-scFvMEL fusion protein. ELISA of different scFvMEL fusion proteins were examined on a plate precoated with Protein L.

The scFvMEL moiety was tested to bind Protein L, which is an immunoglobulin-binding protein that originally comes from the bacteria *Peptostreptococcus magnus*. Protein L has the unique ability to bind through kappa light chain interactions without interfering with an antibody's antigen-binding site. This gives Protein L the unique ability to bind Single Chain Variable Fragments (scFv). The results showed the absorbance at 405 nm concentration-response increase, suggesting scFvMEL bound to Protein L. (FIG. 7). The binding activity of the granzyme B-scFvMEL was the same as that of the scFvMEL-TNF, which could specifically bind to antigen-positive human melanoma cells and was cytotoxic activity to those melanoma cells.

Example 17

In Vitro Cytotoxic Effects of Granzyme B-VEGF121

Figure 8:
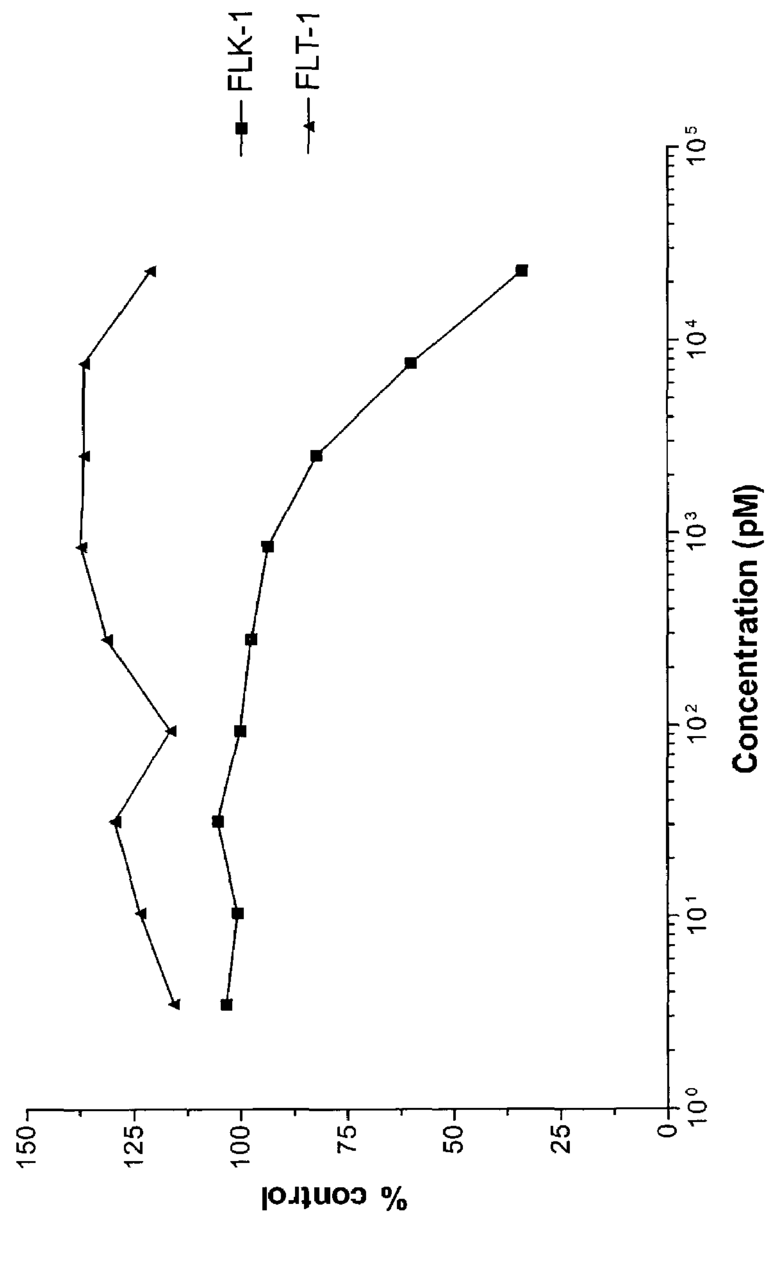
FIG. 8 demonstrates testing of cytotoxicity of granzyme B-vegf121 against log-phase PAE-Flk-1 and PAE-Flt-1

The cytotoxicity of GranzymeB-vegf121 was assessed against log-phase PAE-Flk-1 (Overexpression flk-1/KDR receptor) and PAE-Flt-1 (overexpression flt-1 receptor) in culture, wherein $2.5\times10^3$ cells per well on 96-well plates. A 50% growth inhibitory effect was found at a concentration of ~10 nM on PAE-Flk-1 cells. However, no cytotoxic effects were found on PAE-Flt-1 cells (FIG. 8). It was also shown that VEGF121 could specifically bind to VEGF receptor Flk-1/KDR but not to Flt-1. The cytotoxicity of granzymeB-vegf121 demonstrated that the construct could specifically kill PAE-Flk-1 cells, which indicated that the Vegf121 moiety of the fusion bound to the Flk-1 over-expression cell-surface. Subsequently, there was delivery of granzyme B to the interior of targeted cells, resulting in cytotoxicity to the target cells.

Example 18

In Vitro Cytotoxic Effects of Granzyme B-SCFVMEL

Figure 9:
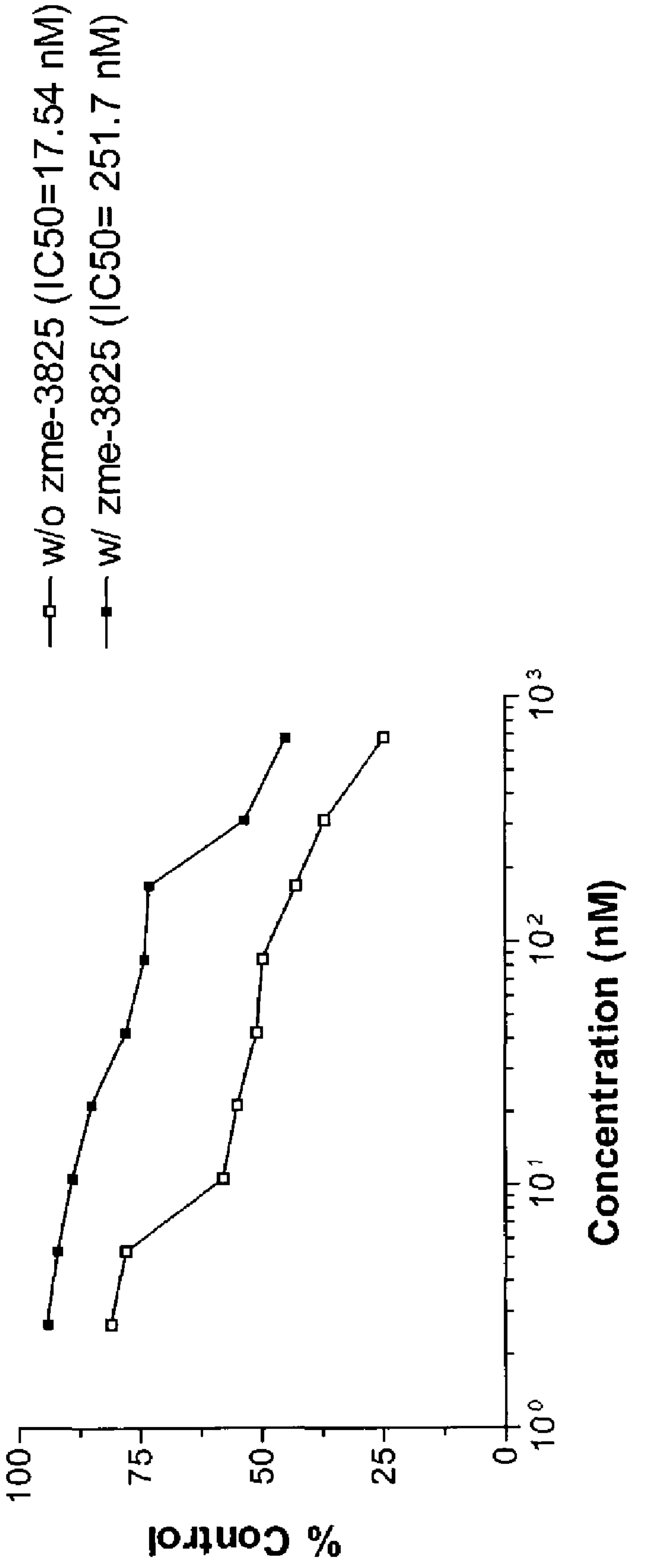
FIG. 9 demonstrates testing of cytotoxicity of granzyme B-scFvMEL on A375-M.

The cytotoxicity of granzyme B-scFvMEL was tested against log-phase human melanoma A375-M cells. The results showed that granzyme B-scFvMEL could kill the A375-M cells, with an $IC_{50}$ concentration of approximately 20 nM. When pre-treated with scFvMEL-3825 at the concentration of 178.5 nM for 6hr, followed by treatment with granzyme B-scFvMEL for 72 hr, a 15-fold higher concentration of granzyme B-scFvMEL was required to exhibit 50% cytotoxicity compared to the absence of scFvMEL-3825 pre-treatment (FIG. 9). In a specific embodiment, this is because the cell-surface antigen gp240 was already occupied by scFvMEL-3825, resulting in a reduced chance for the scFvMEL moiety of granzyme B-scFvMEL binding to the gp240 antigen, consequently inhibiting the cytotoxicity of granzyme B-scFvMEL on these cells. The results suggested that the cytotoxicity, at least in part, is due to the interaction of the antibody with its cell-surface domain.

Example 19

Cloning Human Bax Gene

Total RNA from Namalwa cells was isolated using Glass MAX RNA Microisolation Spin Cartridge System (Gibco BRL). Removal of the genomic DNA was performed by addition of RNase-free DNase I while incubating at room temperature for 15 min. DNase I then was inactivated by adding EDTA solution and heating for 15 min at 65° C. SUPERSCRIPT First-Strand Synthesis System was utilized for RT-PCR (Gibco BRL). First-strand synthesis used Oligo (dT), and then the target cDNA (Bax cDNA) was amplified using the primers: NbaxTA (5' to 3'): GGTGATGGACGGGTCCGGGGAGCA (SEQ ID NO:29) and CbaxTA (5' to 3'): GGCCTCAGCCCATCTTCTTCCAGATGGTGA (SEQ ID NO:30) by PCR with the following cycles: denaturation at 95° C. for 5 min, 30 cycles of 94° C. for 1 min, 50° C. for 1 min, 72° C. for 1 min, and extension at 72° C. for 5 min. A 1% agaro gel was run to check the PCR product. Purified PCR fragment was cloned into PCR 2.1 TA vector (Invitrogen) and designed BaxTA. The BaxTA was transformed into INVαF' competent cells, and the positive clones were screened by blue/white colonies screening or by PCR methods. The DNAs for positive clones were isolated by using QIApre Spin prep kit (Qiagen; Valencia, Cailf.), and sequencing confirmed the human bax gene in the correct clone (BaxTA-35 (clone # 35)).

Example 20

Construction of Bax-Related Fusion Genes

The construction was based on an over-lap PCR method. The scFvMEL genes were fused to Bax, truncated Bax1-5 (that is, comprises exons 1 through 5) or truncated Bax345 (that is, comprises exons 3, 4, and 5) genes with G4S tether in different orientation (designated scFvMEL-bax or Bax-scFvMEL, scFvMEL-Bax1-5 or Bax1-5-scFvMEL, and scFvMEL-Bax345 or Bax345-scFvMEL, respectively). As shown in FIG. 10, a skilled artisan recognizes that the human Bax gene (SEQ ID NO:45), which encodes the polypeptide of SEQ ID NO:46, comprises six exons, with the domain BH1 (DGNFNWGRVVA; SEQ ID NO:47) in exon 4, BH2 (WIQDQGGWD; SEQ ID NO:48) in exon 5, and BH3 (LKRIGDE; SEQ ID NO:49) in exon 3. In a specific embodiment, the Bax chimeric polypeptide comprises the BH1, BH2 and BH3 domains or a combination thereof. In another specific embodiment, the Bax chimeric polypeptide consists essentially of the BH1, BH2 and BH3 domains. In another specific embodiment, the Bax chimeric polypeptide comprises exons 3, 4, and 5 or a combination thereof. In an additional specific embodiment, the Bax chimeric polypeptide consists essentially of exons 3, 4, and 5.

Briefly, scFvMEL coding sequence was amplified from pET32a-scFvMEL/TNF by PCR and full length bax or truncated Bax1-5 or truncated Bax345 was amplified from BaxTA-35 by PCR. Different primers were designed wherein G4S liner sequence was added to the C-terminus or N-terminus in order to link the fused genes together by the second PCR. In order to clone the fused genes into pET32a (+) vector at Nco I and Xho I sites, primers added the Nco I site at the N-terminus and two stop codons, and a Xho I site was added at the C-terminus. The first PCR were performed by 95° C. for 5 min, 30 cycles of 94° C. for 1 min, 50° C. for 1 min and 72° C. for 1 min, and then extension at 72° C. for 5 min. For constructing of scFvMEL-bax, scFvMEL was amplified by using primers: Ncolzme (5' to 3'): GGTGGCG-GTGGCTCCATGGCGGACATTGTGATGAC-CCAGTCTCAAAAATTC (SEQ ID NO:31) and Czme (5' to 3'): CGTCGGAGCCACCGCCACCGCTAGCT-GAGGAGACGGTGAGAGT (SEQ ID NO:32), Bax fragment was amplified by using primers: Nbax2 (5' to 3'): GGTGGCGGTGGCTCCGACGGGTCCGGGGAGCAG (SEQ ID NO:33) and Cbax (5' to 3'): GGAGCCACCGC-CACCCTCGAGCTATCAGCCCATCTTCTTCCAGAT (SEQ ID NO:34). For Bax-scFvMEL construct, primers are Nbax (5' to 3'): GGTGGCGGTGGCTCCATG-GACGGGTCCGGGGAGCAG (SEQ ID NO:35), Cbax2-1 (5' to 3'): GTCCGTGGAGCCACCGCCAC-CGCTAGCGCCCATCTTCTTCCA (SEQ ID NO:36), Nzme2 (5' to 3'): GGTGGCGGTGGCTCCACGGACAT-TGTGATGACCCAGTCTCAAAAATTC (SEQ ID NO:37) and Czme2 (5' to 3'): GGAGCCACCGCCACCCTCGAGC-TATCATGAGGAGACGGTGAGAGTGGT (SEQ ID NO:38). For construction of scFvMEL-Baxl-5 construct, primers are Ncolzme, Czme, Nbax2 and Cxholbax345 (5' to 3'): GGAGCCACCGCCACCCTCGAGCTATCAC-CAACCACCCTGGTC (SEQ ID NO:39). For construction of Bax1-5-scFvMEL fusion construct, primers are Nbax, Cbax345 (5' to 3'): GGAGCCACCGCCACCCCAACCAC-CCTGGTC (SEQ ID NO:40), Nzme2 and Czme2. For construction of scFvMEL-Bax345fusion, primers are NcoIzme, Primer3 (5' to 3'): CCGGAGCCACCGCCAC-CGCTAGCTGAGGAGACTGTGA (SEQ ID NO:41), Nbax345 (5' to 3'): GGTGGCGGTGGCTCCTTCATC-CAGGATCGAG (SEQ ID NO:42), and CxhoIbax345. For construction of Bax345-scFvMEL, NcoIBax345 (5' to 3') is used: GGTGGCGGTGGCTCCATGGTCATCCAG-GATCGAG (SEQ ID NO:43), Cbax345, Nzme2 and Czme2.

Then, the second PCR was performed by 30 cycles of 94° C. for 1 min, 50° C. for 1 min and 72° C. for 1 min, further extension at 72° C. for 5 min. Amplified fragments were separated by 1% agarose gel electrophoresis, purified by PCR purification kit (Qiagen; Valencia, Calif.). The purified PCR products were digested with Nco I and Xho I at 37° C. for 3 hrs and then separated by 1% agarose gel electrophoresis, purified from the gels using geneclean II kit (Quantium Biotechnologies, Inc., Carlsbad, Calif.). The purified gene fragments were cloned into pET32a (+) vector, the ligation mixture was transformed into DH5α competent cells, screened the positive clones by PCR, then sequenced. The clones with correct-frame sequence were transformed into AD494 (DE3)pLysS competent cells for further induction and expression.

For expression of full length Bax and Bax-scFvMEL protein, the Bax and Bax-scFvMEL sequences were subcloned into pBAD/His A vector and designated pBAD/Hisbax and pBAD/Hisbax-scFvMEL, respectively. Briefly, the full length Bax and Bax-scFvMEL genes were amplified by using a PCR method. For amplification of full length Bax, BaxTA-35 was used as template, and the primers were NBAXHIS (5' to 3'): AAACATGCCATGGCTCACCAC-CACCACCACCACGACGGGTCCGGGGAGCAGCCC AGA (SEQ ID NO:44) and Cbax. For amplification of Bax-scFvMEL, pET32-Bax-scFvMEL (clone2) was used as template, and primers were NBAXHIS and Czme2. The NBAXHIS primer was designed as follows: Nco I site for cloning, polyhistidine (6×His) for purification and detection at the N-terminus, followed by the initiation ATG; two stop codons and a Xho I site were added at the C-terminus in Cbax and Czme2 primers. Purified PCR fragments were digested by Nco I and Xho I and purified by using gene clean kit, following ligation into the same restriction endonucleases digested for the pBAD/His A vector. The ligation mixture was transformed into DH5α, and the positive clones were screened by PCR screening, DNA was isolated, and the sequence was checked. The confirmed sequence positive clones were transformed into LMG194 competent cells for expression.

Example 21

Induction and Expression of Bax-Related Fusion Proteins In *E. Coli*

Bacterial colonies transformed with the constructed plasmid were grown in Luria Broth (LB) growth media containing 200 μg/ml ampicillin, 70 μg/ml chloramphenicol, and 15 μg/ml kanamycin, at 37° C. overnight at 24 rpm shaking. The cultures were then diluted 1:100 in fresh LB media plus antibiotics and grown to $A_{600}$=0.6 at 37° C., thereafter, induced by addition of IPTG to a final concentration of 80 μM at 37° C. for 2 hrs. The cells were harvested, resuspended in 10 mM Tris (pH 8.0) and stored frozen at −80° C. for further purification.

Example 22

Induction and Expression of Full Length Bax and Bax-SCFVMEL

Bacterial colonies transformed with the plasmid pBAD/Hisbax and pBAD/Hisbax-scFvMEL were grown in RM medium containing glucose and 100 μg/ml ampicillin, at 37° C. overnight with shaking (225 rpm). The cultures were then diluted by 1: 100 in fresh RM medium containing glucose and 100 μg/ml ampicillin and grown at 37° C. with shaking to maxium $OD_{600}$, then induced by addition of 5% arabinose at 37° C. for 4 hours. The cells were harvested, resuspended in 10 mM Tris (pH 8.0) and stored frozen at −80° C. for further purification.

Example 23

Purification of Bax-Related Fusion Proteins

Re-suspension was lysed by addition of lysozyme to a final concentration of 100 μg/ml tumbling for 30 min at 4° C., followed by sonication. Extracts were centrifuged at 10,800 g for 30 min, and the supernatant was further centrifuged at 40,000 rpm for 1 hr. The supernatant containing only soluble protein was adjusted to 40 mM Tris, pH 8.0, 10 mM Imidazole and was applied to a Nickel-NTA agarose equilibrated with the same buffer. After washing the Nickel-NTA agarose with 500 mM NaCl 20 mM imidazole, the bound proteins were eluted with 500 mM NaCl 500 mM imidazole. Absorbance (280nm) and SDS-PAGE analysis were performed to determine the polyhistidine-tagged proteins. The final proteins were obtained by the addition of recombinant bovine enterokinase (rEK) to remove the polyhistidine-tag according to the manufacturer's instruction (1 unit of rEK cleavage 50 μg protein, incubated at room temperature for 16 hrs). The rEK was then removed by EK capture agarose. The final proteins were analyzed by SDS-PAGE and stored at 4° C.

Example 24

SDS-Page and Western Blot Analysis

Protein samples were analyzed by electrophoresis on a 8.5% or 12% SDS-PAGE under reducing conditions. The gels were stained with Coomassie Blue. For western blotting analysis, proteins were transferred from gels into nitrocellulose membranes. The membranes were blocked with 5% non-fat milk and incubated for 1 hr at room temperature or overnight at 4° C. with rabbit anti-scFvzme antibody (1:2000 dilution) or rabbit anti-bax antibody (1:1000 dilution). After washing, the membranes were incubated with goat anti-rabbit/horseadish peroxidase conjugate (HRP-GAR, 1:5000 dilution). After further washing, the membrane was developed using the Amersham ECL detection system and exposed to X-ray film.

Example 25

Detection of SCFVMEL Moiety of Bax-Related Fusion Proteins

Reacti-Bind TM Protein L Coated Plates from PIERCE (Rockford, Ill.) or 96-well plates containing adherent human melanoma A375-M cells were used for detection of scFvMEL moiety of Bax-related fusion proteins, based on ELISA method. Briefly, Pre-coated Protein L was blocked by 5% BSA and then reacted with scFvMEL bax-related fusion proteins at various concentration. After washing, they were incubated with rabbit anti-scFvZME antibody, followed by incubation with HRP-GAR(1:5000 dilution) for 1 hr at room temperature, and then substrate 2,2' -azino-bis-3-ethylbenzthiazoline-6-sulfonic acid (ABTS) solution with 1 μg/ml 30% $H_2O_2$ added. Absorbance at 405 nm was measured after 30 min.

Example 26

In Vitro Cytotoxicity Assays

Human melanoma A375-M cells cultured in MEM medium with 10% FBS were plated into 96-well plates at a density of 2.5×$10^3$ cells per well and allowed to adhere for 24 hr at 37° C. in 5% $CO_2$. After 24 hr, the medium was replaced with medium containing different concentrations of different scFvMEL-bax-related fusion proteins. After 72 hr, the effect of those fusion proteins on the growth of cells in culture was determined using crystal violet staining, or XTT. Plates were read on a microplate ELISA reader at 540 nm.

Example 27

Cytotoxicity of Bax Chimeric Polypeptides

Figure 11:
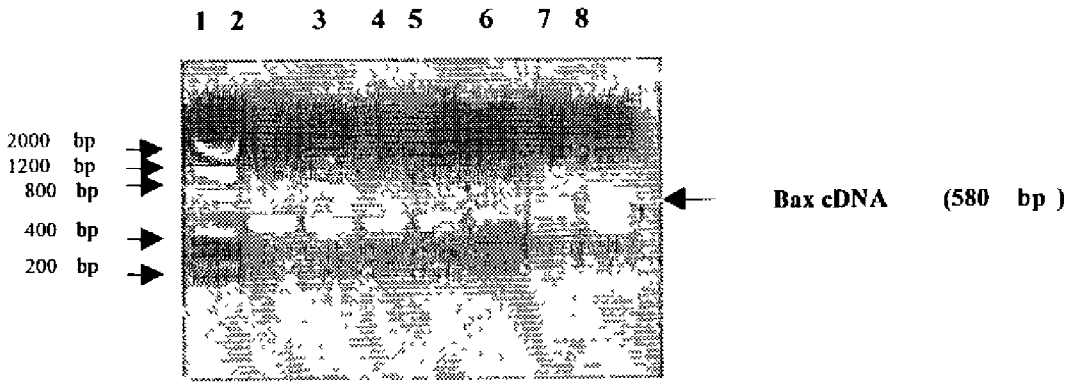
FIG. 11 demonstrates cloning of human Bax cDNA from Namalwa cells by PCR. Lane 1: Low Mass DNA Molecular Marker, lanes 2–6: Control synthesized cDNA (~500 bp), lanes 7–8: Human Bax cDNA (~580 bp) using random primer (lane 7) and using Oligo(dT) primer (lane 8).

As demonstrated in FIG. 11, the human bax gene was cloned by PCR from Namalwa cells. A 1% agarose gel electrophoresis demonstrating human Bax cDNA synthesized from Namalwa cells by RT-PCR.

Figure 12A:
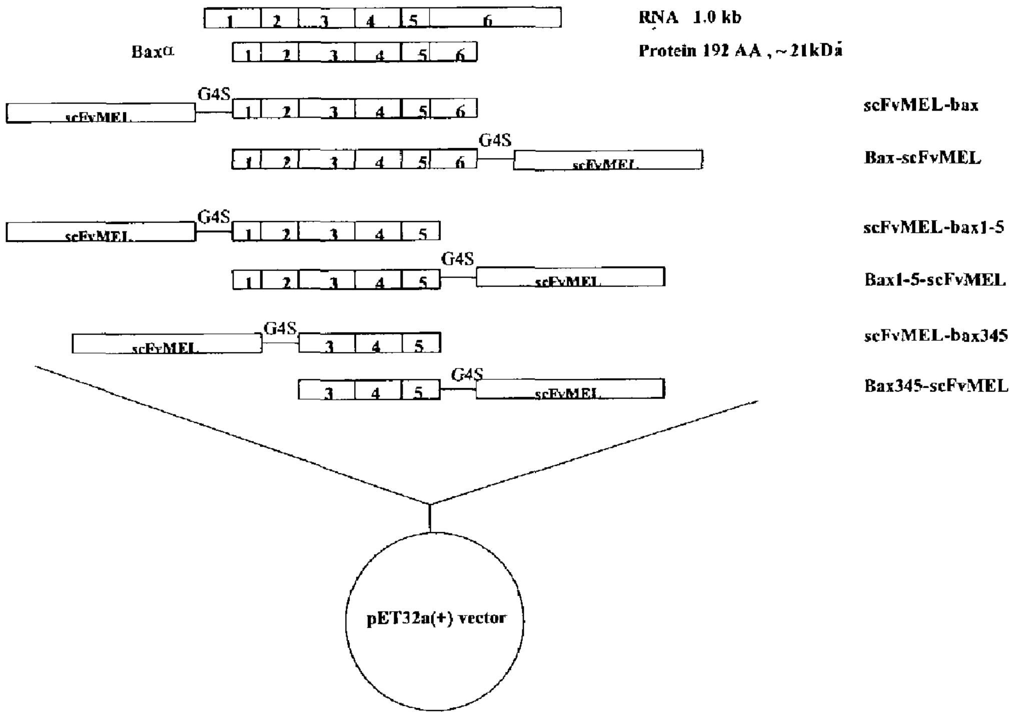
FIGS. 12A and 12B illustrate construction of scFvMEL-bax-related fusion constructs.
Figure 12B:
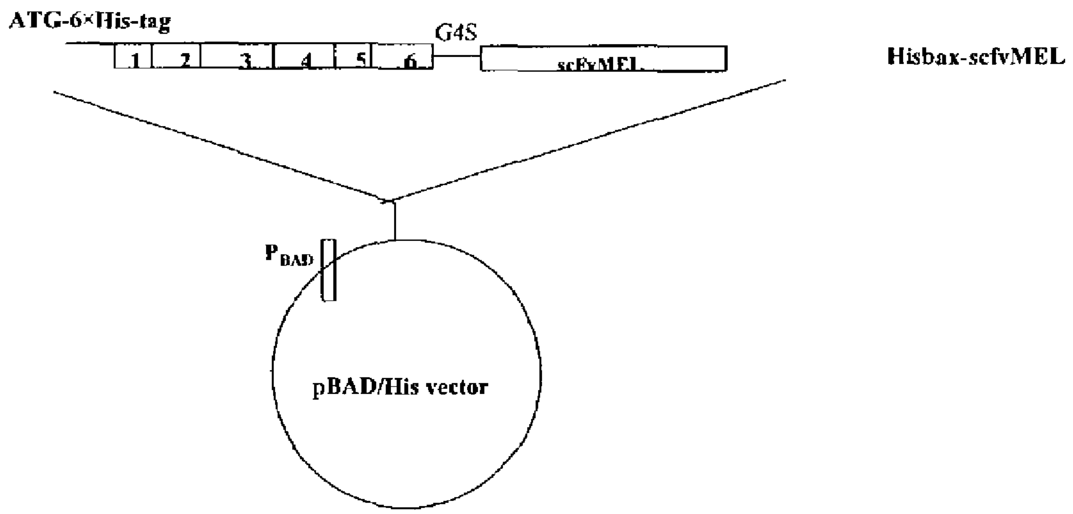

FIGS. 12A and 12B illustrate construction of scFvMEL Bax-related fusion proteins. The Bax gene consists of six exons, and the gene produces alternative transcripts, the predominant form of which encodes a 1.0 kb mRNA and transcript 21 kDa protein which designated Bax α. The boxes indicate exons identified by numbers. Exon 6 is the transmembrane domain. The scFvMEL genes were fused to Bax, truncated Bax1-5 or Bax345 with G4S tether in two different orientations, designated scFvMEL-bax, Bax-scFvMEL, scFvMEL-bax1-5, Bax1-5-scFvMEL, scFvMEL-bax345 and Bax345-scFvMEL. The fusion genes were cloned into pET32a(+) expression vector at Nco I and Xho I sites. Then the plasmid containing fusion genes was transformed into AD494(DE3)pLysS *E. coli* for expression.

Figure 13:
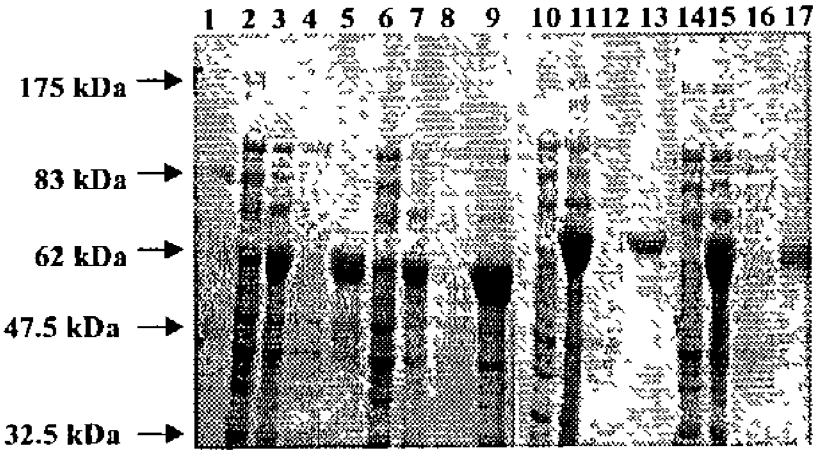
FIG. 13 shows SDS-PAGE and Coomassie Blue Staining analysis of the expression of the fusion proteins.

FIG. 13 demonstrates western blot analysis illustrating expression of scFvMEL Bax-related fusion proteins in pET32a (+) vector. The SDS-PAGE Coomassie Blue staining of truncated bax-related proteins occurred under reducing conditions. The results showed induced expression of scFvMEL and truncated bax fusion proteins in pET32a(+) expression vector. The induced bands were at ~62 kDa for scFvMEL-bax345 and Bax345-scFvMEL and were at ~65 kDa for scFvMEL-Bax1-5 and Bax1-5-scFvMEL, respectively, which also contained a ~20 kDa purification tag.

Figure 14:
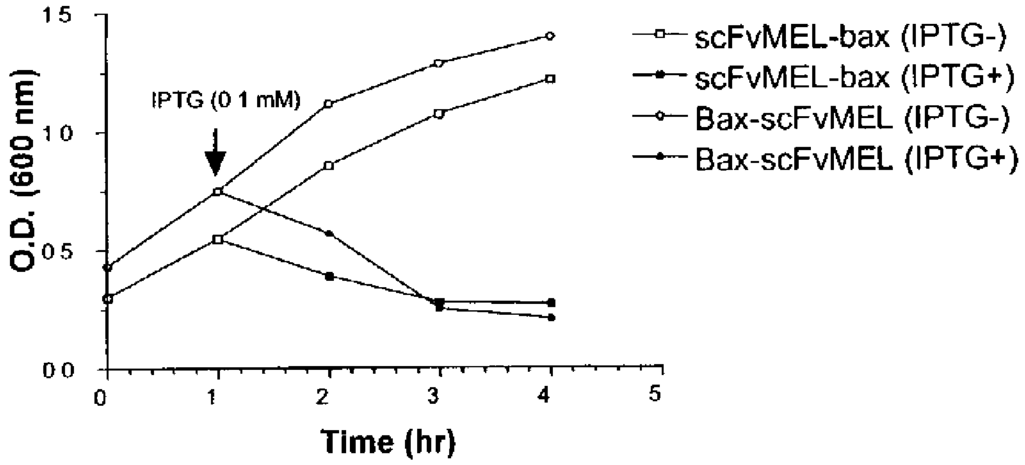
FIG. 14 shows the expression of pET32-scFvMEL-bax and pET32-Bax-scFvMEL transformed into AD494(DE3) pLysS *E coli* and under IPTG induction.

FIG. 14 shows the expression of pET32-scFvMEL-bax and pET32-Bax-scFvMEL transformed into AD494(DE3)

pLysS *E coli* and under IPTG induction. The full-length bax fusion proteins are very toxic to the bacteria because of the highly hydrophobic domain-exon 6. The bacteria containing the plasmid pET32-scFvMEL-Bax or pET32-Bax-scFv were grown in LB media containing 200 μg/ml ampicillin, 70 μg/ml chloramphenicol and 15 μg/ml kanamycin to $OD_{600}$=0.6, induced by addition of IPTG to the final concentration of 0.1 mM, the bacteria died in terms of the decrease value of $OD_{600}$.

Figure 15:
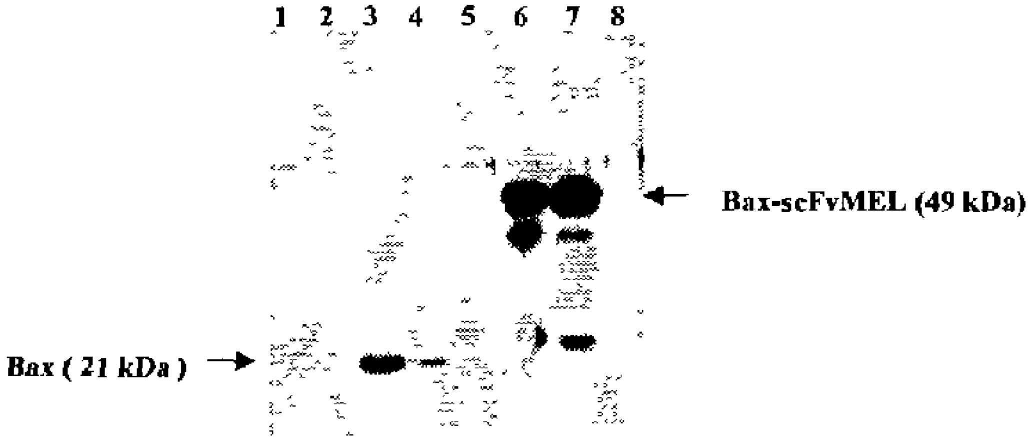
FIG. 15 demonstrates western blotting analysis of the expression of the full length bax and Bax-scFvMEL proteins. Lane 1: pBad/HisA (negative control), Lane 2: pBad/HisLacZ (expression positive control), Lane 3–5: Bax protein (lane 3: expression in RM+glucose+ampicillin, lane 4: expression in RM+ampicillin, lane 5: expression in LB+ampicillin), Lanes 6–8: Bax-scFvMEL protein (lane6: expression in RM+glucose+ampicillin, lane 7: expression in RM+ampicillin, lane 8: expression in LB+ampicillin).

FIG. 15 demonstrates the expression of the full length bax and Bax-scFvMEL in pBAD/HisA vector transformed LMG194 *E coli*. The full length bax gene and Bax-scFvMEL gene were cloned into pBAD/His A vector at Nco I and Xho I sites. The polyhistidine (6 his) tags were followed by the initiation ATG. The plasmids containing either Bax or Bax-scFvMEL were transformed into LMG194 cells for expression, and the expression of the Bax and Bax-scFvMEL proteins was tested in different bacterial growth media (RM containing glucose and 100 μg/ml ampicillin, RM containing 100 μg/ml ampicillin, and LB containing 100 μg/ml ampicillin). The LMG194 transformed pBAD/HisLacZ was used as a positive control, with an expression band at ~120 kDa representing LacZ protein which could be detected by anti-bax antibody. The LMG194 transformed pBAD/HisA (empty vector) was used as a negative control. Western blotting was performed using rabbit anti-Bax monoclonal antibody (1:1000 dilution) as the primary antibody and HRP-Goat-anti-rabbit IgG as the secondary antibody. The results showed that the bands at 21 kDa represent Bax with 6× His-tag, and the bands at ~49 kDa represent Bax-scFvMEL with 6× His-tag.

Figure 16:
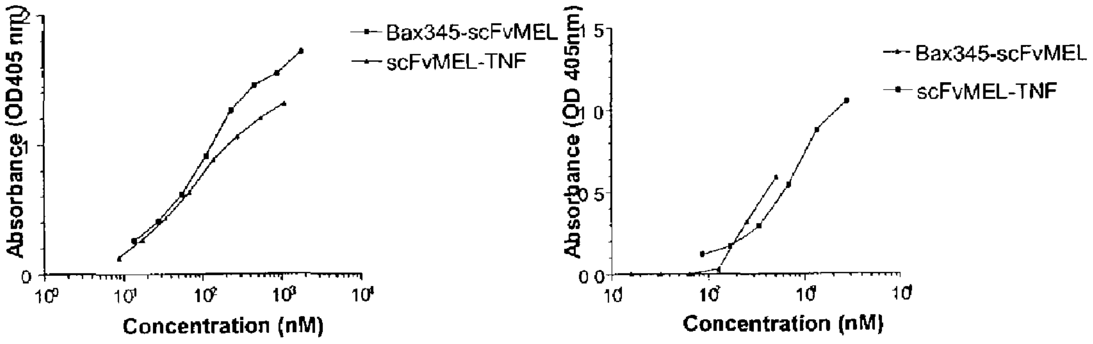
FIGS. 16A and 16B demonstrate the binding activity of scFvMEL moiety of fusion proteins.

Binding activity of scFvMEL moiety of the fusion proteins is demonstrated in FIGS. 16A and 16B. A375-M cells are gp240 antigen-positive human melanoma cell lines. Protein L has the unique ability to bind scFv. The fusion protein Bax345-scFvMEL could bind to either A375-M (FIG. 16A) or Protein L (FIG. 16B) detected with anti-scFvzme antibody. This binding activity is the same as the other fusion protein scFvMEL-TNF.

Figure 17:
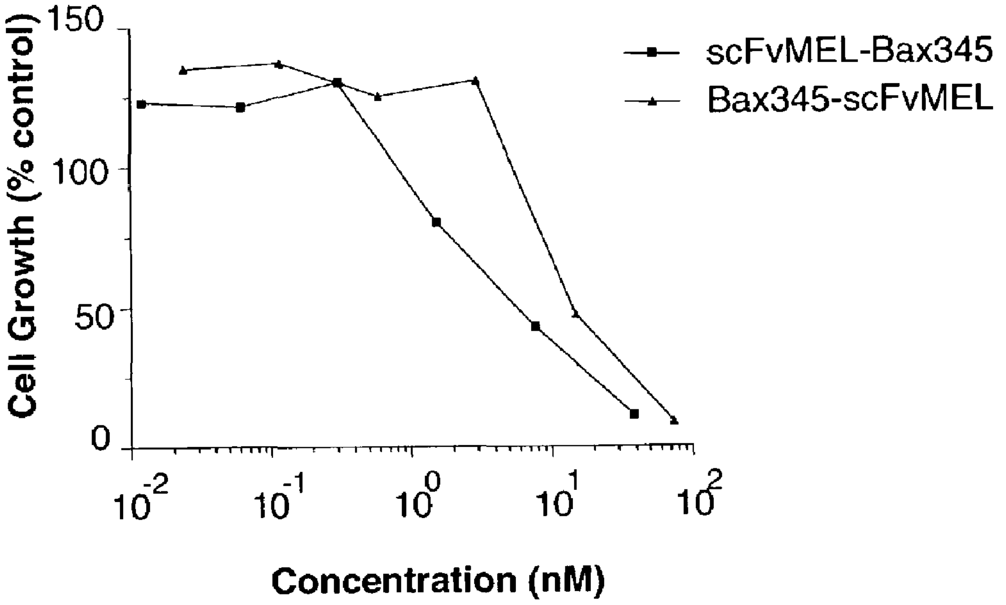
FIG. 17 shows the cytotoxicity of scFvMEL-bax345 and Bax345-scFvMEL fusion proteins on A375-M.

FIG. 17 demonstrates cytotoxicity of scFvMEL-bax345 vs. Bax345-scFvMEL on A375-M. The cytotoxic effects of scFvMEL-bax345 and Bax345-scFvMEL against log-phase human antigen-positive melanoma A375-M cells were assessed. A375-M cells were set up in 96-well plates ($2.5\times10^3$ cells per well). The $IC_{50}$ concentrations of scFvMEL-bax345 and Bax345-scFvMEL were approximately 3 nM and 10 nM, respectively.

Example 28

Elisa of Granzyme B-VEGF121 on Various Cell Lines (Detected with Mouse Anti-VEGF121 Antibody)

ELISA Assay of Binding Activity utilized 96-well plates containing adherent PAE/flk-1, PAE/flt-1, A375-M or SKBR3-HP cells that were blocked by 5% BSA and then reacted with purified Granzyme B-vegf121 at various concentrations. After washing, they were incubated with mouse anti-vegf antibody, followed by HRP-labeled goat anti-mouse IgG. Then as a substrate 2,2'-azino-bis-3-ethylbenzthiazoline-6-sulfonic acid (ABTS) solution with 1 μl/ml of 30% $H_2O_2$ was added. Absorbance at 405 nm was measured after 30 min.

Figure 18:
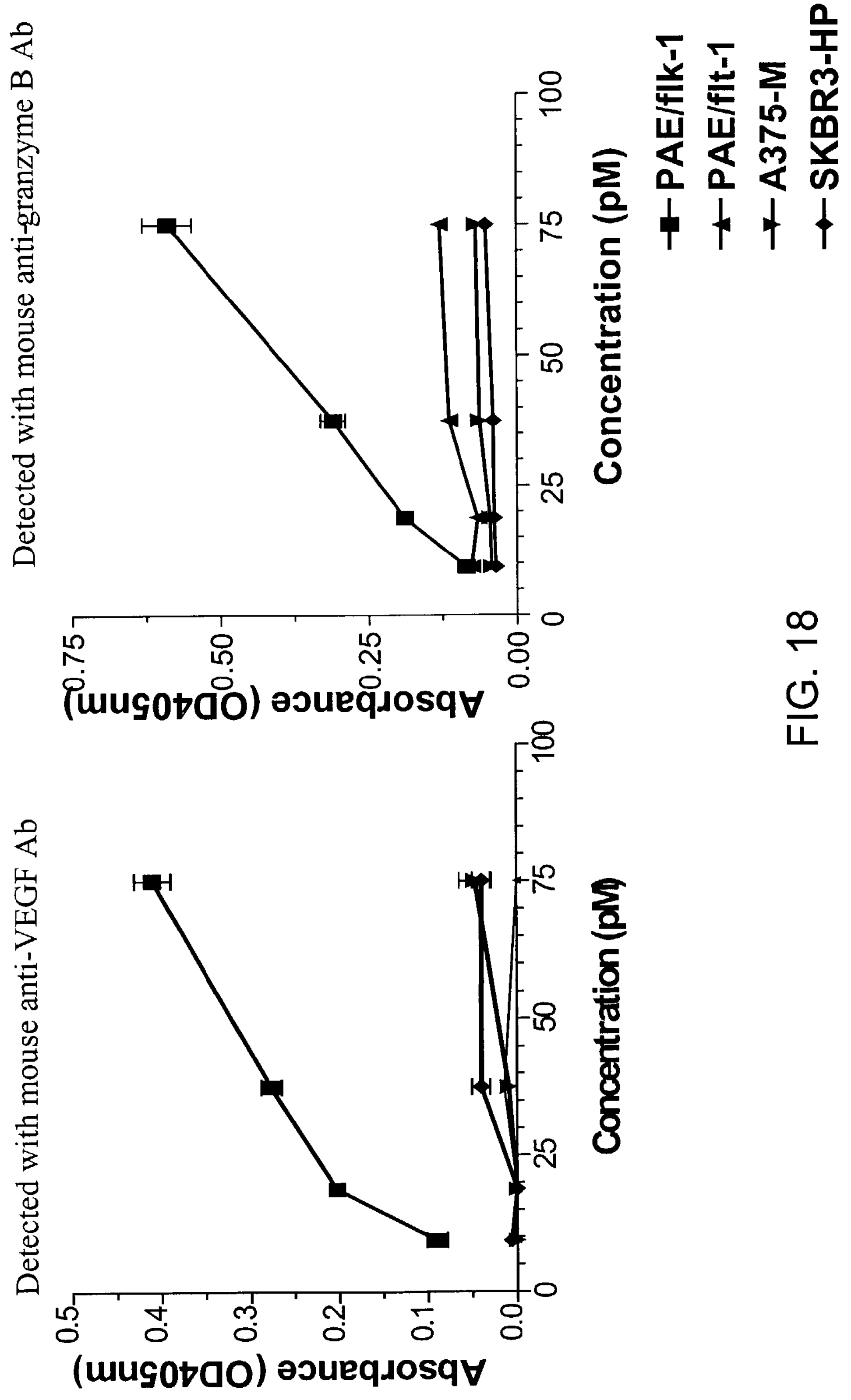
FIG. 18 shows ELISA of granzyme B-Vegf121 on various cell lines (detected with mouse anti-vegf121 antibody and mouse anti-granzyme B antibody).

VEGF121 can specifically bind to the flk-1/KDR receptor on the vascular endothelial cells (FIG. 18). The experiment showed that the fusion protein Granzyme B-vegf121 specifically binds to PAE/flk-1 cells which overexpress flk-1 receptors, but there were no binding activities on PAE/flt-1 (overexpressed flt-1 receptors) or human melanoma A375-M cells and human breast cancer SKBR3-HP cells. That is, GrB/VEGF121 can specifically bind to PAE/flk-1 cells which overexpress flk-1/KDR receptor detected with either VEGF121 antibody or GrB antibody

Example 29

Cytotoxicity of Granzyme B/VEGF121 on Transfected Endothelial Cells

Cytotoxicity of Granzyme B-VEGF121 against PAE/flk-1 vs PAE/flt-1 cells was assessed against log-phase PAE/flk-1 (transfected with flk-1/KDR receptor) and PAE/flt-1 (transfected with flt-1 receptor) in culture. Briefly, PAE cells were plated into 96-well plates at a density of $2.5\times10^3$ cells per well. After 24 hr, the cells were treated with medium containing different concentrations of Granzyme B-VEGF121. The effect on the growth of cells was determined using XTT after 72 hrs. Plates were read on a microplate ELISA reader at 546 nm.

Figure 19:
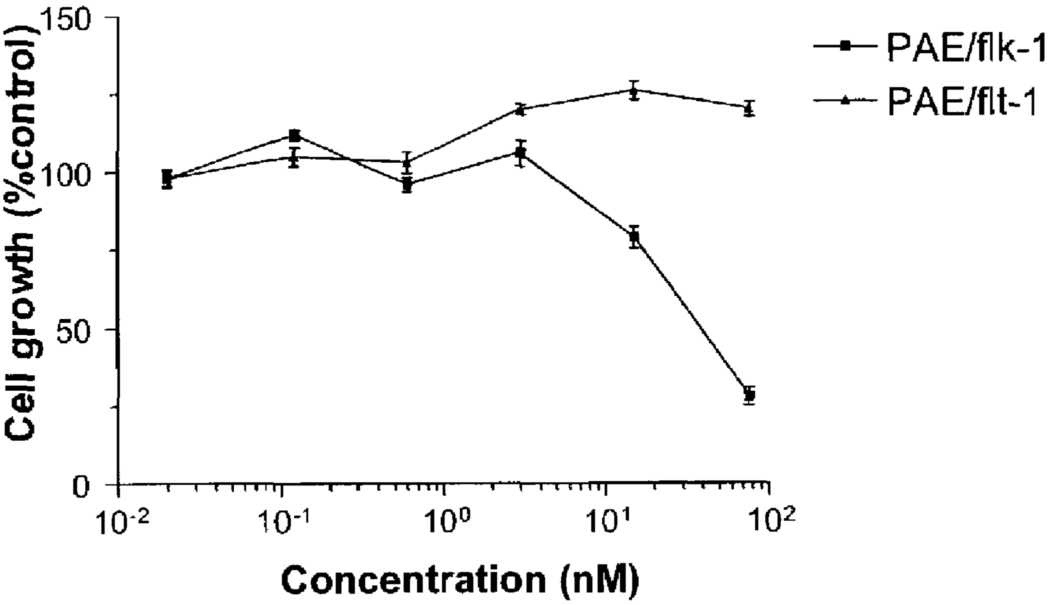
FIG. 19 demonstrates cytotoxicity of Granzyme B-VEGF121 on transfected endothelial cells.

The results showed that a 50% growth inhibitory effect ($I.C._{50}$) was found at a concentration of ~10 nM on PAE/flk-1 cells (FIG. 19). However, no cytotoxic effects were found on PAE/flt-1 cells. The cytotoxicity of Granzyme B-VEGF121 on PAE/flk-1 cells indicates that the VEGF121 moiety of the fusion specifically bound to flk-1 over-expression on the cell-surface, followed by delivery of granzyme B to the interior of targeted cells and cytotoxicity to the target cells.

Example 30

Cytotoxicity Assay of Granzyme B-VEGF121 vs VEGF121-rGel in Vitro Against PAE/FLK-1

PAE cells in Ham's F-12 medium with 10% FBS were plated into 96-well plates at a density of $2.5\times10^3$ cells per well and allowed to adhere for 24 hr at 37° C. in 5% $CO_2$. After 24 hr, the medium was replaced with medium containing different concentrations of Granzyme B-VEGF121 or VEGF121-rGel. After 72 hrs, the effect of Granzyme B-VEGF121 or VEGF121-rGel on the growth of cells in culture was determined using XTT. Plates were read on a microplate ELISA reader at 540 nm.

Figure 20:
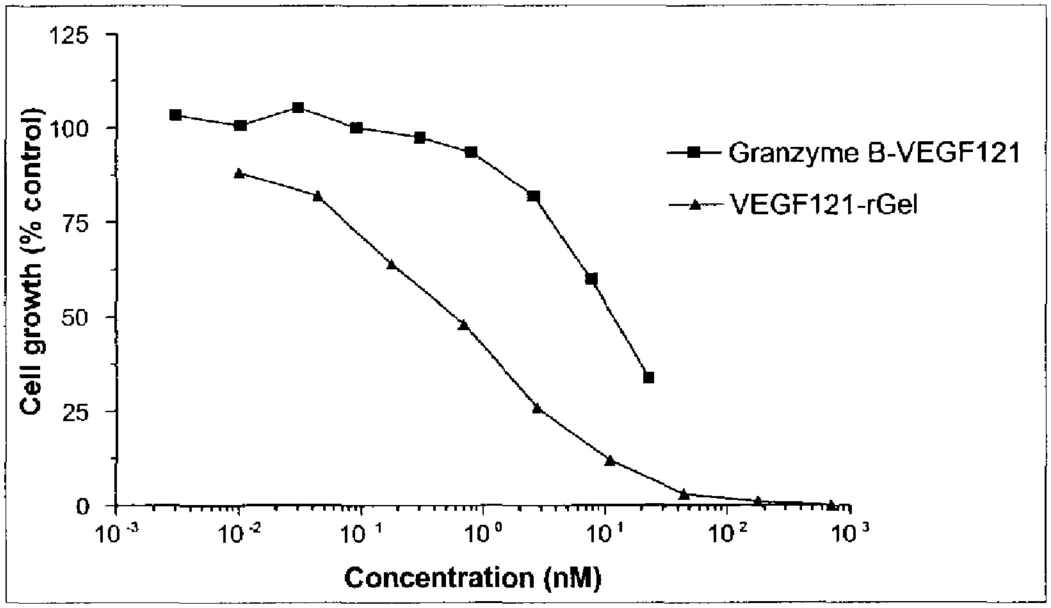
FIG. 20 shows cytotoxicity assay of granzyme B-Vegf121 vs. vegf121 rgel in vitro against PAE/FLK-1.

The results showed that the $I.C._{50}$ of VEGF121-rGel was approximately 1 nM (FIG. 20). The $I.C._{50}$ of Granzyme B-VEGF121 was 10-fold higher than that of VEGF 121-rGel.

Example 31

Caspase Activity of PAE Cells Treated with Granzyme B-VEGF121

Western Blotting analysis of caspase activation was carried out with 30 μg of whole cell lysates. Following SDS-PAGE, the proteins were electrophoretically transferred onto nitrocellulose membranes. The membranes were blocked with phosphate-buffered saline with 0.5% Tween 20 (PBST) containing 5% fat-free milk and then exposed to caspase-8, caspase-3, caspase-6, caspase-7, cleaved caspase-3, PARP or cleaved DFF45 antibodies, respectively. The membranes were washed with PBST and treated with secondary antibodies conjugated to horseradish peroxidase. The antigen-antibody reaction was visualized by an enhanced chemiluminescence (ECL) assay using Amersham ECL develop reagents and exposure to film.

Figure 21:
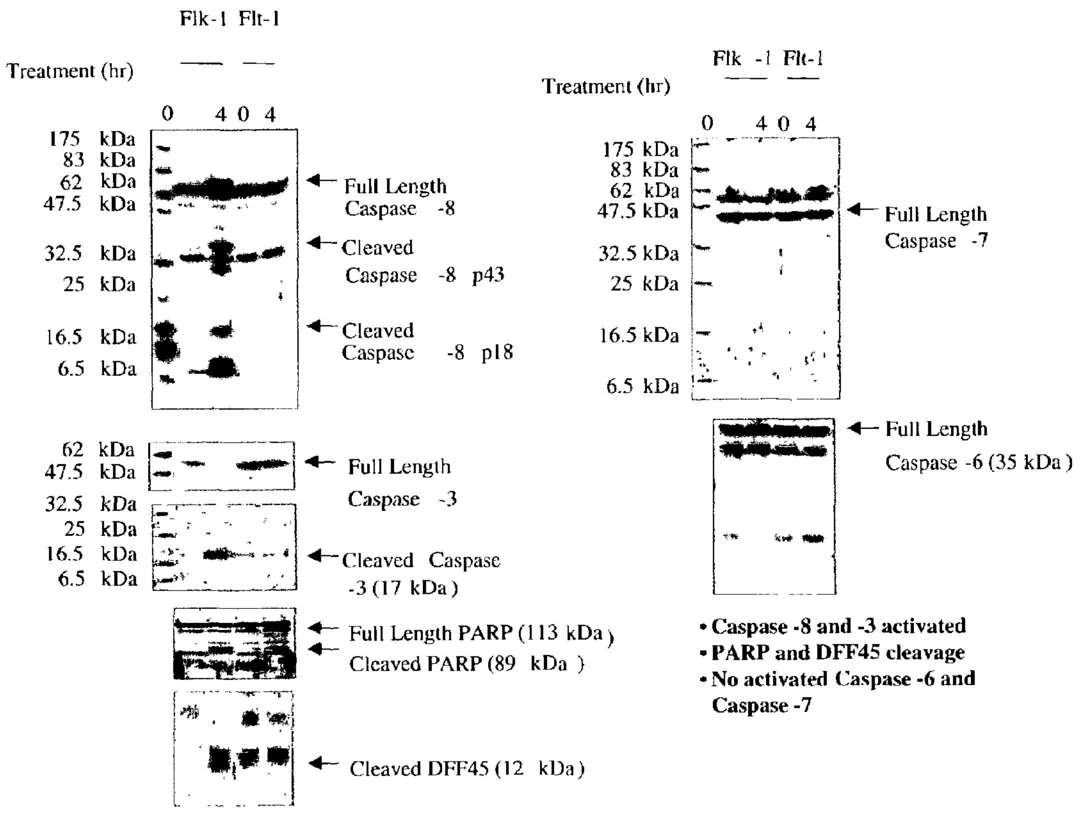
FIG. 21 illustrates caspase activity on PAE cells treated with Granzyme B-Vegf121.

The results showed that after a 4 hr treatment by Granzyme B-VEGF121, cleaved caspase-8, cleaved caspase-3, cleaved PARP and cleaved DFF45 were observed on PAE/flk-1 cells but not on PAE-flt-1 cells (FIG. 21). However, caspase-6 or caspase-7 was not cleaved by Granzyme B-VEGF121, which indicated that Granzyme B-VEGF121 activated caspases only involved in caspase-8, caspase-3 apoptosis pathway.

Example 32

In Situ Cell Death Detection (Tunel)

Cleavage of genomic DNA during apoptosis may yield double-stranded, low molecular weight DNA fragments as well as single strand breaks (nicks) in high molecular weight DNA. Those DNA strand breaks can be identified by labeling free 3'-OH termini with modified nucleotides in an enzymatic reaction. This method uses terminal deoxynucleotidyl transferase (TdT), which catalyzes polymerization of nucleotides to free 3'-OH DNA ends in a template-independent manner, is used to label DNA strand breaks. Incorporated fluorescein is detected by anti-fluofescein antibody Fab fragments from sheep, conjugated with alkaline phosphatase (AP). After substrate reaction, stained cells can be analyzed under light microscope.

For the cell treatments, cells were plated onto 16-well chamber slides, 2500 cells/well, incubated for overnight at 37° C./5% $CO_2$ conditions. Cells were treated with fusion protein GrB-scFvMEL or GrB-vegf121 at I.C-$_{50}$ concentration for different times (24, 48 hr, etc.) and washed briefly with PBS.

For the TUNEL Assay, cells were fixed with 3.7% formaldehyde at room temperature for 20 min, after rinsing with PBS, permeabilzed with 0.1% Triton X-100, 0.1% sodium citrate on ice for 2 min and then washed with PBS twice. Cells were incubated with TUNEL reaction mixture at 37° C. for 60 min, followed by incubation with Converter-AP at 37° C. for 30 min, and finally reacted with Fast Red substrate solution at room temperature for 10 min. After final wash step, the slides were mounted in mounting medium and analyzed under light microscope.

Positive controls were included in each experimental set up. Fixed and permeabilized cells were incubated with 1 mg/ml of DNase I for 10 min at 37° C. to induce DNA strand breaks.

The effect of GrB-scFvMEL on A375-M and SKBR3-HP cells by in situ cell death detection (TUNEL) was determined. TUNEL positive results were observed with respect to GrB-scFvMEL treated antigen-positive human melanoma A375-M cells at 48-hr but not with respect to GrB-scFvMEL treated antigen-negative human breast cancer SKBR-3-HP cells. This indicated that GrB-scFvMEL could specifically target antigen-positive melanoma cells and induce cell apoptosis.

The effect of GrB-vegf121 on PAE/Flk-1 vs. PAE/Flt-1 cells by TUNEL Assay was determined. VEGFR2/KDR was over-expressed on PAE/Flk-1 but not PAE/Flt-1 cell surface. VEGF121 specifically targeted VEGFR2/KDR, delivering GrB into PAE/Flk-1 cells. TUNEL Assay positive results were observed with respect to GrB-vegf121 treated PAE/Flk-1 at 24 hr and 48 hr but not with respect to GrB-vegf121 treated PAE/Flt-1. GrB-vegf121 induced PAE/Flk-1 cell apoptosis.

Example 33

Internalization of GRB/VEGF121 into PAE Cells by Immunofluorescence Microscopy

This example is directed to an internalization analysis of GrB/VEGF121 by immunofluorescence microscopy. Cells were treated as follows. Cells were plated in 16-well chamber slides (Nunc), $1\times10^4$ cells per well, incubated for overnight at 37 ° C./5% $CO_2$ conditions. Cells were treated with 200 nM of GrB/VEGF121 for 4 h and then washed briefly with PBS. The cell surface was stripped by incubations for 10 min with glycine buffer (500 mM NaCl, 0.1 M glycine, pH 2.5), neutralized for 2 min with 0.5 M Tris, pH 7.4, and washed briefly with PBS.

Immunofluorescent staining occurred as follows. Cells were fixed in 3.7% formaldehyde for 15 min at RT, followed by a brief rinse with PBS and then permeabilization for 10 min in PBS containing 0.2% Triton X-100. They were then washed three times with PBS. Samples were incubated with 3% BSA for 1 h at RT to block nonspecific binding sites, then incubated with mouse anti-granzyme B antibody (1:100 dilution) at RT for 1 h, followed by washing three times with PBS. The samples were incubated with fluorescein isothiocyanate (FITC)-coupled anti-mouse IgG (Sigma) (1:100 dilution) at RT for 1 h and then washed three times with PBS. The walls and gaskets were removed carefully. After air drying, the slide was mounted and analyzed under a fluorescence microscope.

The results showed that the GrB moiety of GrB/$VEGF_{121}$ was delivered into the cytosol of PAE/flk-1 but not into that of PAE/flt-1 cells after 4 h treatment.

Example 34

GRB/VEGF121 Induces Apoptosis on PAE/Flk 1 Cells Detected by Tunel Assay

Cleavage of genomic DNA during apoptosis may yield double-stranded, low molecular weight DNA fragments as well as single strand breaks (nicks) in high molecular weight DNA. Those DNA strand breaks can be identified by labeling free 3'-OH termini with modified nucleotides in an enzymatic reaction. This method uses terminal deoxynucleotidyl transferase (TdT), which catalyzes polymerization of nucleotides to free 3'-OH DNA ends in a template-independent manner, to label DNA strand breaks. Incorporated fluorescein is detected by anti-fluorescein antibody Fab fragments from sheep conjugated with alkaline phosphatase (AP). After substrate reaction, stained cells can be analyzed under light microscope.

Cell treatments were as follows. Cells were plated onto 16-well chamber slides, 2500 cells/well, incubated for overnight at 37° C./5% $CO_2$ conditions. Cells were treated with fusion protein GrB-vegf121 at I.C.$_{50}$ concentration for different times (24, 48 hr, etc) and washed briefly with PBS.

The TUNEL Assay was as follows. Cells were fixed with 3.7% formaldehyde at room temperature for 20 min, followed by rinsing with PBS and permeabilization with 0.1% Triton X-100, 0.1% sodium citrate on ice for 2 min. They were then washed with PBS twice. Cells were incubated with TUNEL reaction mixture at 37° C. for 60 min, followed by incubation with Converter-AP at 37° C. for 30 min, and finally reacted with Fast Red substrate solution at room temperature for 10 min. After final wash step, the slides were mounted in mounting medium and analyzed under light microscope.

The results indicated that VEGFR2/KDR over-expressed on PAE/Flk-1 but not the PAE/Flt-1 cell surface. VEGF121 specifically targeted VEGFR2/KDR, delivering GrB into PAE/Flk-1 cells. TUNEL Assay positive results were demonstrated for GrB/$VEGF_{121}$-treated PAE/Flk-1 at 24 hr and 48 hr but not on GrB/VEGF121-treated PAE/Flt-1. Thus, GrB/VEGF121 induced PAE/Flk-1 apoptosis.

Example 35

Cytochrome C Release of PAE Cells Treated with GRB/VEGF121

Cytochrome c plays an important role in apoptosis. The protein is located in the space between the inner and outer mitochonial membranes. An apoptotic stimulus triggers the release of cytochrome c from the mitochondria into the cytosol where it binds to Apaf-1. The cytochrome c/Apaf-1 complex activates caspase-9, which then activates caspase-3 and other downstream caspases.

Materials and methods for the cytochrome c release apoptosis assay: (from Oncogene Research Products; San Diego, Calif.) was as follows. PAE/flk-1 cells and PAE/flt-1 cells ($5\times10^7$) were treated with GrB/VEGF121 at concentrations of 0.1 nM and 20 nM for 24 h. Cells were collected. After washing cells with 10 ml of ice-cold PBS, the cells were resuspended with 0.5 ml of 1× cytosol extraction buffer mix containing DTT and Protease Inhibitors, and incubated on ice for 10 min. Cells were homogenized in an ice-cold glass homogenizer. The homogenate was transferred to a 1.5 ml microcentrifuge tube and centrifuged at 700 μg for 10 min at 4° C. The supernatant was transferred to a fresh 1.5 ml tube and centrifuged at 10,000×g for 30 min at 4° C. Supernatant was collected as a cytosolic fraction. The pellets were resuspended in 0.1 ml mitochondrial extraction buffer mix containing DTT and protease inhibitors, vortexed for 10 seconds, and saved as a mitochondrial fraction. Protein concentrations were determined by using Bio-Rad Laboratories, Inc. (Hercules, Calif.) Bradford Protein Assay. 10 μg of each cytosolic and mitochondrial fraction isolated from non-treated and treated cells were loaded on a 15% SDS-PAGE, followed by standard Western blot procedure and probing with cytochrome c antibody (1 μg ml).

Figure 22:
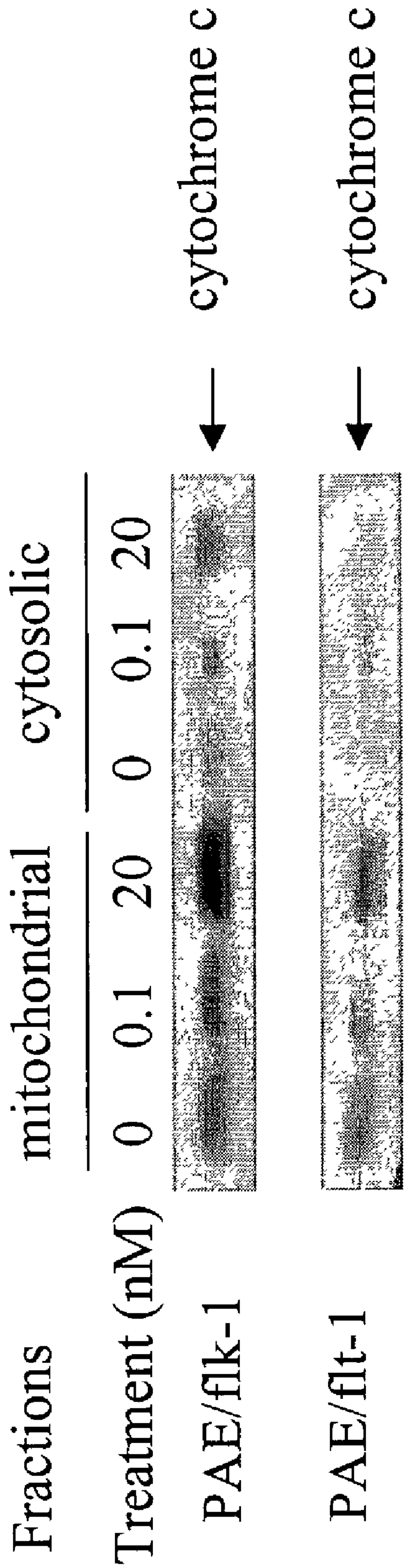
FIG. 22 demonstrates cytochrome c release of PAE cells treated with GRB/VEGF121.

For the cytochrome c release apoptosis assay, PAE cells were treated with GrB/VEGF121 at different concentrations for 24 h. A highly enriched mitochodrial fraction was isolated from the cytosol. Cytochrome c translocation from mitochondria into cytosol during apoptosis was determined by western blotting using cytochrome c antibody. FIG. 22 shows cytochrome c release on PAE/flk-1 but not on PAE/flt-1 cells after GrB/VEGF121 treatment.

Example 36

Bax Translocation of PAE Cells After GRB/VEGF121 Treatment

Bax, a 21 kDa protein with extensive amino acid homology with Bcl-2, is variably expressed by different cells. Bax as a pro-apoptotic member of the Bcl-2 family showed some structural similarities with pore-forming proteins. Hence, it is believed that Bax can form transmembrane pores across the outer mitochondrial membrane, which leads to a loss of membrane potential. The localization of Bax has been shown to change from the cytosol to the mitochondria upon the receipt of an apoptotic stimulus.

Isolation of the cytosolic fraction and mitochondrial fraction was performed using an Oncogene Research Products kit (Cat # QIA87; San Diego, Calif.). Protein concentrations were determined by using Bio-Rad Laboratories, Inc. (Hercules, Calif.) Bradford Protein Assay. 10 μg of each cytosolic and mitochondrial fraction isolated from non-treated and treated cells were loaded on a 12% SDS-PAGE, and then a standard Western blot procedure was performed and probed with Bax antibody (Santa Cruz Biotechnology, Inc.; Santa Cruz, Calif.; 1:200 dilution).

Figure 23:
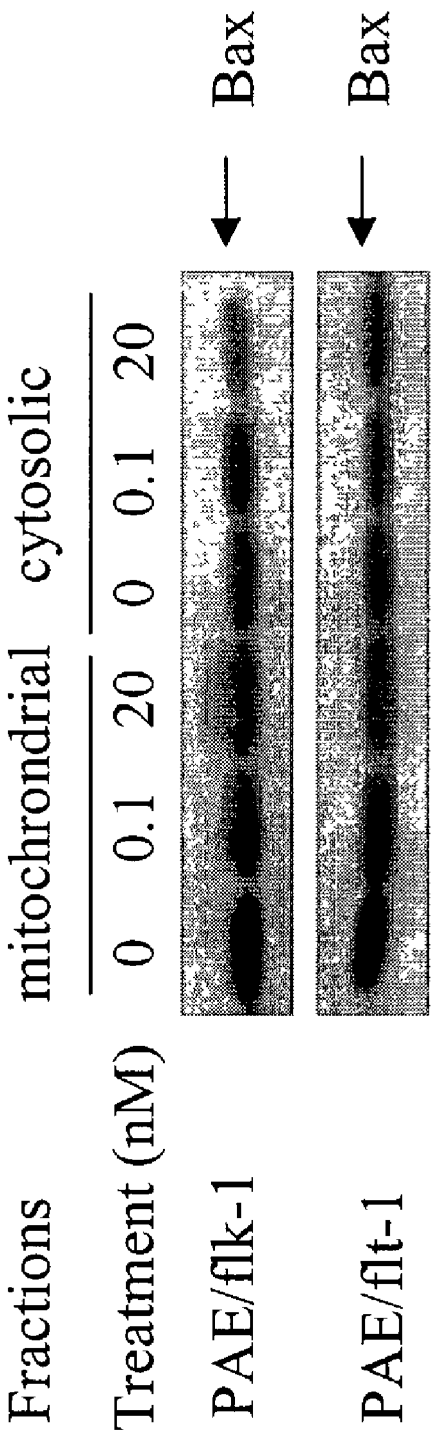
FIG. 23 shows Bax translocation of PAE cells after GRB/$VEGF_{121}$ treatment.

Western blotting analysis was performed of Bax expression on PAE cells after GrB/VEGF121 treatment for 24 h. The results showed that the localization of Bax changed from the cytosol to the mitochondria on PAE/flk-1 but not on PAE/flt-1 cells after treatment with GrB/VEGF121 at the concentration of 20 nM ($I.C._{50}$). FIG. 23 shows that Bax increased in mitochondria and decreased in cytosol on PAE/flk-1 cells after GrB/$VEGF_{121}$ treatment for 24 h at 20 nM concentration, indicating that Bax translocated from the cytosol to the mitochondria during apoptosis.

Example 37

Internalization of GRB/SCFVMEL into A375-M Cells by Immunofluorescence Microscopy Internalization analysis of GrB/scFvMEL by immunofluorescence microscopy utilized the following methods. Cells were plated in 16-well chamber slides (Nunc), $1\times10^4$ cells per well, and incubated for overnight at 37° C./5% $CO_2$ conditions. Cells were treated with 100 nM of GrB/scFvMEL for 1 h and 6 h, then washed briefly with PBS. Cell surface was stripped by incubations of 10 min with glycine buffer (500 mM NaCl, 0.1 M glycine, pH 2.5), neutralized for 2 min with 0.5 M Tris, pH 7.4, washed briefly with PBS.

For immunofluorescent staining, cells were fixed in 3.7% formaldehyde for 15 min at RT, followed by a brief rinse with PBS and then permeabilization for 10 min in PBS containing 0.2% Triton X-100; the cells were then washed three times with PBS. Samples were incubated with 3% BSA for 1 h at RT to block nonspecific binding sites, then incubated with mouse anti-granzyme B antibody (1: 100 dilution) at RT for 1 h followed by washing three times with PBS. The samples were incubated with fluorescein isothiocyanate (FITC)-coupled anti-mouse IgG (Sigma) (1: 100 dilution) at RT for 1 h, washed three times with PBS. The walls and gaskets were removed carefully. After air drying, the slide was mounted and analyzed under light and fluorescence microscope.

The results showed that GrB moiety of GrB/scFvMEL was delivered into the gp240 antigen-positive A375-M cells by scFvMEL binding to gp240 antigen.

Example 38

GRB/SCFVMEL Induces Apoptosis on A375-M Cells Detected by Tunel Assay

Cells (3000 cells per well) were treated with GrB/scFvMEL at $I.C._{50}$ concentration for different times (16 h, 24 h) and washed briefly with PBS. Cells were fixed with 3.7% formaldehyde at room temperature for 20 min, followed by rinsing with PBS and permeabilization with 0.1% Triton X-100, 0.1% sodium citrate on ice for 2 min. They were then washed with PBS twice. Cells were incubated with TUNEL reaction mixture at 37° C. for 60 min. After a final wash step, the cells were analyzed under fluorescence microscopy.

The results demonstrated that GrB/scFvMEL induced apoptosis on antigen-positive A375-M cells but not on antigen-negative SKBR3-HP cells after treatment for 16 h and24 h.

Example 39

Cytochrome C Release in A375-M VS. SKBR3-HP Cells Treated with GRB/SCFVMEL

Cytochrome c release apoptosis assay was performed as described (Oncogene Research Products; San Diego, Calif.; Cat# QIA87). The materials and methods were as follows. Human melanoma A375-M cells and human breast cancer SKBR3-HP cells ($5\times10^7$) were treated with GrB/scFvMEL at concentrations of 5 nM and 50 nM for 24 h. Cells were collected. After washing cells with 10 ml of ice-cold PBS, cells were resuspended with 0.5 ml of 1× cytosol extraction buffer mix containing DTT and protease inhibitors, incubate on ice for 10 min. Cells were homogenized in an ice-cold glass homogenizer. Homogenate was transferred to a 1.5 ml microcentrifuge tube, and centrifuge at 700×g for 10 min at 4° C. The supernatant was transferred to a fresh 1.5 ml tube, and centrifuged at 10,000×g for 30 min at 4 ° C. Supernatant was collected as a cytosolic fraction. The pellet was resuspended in 0.1 ml Mitochondrial Extraction Buffer Mix containing DTT and protease inhibitors, vortexed for 10 seconds, and saved as a mitochondrial fraction. Protein concentrations were determined by using Bio-Rad Laboratories, Inc. (Hercules, Calif.) Bradford Protein Assay. 10 μg of each cytosolic and mitochondrial fraction isolated from non-treated and treated cells were loaded on a 15% SDS-PAGE, and then a standard Western blot procedure was performed and probed with cytochrome c antibody (1 μg/ml).

Figure 24:
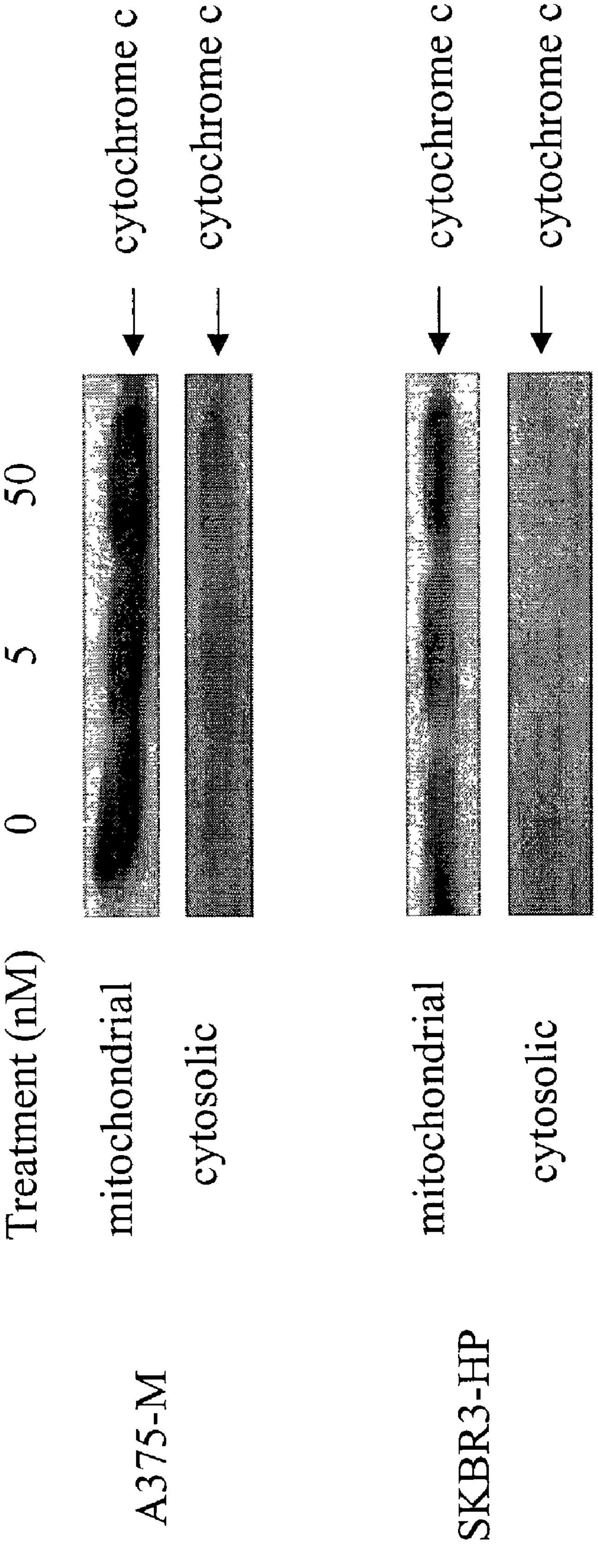
FIG. 24 illustrates cytochrome c release in A375-M vs. SKBR3-HP cells treated with GRB/scFvMEL.

Cytochrome c release apoptosis assay: A375-M and SKBR3-HP cells were treated with GrB/scFvMEL at different concentrations for 24 h. The mitochondrial fraction was isolated from the cytosol, and then cytochrome c release from mitochondria into cytosol during apoptosis was determined by western blotting using cytochrome c antibody. FIG. 24 indicates that cytochrome c release on A375-M but not on SKBR3-HP cells after GrB/scFvMEL treatment.

Example 40

GRB/VEGF$_{121}$ Induces Dna Laddering on PAE/FLK-1 Cells

A DNA laddering assay procedure was followed to analyze influence of GrB/VEGF121 on PAE/FLK-1 cells.

PAE cells ($2\times10^6$) were treated with GrB/VEGF121 at the I.C.$_{50}$ concentration for 24 h. Cells were briefly washed with PBS and then harvested by trypsinization, followed by centrifugation at 200×g for 5 min. Cells were resuspended in 1 ml of PBS, transferred into 10 ml of ice-cold 70% ethanol and stored at −20° C. for 24 h or longer. Fixed cells were centrifuged at 800×g for 5 min, and the ethanol was removed thoroughly. The cell pellets were resuspended in 40 μl phosphate-citrate buffer (PCB), consisting of 192 parts of 0.2 M $Na_2HPO_4$ and 8 parts of 0.1 M citric acid (pH 7.8) and incubated at RT for at least 30 min. After spinning cells down at 1000×g for 5 min, the supernatant was transferred to a new tube. To samples were added 3 μl of 0.25% Nonide NP-40 and 3 μl of RNase (1 mg/ml) and incubated for 30 min at 37° C., followed by addition of 3 μl of proteinase K (1 mg/ml) and incubation for another 30 min at 37° C. An 1.5% agarose gel was run to detect DNA by ethidium bromide under UV light.

Figure 25:
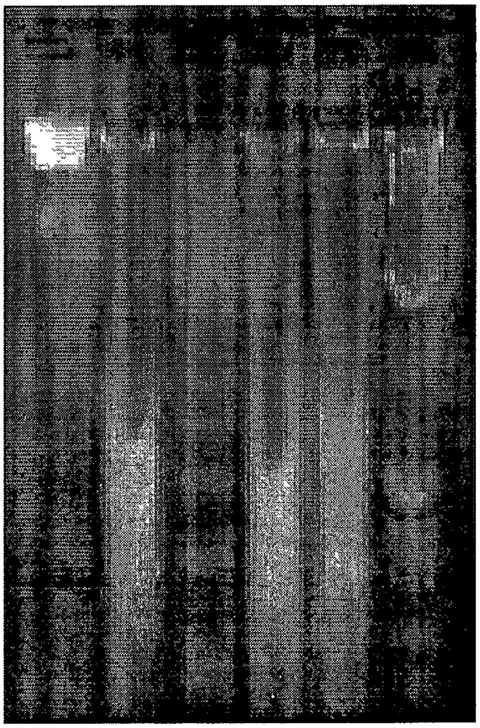
FIG. 25 illustrates GrB/VEGF121 induces DNA laddering on PAE/flk-1 cells.

FIG. 25 shows that GrB/VEGF121 induces DNA laddering on PAE/flk-1 but not on PAE/flt-1 cells.

Example 41

Elisa of GRB/SCFVMEL on gp240 AG-Positive A375-M vs gp240 AG-Negative T-24 Cells Detected by GrB Mouse Mab Binding activity of GrB/scFvMEL to gp240 antigen-positive human melanoma A375-M vs gp240 antigen-negative human bladder cancer T-24 cells was analyzed by ELISA Ninety six-well plates coated with 50,000 cells per well of A375-M or T-24 cells were blocked by 5% BSA, and the cells were then reacted with GrB/scFvMEL at various concentration for 1 h at RT. After washing, the samples were incubated with GrB mouse monoclonal antibody (1 μg/ml) at RT for 1 h, followed by HRP-goat anti-mouse IgG. Then substrate 2,2'-azino-bis-3-ethylbenzthiazoline-6-sulfonic acid (ABTS) solution with 1 μl/ml of 30% $H_2O_2$ added. Absorbance at 405 nm was measured after 30 min.

Figure 26:
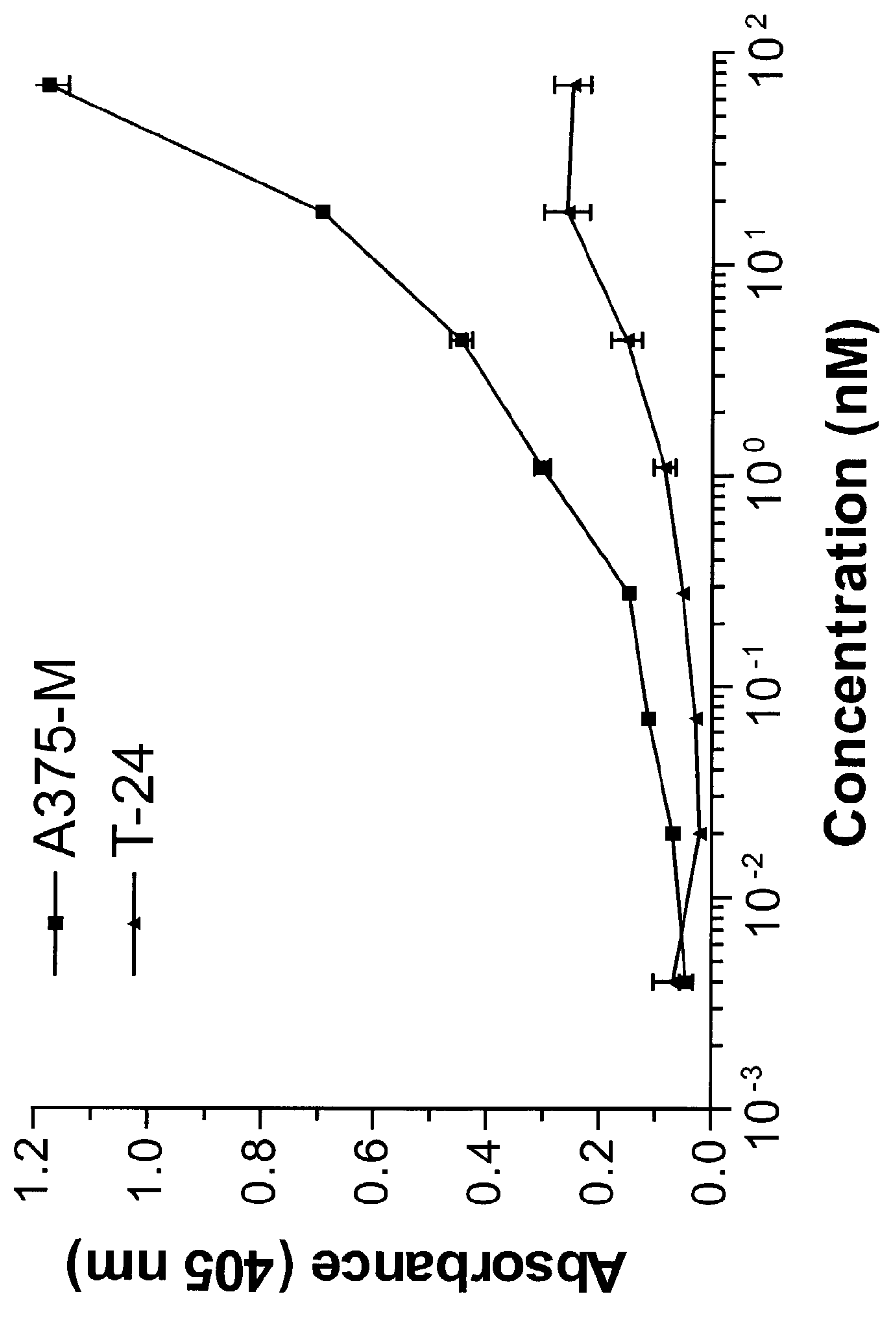
FIG. 26 shows ELISA of GrB/scFvMEL on gp240 Ag-positive A375-M vs gp240 Ag-negative T-24 cells detected by Grb mouse mAb.

FIG. 26 shows that GrB/scFvMEL could specifically bind to Ag-positive A375-M but not bind to Ag-negative T-24 cells, indicating there was binding activity of scFvMEL moiety of the fusion GrB/scFvMEL.

REFERENCES

The following references, to the extent that they provide exemplary procedural or other details supplementary to those set forth herein, are specifically incorporated herein by reference.

Patents

EPO 0273085
EPO 03089
GB 2193095A
PCT/US85/01161
PCT/US89/5040
U.S. Pat. No. 4,162,282
U.S. Pat. No. 4,215,051
U.S. Pat. No. 4,310,505
U.S. Pat. No. 4,376,110
U.S. Pat. No. 4,533,254
U.S. Pat. No. 4,554,101
U.S. Pat. No. 4,676,980
U.S. Pat. No. 4,728,575
U.S. Pat. No. 4,728,578
U.S. Pat. No. 4,737,323
U.S. Pat. No. 4,816,567
U.S. Pat. No. 4,921,706
U.S. Pat. No. 4,946,778
U.S. Pat. No. 5,401,511
U.S. Pat. No. 5,401,511
U.S. Pat. No. 5,432,260
U.S. Pat. No. 5,440,013
U.S. Pat. No. 5,446,128
U.S. Pat. No. 5,475,085
U.S. Pat. No. 5,603,872
U.S. Pat. No. 5,603,872
U.S. Pat. No. 5,618,914

U.S. Pat. No. 5,656,725
U.S. Pat. No. 5,670,155
U.S. Pat. No. 5,672,681
U.S. Pat. No. 5,674,976
U.S. Pat. No. 5,710,245
U.S. Pat. No. 5,786,214
U.S. Pat. No. 5,840,833
U.S. Pat. No. 5,849,718
U.S. Pat. No. 5,859,184
U.S. Pat. No. 5,871,727
U.S. Pat. No. 5,879,703
U.S. Pat. No. 5,889,155
U.S. Pat. No. 5,889,155
U.S. Pat. No. 5,929,237
U.S. Pat. No. 5,939,277
U.S. Pat. No. 6,107,090
U.S. patent Ser. No. 07/715,272
U.S. patent Ser. No. 07/931,811
U.S. patent Ser. No. 07/934,373
WO 91/00360
WO 92/200373
WO 93/06213
WO 93/08829
WO 97/19179
WO 97/22364
WO 97/46259
WO 98/0748
WO 99/18933
WO 99/45128
WO 99/49059

Publications

Adams G P, Schier R. Generating improved single-chain Fv molecules for tumor targeting. J Immunol Methods. 10 Dec. 1999; 231(1–2):249–60.

Adams J. M. and Cory S. The Bcl-2 protein family: arbiters of cell survival. Science, 281:1322–1326, 1998.

Aksentijevich I, Pastan I, Lunardi-Iskandar Y, Gallo R C, Gottesman M M, Thierry A R. In vitro and in vivo liposome-mediated gene transfer leads to human MDR1 expression in mouse bone marrow progenitor cells. Hum Gene Ther. 10 Jun. 1996; 7(9):1111–22.

Andrade F, Roy S, Nicholson D, Thomberry N, Rosen A, Casciola-Rosen L. Granzyme B directly and efficiently cleaves several downstream caspase substrates: implications for CTL-induced apoptosis. Immunity 1998: 8: 451–460.

Antonsson B. et al. Inhibition of Bax channel-forming activity by Bcl-2. Science. 277: 370–372, 1997.

Aqeilan R, Yarkoni S, Lorberboum-Galski H. Interleukin 2-Bax: a novel prototype of human chimeric proteins for targeted therapy. FEBS Lett. 27 Aug. 1999; 457(2):271–6.

Arap et al., 1995.

Ashkenazi A, Dixit V M. Death receptors: signaling and modulation. Science 1998; 281: 1305–1308.

Ausubel et al., In: Current Protocols in Molecular Biology, John, Wiley & Sons, Inc., 1994.

Bangham, et al., “Diffusion of univalent Ions across the Lamellae of Swollen Phospholipids” J. Mol. Biol., 13:238–252, 1965.

Barclay et al. (eds.), The Leucocyl=te Antigen Facts Book, 1993, Academic Press.

Becker K G, Mattson D H, Powers J M, Gado A M, Biddison W E. Analysis of a sequenced cDNA library from multiple sclerosis lesions. J Neuroimmunol. 1997 July; 77(1): 27–38.

Beresford P J. Xia Z, Greenberg A H, Lieberman J. Granzyme A loading induces rapid cytolysis and a novel from of DNA damage independently of caspase activation. Immunity 1999; 10: 585–594.

Berke G. The CTL’s kiss of death, Cell 1995; 81: 9–12.

Bird, R. E. et al., Science 242, 423–426, 1988.

Boise L H, Gonzalez-Garcia M, Postema C E, Ding L, Lindsten T, Turka L A, Mao X, Nunez G, Thompson C B. bcl-x, a bcl-2-related gene that functions as a dominant regulator of apoptotic cell death. Cell. 27 Aug. 1993; 74(4):597–608.

Boldin M P, Goncharov T M, Goltsev Y V, Wallach D. Involvement of MACH, a novel MORT1/FADD-interacting protease, in Fas/APO-1-and TNF receptor-induced cell death. Cell 1996; 85: 803–815.

Boyd J M, Gallo G J, Elangovan B, Houghton A B, Malstrom S, Avery B J, Ebb R G, Subramanian T, Chittenden T, Lutz R J, et al. Bik, a novel death-inducing protein shares a distinct sequence motif with Bcl-2 family proteins and interacts with viral and cellular survival-promoting proteins. Oncogene. 2 Nov. 1995; 11(9):1921–8.

Brinkmann U, Di Carlo A, Vasmatzis G, Kurochkina N, Beers R, Lee B, Pastan I. Stabilization of a recombinant Fv fragment by base-loop interconnection and V(H)-V(L) permutation. J Mol Biol. 25 Apr. 1997; 268(1):107–17.

Brodeur et al., Monoclonal Antibody Production Techniques & Applications, pp. 51–63 (Marcel Dekker Inc., New York, 1987).

Browne, K. A., Blink, E., Sutton, V. R., Groelich, C. J., Jans, D. A., and Trapani, J. A. Mol. Cell. Biol. 1999; 19: 8604–8615.

Canfield L M, Fritz T A, Tarara T E. Incorporation of beta-carotene into mixed micelles. Methods Enzymol. 1990; 189:418–22.

Caruthers M H, Beaucage S L, Efcavitch J W, Fisher E F, Matteucci M D, Stabinsky Y. New chemical methods for synthesizing polynucleotides. Nucleic Acids Symp Ser. 1980; (7):215–23.

Catalysis in Micellar & Macromolecular Systems, 1975.

Cheng J Q, Jhanwar S C, Klein W M, Bell D W, Lee W C, Altomare D A, Nobori T, Olopade O I, Buckler A J, Testa J R. p16 alterations and deletion mapping of 9p21–p22 in malignant mesothelioma. Cancer Res. 1 Nov. 1994; 54(21):5547–51.

Chinnaiyan A. M., Orth K., O’Rourke K., Duan, H., Poirier G. G. and Dixit, V. M. Molecular ordering of the cell death pathway. J. Biol. Chem., 271: 4573–4576, 1996.

Chinnaiyan A M, Orth K, Hanna W L, Duan H J, Poirier G G, Froelich C J, Dixit V M, Cytotoxic T cell-derived granzyme B activates the apoptotic protease ICE-LAP3. Curr Biol 1996; 6: 897–899.

Clackson T, Hoogenboom H R, Griffiths A D, Winter G. Making antibody fragments using phage display libraries. Nature. 15 Aug. 1991; 352(6336):624–8.

Cleary M L, Sklar J. Nucleotide sequence of a t(14; 18) chromosomal breakpoint in follicular lymphoma and demonstration of a breakpoint-cluster region near a transcriptionally active locus on chromosome 18. Proc Natl Acad Sci USA. 1985 November; 82(21):7439–43.

Cohen, 1997, Biochem. J. 326:1–16.

Colbere-Garapin F, Horodniceanu F, Kourilsky P, Garapin A C. A new dominant hybrid selective marker for higher eukaryotic cells. J Mol Biol. 25 Jul. 1981; 150(1):1–14.

Cole S P, Vreeken E H, Roder J C. Antibody production by human X human hybridomas in serum-free medium. J Immunol Methods. 22 Apr. 1985; 78(2):271–8.

Colloidal Surfactant, 1963.

Creighton, 1983, Proteins Structures & Molecular Principles, W.H. Freeman & Co., N. Y., pp. 34–60.
Darmon A J, Ley T J, Nicholson D W, Bleackley R C, Cleavage of CPP32 by granzyme B represents a critical role for granzyme B in the induction of target cell DNA fragmentation. J Biol Chem 1996; 271: 21709–21712.
Darmon A J, Nicholson D W, Bleackley R C. Activation of the apoptotic protease CPP32 by cytotoxic T-cell derived granzyme B. Nature 1995; 377: 446–448.
Deamer and P. Uster, "Liposome Preparation: Methods and Mechanisms," in Liposomes (M. Ostro, ed.), Marcel Dekker, Inc., New York (1983), pp. 27–52.
Doherty P C. Cell-mediated cytotoxicity. Cell 1993; 75: 607–612.
Duan J, Orth K, Chinnaiyan A M, Poirier G G, Froelich C J, He W-W, Dixit V M. ICE-LAP6, a novel member of the ICE/Ced-3 gene family, is activated by the cytotoxic T cell protease granzyme B. J Biol Chem 1996; 271: 16720–16724.
Ebnet K, Hausmann M, Lehmann-Grube F, Mullbacher A, Kopf M, Lamers M, Simon M M, Granzyme A-deficient mice retain potent cell-mediated cytotoxicity. EMBO J 1995; 14: 4230–4239.
El-Gorab M. Solubilization of -carotene and retinol into aqueous solutions of mixed micelles. Biochim Biophys Acta. 13 Apr. 1973; 306(1):58–66.
Felgner P L, Gadek T R, Holm M, Roman R, Chan H W, Wenz M, Northrop J P, Ringold G M, Danielsen M. Lipofection: a highly efficient, lipid-mediated DNA-transfection procedure.Proc Natl Acad Sci USA. 1987 November; 84(21):7413–7.
Fernandes-Alnemri T, Armstrong R C, Krebs J, Srinivasula S M, Wang L, Bullrich F, Fritz L C, Trapani J A, Tomaselli K J, Litwack G, Alnemri E S. In vitro activation of CPP32 and Mch3 by Mch4, a novel human apoptotic cysteine protease containing two FADD-like domains. Proc. Natl Acad Sci USA 1996; 93: 7464–7469.
Fernandes-Alnemri T, Litwack G, Alnemri S. Mch2, a new member of the apoptotic Ced-3/Ice cysteine protease gene family. Cancer Res 1995; 55: 2737–2742.
FernandeS-Alnemri T, Takahashi A, Armstrong R, Krebs J, Fritz L, Tomaselli K J, Wang L, Yu Z, Croce C M, Salvesen G, Earnshaw W C, Litwack G, Alnemri E S. Mch3, a novel human apoptotic cysteine protease highly related to CPP32. Cancer Res 1995; 55: 6045–6052.
Fingl et al., 1975, In: The Pharmacological Basis of Therapeutics, Ch. 1, p. 1.
Fraley and Fornari Kaplan, "Entrapment of a bacterial plasmid in phospholipid vesicles:potential for gene transfer," *Proc. Nat'l. Acad. Sci. USA* 76:3348–3352, 1979.
Froelich C J, Orth K, Turbov J, Seth P, Gottlieb R, Babior B, Shah G M, Bleackley R C, Dixit V M, Hanna W. New paradigm for lymphocyte granule-mediated cytotoxicity. Target cells bind and internalize granzyme B, but an endosomolytic agent is necessary for cytosolic delivery and subsequent apoptosis. J Biol Chem 1996; 271: 29073–29079.
Gazzaniga P, Gradilone A, Vercillo R, Gandini O, Silvestri I, Napolitano M, Albonici L, Vincenzoni A, Gallucci M, Frati L, Agliano A M. Bcl-2/bax mRNA expression ratio as prognostic factor in low-grade urinary bladder cancer. Int J Cancer. 22 Apr. 1996; 69(2): 100–4.
Gershenfeld H K, Weissman I L. Cloning of cDNA for a T cell-specific serine protease from a cytotoxic T lymphocyte. Science 1986; 232: 854–858.
Ghosh and Bachhawat, "Targeting of liposomes to hepatocytes," In: Wu G. Wu C ed., Liver diseases, targeted diagnosis and therapy using specific receptors and ligands, New York: Marel Dekker, pp. 87–104, 1991.
Goding, Monoclonal Antibodies: Principles & Practice, pp. 59–104 (Academic Press, 1986).
Gregoriadis G. and Davis C. "Stability of liposomes in vivo and in vitro is promoted by their cholesterol content and the presence of blood cells," *Biochem Biophys Res Commun.,* 89(4):1287–1293, 1979.
Gregoriadis, *DRUG CARRIERS IN BIOLOGY AND MEDICINE,* G. Gregoriadis (ed.), 1979, pp. 287–341.
Griffiths, G. M., and Isaaz, S. J. Cell Biol. 1993; 120: 885–896.
Gross A., Jockel J., Wie M. C. and Korsmeyer S. J. Enforced dimerization of Bax results in its translocation, mitochondrial dysfunction and apoptosis. EMBO J. 17: 3878–3885, 1998.
Gu Y, Sarnecki C, Fleming M A, Lippke J A, Bleackley R C, Su MS-S. Processing and activation of CMH-1 by granzyme B. J Biol Chem 1996; 271: 10816–10820.
Haddad, P., Jenne, D., Tschopp, J., Clement, M. V., Mathieu-Mahul, D., and Sasportes, M. Int. Immunol. 1991; 3: 57–66.
Hayes M P, Berrebi G A, Henkart P A. Induction of target cell DNA release by the cytotoxic T lymphocyte granule protease granzyme. A. J Exp Med 1980; 170: 933–946.
Heath et al., Chem. Phys. Lipids 40:347 (1986).
Heibein, J. A., Barry, M., Motyka, B., and Bleakley, R. C. J. Immunol. 1999; 163: 4683–4693.
Henkart, P. A. Annu. Rev. Immunol. 1985; 3: 31–58.
Heusel J W, Wesselschmidt R L, Shresta S, Russell J H, Ley T J. Cytotoxic lymphocytes require granzyme B for the rapid induction of DNA fragmentation and apoptosis in allogeneic target cells. Cell 1994; 76: 977–987.
Hockenbery D. M., Oltvai Z. N., Yin X.-M., Milliman C. L. and Korsmeyer S. J. Bcl-2 functions in an antioxidant pathway to prevent apoptosis. Cell, 75: 241–251, 1993.
Hollstein M, Sidransky D, Vogelstein B, Harris C C. p53 mutations in human cancers. Science. 5 Jul. 1991; 253 (5015):49–53.
Huston, J. S. et al., Proc. Natl. Acad. Sci., USA 85, 5879–5883 (1988).
Hsu Y. T. and Youle R. J. Nonionic detergents induce dimerization among members of the Bcl-2 family. J. Biol. Chem., 272: 13829–13834, 1997.
Huiling H., Lam M., McCormic T. S. and Distelhorst C. W. Maintenance of calcium homeostasis in the endoplasmic reticulum by Bcl-2. J. Cell Biol. 138: 1219–1228, 1997.
Hussussian C J, Struewing J P, Goldstein A M, Higgins P A, Ally D S, Sheahan M D, Clark W H Jr, Tucker M A, Dracopoli N C. Germline p16 mutations in familial melanoma. Nat Genet. 1994 September; 8(1):15–21.
Huston J S, Levinson D, Mudgett-Hunter M, Tai M S, Novotny J, Margolies M N, Ridge R J, Bruccoleri R E, Haber E, Crea R, et al. Protein engineering of antibody binding sites: recovery of specific activity in an anti-digoxin single-chain Fv analogue produced in *Escherichia coli*. Proc Natl Acad Sci USA. 1988 August; 85(16): 5879–83.
Inohara N, Ding L, Chen S, Nunez G. harakiri, a novel regulator of cell death, encodes a protein that activates apoptosis and interacts selectively with survival-promoting proteins Bcl-2 and Bcl-X(L). EMBO J. 1 Apr. 1997; 16(7):1686–94.
Jacobson M. D., Weil M, and Raff M. C. Programmed cell death in animal development. Cell, 88: 347–354, 1997.
Jakobovits A, Moore A L, Green L L, Vergara G J, Maynard-Currie C E, Austin H A, Klapholz S. Germ-line transmission and expression of a human-derived yeast artificial chromosome. Nature. 18 Mar. 1993; 362(6417):255–8.

Jans D A, Jans P, Briggs L J, Sutton V, Trapani J A. Nuclear transport of granzyme B (fragmentin-2). J Biol Chem 1996; 271: 30781–30789.

Johannesson et al., 1999, "Bicyclic tripeptide mimetics with reverse turn inducing properties." *J. Med. Chem.* 42:601–608.

Jones P T, Dear P H, Foote J, Neuberger M S, Winter G. Replacing the complementarity-determining regions in a human antibody with those from a mouse. Nature. 1986; May 29–Jun. 4, 321(6069):522–5.

Kagawa S., Gu J., Swisher S. G., Ji L., Roth J. A. Lai D., Stephens L. C. and Fang B. Antitumor effect of adenovirus-mediated Bax gene transfer on p53-sensitive and p53-resistant cancer lines. Cancer Research. 60: 1157–1161, 2000.

Kagawa S., Pearson S. A., Ji L., Xu K., McDonnell T. J., Swisher S. G., Roth J. A. and Fang B. A binary adenoviral vector system for expressing high levels of the proapoptotic gene bax. Gene Therapy., 7: 75–79, 2000.

Kagi D, Lederman B. Burki K, Zinkernagel R M, Hengartner H. Molecular mechanisms of lymphocyte-mediated cytoxicity and their role in immunological protection and pathogenesis in vivo. Ann Rev Immunol 1996; 14:207–232.

Kam, C-M., Hudig D., and Powers, J. C. Biochimica et Biophysica Acta. 2000; 1477: 307–323.

Kamb A, Shattuck-Eidens D, Eeles R, Liu Q, Gruis N A, Ding W, Hussey C, Tran T, Miki Y, Weaver-Feldhaus J, et al. Analysis of the p16 gene (CDKN2) as a candidate for the chromosome 9p melanoma susceptibility locus. Nat Genet. 1994 September; 8(1):23–6.

Kaneda et al., "Increased expression of DNA cointroduced with nuclear protein in adult rat liver," *Science,* 243: 375–378, 1989.

Kaneda et al., "Introduction and expression of the human insulin gene in adult rat liver," *J Biol Chem.,* 264(21): 12126–12129, 1989.

Kato et al., "Expression of hepatitis B virus surface antigen in adult rat liver. Co-introduction of DNA and nuclear protein by a simplified liposome method," *J Biol Chem.,* 266(6):3361–3364, 1991.

Kerr J F, Wyllie A H, Currie A R. Apoptosis: a basic biological phenomenon with wide-ranging implications in tissue kinetics. Br J Cancer. 1972 August; 26(4):239–57.

Kiefer M C, Brauer M J, Powers V C, Wu J J, Umansky S R, Tomei L D, Barr P J. Modulation of apoptosis by the widely distributed Bcl-2 homologue Bak. Nature. 1995; Apr. 20, 374(6524):736–9.

Knudson C M, Korsmeyer S J. Bcl-2 and Bax function independently to regulate cell death. Nat Genet. 1997 August; 16(4):358–63.

Kozbor D, Tripputi P, Roder J C, Croce C M. A human hybrid myeloma for production of human monoclonal antibodies. J Immunol. 1984 December; 133(6):3001–5.

Kozopas K M, Yang T, Buchan H L, Zhou P, Craig R W. MCL1, a gene expressed in programmed myeloid cell differentiation, has sequence similarity to BCL2. Proc Natl Acad Sci USA. 1993; Apr. 15, 90(8):3516–20.

Kuroki M, Arakawa F, Khare P D, Kuroki M, Liao S, Matsumoto H, Abe H, Imakiire T. Specific targeting strategies of cancer gene therapy using a single-chain variable fragment (scFv) with a high affinity for CEA. Anticancer Res. 2000 November–December; 20(6A): 4067–71.

Kyte & Doolittle, 1982.

Lam M., Dubyak G., Chen L., Nunez G., Miesfeld R. L. and Distelhorst C. W. Evidence that Bcl-2 represses apoptosis by regulating endoplasmic reticulum-associated Ca2+ fluxes. Proc. Natl. Acad. Sci. USA, 91: 6569–6573, 1994.

Lang J, Vigo-Pelfrey C, Martin F. Liposomes composed of partially hydrogenated egg phosphatidylcholines: fatty acid composition, thermal phase behavior and oxidative stability. Chem Phys Lipids. 1990 March; 53(1):91–101.

Lin E Y, Orlofsky A, Berger M S, Prystowsky M B. Characterization of A1, a novel hemopoietic-specific early-response gene with sequence similarity to bcl-2. J Immunol. 1993; Aug. 15, 151(4):1979–88.

Liposome Technology, 1984.

Liu Y, Liggitt D, Zhong W, Tu G, Gaensler K, Debs R. Cationic liposome-mediated intravenous gene delivery. J Biol Chem. 1995; Oct. 20, 270(42):24864–70.

Liu X, Kim C N, Pohl J, Wang X. Purification and characterization of an interleukin-1beta-converting enzyme family protease that activates cysteine protease P32 (CPP32). J Biol Chem. 1996; Jun. 7, 271(23):13371–6.

Liu X, Zou H, Slaughter C, Wang X. D F F, a heterodimeric protein that functions downstream of caspase-3 to trigger DNA fragmentation during apoptosis. Cell. 1997; Apr. 18, 89(2): 175–84.

Lobe C G, Havele C, Bleackley R C. Cloning of two genes that are specifically expressed in activated cytotoxic T lymphocytes. Proc Natl Acad Sci USA 1986; 83: 1448–1452.

Lowy I, Pellicer A, Jackson J F, Sim G K, Silverstein S, Axel R. Isolation of transforming DNA: cloning the hamster aprt gene. Cell. 1980 December; 22(3):817–23.

Marks J D, Hoogenboom H R, Bonnert T P, McCafferty J, Griffiths A D, Winter G. By-passing immunization. Human antibodies from V-gene libraries displayed on phage. J Mol Biol. 1991; Dec. 5, 222(3):581–97.

Marks J D, Griffiths A D, Malmqvist M, Clackson T P, Bye J M, Winter G. By-passing immunization: building high affinity human antibodies by chain shuffling. Biotechnology (N Y). 1992 July; 10(7):779–83.

Martin S J, Amarante-Mendes G P, Shi L F, Chuang T H, Casiano C A, O'Brien G A, Fitzgerald P, Tan E M, Bokoch G M, Greenberg A H, Green D R. The cytotoxic cell protease granzyme B initiates apoptosis in a cell-free system by proteolytic processing and activation of the ICE/CED-3 family protease, CPP32, via a novel two-step mechanism. EMBO J 1996: 15: 2407–2416.

Marzo I, et al. The permeability transition pore complex: a target for apoptosis regulation by caspases and bcl-2-related proteins. J. Exp. Med. 187: 1261–1271, 1998.

Masson D, Tschopp J. Isolation of a lytic pore-forming protein (perforin) from cytolytic T lymphocytes. J Biol Chem 1985; 260:9069–9072.

Masson D, Zamai M, Tschopp J. Identification of granzyme A isolated from cytotoxic T-lymphocyte-granules as one of the proteases encoded by CTL-specific genes. FEBS Lett 1986; 208: 84–88.

Mayer L D, Hope M J, Cullis P R. Vesicles of variable sizes produced by a rapid extrusion procedure. Biochim Biophys Acta. 1986; Jun. 13, 858(1):161–8.

Mayhew E, Conroy S, King J, Lazo R, Nikolopoulus G, Siciliano A, Vail W J. High-pressure continuous-flow system for drug entrapment in liposomes. Methods Enzymol. 1987; 149:64–77.

McConlogue, L., 1987, In: Current communications in molecular biology, Cold Spring Harbor Lab ed.)

Medema J P, Toes R E M, Scaffidi C, Zheng T S, Flavell R A, Melief C J M, Peter M E, Offringa R, Krammer P H.

Cleavage of FLICE (caspase-8) by granzyme B during cytotoxic T lymphocyte-induced apoptosis. Eur J Immunol 1997; 27: 3492–3498.

Milstein C, Cuello A C. Hybrid hybridomas and their use in immunohistochemistry. Nature. 1983; Oct. 6–12, 305 (5934):537–40.

Modem Pharmaceutics, 1990.

Montaldo P G, Pagnan G, Pastorino F, Chiesa V, Raffaghello L, Kirchmeier M, Allen T M, Ponzoni M. N-(4-hydroxyphenyl) retinamide is cytotoxic to melanoma cells in vitro through induction of programmed cell death. Int J Cancer. 1999; Apr. 12, 81(2):262–7.

Morrison S L, Johnson M J, Herzenberg L A, Oi V T. Chimeric human antibody molecules: mouse antigen-binding domains with human constant region domains. Proc Natl Acad Sci USA. 1984 November; 81(21):6851–5.

Mujoo K, Spiro R C, Reisfeld R A. Characterization of a unique glycoprotein antigen expressed on the surface of human neuroblastoma cells. J Biol Chem. 1986; Aug. 5, 261(22): 10299–305.

Mullbacher A, Ebnet K, Blanden R V, Hla R T, Stehle T, Museteanu C, Simon M M. Granzyme A is critical for recovery of mice from infection with the natural cytopathic viral pathogen, ectromelia. Proc Natl Acad Sci USA 1996; 93: 5783–5787.

Mulligan R C, Berg P. Factors governing the expression of a bacterial gene in mammalian cells. Mol Cell Biol. 1981 May; 1(5):449–59.

Muzio M, Chinnaiyan A M, Kischkel F C, O'Rourke K, Shevchenko A, Ni J, Scaffidi C, Bretz J D, Zhang M, Gentz R, Mann M, Krammer P H, Peter M E, Dixit V M. FLICE, a novel FADD-homologous ICE/CED-3-like protease, is recruited to the CD95 (Fas/APO-1) death-inducing signaling complex. Cell 1996; 85: 817–827.

Muzio, M., Chinnaiyan, A. M., Kischkel, F. C., O'Rourke, K., Shevchenko, A., Scaffidi, C., Bretz, J. D., Zhang, M., Ni, J., Gentz, R., Mann, M., Krammer, P. H., Peter, M. E., and Dixit, V. M. Cell. 1996; 86: 817–821.

Nagata S, Golstein P. The Fas death factor. Science 1995; 267: 1449–1456.

Nechushtan A, Yarkoni S, Marianovsky I, Lorberboum-Galski H. Adenocarcinoma cells are targeted by the new GnRH-PE66 chimeric toxin through specific gonadotropin-releasing hormone binding sites. J Biol Chem. 1997; Apr. 25, 272(17):11597–603.

Neuberger M S, Williams G T, Fox R O. Recombinant antibodies possessing novel effector functions. Nature. 1984; Dec. 13–19, 312 (5995):604–8.

Nicolau and Sene, "Liposome-mediated DNA transfer in eukaryotic cells: dependence of the transfer efficiency upon the type of liposomes used and the host cell cycle stage," *Biochem. Biophys. Acta,* 721:185–190, 1982.

Nicolau et al., "Liposomes as carriers for in vivo gene transfer and expression," *Methods Enzymol.,* 149:157–176, 1987.

Nygren H. Conjugation of horseradish peroxidase to Fab fragments with different homobifunctional and heterobifunctional cross-linking reagents. A comparative study. J Histochem Cytochem. 1982 May; 30(5):407–12.

O'Hare K, Benoist C, Breathnach R. Transformation of mouse fibroblasts to methotrexate resistance by a recombinant plasmid expressing a prokaryotic dihydrofolate reductase. Proc Natl Acad Sci USA. 1981 March; 78(3): 1527–31.

Odake S, Kam C M, Narasimhan L, Poe M, Blake J T, Krahenbuhl O, Tschopp J, Powers J C. Human and murine cytotoxic T lymphocyte serine proteases: subsite mapping with peptide thioester substrates and inhibition of enzyme activity and cytolysis by isocoumarins. Biochem 1991; 30: 2217–2227.

Oltvai Z. N., Milliman C. L. and Korsmeyer S. J. Bcl-2 heterodimerizes in vivo with a conserved homolog, Bax, that accelerates programmed cell death. Cell, 74: 609–619, 1993.

Orth K, Chinnaiyan A M, Garg M, Froelich C J, Dixit V M. The CED-3/ICE-like protease Mch2 is activated during apoptosis and cleaves the death substrate lamin A. J. Biol Chem 1996; 271: 16443–16446.

Ottilie S, Diaz J L, Home W, Chang J, Wang Y, Wilson G, Chang S, Weeks S, Fritz L C, Oltersdorf T. Dimerization properties of human BAD. Identification of a BH-3 domain and analysis of its binding to mutant BCL-2 and BCL-XL proteins. J Biol Chem. 1997; Dec. 5, 272(49): 30866–72.

Pagnan G, Montaldo P G, Pastorino F, Raffaghello L, Kirchmeier M, Allen T M, Ponzoni M. GD2-mediated melanoma cell targeting and cytotoxicity of liposome-entrapped fenretinide. Int J Cancer. 1999; Apr. 12, 81(2): 268–74.

Perales et al., "Gene transfer in vivo: sustained expression and regulation of genes introduced into the liver by receptor-targeted uptake," *Proc. Natl. Acad. Sci. USA,* 91:4086–4090, 1994.

Pinkoski M J, Heibein J A, Barry M, Bleackley R C. Nuclear translocation of granzyme B in target cell apoptosis. Cell Death Differ 2000; 7: 17–24.

Pinkoski M J, Hobman M, Helbein J A, Tomaselli K, Li F, Seth P, Froelich C J, Bleackley R C. Entry and trafficking of granzyme B in target cells during granzyme B-perforin-mediated apoptosis. Blood 1998;92:1044–1054.

Pinkoski M J, Winkler U, Hudig D, Bleackley R C. Biding of granzyme B in the nucleus of target cells. Recognition of an 80-kilodalton protein. J Biol Chem 1996; 271: 10225–10229.

Podack, E. R. Curr. Top. Microbiol. Immunol. 1992; 178: 175–184.

Poe M, Blake J T, Boulton D A, Gammon M, Sigal N H, Wu J K, Zweerink H J. Human cytotoxic lymphocyte granzyme B: its purification from granules and the characterization of substrate and inhibitor specificity. J Biol Chem 1991; 266: 98–103.

Quan L T, Tewari M, O'Rourke K, Dixit V M, Snipas S J, Poirier G G, Ray C, Pickup D J, Salvesen G S, Proteolytic activation of the cell death protease Yama/CPP32 by granzyme B. Proc Natl Acad Sci USA 1996; 93: 1972–1976.

Remington's Pharmaceutical Sciences, 18th ED. Mack Printing Company, 1990.

Riechmann L, Clark M, Waldmann H, Winter G. Reshaping human antibodies for therapy. Nature. 1988; Mar. 24, 332(6162):323–7.

Ruther U, Muller-Hill B. Easy identification of cDNA clones. EMBO J. 1983; 2(10):1791–4.

Sambrook et al., 1989.

Santerre R F, Allen N E, Hobbs J N Jr, Rao R N, Schmidt R J. Expression of prokaryotic genes for hygromycin B and G418 resistance as dominant-selection markers in mouse L cells. Gene. 1984 October; 30(1–3): 147–56.

Sarin, A., Williams, M. S., Alexander-Miller, M. A., Berzofsky, J. A., Zacharchuk, C. M., and Henkart, P. A. Immunity. 1997; 6: 209–215.

Schendel S L, Xie Z, Montal M O, Matsuyama S, Montal M, Reed J C. Channel formation by antiapoptotic protein Bcl-2. Proc Natl Acad Sci USA. 1997; May 13, 94(10): 5113–8.

Schmid, J., and Weissman, C. J. Immunol. 1987; 139: 250–254.

Schulz G, Cheresh D A, Varki N M, Yu A, Staffileno L K, Reisfeld R A. Detection of ganglioside GD2 in tumor tissues and sera of neuroblastoma patients. Cancer Res. 1984 December; 44(12 Pt 1):5914–20.

Serrano M, Hannon G J, Beach D. A new regulatory motif in cell-cycle control causing specific inhibition of cyclin D/CDK4. Nature. 1993; Dec. 16, 366(6456):704–7.

Serrano M, Gomez-Lahoz E, DePinho R A, Beach D, Bar-Sagi D. Inhibition of ras-induced proliferation and cellular transformation by p16INK4. Science. 1995; Jan. 13, 267(5195):249–52.

Shi L, Chen G, MacDonald G, Bergeron L, Li H, Miura M, Rotello R J, Miller D K, Li P, Seshadri T, Yuan J, Greenberg A H. Activation of an interleukin 1 converting enzyme-dependent apoptosis pathway by granzyme B. Proc Natl Acad Sci USA 1996; 93: 11002–11007.

Shi L, Kraut R P, Aebersold R, Greenberg A H. A natural killer cell granule protein that induces DNA fragmentation and apoptosis. J Exp Med 1992; 175: 553–566.

Shi L, Mai S, Israels S, Browne K, Trapani J A, Greenberg A H. Granzyme B (GraB) autonomously crosses the cell membrane and perforin initiates apoptosis and GraB nuclear localization. J Exp Med 1997; 185: 853–866.

Shinkai, Y., Takio, K., and Okumura, K. Nature. 1988; 334: 525–527.

Shresta S, Graubert T A, Thomas D A, Raptis S Z, Ley T J. Granzyme A initiates an alternative pathway for granule-mediated apoptosis. Immunity 1999; 10: 595–605.

Shresta S, Heusel J W, MacIvor D M, Wesselschmidt R L, Russell J H, Ley T J. Granzyme B plays a critical role in cytotoxic lymphocyte-induced apoptosis. Immunol Rev 1995; 146: 211–221.

Shresta S, MacIvor D M, Heusel J W, Russell J H, Ley T J. Natural killer and lymphokine-activated killer cells require granzyme B for the rapid induction of apoptosis in susceptible target cells. Proc Natl Acad Sci USA 1995; 92: 5679–5683.

Smyth M J, O'Connor M D, Trapani J A. Granzymes: A variety of serine protease specificities encoded by genetically distinct subfamilies. J Leuk Biol 1996; 60: 555–562.

Smyth, M. J., and Trapani, J. A. Immunol. Today. 1995; 16: 202–206.

Smyth, M. J., McGuire, M. J., and Thia, K. Y. J. Immunol. 1995; 154: 6299–6305.

Solodin I, Brown C S, Bruno M S, Chow C Y, Jang E H, Debs R J, Heath T D. A novel series of amphiphilic imidazolinium compounds for in vitro and in vivo gene delivery. Biochemistry. 1995; Oct. 17, 34(41):13537–44.

Spanjer H H, Scherphof G L. Targeting of lactosylceramide-containing liposomes to hepatocytes in vivo. Biochim Biophys Acta. 1983; Sep. 21, 734(1):40–7.

Suresh M R, Cuello A C, Milstein C. Advantages of bispecific hybridomas in one-step immunocytochemistry and immunoassays. Proc Natl Acad Sci USA. 1986 October; 83(20):7989–93.

Suzuki T, Nishiyama K, Yamamoto A, Inazawa J, Iwaki T, Yamada T, Kanazawa I, Sakaki Y. Molecular cloning of a novel apoptosis-related gene, human Nap1 (NCKAP1), and its possible relation to Alzheimer disease. Genomics. 2000 Jan. 15; 63(2):246–54.

Szoka and Papahadjopoulos, "Procedure for Preparation of Liposomes With Large Internal Aqueous Space . . . ", *Proc. Natl. Acad. Sci.,* 75:4194–4198, 1978.

Tai Y-T, Strobel T., Kufe D., and Cannistra S. A. In vivo cytotoxicity of ovarian cancer cells through tumor-selective expression of the Bax gene. Cancer Research. 59: 2121–2126, 1999.

Takeda S, Naito T, Hama K, Noma T, Honjo T. Construction of chimaeric processed immunoglobulin genes containing mouse variable and human constant region sequences. Nature. 1985; Apr. 4–10, 314(6010):452–4.

Talanian R V, Yang X H, Turbov J, Seth P, Ghayur T, Casiano C A, Orth K, Froelich C J. Granule-mediated killing: pathways for granzyme B-initiated apoptosis. J Exp Med 1997; 186: 1323–1331.

Templeton N S, Lasic D D, Frederik P M, Strey H H, Roberts D D, Pavlakis G N. Improved DNA: liposome complexes for increased systemic delivery and gene expression. Nat Biotechnol. 1997 July; 15(7):647–52.

Thierry A R, Lunardi-Iskandar Y, Bryant J L, Rabinovich P, Gallo R C, Mahan L C. Systemic gene therapy: biodistribution and long-term expression of a transgene in mice. Proc Natl Acad Sci USA. 1995; Oct. 10, 92(21):9742–6.

Thompson (ed.) 1994, The Cytokine Handbook, Academic Press, San Diego.

Trapani J A, Browne K A, Smyth M J, Jans D A. Localization of granzyme B in the nucleus. A putative role in the mechanism of cytotoxic lymphocyte-mediated apoptosis. J Biol Chem 1996; 271: 4127–4133.

Trapani, J. A., Jans, D. A., Browne, K. A., Smyth, M. J., Jans, P., and Sutton, V. R. J. Biol. Chem. 1998; 273: 27934–27938.

Trapani, J. A., Klein, J., White, P. C., and Dupont, B. Proc. Natl. Acad. Sci. U.S.A. 1988; 85: 6924–6928.

Traunecker A, Lanzavecchia A, Karjalainen K. Bispecific single chain molecules (Janusins) target cytotoxic lymphocytes on HIV infected cells. EMBO J. 1991 December; 10(12):3655–9.

Tschopp J, Schafer S, Masson D, Peitsch M C, Heusser C. Phosphorylcholine acts as a calcium dependent receptor molecule for lymphocyte perforin. Nature 1989; 337: 272–274.

Tsujimoto Y, Cossman J, Jaffe E, Croce C M. Involvement of the bcl-2 gene in human follicular lymphoma. Science. 1985 Jun. 21; 228(4706):1440–3.

Tsukamoto M, Ochiya T, Yoshida S, Sugimura T, Terada M. Gene transfer and expression in progeny after intravenous DNA injection into pregnant mice. Nat Genet. 1995 March; 9(3):243–8.

Van de Craen M, Van den brande I, Declercq W, Irmler M, Beyaert R, Tschopp J, Fiers W, Vandenabeele P. Cleavage of caspase family members by granzyme B: a comparative study in vitro. Eur J Immunol 1997; 27: 1296–1299.

Van Heeke G, Schuster S M. Expression of human asparagine synthetase in *Escherichia coli*. J Biol Chem. 1989; Apr. 5, 264(10):5503–9.

Vaux D. L., Heacher G, and Strasser A. An evolutionary perspective on apoptosis. Cell, 76: 777–779, 1994.

Verhoeyen M, Milstein C, Winter G. Reshaping human antibodies: grafting an antilysozyme activity. Science. 1988; Mar. 25, 239(4847):1534–6

Vincenz, C., and Dixit, V. M. J. Biol. Chem. 1997; 272: 6578–6583.

Vita et al., 1998, "Novel miniproteins engineered by the transfer of active sites to small natural scaffolds." *Biopolymers* 47:93–100.

Wagner et al., *Science,* 260:1510–1513, 1990.

Wang K, Yin X M, Chao D T, Milliman C L, Korsmeyer S J. BID: a novel BH3 domain-only death agonist. Genes Dev. 1996; Nov. 15, 10(22):2859–69.

Waterhouse P, Griffiths A D, Johnson K S, Winter G. Combinatorial infection and in vivo recombination: a strategy for making large phage antibody repertoires. Nucleic Acids Res. 1993; May 11, 21(9):2265–6.

Weinberg R A. Tumor suppressor genes. Science. 1991; Nov. 22, 254(5035):1138–46.

Weisshoff et al., 1999, "Mimicry of beta II'-turns of proteins in cyclic pentapeptides with one and without D-amino acids." *Eur. J. Biochem.* 259:776–788.

Wigler M, Silverstein S, Lee L S, Pellicer A, Cheng Y, Axel R. Transfer of purified herpes virus thymidine kinase gene to cultured mouse cells. Cell. 1977 May; 11(1):223–32.

Wigler M, Perucho M, Kurtz D, Dana S, Pellicer A, Axel R, Silverstein S. Transformation of mammalian cells with an amplifiable dominant-acting gene. Proc Natl Acad Sci USA. 1980 June; 77(6):3567–70.

Wolter K. G., Hsu Y-T., Smith C. L., Nechushtan A., Xi, X.-G. and Youle R. J. Movement of Bax from the cytosol to mitochondria during apoptosis. J. Cell Biol. 139: 1281–1292, 1997.

Wong et al., "Appearance of beta-lactamase activity in animal cells upon liposome-mediated gene transfer," *Gene.,* 10(2):87–94, 1980.

Wu and Wu, "Receptor-mediated in vitro gene transfections by a soluble DNA carrier system," *J. Biol. Chem.,* 262: 4429–4432, 1987.

Wu and Wu, *Adv. Drug Delivery Rev.,* 12:159–167, 1993.

Yagita, H., Nagata, M., Kawasaki, A., Shinkai, Y., and Okumura, K. Adv. Immunol. 1992; 51: 215–242.

Yang, X., Stennicke, H. R., Wang, B., Green, D. R., Janicke, R. U., Srinivasan, A., Seth, P., Salvesen, G., and Froelich, C. J. J. Biol. Chem. 1998; 273: 34278–34283.

Young J D-E, Hengartner H, Podack E R, Cohn Z A. Purification and characterization of a cytolytic pore-forming protein from granules of cloned lymphocytes with natural killer activity. Cell 1986; 44: 849–859.

Young, J. D. E., and Cohn, Z. A. Cell. 1986; 46: 641–642.

Zamzami N., Susin S. A., Marchetti P., Hirsch T., Gomez-Monterrey I., Castedo M., and Kroemer G. Mitochondrial control of nuclear apoptosis. J. Exp. Med., 183: 1533–1544, 1996.

Zha J, Harada H, Osipov K, Jockel J, Waksman G, Korsmeyer SJ. BH3 domain of BAD is required for heterodimerization with BCL-XL and pro-apoptotic activity. J Biol Chem. 1997; Sep. 26, 272(39):24101–4.

Zola, Monoclonal Antibodies: a Manual of Techniques, pp. 147–158 (CRC Press, Inc., 1987).

Zou H, Henzel W J, Liu X, Lutschg A, Wang X. Apaf-1, a human protein homologous to *C. elegans* CED-4, participates in cytochrome c-dependent activation of caspase-3. Cell. 1997; Aug. 8, 90(3):405–13.

Zunino S J, Bleackley R C, Martinez J, Hudig D. RNKP-1, a novel natural killer cell-associated serine protease gene cloned from RNK-16 cytotoxic lymphocytes. J Immunol 1990; 144: 2001–2009.

All of the methods and compositions disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

We claim:

1. A chimeric polypeptide comprising a cell-specific targeting moiety and an apoptosis-inducing factor, wherein said apoptosis-inducing factor is a granzyme wherein the amino acid sequence of said granzyme is at least 40 contiguous amino acids from SEQ ID NO:60.

2. The polypeptide of claim 1, wherein said granzyme is granzyme B.

3. The polypeptide of claim 1, wherein the amino acid sequence of said granzyme is the granzyme B of SEQ ID NO:60.

4. The polypeptide of claim 1, wherein the amino acid sequence of said granzyme is at least 100 contiguous amino acids from SEQ ID NO:60.

5. The polypeptide of claim 1, wherein the amino acid sequence of said granzyme is at least 75 contiguous amino acids from SEQ ID NO:60.

6. The polypeptide of claim 1, wherein the amino acid sequence of said granzyme comprises SEQ ID NO:60 and which further comprises an N-terminal extension comprising SEQ ID NO:61.

7. The polypeptide of claim 1, wherein the amino acid sequence of said granzyme comprises SEQ ID NO:60, wherein the first twenty amino acids are absent from SEQ ID NO:60.

8. The polypeptide of claim 1, wherein said cell-specific targeting moiety is a cytokine, an antibody, a ligand, or a hormone.

9. The polypeptide of claim 8, wherein said antibody is a single chain antibody.

10. The polypeptide of claim 9, wherein said single chain antibody is scFvMEL.

11. The polypeptide of claim 1, wherein said cell-specific targeting moiety is vegf121.

12. The polypeptide of claim 1, wherein said cell-specific targeting moiety is scFvMEL.

13. The polypeptide of claim 1, further comprising a linker.

14. The polypeptide of claim 13, wherein the linker comprises SEQ ID NO:50, SEQ ID NO:51, or SEQ ID NO:52.

15. The polypeptide of claim 1, wherein the polypeptide is encoded by a recombinant polynucleotide.

16. The polypeptide of claim 1, wherein the granzyme polypeptide is at the N-terminal end and is chemically conjugated to the cell-specific moiety.

17. The polypeptide of claim 16, wherein the granzyme is full-length.

18. The polypeptide of claim 16, wherein the chemical conjugation is through a linker.

19. The polypeptide of claim 18, wherein the linker is an amino acid linker.

20. The polypeptide of claim 1, wherein the granzyme is at the N-terminal end of the polypeptide.

21. The polypeptide of claim 20, wherein the granzyme is granzyme B.

22. The polypeptide of claim 20, wherein the cell-specific targeting moiety is an antibody.

23. The polypeptide of claim 22, wherein the antibody is a single chain antibody.

* * * * *

```
                          SEQUENCE LISTING

<160> NUMBER OF SEQ ID NOS: 61

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 1

ggtggcggtg gctccatgga accaatcctg cttctg                              36


<210> SEQ ID NO 2
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 2

gccaccgcct ccctcgagct attagtagcg tttcatggt                           39


<210> SEQ ID NO 3
<211> LENGTH: 39
<212> TYPE: DNA
```

-continued

<213> ORGANISM: Artificial Sequence
<220> FEATURE:
<223> OTHER INFORMATION: Description of Artificial Sequence: Primer

<400> SEQUENCE: 3
ggtaccgacg acgacgacaa gatcatcggg ggacatgag 39

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 4
ggagccaccg ccaccgtagc gtttcatggt 30

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 5
ggtggcggtg gctccgcacc catggcagaa 30

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 6
aaggctcgtg tcgacctcga gtcattaccg cctcggcttg tc 42

<210> SEQ ID NO 7
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 7
ggtggcggtg gctccacgga cattgtgatg acccagtctc aaaaattc 48

<210> SEQ ID NO 8
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 8
ggagccaccg ccaccctcga gctatcatga ggagacggtg agagtggt 48

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 9
taatacgact cactatag 18

-continued

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 10
cttgtcgtcg tcgtcggtac ccagatctgg 30

<210> SEQ ID NO 11
<211> LENGTH: 247
<212> TYPE: PRT
<213> ORGANISM: Homo sapiens

<400> SEQUENCE: 11

```
Met Gln Pro Ile Leu Leu Leu Leu Ala Phe Leu Leu Leu Pro Arg Ala
  1               5                  10                  15

Asp Ala Gly Glu Ile Ile Gly Gly His Glu Ala Lys Pro His Ser Arg
            20                  25                  30

Pro Tyr Met Ala Tyr Leu Met Ile Trp Asp Gln Lys Ser Leu Lys Arg
        35                  40                  45

Cys Gly Gly Phe Leu Ile Gln Asp Asp Phe Val Leu Thr Ala Ala His
     50                  55                  60

Cys Trp Gly Ser Ser Ile Asn Val Thr Leu Gly Ala His Asn Ile Lys
 65                  70                  75                  80

Glu Gln Glu Pro Thr Gln Gln Phe Ile Pro Val Lys Arg Pro Ile Pro
                 85                  90                  95

His Pro Ala Tyr Asn Pro Lys Asn Phe Ser Asn Asp Ile Met Leu Leu
            100                 105                 110

Gln Leu Glu Arg Lys Ala Lys Arg Thr Arg Ala Val Gln Pro Leu Arg
        115                 120                 125

Leu Pro Ser Asn Lys Ala Gln Val Lys Pro Gly Gln Thr Cys Ser Val
    130                 135                 140

Ala Gly Trp Gly Gln Thr Ala Pro Leu Gly Lys His Ser His Thr Leu
145                 150                 155                 160

Gln Glu Val Lys Met Thr Val Gln Glu Asp Arg Lys Cys Glu Ser Asp
                165                 170                 175

Leu Arg His Tyr Tyr Asp Ser Thr Ile Glu Leu Cys Val Gly Asp Pro
            180                 185                 190

Glu Ile Lys Lys Thr Ser Phe Lys Gly Asp Ser Gly Gly Pro Leu Val
        195                 200                 205

Cys Asn Lys Val Ala Gln Gly Ile Val Ser Tyr Gly Arg Asn Asn Gly
    210                 215                 220

Met Pro Pro Arg Ala Cys Thr Lys Val Ser Ser Phe Val His Trp Ile
225                 230                 235                 240

Lys Lys Thr Met Lys Arg Tyr
                245
```

<210> SEQ ID NO 12
<211> LENGTH: 247
<212> TYPE: PRT
<213> ORGANISM: Homo sapiens

<400> SEQUENCE: 12

```
Met Gln Pro Ile Leu Leu Leu Leu Ala Phe Leu Leu Leu Pro Arg Ala
  1               5                  10                  15
```

-continued

```
Asp Ala Gly Glu Ile Ile Gly Gly His Glu Ala Lys Pro His Ser Arg
            20                  25                  30

Pro Tyr Met Ala Tyr Leu Met Ile Trp Asp Gln Lys Ser Leu Lys Arg
        35                  40                  45

Cys Gly Gly Phe Leu Ile Arg Asp Asp Phe Val Leu Thr Ala Ala His
    50                  55                  60

Cys Trp Gly Ser Ser Ile Asn Val Thr Leu Gly Ala His Asn Ile Lys
65                  70                  75                  80

Glu Gln Glu Pro Thr Gln Gln Phe Ile Pro Val Lys Arg Pro Ile Pro
                85                  90                  95

His Pro Ala Tyr Asn Pro Lys Asn Phe Ser Asn Asp Ile Met Leu Leu
            100                 105                 110

Gln Leu Glu Arg Lys Ala Lys Arg Thr Arg Ala Val Gln Pro Leu Arg
        115                 120                 125

Leu Pro Ser Asn Lys Ala Gln Val Lys Pro Gly Gln Thr Cys Ser Val
    130                 135                 140

Ala Gly Trp Gly Gln Thr Ala Pro Leu Gly Lys His Ser His Thr Leu
145                 150                 155                 160

Gln Glu Val Lys Met Thr Val Gln Glu Asp Arg Lys Cys Glu Ser Asp
                165                 170                 175

Leu Arg His Tyr Tyr Asp Ser Thr Ile Glu Leu Cys Val Gly Asp Pro
            180                 185                 190

Glu Ile Lys Lys Thr Ser Phe Lys Gly Asp Ser Gly Gly Pro Leu Val
        195                 200                 205

Cys Asn Lys Val Ala Gln Gly Ile Val Ser Tyr Gly Arg Asn Asn Gly
    210                 215                 220

Met Pro Pro Arg Ala Cys Thr Lys Val Ser Ser Phe Val His Trp Ile
225                 230                 235                 240

Lys Lys Thr Met Lys Arg Tyr
                245


<210> SEQ ID NO 13
<211> LENGTH: 281
<212> TYPE: PRT
<213> ORGANISM: Homo sapiens

<400> SEQUENCE: 13

Met Lys Ser Leu Ser Leu Leu His Leu Phe Pro Leu Pro Arg Ala Lys
  1               5                  10                  15

Arg Glu Gln Gly Gly Asn Asn Ser Ser Ser Asn Gln Gly Ser Leu Pro
            20                  25                  30

Glu Lys Met Gln Pro Ile Leu Leu Leu Leu Ala Phe Leu Leu Leu Pro
        35                  40                  45

Arg Ala Asp Ala Gly Glu Ile Ile Gly Gly His Glu Ala Lys Pro His
    50                  55                  60

Ser Arg Pro Tyr Met Ala Tyr Leu Met Ile Trp Asp Gln Lys Ser Leu
65                  70                  75                  80

Lys Arg Cys Gly Gly Phe Leu Ile Gln Asp Asp Phe Val Leu Thr Ala
                85                  90                  95

Ala His Cys Trp Gly Ser Ser Ile Asn Val Thr Leu Gly Ala His Asn
            100                 105                 110

Ile Lys Glu Gln Glu Pro Thr Gln Gln Phe Ile Pro Val Lys Arg Pro
        115                 120                 125

Ile Pro His Pro Ala Tyr Asn Pro Lys Asn Phe Ser Asn Asp Ile Met
```

-continued

```
    130                 135                 140

Leu Leu Gln Leu Glu Arg Lys Ala Lys Arg Thr Arg Ala Val Gln Pro
145                 150                 155                 160

Leu Arg Leu Pro Ser Asn Lys Ala Gln Val Lys Pro Gly Gln Thr Cys
                165                 170                 175

Ser Val Ala Gly Trp Gly Gln Thr Ala Pro Leu Gly Lys His Ser His
            180                 185                 190

Thr Leu Gln Glu Val Lys Met Thr Val Gln Glu Asp Arg Lys Cys Glu
        195                 200                 205

Ser Asp Leu Arg His Tyr Tyr Asp Ser Thr Ile Glu Leu Cys Val Gly
    210                 215                 220

Asp Pro Glu Ile Lys Lys Thr Ser Phe Lys Gly Asp Ser Gly Gly Pro
225                 230                 235                 240

Leu Val Cys Asn Lys Val Ala Gln Gly Ile Val Ser Tyr Gly Arg Asn
                245                 250                 255

Asn Gly Met Pro Pro Arg Ala Cys Thr Lys Val Ser Ser Phe Val His
            260                 265                 270

Trp Ile Lys Lys Thr Met Lys Arg Tyr
        275                 280


<210> SEQ ID NO 14
<211> LENGTH: 247
<212> TYPE: PRT
<213> ORGANISM: Homo sapiens

<400> SEQUENCE: 14

Met Gln Pro Ile Leu Leu Leu Leu Ala Phe Leu Leu Leu Pro Arg Ala
  1               5                  10                  15

Asp Ala Gly Glu Ile Ile Gly Gly His Glu Ala Lys Pro His Ser Arg
            20                  25                  30

Pro Tyr Met Ala Tyr Leu Met Ile Trp Asp Gln Lys Ser Leu Lys Arg
        35                  40                  45

Cys Gly Gly Phe Leu Ile Gln Asp Asp Phe Val Leu Thr Ala Ala His
    50                  55                  60

Cys Trp Gly Ser Ser Ile Asn Val Thr Leu Gly Ala His Asn Ile Lys
65                  70                  75                  80

Glu Gln Glu Pro Thr Gln Gln Phe Ile Pro Val Lys Arg Pro Ile Pro
                85                  90                  95

His Pro Ala Tyr Asn Pro Lys Asn Phe Ser Asn Asp Ile Met Leu Leu
            100                 105                 110

Gln Leu Glu Arg Lys Ala Lys Arg Thr Arg Ala Val Gln Pro Leu Arg
        115                 120                 125

Leu Pro Ser Asn Lys Ala Gln Val Lys Pro Gly Gln Thr Cys Ser Val
    130                 135                 140

Ala Gly Trp Gly Gln Thr Ala Pro Leu Gly Lys His Ser His Thr Leu
145                 150                 155                 160

Gln Glu Val Lys Met Thr Val Gln Glu Asp Arg Lys Cys Glu Ser Asp
                165                 170                 175

Leu Arg His Tyr Tyr Asp Ser Thr Ile Glu Leu Cys Val Gly Asp Pro
            180                 185                 190

Glu Ile Lys Lys Thr Ser Phe Lys Gly Asp Ser Gly Gly Pro Leu Val
        195                 200                 205

Cys Asn Lys Val Ala Gln Gly Ile Val Ser Tyr Gly Arg Asn Asn Gly
    210                 215                 220
```

-continued

```
Met Pro Pro Arg Ala Cys Thr Lys Val Ser Ser Phe Val His Trp Ile
225                 230                 235                 240

Lys Lys Thr Met Lys Arg Tyr
                245


<210> SEQ ID NO 15
<211> LENGTH: 227
<212> TYPE: PRT
<213> ORGANISM: Homo sapiens

<400> SEQUENCE: 15

Ile Ile Gly Gly His Val Ala Lys Pro His Ser Arg Pro Tyr Met Ala
  1               5                  10                  15

Tyr Leu Met Ile Trp Asp Gln Lys Ser Leu Lys Arg Cys Gly Gly Phe
             20                  25                  30

Leu Ile Arg Asp Asp Phe Val Leu Thr Ala Ala His Cys Trp Gly Ser
         35                  40                  45

Ser Ile Asn Val Thr Leu Gly Ala His Asn Ile Lys Glu Gln Glu Pro
     50                  55                  60

Thr Gln Gln Phe Ile Pro Val Lys Arg Ala Ile Pro His Pro Ala Tyr
 65                  70                  75                  80

Asn Pro Lys Asn Phe Ser Asn Asp Ile Met Leu Leu Gln Leu Glu Arg
                 85                  90                  95

Lys Ala Lys Arg Thr Arg Ala Val Gln Pro Leu Arg Leu Pro Ser Asn
            100                 105                 110

Lys Ala Gln Val Lys Pro Gly Gln Thr Cys Ser Val Ala Gly Trp Gly
        115                 120                 125

Gln Thr Ala Pro Leu Gly Lys His Ser His Thr Leu Gln Glu Val Lys
    130                 135                 140

Met Thr Val Gln Glu Asp Arg Lys Cys Glu Ser Asp Leu Arg His Tyr
145                 150                 155                 160

Tyr Asp Ser Thr Ile Glu Leu Cys Val Gly Asp Pro Glu Ile Lys Lys
                165                 170                 175

Thr Ser Phe Lys Gly Asp Ser Gly Gly Pro Leu Val Cys Asn Lys Val
            180                 185                 190

Ala Gln Gly Ile Val Ser Tyr Gly Arg Asn Asn Gly Met Pro Pro Arg
        195                 200                 205

Ala Cys Thr Lys Val Ser Ser Phe Val His Trp Ile Lys Lys Thr Met
    210                 215                 220

Lys Arg Tyr
225


<210> SEQ ID NO 16
<211> LENGTH: 247
<212> TYPE: PRT
<213> ORGANISM: Homo sapiens

<400> SEQUENCE: 16

Met Gln Pro Ile Leu Leu Leu Leu Ala Phe Leu Leu Leu Pro Arg Ala
  1               5                  10                  15

Asp Ala Gly Glu Ile Ile Gly Gly His Glu Ala Lys Pro His Ser Arg
             20                  25                  30

Pro Tyr Met Ala Tyr Leu Met Ile Trp Asp Gln Lys Ser Leu Lys Arg
         35                  40                  45

Cys Gly Gly Phe Leu Ile Gln Asp Asp Phe Val Leu Thr Ala Ala His
     50                  55                  60
```

-continued

```
Cys Trp Gly Ser Ser Ile Asn Val Thr Leu Gly Ala His Asn Ile Lys
 65                  70                  75                  80

Glu Gln Glu Pro Thr Gln Gln Phe Ile Pro Val Lys Arg Ala Ile Pro
                 85                  90                  95

His Pro Ala Tyr Asn Pro Lys Asn Phe Ser Asn Asp Ile Met Leu Leu
            100                 105                 110

Gln Leu Glu Arg Lys Ala Lys Arg Thr Arg Ala Val Gln Pro Leu Arg
        115                 120                 125

Leu Pro Ser Asn Lys Ala Gln Val Lys Pro Gly Gln Thr Cys Ser Val
    130                 135                 140

Ala Gly Trp Gly Gln Thr Ala Pro Leu Gly Lys His Ser His Thr Leu
145                 150                 155                 160

Gln Glu Val Lys Met Thr Val Gln Glu Asp Arg Lys Cys Glu Ser Asp
                165                 170                 175

Leu Arg His Tyr Tyr Asp Ser Thr Ile Glu Leu Cys Val Gly Asp Pro
            180                 185                 190

Glu Ile Lys Lys Thr Ser Phe Lys Gly Asp Ser Gly Gly Pro Leu Val
        195                 200                 205

Cys Asn Lys Val Ala Gln Gly Ile Val Ser Tyr Gly Arg Asn Asn Gly
    210                 215                 220

Met Pro Pro Arg Ala Cys Thr Lys Val Ser Ser Phe Val His Trp Ile
225                 230                 235                 240

Lys Lys Thr Met Lys Arg Tyr
                245
```

<210> SEQ ID NO 17
<211> LENGTH: 889
<212> TYPE: DNA
<213> ORGANISM: Homo sapiens

<400> SEQUENCE: 17

```
gcagctccaa ccagggcagc cttcctgaga agatgcaacc aatcctgctt ctgctggcct     60

tcctcctgct gcccagggca gatgcagggg agatcatcgg gggacatgag gccaagcccc    120

actcccgccc ctacatggct tatcttatga tctgggatca gaagtctctg aagaggtgcg    180

gtggcttcct gatacgagac gacttcgtgc tgacagctgc tcactgttgg ggaagctcca    240

taaatgtcac cttgggggcc cacaatatca aagaacagga gccgacccag cagtttatcc    300

ctgtgaaaag acccatcccc catccagcct ataatcctaa gaacttctcc aacgacatca    360

tgctactgca gctggagaga aaggccaagc ggaccagagc tgtgcagccc ctcaggctac    420

ctagcaacaa ggcccaggtg aagccagggc agacatgcag tgtggccggc tgggggcaga    480

cggcccccct gggaaaacac tcacacacac tacaagaggt gaagatgaca gtgcaggaag    540

atcgaaagtg cgaatctgac ttacgccatt attacgacag taccattgag ttgtgcgtgg    600

gggacccaga gattaaaaag acttccttta agggggactc tggaggccct cttgtgtgta    660

acaaggtggc ccagggcatt gtctcctatg gacgaaacaa tggcatgcct ccacgagcct    720

gcaccaaagt ctcaagcttt gtacactgga taaagaaaac catgaaacgc tactaactac    780

aggaagcaaa ctaagccccc gctgtaatga aacaccttct ctggagccaa gtccagattt    840

acactgggag aggtgccagc aactgaataa atacctctta gctgagtgg               889
```

<210> SEQ ID NO 18
<211> LENGTH: 475
<212> TYPE: DNA
<213> ORGANISM: Homo sapiens -continued

<400> SEQUENCE: 18

```
ttccactcag ctaagaggta tttattcagt tgctggcacc tctcccagtg taaatctgga     60
cttggctcca gagaaggtgt ttcattacag cgggggctta gtttgcttcc tgtagttagt    120
agcgtttcat ggttttcttt atccagtgta caaagcttga gactttggtg caggctcgtg    180
gaggcatgcc attgtttcgt ccataggaga caatgccctg ggccaccttg ttacacacaa    240
gagggcctcc agagtccccc ttaaaggaag tctttttaat ctctgggtcc cccacgcaca    300
actcaatggt actgtcgtaa taatggcgta agtcagattc gcactttcga tcttcctgca    360
ctgtcatctt cacctcttgt agtgtgtgtg agtgttttcc caagggggcc gtctgccccc    420
aaccggccac actggatgtt tgccctggct tttacctggc cttgttgcta tgtaa         475
```

<210> SEQ ID NO 19
<211> LENGTH: 484
<212> TYPE: DNA
<213> ORGANISM: Homo sapiens
<220> FEATURE:
<221> NAME/KEY: modified_base
<222> LOCATION: (438)
<223> OTHER INFORMATION: N = A, C, G or T/U

<400> SEQUENCE: 19

```
tttttccact cagctaagag gtatttattc agttgctggc accctctccc agtgtaaatc     60
tggacttggc tccagagaag gtgtttcatt acagcggggg cttagtttgc ttcctgtagt    120
tagtagcgtt tcatggtttt ctttatccag tgtacaaagc ttgagacttt ggtgcaggct    180
cgtggaggca tgccattgtt tcgtccatag gagacaatgc cctgggccac cttgttacac    240
acaagagggc ctccagagtc cccottaaag gaagtctttt taatctctgg gtcccccacg    300
cacaactcaa tggtactgtc gtaataatgg cgtaagtcag attcgcactt tcgatcttcc    360
tgcactgtca tcttcacctc ttgtagtgtg tgtgagtgtt ttcccagggg ggccgtttgc    420
cccaaccggc cacactgnat gtttgtcctt ggttcacctg ggcccttggt gctaggtagc    480
cccg                                                                 484
```

<210> SEQ ID NO 20
<211> LENGTH: 960
<212> TYPE: DNA
<213> ORGANISM: Homo sapiens

<400> SEQUENCE: 20

```
agcagctcca accagggcag ccttcctgag aagatgcaac caatcctgct tctgctggcc     60
ttcctcctgc tgcccagggc agatgcaggg gagatcatcg gggacatga ggccaagccc     120
cactcccgcc cctacatggc ttatcttatg atctgggatc agaagtctct gaagaggtgc    180
ggtggcttcc tgatacaaga cgacttcgtg ctgacagctg ctcactgttg gggaagctcc    240
ataaatgtca ccttgggggc ccacaatatc aaagaacagg agccgaccca gcagtttatc    300
cctgtgaaaa gacccatccc ccatccagcc tataatccta agaacttctc caacgacatc    360
atgctactgc agctggagag aaaggccaag cggaccagag ctgtgcagcc cctcaggcta    420
cctagcaaca aggcccaggt gaagccaggg cagacatgca gtgtggccgg ctgggggcag    480
acggcccccc tgggaaaaca ctcacacaca ctacaagagg tgaagatgac agtgcaggaa    540
gatcgaaagt gcgaatctga cttacgccat tattacgaca gtaccattga gttgtgcgtg    600
gggacccag agattaaaaa gacttccttt aaggggact ctggaggccc tcttgtgtgt    660
```

-continued

```
aacaaggtgg cccagggcat tgtctcctat ggacgaaaca atggcatgcc tccacgagcc    720

tgcaccaaag tctcaagctt tgtacactgg ataaagaaaa ccatgaaacg ctactaacta    780

caggaagcaa actaagcccc cgctgtaatg aaacaccttc tctggagcca agtccagatt    840

tacactggga gaggtgccag caactgaata aatacctctc ccagtgtaaa tctggagcca    900

agtccagatt tacactggga gaggtgccag caactgaata aatacctctt agctgagtgg    960
```

<210> SEQ ID NO 21
<211> LENGTH: 831
<212> TYPE: DNA
<213> ORGANISM: Homo sapiens

<400> SEQUENCE: 21

```
atcatcgggg gacatgtggc caagccccac tcccgcccct acatggctta tcttatgatc     60

tgggatcaga agtctctgaa gaggtgcggt ggcttcctga tacgagacga cttcgtgctg    120

acagctgctc actgttgggg aagctccata aatgtcacct tgggggccca caatatcaag    180

gaacaggagc cgacccagca gtttatccct gtgaaaagag ccatccccca tccagcctat    240

aatcctaaga acttctccaa tgacatcatg ctactgcagc tggagagaaa ggccaagcgg    300

accagagctg tgcagcccct caggctacct agcaacaagg cccaggtgaa gccagggcag    360

acatgcagtg tggccggctg gggggcagacg gcccccctgg gaaaacattc acacacacta    420

caagaggtga agatgacagt gcaggaagat cgaaagtgcg aatctgactt acgccattat    480

tacgacagta ccattgagtt gtgcgtgggg gacccagaga ttaaaaagac ttcctttaag    540

ggggactctg gaggccctct tgtgtgtaac aaggtggccc agggcattgt ctcctatgga    600

cgaaacaatg gcatgcctcc acgagcctgc accaaagtct caagctttgt acactggata    660

aagaaaacca tgaaacgcta ctaactacag gaagcaaact aagcccccgc tgtaatgcta    720

caggaagcaa actaagcccc cgctgtaatg aaacaccttc tctggagcca agtccagatt    780

tacactggga gaggtgccag caactgaata aatacctctt agctgagtgg t             831
```

<210> SEQ ID NO 22
<211> LENGTH: 4751
<212> TYPE: DNA
<213> ORGANISM: Homo sapiens

<400> SEQUENCE: 22

```
gaattctata ttttgagata taccattcct catagaaaaa tttcctcaca gaaaatataa     60

aggtggaaac aaatcacaag aatcgaacca tgtagagaga cttagttgtc ttttaacaga    120

attgggcacg ggctgttcag aaacaacaat ctttcacatc cattataatg atagcattag    180

tgtagtttgt ttagcaaatg tttactgcga gcctgttatg tgctgagcct gctatgtaag    240

aagtgtggct ctctggacag gagacagaat actaaacaac acaactactg atctttggct    300

gcctggcatg cttcctcact tcatatggta tcagcaattt agcaccacaa acgtccttta    360

gagaccagcc ctttctcatt cttggttcta gtggcttgag tagactgacc ccactaccca    420

agtggatttg actcctagca attcattaat ctagcccata aatgtcaagt acaggacttt    480

attgaagcat tcagaaagag gaatagggga tgttagaatc tctagaaagg aagctatgat    540

aataaatggg ttgctagatg ggtctagtag atggtggcca tgctttgtta ctgccttgtg    600

tattgtgcta ccatagccct ccccaaactg tactctggct cctggcattt ccgtctcttc    660

aaccagatgg tcagctctct aagtgaagga gacacatctc caacatgctt ggttctagca    720

caacagaagg gctcaaacac atacctgcta aagaaactat cctgatggat ttagcagcat    780
```

-continued

```
ggccatgagg cattggcggt tctatcactg ggaactcagg tttctggtgc tccagtacct    840
ctactggctg ataccacatc ctacagttca cttcataggc ttgggttcct gctctgggct    900
gaataggtgg tccactctga gtcatcagct gtggtgatga tgtggtcact gcatgattct    960
cacacaagca cccagaggac gtcatcaggc agaggcagtg ggggtgggca gcatttacag   1020
aaaatctgtg atgagacacc acaaaaccag aggggaacat gaagtcactg agcctgctcc   1080
acctctttcc tctcccaaga gctaaaagag agcaaggagg aaacaacagc agctccaacc   1140
agggcagcct tcctgagaag atgcaaccaa tcctgcttct gctggccttc ctcctgctgc   1200
ccagggcaga tgcaggtgag tgaccgtctt ccaacctcgg ggcccaaccc atcccacagg   1260
tctcctgccc tttctccaca ttcctgatcc atctatctac caggaatgtt ctgaactcca   1320
gctcccattc taccaagacc ccccaagtgt gatgctggat aagctatcag caggaatggc   1380
agagcagcag gccattctca agaagagcca gtgggtacta tcccttcccc agagcccacc   1440
tttgtcacct ggagagtagg actttcctag aagtaaatgg cagaggatgg gaaactagaa   1500
aagagaaata ttaaattatt ctagagtagg cctggcttct gtttctggga taagacaggt   1560
gcttctctca ctgtacttag gagagaaacc cagagctcag ctgacagcag aattggtaca   1620
atcactgtcc tcagaacact gttaatgtgt ttgctcagtc ccattctcca actctgcttt   1680
tcttccctgg cctttggtgg ctcccctctt tccaaggatg aggcactacg gcaggcccca   1740
gcttccctgc tttctagaat tccaccagca ctgctctacc agccctcatc cagaggctaa   1800
ctggagccag tccatcatgc agccatgaac atttactggg cacccactac atgtcaggct   1860
ctaggaaaca ggatatgaca gtatctagat ccctccactt acaccctggc cattagaaag   1920
cagcactatc ctagacacca caggactcat aagggtcttg gaaactcacc tgaaacaaag   1980
caaagtcagg agaggaatga tcaggagcct ctgggatttc actgtcccta agacaggtat   2040
gctcgccttc aactacatat ggaagaaaga tttacagacc aaagtctgct gttcttccct   2100
ttttcagagc aggaaattga agccccttcc tccaggccac tcccaactcc aggctatccc   2160
aggctcccaa atgcccagga gttctggagc cactaagcag gtgcccaccc agcagattcc   2220
atgggtgccc acaagcagac agacttttcc ttcaggggag atcatcgggg gacatgaggc   2280
caagccccac tcccgcccct acatggctta tcttatgatc tgggatcaga agtctctgaa   2340
gaggtgcggt ggcttcctga tacaagacga cttcgtgctg acagctgctc actgttgggg   2400
aaggtgagga gcagaaaaca gcccacaccc tcctggaaac actccacaga gacccctgcc   2460
ttcttcccaa ggagctccct gggctcctgt gaacacacat gccaggaggt ctccttagag   2520
ggtgagaaaa gggcagttaa gtttgtggag agaggggaag gttggttcca gaggtgctgc   2580
tgaagtaaga aacagcagag tgaccaagcc tgccatattt agaactgggg gcatactttg   2640
gcatagaata caaactgaag caattccacc tgtgtttcta gggggaaccg aaccctgaga   2700
aacctggtgc aattaccaga attccaattc ctggggaccg actgtcctta atttcccctc   2760
agctgcagcc ctgccccagc tgtcacctgc tcttcactgt ctctgggctg tatacactgt   2820
gactccaccc ccatcctcac tctgctctct gtgcagctcc ataaatgtca ccttgggggc   2880
ccacaatatc aaggaacagg agccgaccca gcagtttatc cctgtgaaaa gagccatccc   2940
ccatccagcc tataatccta agaacttctc caatgacatc atgctactgc aggtgaggca   3000
cactcctgcc actcttgctc ttcttggtcc agttggttcc actccccctg gaatgccggc   3060
ccttccctcc tttccatcct ggcctcttgg ttagttccta tgcctcagag gagagaggga   3120
```

-continued

```
agattgtgca gccccatcac tgtgtcgggg cccagaagtt cgttggctga cctggacttt   3180

cttgcctctt ccccaccagc tggagagaaa ggccaagcgg accagagctg tgcagcccct   3240

caggctacct agcaacaagg cccaggtgaa gccagggcag acatgcagtg tggccggctg   3300

ggggcagacg gcccccctgg gaaaacactc acacacacta caagaggtga agatgacagt   3360

gcaggaagat cgaaagtgcg aatctgactt acgccattat tacgacagta ccattgagtt   3420

gtgcgtgggg gacccagaga ttaaaaagac ttcctttaag gtaagactat gcacctgcct   3480

ggattggctc ttgggagaaa gatgtttggg gaatatctga gacctggaga ctcaagtagt   3540

gggggactcc ttcacccact agactgtgat atttctctct ggaaagagaa aaggggacta   3600

gactgagctg gggagaaatt agggcctctg caaacttacc aagaggcctt atggtggatg   3660

gtgccttctt tggaaggatg aatttgcaac actccaccca ctccaggtca cagatattag   3720

gaaactgtgc ccatgggggt gcagctaatt ataaccaggt gtgtcttcag aggctggtac   3780

ccaacgtggt taatgggctg gtcctccatg gtggacatca gccctccttg cccacttctg   3840

ggtccttaaa cagccaacgg tcccacatac ctccgatctc aggatctggg ggacatgacg   3900

gaggctggcc cctgggatga ggtgaagcag taacaatgtc cagggccaga gcttggcagc   3960

tggggccacc agcggcctgc cctgccctct ggtctcccac atgtaggctg tgcaagttgg   4020

ccttttctaa aagggggctt gagatggaag agagggcagg acccggagga gcatcagctc   4080

agtccttcca ctctctattc acagggggac tctggaggcc ctcttgtgtg taacaaggtg   4140

gcccagggca ttgtctccta tggacgaaac aatggcatgc ctccacgagc ctgcaccaaa   4200

gtctcaagct ttgtacactg gataaagaaa accatgaaac gctactaact acaggaagca   4260

aactaagccc ccgctgtaat gaaacacctt ctctggagcc aagtccagat ttacactggg   4320

agaggtgcca gcaactgaat aaatacctct tagctgagtg gaaagctggt ttcttgttta   4380

ttcattgacc ctcattctca ggcaccacat ctgcgctatg caggccaatg acacaatttt   4440

gctgttttct gctttctcct ctcccctcac cccttgccac ctccccaaac cccacatga    4500

agctgatact cagctccttc ctatccacac cagtttctcc agggcctgcc ttctgccaag   4560

gctgaagctg agcaccatca ggagacaaca tggaccactt tggtcctggg gctttgggta   4620

aacttcttac ctccttctcc agtgttacat tgacagagaa aaaagggata ataccatggg   4680

acctaactcc tcatcccact ggggctcctc attctcccct gggcttagtt tctctaccct   4740

cctctgagct c                                                        4751
```

<210> SEQ ID NO 23
<211> LENGTH: 262
<212> TYPE: PRT
<213> ORGANISM: Homo sapiens

<400> SEQUENCE: 23

```
Met Arg Asn Ser Tyr Arg Phe Leu Ala Ser Ser Leu Ser Val Val Val
  1               5                  10                  15

Ser Leu Leu Leu Ile Pro Glu Asp Val Cys Glu Lys Ile Ile Gly Gly
             20                  25                  30

Asn Glu Val Thr Pro His Ser Arg Pro Tyr Met Val Leu Leu Ser Leu
         35                  40                  45

Asp Arg Lys Thr Ile Cys Ala Gly Ala Leu Ile Ala Lys Asp Trp Val
     50                  55                  60

Leu Thr Ala Ala His Cys Asn Leu Asn Lys Arg Ser Gln Val Ile Leu
 65                  70                  75                  80
```

-continued

```
Gly Ala His Ser Ile Thr Arg Glu Glu Pro Thr Lys Gln Ile Met Leu
                85                  90                  95

Val Lys Lys Glu Phe Pro Tyr Pro Cys Tyr Asp Pro Ala Thr Arg Glu
            100                 105                 110

Gly Asp Leu Lys Leu Leu Gln Leu Thr Glu Lys Ala Lys Ile Asn Lys
        115                 120                 125

Tyr Val Thr Ile Leu His Leu Pro Lys Lys Gly Asp Asp Val Lys Pro
    130                 135                 140

Gly Thr Met Cys Gln Val Ala Gly Trp Gly Arg Thr His Asn Ser Ala
145                 150                 155                 160

Ser Trp Ser Asp Thr Leu Arg Glu Val Asn Ile Thr Ile Ile Asp Arg
                165                 170                 175

Lys Val Cys Asn Asp Arg Asn His Tyr Asn Phe Asn Pro Val Ile Gly
            180                 185                 190

Met Asn Met Val Cys Ala Gly Ser Leu Arg Gly Gly Arg Asp Ser Cys
        195                 200                 205

Asn Gly Asp Ser Gly Ser Pro Leu Leu Cys Glu Gly Val Phe Arg Gly
    210                 215                 220

Val Thr Ser Phe Gly Leu Glu Asn Lys Cys Gly Asp Pro Arg Gly Pro
225                 230                 235                 240

Gly Val Tyr Ile Leu Leu Ser Lys Lys His Leu Asn Trp Ile Ile Met
                245                 250                 255

Thr Ile Lys Gly Ala Val
        260


<210> SEQ ID NO 24
<211> LENGTH: 262
<212> TYPE: PRT
<213> ORGANISM: Homo sapiens

<400> SEQUENCE: 24

Met Arg Asn Ser Tyr Arg Phe Leu Ala Ser Ser Leu Ser Val Val Val
  1               5                  10                  15

Ser Leu Leu Leu Ile Pro Glu Asp Val Cys Glu Lys Ile Ile Gly Gly
             20                  25                  30

Asn Glu Val Thr Pro His Ser Arg Pro Tyr Met Val Leu Leu Ser Leu
         35                  40                  45

Asp Arg Lys Thr Ile Cys Ala Gly Ala Leu Ile Ala Lys Asp Trp Val
     50                  55                  60

Leu Thr Ala Ala His Cys Asn Leu Asn Lys Arg Ser Gln Val Ile Leu
 65                  70                  75                  80

Gly Ala His Ser Ile Thr Arg Glu Glu Pro Thr Lys Gln Ile Met Leu
                85                  90                  95

Val Lys Lys Glu Phe Pro Tyr Pro Cys Tyr Asp Pro Ala Thr Arg Glu
            100                 105                 110

Gly Asp Leu Lys Leu Leu Gln Leu Met Glu Lys Ala Lys Ile Asn Lys
        115                 120                 125

Tyr Val Thr Ile Leu His Leu Pro Lys Lys Gly Asp Asp Val Lys Pro
    130                 135                 140

Gly Thr Met Cys Gln Val Ala Gly Trp Gly Arg Thr His Asn Ser Ala
145                 150                 155                 160

Ser Trp Ser Asp Thr Leu Arg Glu Val Asn Ile Thr Ile Ile Asp Arg
                165                 170                 175

Lys Val Cys Asn Asp Arg Asn His Tyr Asn Phe Asn Pro Val Ile Gly
            180                 185                 190
```

-continued

```
Met Asn Met Val Cys Ala Gly Ser Leu Arg Gly Gly Arg Asp Ser Cys
        195                 200                 205

Asn Gly Asp Ser Gly Ser Pro Leu Leu Cys Glu Gly Val Phe Arg Gly
    210                 215                 220

Val Thr Ser Phe Gly Leu Glu Asn Lys Cys Gly Asp Pro Arg Gly Pro
225                 230                 235                 240

Gly Val Tyr Ile Leu Leu Ser Lys Lys His Leu Asn Trp Ile Ile Met
                245                 250                 255

Thr Ile Lys Gly Ala Val
            260


<210> SEQ ID NO 25
<211> LENGTH: 262
<212> TYPE: PRT
<213> ORGANISM: Homo sapiens
<220> FEATURE:
<221> NAME/KEY: MOD_RES
<222> LOCATION: (121)
<223> OTHER INFORMATION: x = t or m

<400> SEQUENCE: 25

Met Arg Asn Ser Tyr Arg Phe Leu Ala Ser Ser Leu Ser Val Val Val
  1               5                  10                  15

Ser Leu Leu Leu Ile Pro Glu Asp Val Cys Glu Lys Ile Ile Gly Gly
            20                  25                  30

Asn Glu Val Thr Pro His Ser Arg Pro Tyr Met Val Leu Leu Ser Leu
        35                  40                  45

Asp Arg Lys Thr Ile Cys Ala Gly Ala Leu Ile Ala Lys Asp Trp Val
     50                  55                  60

Leu Thr Ala Ala His Cys Asn Leu Asn Lys Arg Ser Gln Val Ile Leu
 65                  70                  75                  80

Gly Ala His Ser Ile Thr Arg Glu Glu Pro Thr Lys Gln Ile Met Leu
                85                  90                  95

Val Lys Lys Glu Phe Pro Tyr Pro Cys Tyr Asp Pro Ala Thr Arg Glu
            100                 105                 110

Gly Asp Leu Lys Leu Leu Gln Leu Xaa Glu Lys Ala Lys Ile Asn Lys
        115                 120                 125

Tyr Val Thr Ile Leu His Leu Pro Lys Lys Gly Asp Asp Val Lys Pro
    130                 135                 140

Gly Thr Met Cys Gln Val Ala Gly Trp Gly Arg Thr His Asn Ser Ala
145                 150                 155                 160

Ser Trp Ser Asp Thr Leu Arg Glu Val Asn Ile Thr Ile Ile Asp Arg
                165                 170                 175

Lys Val Cys Asn Asp Arg Asn His Tyr Asn Phe Asn Pro Val Ile Gly
            180                 185                 190

Met Asn Met Val Cys Ala Gly Ser Leu Arg Gly Gly Arg Asp Ser Cys
        195                 200                 205

Asn Gly Asp Ser Gly Ser Pro Leu Leu Cys Glu Gly Val Phe Arg Gly
    210                 215                 220

Val Thr Ser Phe Gly Leu Glu Asn Lys Cys Gly Asp Pro Arg Gly Pro
225                 230                 235                 240

Gly Val Tyr Ile Leu Leu Ser Lys Lys His Leu Asn Trp Ile Ile Met
                245                 250                 255

Thr Ile Lys Gly Ala Val
            260
```

-continued

<210> SEQ ID NO 26
<211> LENGTH: 878
<212> TYPE: DNA
<213> ORGANISM: Homo sapiens

<400> SEQUENCE: 26
cagattttca ggttgattga tgtgggacag cagccacaat gaggaactcc tatagatttc 60
tggcatcctc tctctcagtt gtcgtttctc tcctgctaat tcctgaagat gtctgtgaaa 120
aaattattgg aggaaatgaa gtaactcctc attcaagacc ctacatggtc ctacttagtc 180
ttgacagaaa aaccatctgt gctggggctt tgattgcaaa agactgggtg ttgactgcag 240
ctcactgtaa cttgaacaaa aggtcccagg tcattcttgg ggctcactca ataaccaggg 300
aagagccaac aaaacagata atgcttgtta agaaagagtt tccctatcca tgctatgacc 360
cagccacacg cgaaggtgac cttaaacttt tacagctgat ggaaaaagca aaaattaaca 420
aatatgtgac tatccttcat ctacctaaaa agggggacga tgtgaaacca ggaaccatgt 480
gccaagttgc agggtggggc aggactcaca atagtgcatc ttggtccgat actctgagag 540
aagtcaatat caccatcata gacagaaaag tctgcaatga tcgaaatcac tataatttta 600
accctgtgat tggaatgaat atggtttgtg ctggaagcct ccgaggtgga agagactcgt 660
gcaatggaga ttctggaagc cctttgttgt gcgagggtgt tttccgaggg gtcacttcct 720
ttggccttga aaataaatgc ggagaccctc gtgggcctgg tgtctatatt cttctctcaa 780
agaaacacct caactggata attatgacta tcaagggagc agtttaaata accgtttcct 840
ttcatttact gtggcttctt aatcttttca caaataaa 878

<210> SEQ ID NO 27
<211> LENGTH: 878
<212> TYPE: DNA
<213> ORGANISM: Homo sapiens

<400> SEQUENCE: 27
cagattttca ggttgattga tgtgggacag cagccacaat gaggaactcc tatagatttc 60
tggcatcctc tctctcagtt gtcgtttctc tcctgctaat tcctgaagat gtctgtgaaa 120
aaattattgg aggaaatgaa gtaactcctc attcaagacc ctacatggtc ctacttagtc 180
ttgacagaaa aaccatctgt gctggggctt tgattgcaaa agactgggtg ttgactgcag 240
ctcactgtaa cttgaacaaa aggtcccagg tcattcttgg ggctcactca ataaccaggg 300
aagagccaac aaaacagata atgcttgtta agaaagagtt tccctatcca tgctatgacc 360
cagccacacg cgaaggtgac cttaaacttt tacagctgac ggaaaaagca aaaattaaca 420
aatatgtgac tatccttcat ctacctaaaa agggggatga tgtgaaacca ggaaccatgt 480
gccaagttgc agggtggggg aggactcaca atagtgcatc ttggtccgat actctgagag 540
aagtcaatat caccatcata gacagaaaag tctgcaatga tcgaaatcac tataatttta 600
accctgtgat tggaatgaat atggtttgtg ctggaagcct ccgaggtgga agagactcgt 660
gcaatggaga ttctggaagc cctttgttgt gcgagggtgt tttccgaggg gtcacttcct 720
ttggccttga aaataaatgc ggagaccctc gtgggcctgg tgtctatatt cttctctcaa 780
agaaacacct caactggata attatgacta tcaagggagc agtttaaata accgtttcct 840
ttcatttact gtggcttctt aatcttttca caaataaa 878

<210> SEQ ID NO 28
<211> LENGTH: 1610

-continued

<212> TYPE: DNA
<213> ORGANISM: Homo sapiens

<400> SEQUENCE: 28
aagcttccaa tgactttctt cacagaattg gaaaaaacta ctttaaagtt catatggaac 60
caaacaagag cccacattgc caagacaatc ctaagccaaa agaacaaagc tggaagcatc 120
atgctacctg acttcaacaa tactacaagg ctacgtaacc aaaacagatg gactggtaat 180
ggctgcacaa ctatgcatat atactaaatc cattgactat acactctaaa tgggtgacct 240
tatggtgtgt gaattatgtc tcataaagtt gttagaagtc gacataaatg gaagagcaac 300
cattcacata aaaataaaca aaattgtcaa tgttttaaga atttttcagt aggtgtagtt 360
aattacaatt tgactttttt aagtctgcac taaattactc accaaaacca atagcagggt 420
cctcactgct gttactgaaa atgattaacc tttgatacac ttgtaatatc tgagaaaaag 480
aaatgcaggg gtctcagcag ggctcccttc taaggtcact tgatttctaa agaagtaacc 540
actaggtttg aagtcatcag gatgttaact atggggatgg ttggttcagt acccaacatc 600
ctgacagcac atctgaccat gtatattgta tcggagacca catcctcagc tcagaaaaag 660
agctgaactc atttcaaata gaagcacacc tgcatactgt tcctccaggg actgaggttg 720
actcttctta gagtgagaca ttccccaaca ttggaacaaa aatgactccc acttcttttc 780
tcacctaaac ctgttcagaa gaaagaagaa aggcaggaag caggggtcgg ggggggcggg 840
gagggaggga aactcggaga tactttcagt atctaaagtt gtgaaactag acaatcagga 900
acgcacaatc agagggctga aaagggccaa gagcccccta ccctcctcca gcccatgttc 960
ccacacctgc cacagaccag gcaggagcag aataaacact cacacaaagt gggaaggaaa 1020
atccagcagg agcctctatg taaataaatc tccctcctgt cctgagcttg cacttggcct 1080
gctaattcta tataacccaa ggagacagct agaaagaatt ttgattggtg accaattttg 1140
aggactttta ttaaaattct aatttaagtc ttcgagagtt tccagtcatg gatagtacag 1200
ataatattgc agatgatgaa agcgtcttca aaatcatagc tgagaccttc acgtcttccc 1260
tggtgtactc tgatggcaac aaggtccctt gcccctctcc tacccatgta gaattccagc 1320
gcccccctca gcagtcctag caaaggaaag cctgcctgct ggcagtgagc catcatccac 1380
cattctcact tatttggatt tggtttccta atgctaaact ttgaaacttg aaaaaaaaaa 1440
tgaaaggaaa ccacatcctt tttactctca gtatatagat agaggcagtt aagaactgaa 1500
aacagatttt caggttgatt gatgtgggac agcagccaca atgaggaact cctatagatt 1560
tctggcatcc tctctctcag ttgtcgtttc tctcctgcta attcctgaag 1610

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 29
ggtgatggac gggtccgggg agca 24

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Primer -continued

<400> SEQUENCE: 30
ggcctcagcc catcttcttc cagatggtga 30

<210> SEQ ID NO 31
<211> LENGTH: 51
<212> TYPE: DNA
<213> ORGANISM: Artificial Sequence
<220> FEATURE:
<223> OTHER INFORMATION: Description of Artificial Sequence: Primer

<400> SEQUENCE: 31
ggtggcggtg gctccatggc ggacattgtg atgacccagt ctcaaaaatt c 51

<210> SEQ ID NO 32
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 32
cgtcggagcc accgccaccg ctagctgagg agacggtgag agt 43

<210> SEQ ID NO 33
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 33
ggtggcggtg gctccgacgg gtccggggag cag 33

<210> SEQ ID NO 34
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 34
ggagccaccg ccaccctcga gctatcagcc catcttcttc cagat 45

<210> SEQ ID NO 35
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 35
ggtggcggtg gctccatgga cgggtccggg gagcag 36

<210> SEQ ID NO 36
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 36
gtccgtggag ccaccgccac cgctagcgcc catcttcttc ca 42

<210> SEQ ID NO 37
<211> LENGTH: 48

-continued

<212> TYPE: DNA
<213> ORGANISM: Artificial Sequence
<220> FEATURE:
<223> OTHER INFORMATION: Description of Artificial Sequence: Primer

<400> SEQUENCE: 37
ggtggcggtg gctccacgga cattgtgatg acccagtctc aaaaattc 48

<210> SEQ ID NO 38
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 38
ggagccaccg ccaccctcga gctatcatga ggagacggtg agagtggt 48

<210> SEQ ID NO 39
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 39
ggagccaccg ccaccctcga gctatcacca accaccctgg tc 42

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 40
ggagccaccg ccaccccaac caccctggtc 30

<210> SEQ ID NO 41
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 41
ccggagccac cgccaccgct agctgaggag actgtga 37

<210> SEQ ID NO 42
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 42
ggtggcggtg gctccttcat ccaggatcga g 31

<210> SEQ ID NO 43
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 43

-continued ggtggcggtg gctccatggt catccaggat cgag 34

<210> SEQ ID NO 44
<211> LENGTH: 57
<212> TYPE: DNA
<213> ORGANISM: Artificial Sequence
<220> FEATURE:
<223> OTHER INFORMATION: Description of Artificial Sequence: Primer

<400> SEQUENCE: 44
aaacatgcca tggctcacca ccaccaccac cacgacgggt ccggggagca gcccaga 57

<210> SEQ ID NO 45
<211> LENGTH: 573
<212> TYPE: DNA
<213> ORGANISM: Homo sapiens

<400> SEQUENCE: 45
gacgggtccg gggagcagcc cagaggcggg gggcccacca gctctgagca gatcatgaag 60
acaggggccc ttttgcttca gggtttcatc caggatcgag cagggcgaat gggggggag 120 gcacccgagc tggccctgga cccggtgcct caggatgcgt ccaccaagaa gctgagcgag 180
tgtctcaagc gcatcgggga cgaactggac agtaacatgg agctgcagag gatgattgcc 240
gccgtggaca cagactcccc ccgagaggtc tttttccgag tggcagctga catgttttct 300
gacggcaact tcaactgggg ccgggttgtc gcccttttct actttgccag caaactggtg 360
ctcaaggccc tgtgcaccaa ggtgccggaa ctgatcagaa ccatcatggg ctggacattg 420
gacttcctcc gggagcggct gttgggctgg atccaagacc agggtggttg ggacggcctc 480
ctctcctact ttgggacgcc cacgtggcag accgtgacca tctttgtggc gggagtgctc 540
accgcctcgc tcaccatctg gaagaagatg ggc 573

<210> SEQ ID NO 46
<211> LENGTH: 191
<212> TYPE: PRT
<213> ORGANISM: Homo sapiens

<400> SEQUENCE: 46

Asp Gly Ser Gly Glu Gln Pro Arg Gly Gly Gly Pro Thr Ser Ser Glu
1 5 10 15

Gln Ile Met Lys Thr Gly Ala Leu Leu Leu Gln Gly Phe Ile Gln Asp
20 25 30

Arg Ala Gly Arg Met Gly Gly Glu Ala Pro Glu Leu Ala Leu Asp Pro
35 40 45

Val Pro Gln Asp Ala Ser Thr Lys Lys Leu Ser Glu Cys Leu Lys Arg
50 55 60

Ile Gly Asp Glu Leu Asp Ser Asn Met Glu Leu Gln Arg Met Ile Ala
65 70 75 80

Ala Val Asp Thr Asp Ser Pro Arg Glu Val Phe Phe Arg Val Ala Ala
85 90 95

Asp Met Phe Ser Asp Gly Asn Phe Asn Trp Gly Arg Val Val Ala Leu
100 105 110

Phe Tyr Phe Ala Ser Lys Leu Val Leu Lys Ala Leu Val Thr Lys Val
115 120 125

Pro Glu Leu Ile Arg Thr Ile Met Gly Trp Thr Leu Asp Phe Leu Arg
130 135 140

Glu Arg Leu Leu Gly Trp Ile Gln Asp Gln Gly Gly Trp Asp Gly Leu
145 150 155 160

-continued

Leu Ser Tyr Phe Gly Thr Pro Thr Trp Gln Thr Val Thr Ile Phe Val
165 170 175

Ala Gly Val Leu Thr Ala Ser Leu Thr Ile Trp Lys Lys Met Gly
180 185 190

<210> SEQ ID NO 47
<211> LENGTH: 11
<212> TYPE: PRT
<213> ORGANISM: Homo sapiens

<400> SEQUENCE: 47

Asp Gly Asn Phe Asn Trp Gly Arg Val Val Ala
1 5 10

<210> SEQ ID NO 48
<211> LENGTH: 9
<212> TYPE: PRT
<213> ORGANISM: Homo sapiens

<400> SEQUENCE: 48

Trp Ile Gln Asp Gln Gly Gly Trp Asp
1 5

<210> SEQ ID NO 49
<211> LENGTH: 7
<212> TYPE: PRT
<213> ORGANISM: Homo sapiens

<400> SEQUENCE: 49

Leu Lys Arg Ile Gly Asp Glu
1 5

<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: Linker

<400> SEQUENCE: 50

Gly Gly Gly Gly Ser
1 5

<210> SEQ ID NO 51
<211> LENGTH: 14
<212> TYPE: PRT
<213> ORGANISM: Artificial Sequence
<220> FEATURE:
<223> OTHER INFORMATION: Description of Artificial Sequence: Linker

<400> SEQUENCE: 51

Glu Gly Lys Ser Ser Gly Ser Gly Ser Glu Ser Lys Val Asp
1 5 10

<210> SEQ ID NO 52
<211> LENGTH: 18
<212> TYPE: PRT
<213> ORGANISM: Artificial Sequence
<220> FEATURE:
<223> OTHER INFORMATION: Description of Artificial Sequence: Linker

<400> SEQUENCE: 52

Lys Glu Ser Gly Ser Val Ser Ser Glu Gln Leu Ala Gln Phe Arg Ser
1 5 10 15

-continued

Leu Asp

<210> SEQ ID NO 53
<211> LENGTH: 4
<212> TYPE: PRT
<213> ORGANISM: Artificial Sequence
<220> FEATURE:
<223> OTHER INFORMATION: Description of Artificial Sequence:
Enterokinase cleavage site

<400> SEQUENCE: 53

Asp Asp Asp Lys
1

<210> SEQ ID NO 54
<211> LENGTH: 744
<212> TYPE: DNA
<213> ORGANISM: Homo sapiens

<400> SEQUENCE: 54
atgcaaccaa tcctgcttct gctggccttc ctcctgctgc ccagggcaga tgcaggggag 60
atcatcgggg gacatgaggc caagccccac tcccgcccct acatggctta tcttatgatc 120
tgggatcaga agtctctgaa gaggtgcggt ggcttcctga tacaagacga cttcgtgctg 180
acagctgctc actgttgggg aagctccata aatgtcacct tgggggccca caatatcaaa 240
gaacaggagc cgacccagca gtttatccct gtgaaaagac ccatccccca tccagcctat 300
aatcctaaga acttctccaa cgacatcatg ctactgcagc tggagagaaa ggccaagcgg 360
accagagctg tgcagcccct caggctacct agcaacaagg cccaggtgaa gccagggcag 420
acatgcagtg tggccggctg gggcagacg gcccccctgg gaaaacactc acacacacta 480
caagaggtga agatgacagt gcaggaagat cgaaagtgcg aatctgactt acgccattat 540
tacgacagta ccattgagtt gtgcgtgggg gacccagaga ttaaaaagac ttcctttaag 600
ggggactctg gaggccctct tgtgtgtaac aaggtggccc agggcattgt ctcctatgga 660
cgaaacaatg gcatgcctcc acgagcctgc accaaagtct caagctttgt acactggata 720
aagaaaacca tgaaacgcta ctaa 744

<210> SEQ ID NO 55
<211> LENGTH: 247
<212> TYPE: PRT
<213> ORGANISM: Homo sapiens

<400> SEQUENCE: 55

Met Gln Pro Ile Leu Leu Leu Leu Ala Phe Leu Leu Leu Pro Arg Ala
1 5 10 15

Asp Ala Gly Glu Ile Ile Gly Gly His Glu Ala Lys Pro His Ser Arg
20 25 30

Pro Tyr Met Ala Tyr Leu Met Ile Trp Asp Gln Lys Ser Leu Lys Arg
35 40 45

Cys Gly Gly Phe Leu Ile Gln Asp Asp Phe Val Leu Thr Ala Ala His
50 55 60

Cys Trp Gly Ser Ser Ile Asn Val Thr Leu Gly Ala His Asn Ile Lys
65 70 75 80

Glu Gln Glu Pro Thr Gln Gln Phe Ile Pro Val Lys Arg Pro Ile Pro
85 90 95

His Pro Ala Tyr Asn Pro Lys Asn Phe Ser Asn Asp Ile Met Leu Leu
100 105 110

-continued

```
Gln Leu Glu Arg Lys Ala Lys Arg Thr Arg Ala Val Gln Pro Leu Arg
        115                 120                 125

Leu Pro Ser Asn Lys Ala Gln Val Lys Pro Gly Gln Thr Cys Ser Val
    130                 135                 140

Ala Gly Trp Gly Gln Thr Ala Pro Leu Gly Lys His Ser His Thr Leu
145                 150                 155                 160

Gln Glu Val Lys Met Thr Val Gln Glu Asp Arg Lys Cys Glu Ser Asp
                165                 170                 175

Leu Arg His Tyr Tyr Asp Ser Thr Ile Glu Leu Cys Val Gly Asp Pro
            180                 185                 190

Glu Ile Lys Lys Thr Ser Phe Lys Gly Asp Ser Gly Gly Pro Leu Val
        195                 200                 205

Cys Asn Lys Val Ala Gln Gly Ile Val Ser Tyr Gly Arg Asn Asn Gly
    210                 215                 220

Met Pro Pro Arg Ala Cys Thr Lys Val Ser Ser Phe Val His Trp Ile
225                 230                 235                 240

Lys Lys Thr Met Lys Arg Tyr
                245
```

<210> SEQ ID NO 56
<211> LENGTH: 1059
<212> TYPE: DNA
<213> ORGANISM: Artificial Sequence
<220> FEATURE:
<223> OTHER INFORMATION: Description of Artificial Sequence: Granhzyme B-vegf121

<400> SEQUENCE: 56

```
atcatcgggg gacatgaggc caagccccac tcccgcccct acatggctta tcttatgatc     60

tgggatcaga agtctctgaa gaggtgcggt ggcttcctga tacaagacga cttcgtgctg    120

acagctgctc actgttgggg aagctccata aatgtcacct tgggggccca caatatcaaa    180

gaacaggagc cgacccagca gtttatccct gtgaaaagac ccatccccca tccagcctat    240

aatcctaaga acttctccaa cgacatcatg ctactgcagc tggagagaaa ggccaagcgg    300

accagagctg tgcagcccct caggctacct agcaacaagg cccaggtgaa gccagggcag    360

acatgcagtg tggccggctg gggcagacg gcccccctgg gaaaacactc acacacacta    420

caagaggtga agatgacagt gcaggaagat cgaaagtgcg aatctgactt acgccattat    480

tacgacagta ccattgagtt gtgcgtgggg gacccagaga ttaaaaagac ttcctttaag    540

ggggactctg gaggccctct tgtgtgtaac aaggtggccc agggcattgt ctcctatgga    600

cgaaacaatg gcatgcctcc acgagcctgc accaaagtct caagctttgt acactggata    660

aagaaaacca tgaaacgcta cggtggcggt ggctccgcac ccatggcaga aggaggaggg    720

cagaatcatc acgaagtggt gaagttcatg gatgtctatc agcgcagcta ctgccatcca    780

atcgagaccc tggtggacat cttccaggag taccctgatg agatcgagta catcttcaag    840

ccatcctgtg tgcccctgat gcgatgcggg ggctgctgca atgacgaggg cctggagtgt    900

gtgcccactg aggagtccaa catcaccatg cagattatgc ggatcaaacc tcaccaaggc    960

cagcacatag gagagatgag cttcctacag cacaacaaat gtgaatgcag accaaagaaa   1020

gatagagcaa gacaagaaaa ttgtgacaag ccgaggcgg                          1059
```

<210> SEQ ID NO 57
<211> LENGTH: 353
<212> TYPE: PRT
<213> ORGANISM: Artificial Sequence -continued

```
<220> FEATURE:
<223> OTHER INFORMATION: Description of Artificial Sequence:  Granzyme
      B-vegf121

<400> SEQUENCE: 57

Ile Ile Gly Gly His Glu Ala Lys Pro His Ser Arg Pro Tyr Met Ala
  1               5                  10                  15

Tyr Leu Met Ile Trp Asp Gln Lys Ser Leu Lys Arg Cys Gly Gly Phe
             20                  25                  30

Leu Ile Gln Asp Asp Phe Val Leu Thr Ala Ala His Cys Trp Gly Ser
         35                  40                  45

Ser Ile Asn Val Thr Leu Gly Ala His Asn Ile Lys Glu Gln Glu Pro
     50                  55                  60

Thr Gln Gln Phe Ile Pro Val Lys Arg Pro Ile Pro His Pro Ala Tyr
 65                  70                  75                  80

Asn Pro Lys Asn Phe Ser Asn Asp Ile Met Leu Leu Gln Leu Glu Arg
                 85                  90                  95

Lys Ala Lys Arg Thr Arg Ala Val Gln Pro Leu Arg Leu Pro Ser Asn
            100                 105                 110

Lys Ala Gln Val Lys Pro Gly Gln Thr Cys Ser Val Ala Gly Trp Gly
        115                 120                 125

Gln Thr Ala Pro Leu Gly Lys His Ser His Thr Leu Gln Glu Val Lys
    130                 135                 140

Met Thr Val Gln Glu Asp Arg Lys Cys Glu Ser Asp Leu Arg His Tyr
145                 150                 155                 160

Tyr Asp Ser Thr Ile Glu Leu Cys Val Gly Asp Pro Glu Ile Lys Lys
                165                 170                 175

Thr Ser Phe Lys Gly Asp Ser Gly Gly Pro Leu Val Cys Asn Lys Val
            180                 185                 190

Ala Gln Gly Ile Val Ser Tyr Gly Arg Asn Asn Gly Met Pro Pro Arg
        195                 200                 205

Ala Cys Thr Lys Val Ser Ser Phe Val His Trp Ile Lys Lys Thr Met
    210                 215                 220

Lys Arg Tyr Gly Gly Gly Gly Ser Ala Pro Met Ala Glu Gly Gly Gly
225                 230                 235                 240

Gln Asn His His Glu Val Val Lys Phe Met Asp Val Tyr Gln Arg Ser
                245                 250                 255

Tyr Cys His Pro Ile Glu Thr Leu Val Asp Ile Phe Gln Glu Tyr Pro
            260                 265                 270

Asp Glu Ile Glu Tyr Ile Phe Lys Pro Ser Cys Val Pro Leu Met Arg
        275                 280                 285

Cys Gly Gly Cys Cys Asn Asp Glu Gly Leu Glu Cys Val Pro Thr Glu
    290                 295                 300

Glu Ser Asn Ile Thr Met Gln Ile Met Arg Ile Lys Pro His Gln Gly
305                 310                 315                 320

Gln His Ile Gly Glu Met Ser Phe Leu Gln His Asn Lys Cys Glu Cys
                325                 330                 335

Arg Pro Lys Lys Asp Arg Ala Arg Gln Glu Asn Cys Asp Lys Pro Arg
            340                 345                 350

Arg


<210> SEQ ID NO 58
<211> LENGTH: 1440
<212> TYPE: DNA
<213> ORGANISM: Artificial Sequence
```

-continued

<220> FEATURE:
<223> OTHER INFORMATION: Description of Artificial Sequence: Granzyme
B-scFvMEL

<400> SEQUENCE: 58

```
atcatcgggg gacatgaggc caagccccac tcccgcccct acatggctta tcttatgatc      60

tgggatcaga agtctctgaa gaggtgcggt ggcttcctga tacaagacga cttcgtgctg     120

acagctgctc actgttgggg aagctccata aatgtcacct tgggggccca caatatcaaa     180

gaacaggagc cgacccagca gtttatccct gtgaaaagac ccatccccca tccagcctat     240

aatcctaaga acttctccaa cgacatcatg ctactgcagc tggagagaaa ggccaagcgg     300

accagagctg tgcagcccct caggctacct agcaacaagg cccaggtgaa gccagggcag     360

acatgcagtg tggccggctg ggggcagacg gcccccctgg gaaaacactc acacacacta     420

caagaggtga agatgacagt gcaggaagat cgaaagtgcg aatctgactt acgccattat     480

tacgacagta ccattgagtt gtgcgtgggg gacccagaga ttaaaaagac ttcctttaag     540

ggggactctg gaggccctct tgtgtgtaac aaggtggccc agggcattgt ctcctatgga     600

cgaaacaatg gcatgcctcc acgagcctgc accaaagtct caagctttgt acactggata     660

aagaaaacca tgaaacgcta cggtggcggt ggctccacgg acattgtgat gacccagtct     720

caaaaattca tgtccacatc agtaggagac agggtcagcg tcacctgcaa ggccagtcag     780

aatgtggata ctaatgtagc ctggtatcaa caaaaaccag ggcaatctcc tgaaccactg     840

cttttctcgg catcctaccg ttacactgga gtccctgatc gcttcacagg cagtggatct     900

gggacagatt tcactctcac catcagcaat gtgcagtctg aagacttggc agagtatttc     960

tgtcagcaat ataacagcta tcctctgacg ttcggtggag gcaccaagct ggagatcaaa    1020

ggctccacca gcggcagcgg taagccaggc tccggcgaag gcagcaccaa aggcgaagtg    1080

aaggttgagg agtctggagg aggcttggtg caacctggag gatccatgaa actctcctgt    1140

gttgtctctg gattcacttt cggtaattac tggatgaact gggtccgcca gtctccagag    1200

aaggggcttg agtggattgc agaaattaga ttgaaatcca ataattttgc aagatattat    1260

gcggagtctg tgaaagggag gttcaccatc tcaagagatg attccaaaag tagtgtctac    1320

ctgcaaatga tcaacctaag agctgaagat actggcattt attactgtac cagttatggt    1380

aactacgttg ggcactattt tgaccactgg ggccaaggca ccactctcac cgtctcctca    1440
```

<210> SEQ ID NO 59
<211> LENGTH: 480
<212> TYPE: PRT
<213> ORGANISM: Artificial Sequence
<220> FEATURE:
<223> OTHER INFORMATION: Description of Artificial Sequence: Granzyme
B-scFvMEL

<400> SEQUENCE: 59

```
Ile Ile Gly Gly His Glu Ala Lys Pro His Ser Arg Pro Tyr Met Ala
  1               5                  10                  15

Tyr Leu Met Ile Trp Asp Gln Lys Ser Leu Lys Arg Cys Gly Gly Phe
             20                  25                  30

Leu Ile Gln Asp Asp Phe Val Leu Thr Ala Ala His Cys Trp Gly Ser
         35                  40                  45

Ser Ile Asn Val Thr Leu Gly Ala His Asn Ile Lys Glu Gln Glu Pro
     50                  55                  60

Thr Gln Gln Phe Ile Pro Val Lys Arg Pro Ile Pro His Pro Ala Tyr
 65                  70                  75                  80
```

-continued

```
Asn Pro Lys Asn Phe Ser Asn Asp Ile Met Leu Leu Gln Leu Glu Arg
                85                  90                  95

Lys Ala Lys Arg Thr Arg Ala Val Gln Pro Leu Arg Leu Pro Ser Asn
            100                 105                 110

Lys Ala Gln Val Lys Pro Gly Gln Thr Cys Ser Val Ala Gly Trp Gly
        115                 120                 125

Gln Thr Ala Pro Leu Gly Lys His Ser His Thr Leu Gln Glu Val Lys
    130                 135                 140

Met Thr Val Gln Glu Asp Arg Lys Cys Glu Ser Asp Leu Arg His Tyr
145                 150                 155                 160

Tyr Asp Ser Thr Ile Glu Leu Cys Val Gly Asp Pro Glu Ile Lys Lys
                165                 170                 175

Thr Ser Phe Lys Gly Asp Ser Gly Gly Pro Leu Val Cys Asn Lys Val
            180                 185                 190

Ala Gln Gly Ile Val Ser Tyr Gly Arg Asn Asn Gly Met Pro Pro Arg
        195                 200                 205

Ala Cys Thr Lys Val Ser Ser Phe Val His Trp Ile Lys Lys Thr Met
    210                 215                 220

Lys Arg Tyr Gly Gly Gly Gly Ser Thr Asp Ile Val Met Thr Gln Ser
225                 230                 235                 240

Gln Lys Phe Met Ser Thr Ser Val Gly Asp Arg Val Ser Val Thr Cys
                245                 250                 255

Lys Ala Ser Gln Asn Val Asp Thr Asn Val Ala Trp Tyr Gln Gln Lys
            260                 265                 270

Pro Gly Gln Ser Pro Glu Pro Leu Leu Phe Ser Ala Ser Tyr Arg Tyr
        275                 280                 285

Thr Gly Val Pro Asp Arg Phe Thr Gly Ser Gly Ser Gly Thr Asp Phe
    290                 295                 300

Thr Leu Thr Ile Ser Asn Val Gln Ser Glu Asp Leu Ala Glu Tyr Phe
305                 310                 315                 320

Cys Gln Gln Tyr Asn Ser Tyr Pro Leu Thr Phe Gly Gly Gly Thr Lys
                325                 330                 335

Leu Glu Ile Lys Gly Ser Thr Ser Gly Ser Gly Lys Pro Gly Ser Gly
            340                 345                 350

Glu Gly Ser Thr Lys Gly Glu Val Lys Val Glu Glu Ser Gly Gly Gly
        355                 360                 365

Leu Val Gln Pro Gly Gly Ser Met Lys Leu Ser Cys Val Val Ser Gly
    370                 375                 380

Phe Thr Phe Gly Asn Tyr Trp Met Asn Trp Val Arg Gln Ser Pro Glu
385                 390                 395                 400

Lys Gly Leu Glu Trp Ile Ala Glu Ile Arg Leu Lys Ser Asn Asn Phe
                405                 410                 415

Ala Arg Tyr Tyr Ala Glu Ser Val Lys Gly Arg Phe Thr Ile Ser Arg
            420                 425                 430

Asp Asp Ser Lys Ser Ser Val Tyr Leu Gln Met Ile Asn Leu Arg Ala
        435                 440                 445

Glu Asp Thr Gly Ile Tyr Tyr Cys Thr Ser Tyr Gly Asn Tyr Val Gly
    450                 455                 460

His Tyr Phe Asp His Trp Gly Gln Gly Thr Thr Leu Thr Val Ser Ser
465                 470                 475                 480
```

<210> SEQ ID NO 60
<211> LENGTH: 247

-continued

<212> TYPE: PRT
<213> ORGANISM: Homo sapiens
<220> FEATURE:
<221> NAME/KEY: MOD_RES
<222> LOCATION: (55)
<223> OTHER INFORMATION: x = q or r
<220> FEATURE:
<221> NAME/KEY: MOD_RES
<222> LOCATION: (94)
<223> OTHER INFORMATION: z = p or a

<400> SEQUENCE: 60

```
Met Gln Pro Ile Leu Leu Leu Leu Ala Phe Leu Leu Leu Pro Arg Ala
  1               5                  10                  15

Asp Ala Gly Glu Ile Ile Gly Gly His Glu Ala Lys Pro His Ser Arg
             20                  25                  30

Pro Tyr Met Ala Tyr Leu Met Ile Trp Asp Gln Lys Ser Leu Lys Arg
         35                  40                  45

Cys Gly Gly Phe Leu Ile Xaa Asp Asp Phe Val Leu Thr Ala Ala His
     50                  55                  60

Cys Trp Gly Ser Ser Ile Asn Val Thr Leu Gly Ala His Asn Ile Lys
 65                  70                  75                  80

Glu Gln Glu Pro Thr Gln Gln Phe Ile Pro Val Lys Arg Glx Ile Pro
                 85                  90                  95

His Pro Ala Tyr Asn Pro Lys Asn Phe Ser Asn Asp Ile Met Leu Leu
            100                 105                 110

Gln Leu Glu Arg Lys Ala Lys Arg Thr Arg Ala Val Gln Pro Leu Arg
        115                 120                 125

Leu Pro Ser Asn Lys Ala Gln Val Lys Pro Gly Gln Thr Cys Ser Val
    130                 135                 140

Ala Gly Trp Gly Gln Thr Ala Pro Leu Gly Lys His Ser His Thr Leu
145                 150                 155                 160

Gln Glu Val Lys Met Thr Val Gln Glu Asp Arg Lys Cys Glu Ser Asp
                165                 170                 175

Leu Arg His Tyr Tyr Asp Ser Thr Ile Glu Leu Cys Val Gly Asp Pro
            180                 185                 190

Glu Ile Lys Lys Thr Ser Phe Lys Gly Asp Ser Gly Gly Pro Leu Val
        195                 200                 205

Cys Asn Lys Val Ala Gln Gly Ile Val Ser Tyr Gly Arg Asn Asn Gly
    210                 215                 220

Met Pro Pro Arg Ala Cys Thr Lys Val Ser Ser Phe Val His Trp Ile
225                 230                 235                 240

Lys Lys Thr Met Lys Arg Tyr
                245
```

<210> SEQ ID NO 61
<211> LENGTH: 34
<212> TYPE: PRT
<213> ORGANISM: Homo sapiens

<400> SEQUENCE: 61

```
Met Lys Ser Leu Ser Leu Leu His Leu Phe Pro Leu Pro Arg Ala Lys
  1               5                  10                  15

Arg Glu Gln Gly Gly Asn Asn Ser Ser Ser Asn Gln Gly Ser Leu Pro
             20                  25                  30

Glu Lys
```